(12) United States Patent
O'Toole et al.

(10) Patent No.: US 7,109,294 B2
(45) Date of Patent: Sep. 19, 2006

(54) BACTERIAL GLYCOSYLTRANSFERASE POLYPEPTIDES INVOLVED IN ANTIBIOTIC RESISTANCE

(75) Inventors: George A. O'Toole, Hanover, NH (US); Thien-Fah Mah, Hanover, NH (US)

(73) Assignee: Trustees of Dartmouth College, Hanover, NH (US)

( * ) Notice: Subject to any disclaimer, the term of this patent is extended or adjusted under 35 U.S.C. 154(b) by 412 days.

(21) Appl. No.: 10/246,330

(22) Filed: Sep. 18, 2002

(65) Prior Publication Data

US 2003/0166030 A1    Sep. 4, 2003

Related U.S. Application Data

(60) Provisional application No. 60/323,241, filed on Sep. 18, 2001.

(51) Int. Cl.
*C07K 1/00* (2006.01)
(52) U.S. Cl. ............... 530/350; 530/300; 435/7.32; 435/252.1; 435/32; 435/7.1; 435/69.1; 435/193; 514/2; 514/12
(58) Field of Classification Search ............... 435/193
See application file for complete search history.

(56) References Cited

U.S. PATENT DOCUMENTS

| | | | |
|---|---|---|---|
| 5,989,832 A | 11/1999 | Trias et al. | 435/7.2 |
| 6,020,121 A | 2/2000 | Bao et al. | 435/4 |
| 6,037,123 A | 3/2000 | Benton et al. | 435/6 |
| 6,114,310 A | 9/2000 | Chamberland et al. | 514/39 |
| 6,187,541 B1 | 2/2001 | Benton et al. | 435/6 |
| 6,228,588 B1 | 5/2001 | Benton et al. | 435/6 |
| 6,245,746 B1 | 6/2001 | Chamberland et al. | 514/39 |
| 6,399,629 B1 | 6/2002 | Chamberland et al. | 514/313 |

OTHER PUBLICATIONS

Ielpi et al. The ndvB Locus of Rhizobium meliloti Encodes a 319-kDa Protein Involved in the Production of beta-1-2-glucan. J. Biol. Chem. (1990) 265(5): 2843-2851.*
Stover et al. Complete genome sequence of Pseudomonas aeruginosa PA01, an opportunistic pathogen. Nature (2000) 406: 959-964 including supplemental materials at http://www.pseudomonas.com.*
Bhagwat et al. Site-Directed Mutagenesis of the beta-1-3, beta-1-6-D-Glucan Synthesis Locus of Bradyrhizobium japonicum. Molecular Plant-Microbe Interactions (1995) 8(3): 366-370.*
GenBank Accession No. H83500. probably glucosyl transferase PA1163 (2000).*
GenBank Accession No. AAC62210. beta-(1-3)- glucosyl transferase (1998).*
GenBank Accession No. NP_357541. hypothetical protein AGR_L_3500 (2001).*
GenBank Accession No. AAN67147. beta-(1-3)-glucosyl transferase (2002).*
GenBank Accession No. NP_791349. glycosyl transferase, group 2 family protein (2003).*
Bhagwat et al. J. Bacteriol. (1996) 178(15): 4635-4642.*
Mah et al. Nature (2003) 426: 306-310.*
Mah et al., TRENDS in Microbiology, vol. 9, No. 1, Jan. 2001.*
Hancock et al., Pseudomonas Genome Project, "Approach for primary Annotation of the *P. Aeruginosa* PAO1 genome" 2000.

* cited by examiner

*Primary Examiner*—Hope Robinson
(74) *Attorney, Agent, or Firm*—Licata & Tyrrell P.C.

(57) ABSTRACT

Disclosed are various genes encoding proteins that are shown to play a role, direct or indirect, in microbial resistance of an organism in a biofilm and homologs thereof. Also disclosed are methods of identifying a compound that modulates microbial resistance of an organism in a biofilm, and methods of identifying genes that encode proteins that play a role, direct or indirect, in biofilm resistance.

1 Claim, 43 Drawing Sheets

NdvB

| | | | | | | | | | | | | | | | | |
|---|---|---|---|---|---|---|---|---|---|---|---|---|---|---|---|---|
| atg | tct | tca | cgc | aag | atc | ggg | ctc | aac | ctg | gtg | gtc | atc | gtc | gcc | ctg | 48 |
| Met | Ser | Ser | Arg | Lys | Ile | Gly | Leu | Asn | Leu | Val | Val | Ile | Val | Ala | Leu | |
| 1 | | | | 5 | | | | | 10 | | | | | 15 | | |

| gcc | gcc | ctc | ttc | acc | ggc | atc | tgg | gcc | ctg | tac | aac | cgt | ccg | gtc | agc | 96 |
|---|---|---|---|---|---|---|---|---|---|---|---|---|---|---|---|---|
| Ala | Ala | Leu | Phe | Thr | Gly | Ile | Trp | Ala | Leu | Tyr | Asn | Arg | Pro | Val | Ser | |
| | | | 20 | | | | 25 | | | | | 30 | | | | |

| gta | ccg | gac | tgg | ccg | gaa | cgc | atc | tcc | ggc | ttc | tcc | ttc | tcg | ccg | ttc | 144 |
|---|---|---|---|---|---|---|---|---|---|---|---|---|---|---|---|---|
| Val | Pro | Asp | Trp | Pro | Glu | Arg | Ile | Ser | Gly | Phe | Ser | Phe | Ser | Pro | Phe | |
| | | 35 | | | | | 40 | | | | | 45 | | | | |

| cgc | ctc | aac | cag | aac | ccg | cag | agc | ggc | cgc | tac | ccc | agc | gcc | gaa | cag | 192 |
|---|---|---|---|---|---|---|---|---|---|---|---|---|---|---|---|---|
| Arg | Leu | Asn | Gln | Asn | Pro | Gln | Ser | Gly | Arg | Tyr | Pro | Ser | Ala | Glu | Gln | |
| | 50 | | | | | 55 | | | | | 60 | | | | | |

| atg | cgc | acc | gac | ctg | gaa | ctg | gtc | gcc | cgg | cac | acc | cac | agc | atc | cgc | 240 |
|---|---|---|---|---|---|---|---|---|---|---|---|---|---|---|---|---|
| Met | Arg | Thr | Asp | Leu | Glu | Leu | Val | Ala | Arg | His | Thr | His | Ser | Ile | Arg | |
| 65 | | | | | 70 | | | | | 75 | | | | | 80 | |

| acc | tat | tcg | gtc | cag | ggc | gcg | ctc | ggc | gac | atc | ccg | gcg | ctg | gcc | gag | 288 |
|---|---|---|---|---|---|---|---|---|---|---|---|---|---|---|---|---|
| Thr | Tyr | Ser | Val | Gln | Gly | Ala | Leu | Gly | Asp | Ile | Pro | Ala | Leu | Ala | Glu | |
| | | | | 85 | | | | | 90 | | | | | 95 | | |

| gcg | ttc | ggc | ctg | cgc | gtc | agc | ctg | ggc | atc | tgg | ctc | ggc | ccg | gac | ctg | 336 |
|---|---|---|---|---|---|---|---|---|---|---|---|---|---|---|---|---|
| Ala | Phe | Gly | Leu | Arg | Val | Ser | Leu | Gly | Ile | Trp | Leu | Gly | Pro | Asp | Leu | |
| | | | 100 | | | | | 105 | | | | | 110 | | | |

| gcc | agc | aac | gag | gcc | gag | atc | gcc | cgc | gcc | atc | cgc | atc | gcc | aac | gag | 384 |
|---|---|---|---|---|---|---|---|---|---|---|---|---|---|---|---|---|
| Ala | Ser | Asn | Glu | Ala | Glu | Ile | Ala | Arg | Ala | Ile | Arg | Ile | Ala | Asn | Glu | |
| | | 115 | | | | | 120 | | | | | 125 | | | | |

| tcg | ccg | agc | gtg | gtg | cga | gtg | ata | gtc | ggc | aac | gag | gcg | ctg | ttc | cgc | 432 |
|---|---|---|---|---|---|---|---|---|---|---|---|---|---|---|---|---|
| Ser | Pro | Ser | Val | Val | Arg | Val | Ile | Val | Gly | Asn | Glu | Ala | Leu | Phe | Arg | |
| | 130 | | | | | 135 | | | | | 140 | | | | | |

| cgc | gag | gtg | acg | gcg | gaa | cag | ttg | atc | gcc | tac | ctc | gac | cgg | gtc | cgc | 480 |
|---|---|---|---|---|---|---|---|---|---|---|---|---|---|---|---|---|
| Arg | Glu | Val | Thr | Ala | Glu | Gln | Leu | Ile | Ala | Tyr | Leu | Asp | Arg | Val | Arg | |
| 145 | | | | | 150 | | | | | 155 | | | | | 160 | |

| gcg | gcg | gtc | aag | gtt | ccg | gtg | acc | acc | gcc | gaa | cag | tgg | cac | gtc | tac | 528 |
|---|---|---|---|---|---|---|---|---|---|---|---|---|---|---|---|---|
| Ala | Ala | Val | Lys | Val | Pro | Val | Thr | Thr | Ala | Glu | Gln | Trp | His | Val | Tyr | |
| | | | | 165 | | | | | 170 | | | | | 175 | | |

| cgc | gaa | cac | ccg | gaa | ctg | gcg | caa | cac | gtc | gac | ctg | atc | gcc | gcc | cac | 576 |
|---|---|---|---|---|---|---|---|---|---|---|---|---|---|---|---|---|
| Arg | Glu | His | Pro | Glu | Leu | Ala | Gln | His | Val | Asp | Leu | Ile | Ala | Ala | His | |
| | | | 180 | | | | | 185 | | | | | 190 | | | |

| gtc | ctg | ccc | tac | tgg | gag | gcc | acg | ccg | gtg | gcc | gac | gcg | gtg | gac | ttc | 624 |
|---|---|---|---|---|---|---|---|---|---|---|---|---|---|---|---|---|
| Val | Leu | Pro | Tyr | Trp | Glu | Ala | Thr | Pro | Val | Ala | Asp | Ala | Val | Asp | Phe | |
| | | | 195 | | | | | 200 | | | | | 205 | | | |

| gtg | ctc | gaa | cgc | gcg | cgc | gaa | ctc | aag | gcc | gcc | ttc | ccg | agg | aag | ccg | 672 |
|---|---|---|---|---|---|---|---|---|---|---|---|---|---|---|---|---|
| Val | Leu | Glu | Arg | Ala | Arg | Glu | Leu | Lys | Ala | Ala | Phe | Pro | Arg | Lys | Pro | |
| | 210 | | | | | 215 | | | | | 220 | | | | | |

FIG. 6A

```
ctg ctg ctc gcc gag gtc ggc tgg ccg agc aac ggg cgc atg cgc ggc    720
Leu Leu Leu Ala Glu Val Gly Trp Pro Ser Asn Gly Arg Met Arg Gly
225             230             235             240 agc gcc gag gcg aca ccc gcg gac cag gcc atc tac ctg cgg cgc ctg    768
Ser Ala Glu Ala Thr Pro Ala Asp Gln Ala Ile Tyr Leu Arg Arg Leu
                245             250             255 acc aac gcg ctc aac ggc gaa ggc tac agc tac ttc gtc atc gaa gcc    816
Thr Asn Ala Leu Asn Gly Glu Gly Tyr Ser Tyr Phe Val Ile Glu Ala
            260             265             270 ttc gac cag ccc tgg aag gtc agc gcc gaa ggc tcg gtg ggc gcc tac    864
Phe Asp Gln Pro Trp Lys Val Ser Ala Glu Gly Ser Val Gly Ala Tyr
        275             280             285 tgg ggc gtc tac aac gcc gac cgc aag gcc aag ttc aac ttc acc ggg    912
Trp Gly Val Tyr Asn Ala Asp Arg Lys Ala Lys Phe Asn Phe Thr Gly
    290             295             300 ccg gtg gtg ccg att ccc aag tgg cgc gcc ctg gcc atc gcc tcg gcg    960
Pro Val Val Pro Ile Pro Lys Trp Arg Ala Leu Ala Ile Ala Ser Ala
305             310             315             320 gta ctc gcg gta ctc gcc ttc acc ctg ctg ctg atc gac agt tcc tcg    1008
Val Leu Ala Val Leu Ala Phe Thr Leu Leu Leu Ile Asp Ser Ser Ser
                325             330             335 ctg cgc cag cgc ggg agg acc ttc ctc gcc gtg gtc tcg ttc gcc tgc    1056
Leu Arg Gln Arg Gly Arg Thr Phe Leu Ala Val Val Ser Phe Ala Cys
            340             345             350 gcc tcg gtg ctg gtg tgg atc gcc tac gac tac agc cag cag tac agc    1104
Ala Ser Val Leu Val Trp Ile Ala Tyr Asp Tyr Ser Gln Gln Tyr Ser
        355             360             365 acc tgg ttc agc ctg acc gtc ggc gcg ttg ctg ggc gtc ggc gcg cta    1152
Thr Trp Phe Ser Leu Thr Val Gly Ala Leu Leu Gly Val Gly Ala Leu
    370             375             380 ggg gtg gtc atc gtg ctg ttc acc gag gcc cac gag ctg gcc gag gcg    1200
Gly Val Val Ile Val Leu Phe Thr Glu Ala His Glu Leu Ala Glu Ala
385             390             395             400 gtc tgg acg cgc aag cgg cgc cgg cca ttc ctg ccg atc acc gcc gcg    1248
Val Trp Thr Arg Lys Arg Arg Arg Pro Phe Leu Pro Ile Thr Ala Ala
                405             410             415 cgg gcc tat cgg ccc aag gtg tcg atc cac gtg ccc tgc tac aac gag    1296
Arg Ala Tyr Arg Pro Lys Val Ser Ile His Val Pro Cys Tyr Asn Glu
            420             425             430 ccg ccg gaa ctg ctg aag cag acc ctc gac gcc ctt gcc cgc ctc gac    1344
Pro Pro Glu Leu Leu Lys Gln Thr Leu Asp Ala Leu Ala Arg Leu Asp
        435             440             445
```

FIG. 6B

```
tac ccg gac tac gaa gtc ctg gtg atc gac aac aac acc cgc gac ccg    1392
Tyr Pro Asp Tyr Glu Val Leu Val Ile Asp Asn Asn Thr Arg Asp Pro
    450             455             460 gcc gtc tgg cag ccg gtc gag gcg cac tgc gcg cgc ctg ggc gag cgc    1440
Ala Val Trp Gln Pro Val Glu Ala His Cys Ala Arg Leu Gly Glu Arg
465             470             475             480 ttc cgc ttc ttc cac gtt gcc ccg ctg gaa ggc ttc aag gcc ggc gcg    1488
Phe Arg Phe Phe His Val Ala Pro Leu Glu Gly Phe Lys Ala Gly Ala
                485             490             495 ctg aac ttc gcc ctg ggc cac gtg gcg gcg gac gtc gag gtg gtc gcg    1536
Leu Asn Phe Ala Leu Gly His Val Ala Ala Asp Val Glu Val Val Ala
        500             505             510 gtg atc gac gcc gac tac tgc gtc gac ccc gac tgg ctc agg cac atg    1584
Val Ile Asp Ala Asp Tyr Cys Val Asp Pro Asp Trp Leu Arg His Met
    515             520             525 gtg ccg cac ttc ggc gac ccg cgg atc gcc gtg gtg cag tcg ccg cag    1632
Val Pro His Phe Gly Asp Pro Arg Ile Ala Val Val Gln Ser Pro Gln
530             535             540 gac tac cgc gac cag cac gag agc gcc ttc aag cgg ctc tgc tac gcc    1680
Asp Tyr Arg Asp Gln His Glu Ser Ala Phe Lys Arg Leu Cys Tyr Ala
545             550             555             560 gag tac aag ggc ttc ttc cac atc ggc atg gtc acc cgc aac gac cgc    1728
Glu Tyr Lys Gly Phe Phe His Ile Gly Met Val Thr Arg Asn Asp Arg
                565             570             575 gac gcg atc atc gag cac ggc acc atg acc atg atc cgg cgc agc gtg    1776
Asp Ala Ile Ile Glu His Gly Thr Met Thr Met Ile Arg Arg Ser Val
        580             585             590 ctg gac gag ctg aga tgg ccg gaa tgg tgc atc acc gag gac gcc gag    1824
Leu Asp Glu Leu Arg Trp Pro Glu Trp Cys Ile Thr Glu Asp Ala Glu
    595             600             605 ctg ggc ctg cgg gtg ttc gag aag ggc ctg tcg gcc gcc tac ttc gag    1872
Leu Gly Leu Arg Val Phe Glu Lys Gly Leu Ser Ala Ala Tyr Phe Glu
610             615             620 cgc agc tac ggc aag ggg gtg atg ccc gat acc ttc atc gat ttc aag    1920
Arg Ser Tyr Gly Lys Gly Val Met Pro Asp Thr Phe Ile Asp Phe Lys
625             630             635             640 aag cag cgc ttc cgc tgg gcc tac ggc gcg atc cag atc atg aag cgg    1968
Lys Gln Arg Phe Arg Trp Ala Tyr Gly Ala Ile Gln Ile Met Lys Arg
                645             650             655 cat acc gac gcc ctg ctg cgc ggc cgc ggt ccc gac ggc agc cgc ctg    2016
His Thr Asp Ala Leu Leu Arg Gly Arg Gly Pro Asp Gly Ser Arg Leu
        660             665             670
```

FIG. 6C

```
acc cgc ggc cag cgc tac cac ttc gtg gcc ggc tgg ctg ccg tgg atc    2064
Thr Arg Gly Gln Arg Tyr His Phe Val Ala Gly Trp Leu Pro Trp Ile
        675             680             685 gcc gac ggc ctg aac atc ttc ttc acc ctc ggc gcg ctg ctc tgg tcg    2112
Ala Asp Gly Leu Asn Ile Phe Phe Thr Leu Gly Ala Leu Leu Trp Ser
        690             695             700 gcg gcg atg atc atc gtg ccc aag cgc gtc gac ccg ccg ctg ctg atc    2160
Ala Ala Met Ile Ile Val Pro Lys Arg Val Asp Pro Pro Leu Leu Ile
705             710             715             720 ttc gcg atc ctg ccg ctg gcc ctg ttc gtc ttc aag gtc ggc aag atc    2208
Phe Ala Ile Leu Pro Leu Ala Leu Phe Val Phe Lys Val Gly Lys Ile
                725             730             735 ctc ttc ctc tac cgg cgc acc gtc ggc gtc gac ctg cgc gac tcg ttc    2256
Leu Phe Leu Tyr Arg Arg Thr Val Gly Val Asp Leu Arg Asp Ser Phe
            740             745             750 ttc gcc gcc ctc gcc ggc ctg tcg ctc tcg cac acc att gcc aag gcg    2304
Phe Ala Ala Leu Ala Gly Leu Ser Leu Ser His Thr Ile Ala Lys Ala
        755             760             765 gtg ctg tac ggc ttc gtc acc cgc ggc atc ccg ttc ttc cgc acg ccg    2352
Val Leu Tyr Gly Phe Val Thr Arg Gly Ile Pro Phe Phe Arg Thr Pro
    770             775             780 aag atg cgc tcc agc cac ggc ctg ctg gtg gcc ctg gcg gag gcc cgc    2400
Lys Met Arg Ser Ser His Gly Leu Leu Val Ala Leu Ala Glu Ala Arg
785             790             795             800 gag gaa gtc ttc gtg atg ctc ctg ctg tgg ggc gcg gcg gcc ggc atc    2448
Glu Glu Val Phe Val Met Leu Leu Leu Trp Gly Ala Ala Ala Gly Ile
                805             810             815
```

FIG. 6D

```
gtg gcg gtt cag ggc gtg ccg agc cgc gac ctg ctg atc tgg gtc gcc    2496
Val Ala Val Gln Gly Val Pro Ser Arg Asp Leu Leu Ile Trp Val Ala
            820                 825                 830 atg ctc ctg gtg caa tcg ctg ccc tac ctg gcg gcg ctg gtc atg gcc    2544
Met Leu Leu Val Gln Ser Leu Pro Tyr Leu Ala Ala Leu Val Met Ala
            835                 840                 845 ttg ctc tcg tcg ctg ccg aaa ccg cgc gag gaa ctg gcc ggc ggc gcc    2592
Leu Leu Ser Ser Leu Pro Lys Pro Arg Glu Glu Leu Ala Gly Gly Ala
            850                 855                 860 gag cag atc ggc ggt tga                                            2610
Glu Gln Ile Gly Gly *
```

| | | | | | | | | | | | | | | | | |
|---|---|---|---|---|---|---|---|---|---|---|---|---|---|---|---|---|
| atg | tcg | atc | cag | gcg | aaa | gtt | acc | cct | atc | gat | cag | agt | att | tct | tct | 48 |
| Met | Ser | Ile | Gln | Ala | Lys | Val | Thr | Pro | Ile | Asp | Gln | Ser | Ile | Ser | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcg | gct | gcc | gtc | gag | gtt | ccg | gaa | aac | ggg | ata | ctc | aaa | ctc | tcc | cag | 96 |
| Ala | Ala | Ala | Val | Glu | Val | Pro | Glu | Asn | Gly | Ile | Leu | Lys | Leu | Ser | Gln | |
| | | | 20 | | | | | 25 | | | | | 30 | | | |

| | | | | | | | | | | | | | | | | |
|---|---|---|---|---|---|---|---|---|---|---|---|---|---|---|---|---|
| agc | agt | aat | gtc | gcg | ctc | gat | gtc | gca | ccg | gag | tcg | gtg | gcg | gga | tac | 144 |
| Ser | Ser | Asn | Val | Ala | Leu | Asp | Val | Ala | Pro | Glu | Ser | Val | Ala | Gly | Tyr | |
| | | 35 | | | | | 40 | | | | | 45 | | | | |

| | | | | | | | | | | | | | | | | |
|---|---|---|---|---|---|---|---|---|---|---|---|---|---|---|---|---|
| tcg | aag | agc | ggt | tcg | gac | ctg | atc | gtc | cag | ctg | aag | acc | ggg | gaa | agc | 192 |
| Ser | Lys | Ser | Gly | Ser | Asp | Leu | Ile | Val | Gln | Leu | Lys | Thr | Gly | Glu | Ser | |
| | 50 | | | | | 55 | | | | | 60 | | | | | |

| | | | | | | | | | | | | | | | | |
|---|---|---|---|---|---|---|---|---|---|---|---|---|---|---|---|---|
| gtc | cgg | atc | gcc | aac | ttc | tat | gcg | gaa | ggc | cag | cct | tcc | agc | caa | ctg | 240 |
| Val | Arg | Ile | Ala | Asn | Phe | Tyr | Ala | Glu | Gly | Gln | Pro | Ser | Ser | Gln | Leu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttc | ctg | gcc | gac | aag | gac | aag | ctg | gtg | gcg | gta | gat | ctg | ccg | ccg | gtc | 288 |
| Phe | Leu | Ala | Asp | Lys | Asp | Lys | Leu | Val | Ala | Val | Asp | Leu | Pro | Pro | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| gct | gcc | gac | ggg | ccg | ctg | atg | gcc | ggc | tac | atc | ccg | cag | gaa | agc | ctg | 336 |
| Ala | Ala | Asp | Gly | Pro | Leu | Met | Ala | Gly | Tyr | Ile | Pro | Gln | Glu | Ser | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| gcc | ggt | ttc | gag | tcg | ctg | acc | ggc | gcc | ggt | gtg | ctc | ggt | ggc | atg | agc | 384 |
| Ala | Gly | Phe | Glu | Ser | Leu | Thr | Gly | Ala | Gly | Val | Leu | Gly | Gly | Met | Ser | |
| | | | 115 | | | | | 120 | | | | | 125 | | | |

| | | | | | | | | | | | | | | | | |
|---|---|---|---|---|---|---|---|---|---|---|---|---|---|---|---|---|
| gca | ggg | act | gcg | ctg | ctg | gtc | ggt | gcg | gcg | gcc | atc | ggc | gcc | ggg | gtg | 432 |
| Ala | Gly | Thr | Ala | Leu | Leu | Val | Gly | Ala | Ala | Ala | Ile | Gly | Ala | Gly | Val | |
| | | 130 | | | | | 135 | | | | | 140 | | | | |

| | | | | | | | | | | | | | | | | |
|---|---|---|---|---|---|---|---|---|---|---|---|---|---|---|---|---|
| gcg | att | tcc | aac | agc | agc | ggc | ggc | ggt | ggc | ggc | ggc | ggt | tct | tcg | gtg | 480 |
| Ala | Ile | Ser | Asn | Ser | Ser | Gly | Gly | Gly | Gly | Gly | Gly | Gly | Ser | Ser | Val | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ccc | ccg | gac | acc | act | ccg | ccg | aag | gcg | gcc | agc | ggc | ctg | aag | ata | gcg | 528 |
| Pro | Pro | Asp | Thr | Thr | Pro | Pro | Lys | Ala | Ala | Ser | Gly | Leu | Lys | Ile | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| cct | gac | ggc | agc | agc | atc | agc | ggc | cag | gcc | gag | gcc | ggc | gcg | agc | gtc | 576 |
| Pro | Asp | Gly | Ser | Ser | Ile | Ser | Gly | Gln | Ala | Glu | Ala | Gly | Ala | Ser | Val | |
| | | | 180 | | | | | 185 | | | | | 190 | | | |

| | | | | | | | | | | | | | | | | |
|---|---|---|---|---|---|---|---|---|---|---|---|---|---|---|---|---|
| ggc | atc | gat | acc | aat | ggc | gac | ggc | aag | ccg | gac | ctc | acc | gtg | atc | gcc | 624 |
| Gly | Ile | Asp | Thr | Asn | Gly | Asp | Gly | Lys | Pro | Asp | Leu | Thr | Val | Ile | Ala | |
| | | 195 | | | | | 200 | | | | | 205 | | | | |

| | | | | | | | | | | | | | | | | |
|---|---|---|---|---|---|---|---|---|---|---|---|---|---|---|---|---|
| gat | gcc | aac | ggc | aat | ttc | acc | gct | ccg | ctg | aac | ccg | ccg | ctg | acc | aat | 672 |
| Asp | Ala | Asn | Gly | Asn | Phe | Thr | Ala | Pro | Leu | Asn | Pro | Pro | Leu | Thr | Asn | |
| | 210 | | | | | 215 | | | | | 220 | | | | | |

FIG. 7A

```
ggc cag acg gtc acc gtg gtg gtc acc gac ccg gct ggc aac gcc agc    720
Gly Gln Thr Val Thr Val Val Val Thr Asp Pro Ala Gly Asn Ala Ser
225             230             235             240 ccg ccg gcc cag gtc acc gct ccg gac act acc gcc ccg gcg ccg gct    768
Pro Pro Ala Gln Val Thr Ala Pro Asp Thr Thr Ala Pro Ala Pro Ala
                245             250             255 acc gac gtg cag gtg gcg ccg gac ggc agc agc gtc acc ggc aag gcc    816
Thr Asp Val Gln Val Ala Pro Asp Gly Ser Ser Val Thr Gly Lys Ala
                260             265             270 gaa ccc ggc tcg acg gtg ggc gtc gat acc gac ggc gac ggc cag ccg    864
Glu Pro Gly Ser Thr Val Gly Val Asp Thr Asp Gly Asp Gly Gln Pro
            275             280             285 gac acc acc gtg gtg gtc ggc ccc ggc ggc agc ttc gag gtt ccg ctg    912
Asp Thr Thr Val Val Val Gly Pro Gly Gly Ser Phe Glu Val Pro Leu
        290             295             300 aac ccg ccg ctg acc aat ggc gag acg gtg acg gtg atc gtt acc gac    960
Asn Pro Pro Leu Thr Asn Gly Glu Thr Val Thr Val Ile Val Thr Asp
305             310             315             320 ccg gcc ggc aac aac agc acc ccg gtg acc gtc gag gcg ccg gac acc   1008
Pro Ala Gly Asn Asn Ser Thr Pro Val Thr Val Glu Ala Pro Asp Thr
                325             330             335 acc gcc ccg gcg ccg gcc acc gac gtg cag gtg gcg ccg gac ggc agc   1056
Thr Ala Pro Ala Pro Ala Thr Asp Val Gln Val Ala Pro Asp Gly Ser
                340             345             350 agc gtc acc ggc aac gca gag ccg ggc gcc acc gtc ggt gtc gac acc   1104
Ser Val Thr Gly Asn Ala Glu Pro Gly Ala Thr Val Gly Val Asp Thr
            355             360             365 gat ggc gac ggc cag ccg gac acc acc gtg gtg gtc ggt ccc ggc ggc   1152
Asp Gly Asp Gly Gln Pro Asp Thr Thr Val Val Val Gly Pro Gly Gly
        370             375             380 agc ttc gag gtt ccg ctg aac ccg ccg ctg acc aat ggc gag acg gtg   1200
Ser Phe Glu Val Pro Leu Asn Pro Pro Leu Thr Asn Gly Glu Thr Val
385             390             395             400 acg gtg atc gtt acc gac ccg gcc ggc aac agc agc acc ccg gtc acc   1248
Thr Val Ile Val Thr Asp Pro Ala Gly Asn Ser Ser Thr Pro Val Thr
                405             410             415 gcc gaa gcc ccc gac ttc ccc gac gcg ccc cag gtc aat gcc agc aac   1296
Ala Glu Ala Pro Asp Phe Pro Asp Ala Pro Gln Val Asn Ala Ser Asn
                420             425             430 ggc agc gtc ctc agt ggt acg gcg gaa gcg ggc gtg acc atc gtg atc   1344
Gly Ser Val Leu Ser Gly Thr Ala Glu Ala Gly Val Thr Ile Val Ile
            435             440             445
```

FIG. 7B

```
acc gac ggc aac ggc aat ccg atc ggc cag acc agc gcc gat gcc aac   1392
Thr Asp Gly Asn Gly Asn Pro Ile Gly Gln Thr Ser Ala Asp Ala Asn
    450                 455                 460 ggc aac tgg agc ttc acc ccc ggt agc caa ctg ccg gat ggc acc gtg   1440
Gly Asn Trp Ser Phe Thr Pro Gly Ser Gln Leu Pro Asp Gly Thr Val
465                 470                 475                 480 gtc aat gtg gtg gcc agg gac gcc gcc ggc aac agc agc ccg gcg acc   1488
Val Asn Val Val Ala Arg Asp Ala Ala Gly Asn Ser Ser Pro Ala Thr
                485                 490                 495 tcc atc acc gtc gac ggc gtg gcg ccg aac gcg ccg gtg gtc gag ccg   1536
Ser Ile Thr Val Asp Gly Val Ala Pro Asn Ala Pro Val Val Glu Pro
            500                 505                 510 agc aac ggc agc gaa ctc agc ggg act gcc gaa ccg ggc agc agc gtg   1584
Ser Asn Gly Ser Glu Leu Ser Gly Thr Ala Glu Pro Gly Ser Ser Val
        515                 520                 525 acc ctg acc gac ggc aat ggc aat ccg atc ggc cag acc acc gcc gat   1632
Thr Leu Thr Asp Gly Asn Gly Asn Pro Ile Gly Gln Thr Thr Ala Asp
    530                 535                 540 gcc aac ggc aac tgg tct ttc acg ccg tcc acc ccg ttg ccg gac ggt   1680
Ala Asn Gly Asn Trp Ser Phe Thr Pro Ser Thr Pro Leu Pro Asp Gly
545                 550                 555                 560 acc gtg gtc aac gtg gtg gcc agg gat gcc gcc ggc aac agc agt ccg   1728
Thr Val Val Asn Val Val Ala Arg Asp Ala Ala Gly Asn Ser Ser Pro
                565                 570                 575 ccg gcc agc gtt acc gtg gat gcc gtc gcg ccg gcc acg ccc acc gtc   1776
Pro Ala Ser Val Thr Val Asp Ala Val Ala Pro Ala Thr Pro Thr Val
            580                 585                 590 gat ccg agc aac ggt acg acc ctc agc ggc acc gcc gag ccg ggc agt   1824
Asp Pro Ser Asn Gly Thr Thr Leu Ser Gly Thr Ala Glu Pro Gly Ser
        595                 600                 605 agc gtg acc ctg acc gac ggc aac ggt aac ccg ata ggg cag gtc acc   1872
Ser Val Thr Leu Thr Asp Gly Asn Gly Asn Pro Ile Gly Gln Val Thr
    610                 615                 620 gcc gac ggc agc ggc aac tgg acc ttc acc ccg agc acg ccg ttg ccc   1920
Ala Asp Gly Ser Gly Asn Trp Thr Phe Thr Pro Ser Thr Pro Leu Pro
625                 630                 635                 640 aac ggc acg gtg gtc aac gcc acg gct acc gac ccg tcc ggc aac gcc   1968
Asn Gly Thr Val Val Asn Ala Thr Ala Thr Asp Pro Ser Gly Asn Ala
                645                 650                 655 agt tcg ccg gcc agc gtc acc gtg gac gcc gtg gca ccg gcc acg cca   2016
Ser Ser Pro Ala Ser Val Thr Val Asp Ala Val Ala Pro Ala Thr Pro
            660                 665                 670
```

FIG. 7C

```
gtg gtc aac ccg agc aac ggc acc acg ctc agc ggc acc gcc gag ccg    2064
Val Val Asn Pro Ser Asn Gly Thr Thr Leu Ser Gly Thr Ala Glu Pro
        675                 680                 685 ggc gcc acc gtg acc ctg acc gat ggc aac ggc aat ccc atc ggg cag    2112
Gly Ala Thr Val Thr Leu Thr Asp Gly Asn Gly Asn Pro Ile Gly Gln
    690                 695                 700 gtc acc gcc gat ggc agc ggc aac tgg agc ttc act ccg acc acg ccg    2160
Val Thr Ala Asp Gly Ser Gly Asn Trp Ser Phe Thr Pro Thr Thr Pro
705                 710                 715                 720 ttg ccc aac ggc acc gtg gtc aac gcc acg gcc acc gac gcc tcc ggc    2208
Leu Pro Asn Gly Thr Val Val Asn Ala Thr Ala Thr Asp Ala Ser Gly
                725                 730                 735 aac acc agt gcg ggc agc agt gtc acc gtg gac tcg gta gcc ccg gcc    2256
Asn Thr Ser Ala Gly Ser Ser Val Thr Val Asp Ser Val Ala Pro Ala
            740                 745                 750 acg cca gtg atc aac ccc agc aac ggc acc acg ctc agc ggc acc gcc    2304
Thr Pro Val Ile Asn Pro Ser Asn Gly Thr Thr Leu Ser Gly Thr Ala
        755                 760                 765 gag ccg ggc agc agc gtg act ctg acc gat ggc aac ggc aac ccg att    2352
Glu Pro Gly Ser Ser Val Thr Leu Thr Asp Gly Asn Gly Asn Pro Ile
    770                 775                 780 ggc cag gtc acc gcc gac ggc agc ggc aac tgg agc ttc acc ccg tcc    2400
Gly Gln Val Thr Ala Asp Gly Ser Gly Asn Trp Ser Phe Thr Pro Ser
785                 790                 795                 800 acg ccg ctg gcg gat gga acc gtg gtc aac gcc acg gcc acc gat ccg    2448
Thr Pro Leu Ala Asp Gly Thr Val Val Asn Ala Thr Ala Thr Asp Pro
                805                 810                 815 gcg ggc aac acc agc ggc cag ggc agc acc acc gtc gat ggc gtg gcg    2496
Ala Gly Asn Thr Ser Gly Gln Gly Ser Thr Thr Val Asp Gly Val Ala
            820                 825                 830 ccg acc acg ccg acc gtc aac ctg agc aac ggc agc agc ctc agc ggc    2544
Pro Thr Thr Pro Thr Val Asn Leu Ser Asn Gly Ser Ser Leu Ser Gly
        835                 840                 845 act gcg gaa ccg ggc agc acg gtg atc ctc acc gac ggc aac ggc aat    2592
Thr Ala Glu Pro Gly Ser Thr Val Ile Leu Thr Asp Gly Asn Gly Asn
    850                 855                 860 ccg atc gcc gag gtc acc gcc gac ggc agc ggc aac tgg acc tac acc    2640
Pro Ile Ala Glu Val Thr Ala Asp Gly Ser Gly Asn Trp Thr Tyr Thr
865                 870                 875                 880 ccg tcc acg ccg atc gcc aac ggc acc gtg gtc aac gtg gtg gcc cag    2688
Pro Ser Thr Pro Ile Ala Asn Gly Thr Val Val Asn Val Val Ala Gln
                885                 890                 895
```

FIG. 7D

```
gac gcc gcc ggc aat agc agc ccg ggc gcc agc gtc acc gtg gac tcg    2736
Asp Ala Ala Gly Asn Ser Ser Pro Gly Ala Ser Val Thr Val Asp Ser
            900             905             910 cag gcc ccg gcg gct ccg gtg gtc aac ccg agc aac ggc act acg ctc    2784
Gln Ala Pro Ala Ala Pro Val Val Asn Pro Ser Asn Gly Thr Thr Leu
            915             920             925 agc ggc acc gcc gag ccg ggc gct acc gtg acc ctg acc gac ggc aac    2832
Ser Gly Thr Ala Glu Pro Gly Ala Thr Val Thr Leu Thr Asp Gly Asn
            930             935             940 ggc aac ccg att ggc cag gtc acc gcc gac ggc agc ggc aac tgg agc    2880
Gly Asn Pro Ile Gly Gln Val Thr Ala Asp Gly Ser Gly Asn Trp Ser
945             950             955             960 ttc aca ccg ggc acg ccg ctg gcc aac ggc acc gtg gtc aac gcc acg    2928
Phe Thr Pro Gly Thr Pro Leu Ala Asn Gly Thr Val Val Asn Ala Thr
                965             970             975 gcc agc gac ccg acc ggc aat acc agc gct ccg gcc agc acc acc gtg    2976
Ala Ser Asp Pro Thr Gly Asn Thr Ser Ala Pro Ala Ser Thr Thr Val
            980             985             990 gac tcg gtg gcg ccg gcc gcg ccg gtg gtc aat ccg agc aac ggc gcg    3024
Asp Ser Val Ala Pro Ala Ala Pro Val Val Asn Pro Ser Asn Gly Ala
            995             1000            1005 gag atc agc ggc acc gcc gaa ccg ggc gcc acc gtg acc ctg acc gat    3072
Glu Ile Ser Gly Thr Ala Glu Pro Gly Ala Thr Val Thr Leu Thr Asp
    1010            1015            1020 ggc agc ggc aat ccg atc ggg cag gtc acc gcc gac ggc agc ggc aac    3120
Gly Ser Gly Asn Pro Ile Gly Gln Val Thr Ala Asp Gly Ser Gly Asn
1025            1030            1035            1040 tgg agc ttc acc ccg tcc acg ccg ctg gcg gat gga acc gtg gtc aac    3168
Trp Ser Phe Thr Pro Ser Thr Pro Leu Ala Asp Gly Thr Val Val Asn
                1045            1050            1055 gcc acc gct acc gac ccg gcc ggc aat acc ggc ggc cag ggc agc acc    3216
Ala Thr Ala Thr Asp Pro Ala Gly Asn Thr Gly Gly Gln Gly Ser Thr
            1060            1065            1070 acc gtg gac gcc atc gcg ccg gcc acg ccg acc gtc aac ctg agc aat    3264
Thr Val Asp Ala Ile Ala Pro Ala Thr Pro Thr Val Asn Leu Ser Asn
            1075            1080            1085 ggc agc agc ctc agc ggc acc gcc gag ccg ggc agc acg gtg att ctc    3312
Gly Ser Ser Leu Ser Gly Thr Ala Glu Pro Gly Ser Thr Val Ile Leu
            1090            1095            1100 acc gac ggc aac ggc aat ccg atc gcc gag gtc acc gcc gac ggc agc    3360
Thr Asp Gly Asn Gly Asn Pro Ile Ala Glu Val Thr Ala Asp Gly Ser
1105            1110            1115            1120
```

FIG. 7E

```
ggc aac tgg acc tac acc ccg tcc acg ccg atc gcc aac ggt act gtg    3408
Gly Asn Trp Thr Tyr Thr Pro Ser Thr Pro Ile Ala Asn Gly Thr Val
            1125                1130                1135 gtc aac gtg gtg gcc cag gac gcc tcc ggt aac agc agc ccg ccg gcg    3456
Val Asn Val Val Ala Gln Asp Ala Ser Gly Asn Ser Ser Pro Pro Ala
            1140                1145                1150 acg gtg acc gtc gat tcc agc gcg ccg ccg gcg ccg gtg atc aac ccg    3504
Thr Val Thr Val Asp Ser Ser Ala Pro Pro Ala Pro Val Ile Asn Pro
            1155                1160                1165 agc aac ggc gtc gtc atc agc ggc acc gcc gag gcc ggt gcc acg gtg    3552
Ser Asn Gly Val Val Ile Ser Gly Thr Ala Glu Ala Gly Ala Thr Val
            1170                1175                1180 acc ctc acc gat gcc ggc ggc aac ccg ata ggg cag gtc acc gcc gac    3600
Thr Leu Thr Asp Ala Gly Gly Asn Pro Ile Gly Gln Val Thr Ala Asp
1185                1190                1195                1200 ggc agc ggc aac tgg agc ttc acg ccg ggc acc ccg ctg gcc aac ggc    3648
Gly Ser Gly Asn Trp Ser Phe Thr Pro Gly Thr Pro Leu Ala Asn Gly
            1205                1210                1215 acg gtg atc gtc gcc acg gcc acc gac ccg acc ggc aat acc ggc ccg    3696
Thr Val Ile Val Ala Thr Ala Thr Asp Pro Thr Gly Asn Thr Gly Pro
            1220                1225                1230 cag gcc gcc acc acg gtg gac gcg gtg gcg ccg ccg gcg ccg gtg atc    3744
Gln Ala Ala Thr Thr Val Asp Ala Val Ala Pro Pro Ala Pro Val Ile
            1235                1240                1245 gat ccg agc aac ggc acg acc atc agc ggc acc gcg gag gcc ggg gcc    3792
Asp Pro Ser Asn Gly Thr Thr Ile Ser Gly Thr Ala Glu Ala Gly Ala
            1250                1255                1260 aag gtg atc ctc acc gac ggc aac ggc aac ccg atc ggc gaa acc acc    3840
Lys Val Ile Leu Thr Asp Gly Asn Gly Asn Pro Ile Gly Glu Thr Thr
1265                1270                1275                1280 gcc gac ggc agc ggc aac tgg agc ttc acg ccc ggc acg ccg ctg gcc    3888
Ala Asp Gly Ser Gly Asn Trp Ser Phe Thr Pro Gly Thr Pro Leu Ala
            1285                1290                1295 aac ggc acg gtg gtc aac gcc gtg gcc cag gac cct gcg ggc aat acc    3936
Asn Gly Thr Val Val Asn Ala Val Ala Gln Asp Pro Ala Gly Asn Thr
            1300                1305                1310 ggc ccg cag ggc agc act acc gtg gac gcg gtg gcg ccg aac acg cct    3984
Gly Pro Gln Gly Ser Thr Thr Val Asp Ala Val Ala Pro Asn Thr Pro
            1315                1320                1325 gtg gtc aat ccg agc aac ggc aac ctg ctc aac ggt acc gcc gag ccg    4032
Val Val Asn Pro Ser Asn Gly Asn Leu Leu Asn Gly Thr Ala Glu Pro
            1330                1335                1340
```

FIG. 7F

```
ggc agc acc gtg acc ttg acc gac ggc aac ggc aac ccg atc ggc cag    4080
Gly Ser Thr Val Thr Leu Thr Asp Gly Asn Gly Asn Pro Ile Gly Gln
1345                1350                1355                1360 acc acc gcc gat ggc agc ggc aac tgg agc ttc acg ccc ggc tcg caa    4128
Thr Thr Ala Asp Gly Ser Gly Asn Trp Ser Phe Thr Pro Gly Ser Gln
                1365                1370                1375 ctg ccc aac ggc acc gtg gtc aac gtg acc gcg agc gac gcc gcc ggc    4176
Leu Pro Asn Gly Thr Val Val Asn Val Thr Ala Ser Asp Ala Ala Gly
            1380                1385                1390 aat acc agc ctt ccc gct acc acg acg gtg gat tcc tcg ctg ccg tcg    4224
Asn Thr Ser Leu Pro Ala Thr Thr Thr Val Asp Ser Ser Leu Pro Ser
        1395                1400                1405 atc ccg cag gtg gat ccg agc aac ggt tcg gtg atc agc ggc acc gcg    4272
Ile Pro Gln Val Asp Pro Ser Asn Gly Ser Val Ile Ser Gly Thr Ala
    1410                1415                1420 gac gcc ggc aac acc atc atc atc acc gat ggc aac ggc aac ccg att    4320
Asp Ala Gly Asn Thr Ile Ile Ile Thr Asp Gly Asn Gly Asn Pro Ile
1425                1430                1435                1440 ggc cag gtc acc gcc gac ggc agc ggc aac tgg tcc ttc act cca ggc    4368
Gly Gln Val Thr Ala Asp Gly Ser Gly Asn Trp Ser Phe Thr Pro Gly
                1445                1450                1455 atc ccg ctg ccg gat ggc acg gtg gtc aac gtg gtg gcg cgc agc cca    4416
Ile Pro Leu Pro Asp Gly Thr Val Val Asn Val Val Ala Arg Ser Pro
            1460                1465                1470 agc aat gtc gac agt gcg ccg gcg gtg atc act gtg gat ggc gtg gcc    4464
Ser Asn Val Asp Ser Ala Pro Ala Val Ile Thr Val Asp Gly Val Ala
        1475                1480                1485 ccg gcg gcg ccg gtg atc gat ccg agc aac ggc acc gag ata agc ggt    4512
Pro Ala Ala Pro Val Ile Asp Pro Ser Asn Gly Thr Glu Ile Ser Gly
    1490                1495                1500 acc gcg gag gcc ggc gcg acg gtg atc ctc acc gat ggc ggc ggc aac    4560
Thr Ala Glu Ala Gly Ala Thr Val Ile Leu Thr Asp Gly Gly Gly Asn
1505                1510                1515                1520 ccg atc ggc cag gcc acc gcc gac ggc agc ggc aac tgg acg ttc acc    4608
Pro Ile Gly Gln Ala Thr Ala Asp Gly Ser Gly Asn Trp Thr Phe Thr
                1525                1530                1535 ccg agc acc ccg ctg gcc aac ggc acc gtg atc aac gcc gtg gcc cag    4656
Pro Ser Thr Pro Leu Ala Asn Gly Thr Val Ile Asn Ala Val Ala Gln
            1540                1545                1550 gac ccg gcc ggc aat acc agc ggt ccg gcc agc gtc acc gtc gat gcc    4704
Asp Pro Ala Gly Asn Thr Ser Gly Pro Ala Ser Val Thr Val Asp Ala
        1555                1560                1565
```

FIG. 7G

```
atc gcc ccg ccg gcg ccg gtg atc aat ccg agc aat gga gtc gtc atc    4752
Ile Ala Pro Pro Ala Pro Val Ile Asn Pro Ser Asn Gly Val Val Ile
    1570            1575            1580 agc ggt acg gcg gaa gcc ggg gcc acg gtg atc ctc acc gac ggc aac    4800
Ser Gly Thr Ala Glu Ala Gly Ala Thr Val Ile Leu Thr Asp Gly Asn
1585            1590            1595            1600 ggc aac ccg atc ggc cag gtc acc gcc gac ggc agc ggc aac tgg agc    4848
Gly Asn Pro Ile Gly Gln Val Thr Ala Asp Gly Ser Gly Asn Trp Ser
            1605            1610            1615 ttc acg ccc ggc acg ccg ctg gcc aac ggc tcg gtg atc aat gcg ctg    4896
Phe Thr Pro Gly Thr Pro Leu Ala Asn Gly Ser Val Ile Asn Ala Leu
        1620            1625            1630 gcc cag gac gcc gcc ggc aac aac agc agt ccc acc agc gcc acc gtc    4944
Ala Gln Asp Ala Ala Gly Asn Asn Ser Ser Pro Thr Ser Ala Thr Val
        1635            1640            1645 gac tcg ctg gcg cca gca gcc ccg gtg atc gat ccg agc aac ggt agc    4992
Asp Ser Leu Ala Pro Ala Ala Pro Val Ile Asp Pro Ser Asn Gly Ser
        1650            1655            1660 gtg atc gcc ggt acc gcc gag gct ggt gcc acg gtg atc ctc acc gac    5040
Val Ile Ala Gly Thr Ala Glu Ala Gly Ala Thr Val Ile Leu Thr Asp
1665            1670            1675            1680 ggc aac ggc aac ccg atc ggc cag gtc acc gcc gat ggc agc ggc aac    5088
Gly Asn Gly Asn Pro Ile Gly Gln Val Thr Ala Asp Gly Ser Gly Asn
            1685            1690            1695 tgg agc ttc acg ccc ggc acg ccg ctg tcc aat ggc acg gtg gtc aat    5136
Trp Ser Phe Thr Pro Gly Thr Pro Leu Ser Asn Gly Thr Val Val Asn
        1700            1705            1710 gcg gtg gcc cag gac gct gcc ggc aac acc agc ggc ccg gtc agc acc    5184
Ala Val Ala Gln Asp Ala Ala Gly Asn Thr Ser Gly Pro Val Ser Thr
    1715            1720            1725 acg gtg gac gcg gtg gcc ccg gcc acc ccg gtg atc gac ccg agc aac    5232
Thr Val Asp Ala Val Ala Pro Ala Thr Pro Val Ile Asp Pro Ser Asn
    1730            1735            1740 ggt gtc gaa ctc agc ggc acc gcc gaa ccc ggc gtc cgg gtg atc ctc    5280
Gly Val Glu Leu Ser Gly Thr Ala Glu Pro Gly Val Arg Val Ile Leu
1745            1750            1755            1760 acc gat ggc aat ggc aat ccg atc ggc cag acc ctt gcc gac ggc agc    5328
Thr Asp Gly Asn Gly Asn Pro Ile Gly Gln Thr Leu Ala Asp Gly Ser
            1765            1770            1775 ggc aac tgg agc ttc acg ccg ggc acg ccg ctg gcc aac ggc acg gtg    5376
Gly Asn Trp Ser Phe Thr Pro Gly Thr Pro Leu Ala Asn Gly Thr Val
        1780            1785            1790
```

FIG. 7H

```
gtc aat gcc gtg gcc cag gac ccg gcc ggc aat acc agc ggc ccg gcc    5424
Val Asn Ala Val Ala Gln Asp Pro Ala Gly Asn Thr Ser Gly Pro Ala
    1795                1800                1805 agc acc acg gtg gac acg gtg gct ccg gcc acg ccg gtg atc aat ccc    5472
Ser Thr Thr Val Asp Thr Val Ala Pro Ala Thr Pro Val Ile Asn Pro
    1810                1815                1820 agc aac ggc agc gtg atc acc ggc acc gcc gag gtc ggc gcc aag gtg    5520
Ser Asn Gly Ser Val Ile Thr Gly Thr Ala Glu Val Gly Ala Lys Val
1825                1830                1835                1840 atc ctc acc gat ggc aac ggc aac ccg atc ggc gag acc acc gcc gac    5568
Ile Leu Thr Asp Gly Asn Gly Asn Pro Ile Gly Glu Thr Thr Ala Asp
                1845                1850                1855 ggc agt ggt aac tgg acc ttc acc ccc ggc acg ccg ctg gcc aac ggt    5616
Gly Ser Gly Asn Trp Thr Phe Thr Pro Gly Thr Pro Leu Ala Asn Gly
            1860                1865                1870 acg gtg atc aac gcc gtc gcc gag gac gcc gcg ggc aac gcc agc ggt    5664
Thr Val Ile Asn Ala Val Ala Glu Asp Ala Ala Gly Asn Ala Ser Gly
        1875                1880                1885 ccg gcc agc acc acg gtg gac tcg gtg gcg ccg tcc gct ccg ctg ctg    5712
Pro Ala Ser Thr Thr Val Asp Ser Val Ala Pro Ser Ala Pro Leu Leu
    1890                1895                1900 agc atc agc gcc gac ggc gcg ctg ctg acc ggc acc gcc gag ccg aac    5760
Ser Ile Ser Ala Asp Gly Ala Leu Leu Thr Gly Thr Ala Glu Pro Asn
1905                1910                1915                1920 agc cag gtg cgc atc gtg gtc aac ggc gac acc gcc aac ccg atc acg    5808
Ser Gln Val Arg Ile Val Val Asn Gly Asp Thr Ala Asn Pro Ile Thr
                1925                1930                1935 gtc acc gtc gac ggc gcc ggc aac ttc agc ctg ccg ttc gcg ccg ccg    5856
Val Thr Val Asp Gly Ala Gly Asn Phe Ser Leu Pro Phe Ala Pro Pro
            1940                1945                1950 ctg atc acc ggc gag ctg atc gcc ggg gtc gcc gtc gac gcc gcc ggc    5904
Leu Ile Thr Gly Glu Leu Ile Ala Gly Val Ala Val Asp Ala Ala Gly
        1955                1960                1965 aac gtc agc ggg ccg gcc acc atc aac gcc ccg gac ctg gcg ccg ccg    5952
Asn Val Ser Gly Pro Ala Thr Ile Asn Ala Pro Asp Leu Ala Pro Pro
    1970                1975                1980 acc atc agc gtg ccg gaa gcc gcc gat acc tgg atc aat gcc gcg gag    6000
Thr Ile Ser Val Pro Glu Ala Ala Asp Thr Trp Ile Asn Ala Ala Glu
1985                1990                1995                2000 atc ggc gac ggt atc cag gtc gat gtg acg gtc cgt ccg acc atg cag    6048
Ile Gly Asp Gly Ile Gln Val Asp Val Thr Val Arg Pro Thr Met Gln
                2005                2010                2015
```

FIG. 7I

```
gtc ggc cag gtg gtc acg gtc aag ttc gcc ggg cag aac ggc tac gag    6096
Val Gly Gln Val Val Thr Val Lys Phe Ala Gly Gln Asn Gly Tyr Glu
            2020                2025                2030 gcc gag gtc agc cat acc ctc acc gcc ggc gac atc gcc gcc ggc aac    6144
Ala Glu Val Ser His Thr Leu Thr Ala Gly Asp Ile Ala Ala Gly Asn
            2035                2040                2045 ctg acc ctg acc ctg acg cct ccc ggc ggc atg ggc ccg ttc ccg gag    6192
Leu Thr Leu Thr Leu Thr Pro Pro Gly Gly Met Gly Pro Phe Pro Glu
            2050                2055                2060 ggt gcc tcg acc gtc acc gcc gac atc aac ggc ggc acc gcg tcg acc    6240
Gly Ala Ser Thr Val Thr Ala Asp Ile Asn Gly Gly Thr Ala Ser Thr
2065                2070                2075                2080 ccg gtg ccg ttc acc atc gac acc att ccg ccg gcg acc ccg gtg ctg    6288
Pro Val Pro Phe Thr Ile Asp Thr Ile Pro Pro Ala Thr Pro Val Leu
                2085                2090                2095 tcc ctg gtc ggc aac atc ctg acc atc tcg gcg gag cca ggg acc gag    6336
Ser Leu Val Gly Asn Ile Leu Thr Ile Ser Ala Glu Pro Gly Thr Glu
            2100                2105                2110 ttg acg gtg acc gtc gac gtc ggc ggg gtg acc gcc acc gcc acg gtg    6384
Leu Thr Val Thr Val Asp Val Gly Gly Val Thr Ala Thr Ala Thr Val
            2115                2120                2125 acc gcc gac aac agc ggg ctg gcg tcg ctg aac ctg ctc acc gac ctg    6432
Thr Ala Asp Asn Ser Gly Leu Ala Ser Leu Asn Leu Leu Thr Asp Leu
            2130                2135                2140 gac atc gac ttc agt tgg gac cag ttg ctc aat gcc cag gtg tcg gtg    6480
Asp Ile Asp Phe Ser Trp Asp Gln Leu Leu Asn Ala Gln Val Ser Val
2145                2150                2155                2160 gtc gga cgc gac ccg gcc ggc aac ccg agc aac acg gcg agc atc ggc    6528
Val Gly Arg Asp Pro Ala Gly Asn Pro Ser Asn Thr Ala Ser Ile Gly
            2165                2170                2175 gtc ggc acc agc atc gag caa ccg gtg acc atc ggc aac ttc ggc ctc    6576
Val Gly Thr Ser Ile Glu Gln Pro Val Thr Ile Gly Asn Phe Gly Leu
            2180                2185                2190 gac gtc agc ctc aac ccg ctg aac ccg cgt ttc ggt ttc agc gga acc    6624
Asp Val Ser Leu Asn Pro Leu Asn Pro Arg Phe Gly Phe Ser Gly Thr
            2195                2200                2205 acc gag cct gac tcc agc gtg gtg atc cgg gtc atc acc ccg gcg ttg    6672
Thr Glu Pro Asp Ser Ser Val Val Ile Arg Val Ile Thr Pro Ala Leu
            2210                2215                2220 aac gtc gaa ttg ctg ccg atc cag gcg gat tcg tcc gga aac ttc tcg    6720
Asn Val Glu Leu Leu Pro Ile Gln Ala Asp Ser Ser Gly Asn Phe Ser
2225                2230                2235                2240
```

FIG. 7J

```
ctg aac ctg ctg agc ccg acc atc ctc acc cag ttg ggg ctg aac atc      6768
Leu Asn Leu Leu Ser Pro Thr Ile Leu Thr Gln Leu Gly Leu Asn Ile
            2245            2250            2255 acc gac atc ctc aac ctc ggc tcg cag atc tcg ttc aac ctg gtg tcc      6816
Thr Asp Ile Leu Asn Leu Gly Ser Gln Ile Ser Phe Asn Leu Val Ser
            2260            2265            2270 acc gac tcc aat ggc aac gac agc gcc gcc tac ggg atc acc ctg acc      6864
Thr Asp Ser Asn Gly Asn Asp Ser Ala Ala Tyr Gly Ile Thr Leu Thr
            2275            2280            2285 ccc aac gga ctg tcg ctc aat atc ggc cag atc gat gtc aac ggt act      6912
Pro Asn Gly Leu Ser Leu Asn Ile Gly Gln Ile Asp Val Asn Gly Thr
            2290            2295            2300 tcc ggc gac gac gtg ctg tcc ggc gcc aac ggc agt tcg gag cac atc      6960
Ser Gly Asp Asp Val Leu Ser Gly Ala Asn Gly Ser Ser Glu His Ile
2305            2310            2315            2320 aac ggc ggc gac ggc agc gac ctg atc ttc aac gtg ggc acc ggc gat      7008
Asn Gly Gly Asp Gly Ser Asp Leu Ile Phe Asn Val Gly Thr Gly Asp
            2325            2330            2335 cac gtg gtg gcc ggc aac ggc aac gac acc atc cag atc acc gcg acc      7056
His Val Val Ala Gly Asn Gly Asn Asp Thr Ile Gln Ile Thr Ala Thr
            2340            2345            2350 gat ttc gtc agc atc gat ggc ggc gcc ggg ttc gac acc ctg gtc ctg      7104
Asp Phe Val Ser Ile Asp Gly Gly Ala Gly Phe Asp Thr Leu Val Leu
            2355            2360            2365 gcc aac ggc atc gac ctc gac tac aac gcc gtc ggc gtc ggc acg ctc      7152
Ala Asn Gly Ile Asp Leu Asp Tyr Asn Ala Val Gly Val Gly Thr Leu
            2370            2375            2380 agc aac ctc gag cgc atc gac ctc ggc aag ggc gat tcg ggt agc gtg      7200
Ser Asn Leu Glu Arg Ile Asp Leu Gly Lys Gly Asp Ser Gly Ser Val
2385            2390            2395            2400 ctg acc ctg acc gcg gcg gag gtg gat gcc atc acc gat gcc aac aac      7248
Leu Thr Leu Thr Ala Ala Glu Val Asp Ala Ile Thr Asp Ala Asn Asn
            2405            2410            2415 acg ttg cag atc acc ggc gag aac aac gac acc ctg aac gtg gtg ggc      7296
Thr Leu Gln Ile Thr Gly Glu Asn Asn Asp Thr Leu Asn Val Val Gly
            2420            2425            2430 gcg gtg aat acc ggt acc acg caa ctg atc aac ggc att acc tac gac      7344
Ala Val Asn Thr Gly Thr Thr Gln Leu Ile Asn Gly Ile Thr Tyr Asp
            2435            2440            2445 gtc tac acc ttc ggc agt acc acc ctg ctg atc gag gac aac acg gta      7392
Val Tyr Thr Phe Gly Ser Thr Thr Leu Leu Ile Glu Asp Asn Thr Val
            2450            2455            2460 cag gtc gtg gtc tga                                                  7407
Gln Val Val Val  *
```

| | | | | | | | | | | | | | | | | |
|---|---|---|---|---|---|---|---|---|---|---|---|---|---|---|---|---|
| atg | cgc | ggg | cgc | agg | cag | tac | gcg | cgc | aag | gga | cgg | cgg | cat | ggg | aag | 48 |
| Met | Arg | Gly | Arg | Arg | Gln | Tyr | Ala | Arg | Lys | Gly | Arg | Arg | His | Gly | Lys | |
| 1 | | | | 5 | | | | | 10 | | | | | 15 | | |

| gga | gcc | atc | tgg | ctc | ctt | tcc | ctg | ggt | ctg | ccg | atg | ttc | gcg | tcg | gcc | 96 |
|---|---|---|---|---|---|---|---|---|---|---|---|---|---|---|---|---|
| Gly | Ala | Ile | Trp | Leu | Leu | Ser | Leu | Gly | Leu | Pro | Met | Phe | Ala | Ser | Ala | |
| | | | 20 | | | | | 25 | | | | | 30 | | | |

| atg | ccc | ctc | gac | cag | gcg | gtc | agg | gca | ggg | ctg | gcg | atc | cac | ccg | gaa | 144 |
|---|---|---|---|---|---|---|---|---|---|---|---|---|---|---|---|---|
| Met | Pro | Leu | Asp | Gln | Ala | Val | Arg | Ala | Gly | Leu | Ala | Ile | His | Pro | Glu | |
| | | 35 | | | | | 40 | | | | | 45 | | | | |

| gta | cga | tcc | gcg | atg | gcc | gaa | gcg | gac | cgt | gca | ggc | acc | gag | gtg | gag | 192 |
|---|---|---|---|---|---|---|---|---|---|---|---|---|---|---|---|---|
| Val | Arg | Ser | Ala | Met | Ala | Glu | Ala | Asp | Arg | Ala | Gly | Thr | Glu | Val | Glu | |
| | 50 | | | | | 55 | | | | | 60 | | | | | |

| atg | gcc | aaa | ggg | ggg | tac | tac | ccc | tcc | gtg | acg | atg | tcc | ggg | ggg | ccg | 240 |
|---|---|---|---|---|---|---|---|---|---|---|---|---|---|---|---|---|
| Met | Ala | Lys | Gly | Gly | Tyr | Tyr | Pro | Ser | Val | Thr | Met | Ser | Gly | Gly | Pro | |
| 65 | | | | | 70 | | | | | 75 | | | | | 80 | |

| cag | gag | ttc | gac | ttc | ggc | gag | atc | gtc | tac | gat | ctc | acc | gcg | tcg | cag | 288 |
|---|---|---|---|---|---|---|---|---|---|---|---|---|---|---|---|---|
| Gln | Glu | Phe | Asp | Phe | Gly | Glu | Ile | Val | Tyr | Asp | Leu | Thr | Ala | Ser | Gln | |
| | | | | 85 | | | | | 90 | | | | | 95 | | |

| atg | ctg | tac | gac | tgg | ggt | cgg | gtg | acg | agc | aag | gtc | gac | agc | gcc | agc | 336 |
|---|---|---|---|---|---|---|---|---|---|---|---|---|---|---|---|---|
| Met | Leu | Tyr | Asp | Trp | Gly | Arg | Val | Thr | Ser | Lys | Val | Asp | Ser | Ala | Ser | |
| | | | 100 | | | | | 105 | | | | | 110 | | | |

| gcg | acc | cag | cgc | aag | ctg | tcc | gag | gcg | gtg | ctg | gtg | gcg | cgc | gac | gat | 384 |
|---|---|---|---|---|---|---|---|---|---|---|---|---|---|---|---|---|
| Ala | Thr | Gln | Arg | Lys | Leu | Ser | Glu | Ala | Val | Leu | Val | Ala | Arg | Asp | Asp | |
| | | 115 | | | | | 120 | | | | | 125 | | | | |

| gcg | gcg | ctg | gat | atc | gtc | gag | acc | tac | ctc | gat | gtg | ctt | gcc | tcg | gag | 432 |
|---|---|---|---|---|---|---|---|---|---|---|---|---|---|---|---|---|
| Ala | Ala | Leu | Asp | Ile | Val | Glu | Thr | Tyr | Leu | Asp | Val | Leu | Ala | Ser | Glu | |
| | 130 | | | | | 135 | | | | | 140 | | | | | |

| cgc | cgg | gtg | gag | gcg | gtg | cgc | gaa | cac | atc | cag | cgc | ctc | gac | ggc | atc | 480 |
|---|---|---|---|---|---|---|---|---|---|---|---|---|---|---|---|---|
| Arg | Arg | Val | Glu | Ala | Val | Arg | Glu | His | Ile | Gln | Arg | Leu | Asp | Gly | Ile | |
| 145 | | | | | 150 | | | | | 155 | | | | | 160 | |

| cgc | gag | atg | acc | cag | gcg | cgc | ggc | ggc | gac | ggc | tac | gcc | gac | cgc | agc | 528 |
|---|---|---|---|---|---|---|---|---|---|---|---|---|---|---|---|---|
| Arg | Glu | Met | Thr | Gln | Ala | Arg | Gly | Gly | Asp | Gly | Tyr | Ala | Asp | Arg | Ser | |
| | | | | 165 | | | | | 170 | | | | | 175 | | |

| gag | ctg | gat | cgc | gcc | aat | ctg | gaa | ctg | tcg | cgg | gcc | cag | gag | cag | ttg | 576 |
|---|---|---|---|---|---|---|---|---|---|---|---|---|---|---|---|---|
| Glu | Leu | Asp | Arg | Ala | Asn | Leu | Glu | Leu | Ser | Arg | Ala | Gln | Glu | Gln | Leu | |
| | | | 180 | | | | | 185 | | | | | 190 | | | |

| tcg | ctg | gag | aag | ggc | aac | ctg | cag | gac | gcg | cgc | aac | cag | tac | gcg | atc | 624 |
|---|---|---|---|---|---|---|---|---|---|---|---|---|---|---|---|---|
| Ser | Leu | Glu | Lys | Gly | Asn | Leu | Gln | Asp | Ala | Arg | Asn | Gln | Tyr | Ala | Ile | |
| | | 195 | | | | | 200 | | | | | 205 | | | | |

| ctg | gtc | ggc | cag | gag | ccc | gcc | gac | ctg | gtg | gag | ccc | gag | ccg | atg | tcg | 672 |
|---|---|---|---|---|---|---|---|---|---|---|---|---|---|---|---|---|
| Leu | Val | Gly | Gln | Glu | Pro | Ala | Asp | Leu | Val | Glu | Pro | Glu | Pro | Met | Ser | |
| | 210 | | | | | 215 | | | | | 220 | | | | | |

FIG. 8A

```
ctg caa cgc tac ctg gcg gcc agc gat atg gcg cgg gtg atc cgc gaa    720
Leu Gln Arg Tyr Leu Ala Ala Ser Asp Met Ala Arg Val Ile Arg Glu
225              230                 235                 240 tcg cct ttg cag cgc aag gcc ctg gag gac gcc aat gtc gcc gag gcc    768
Ser Pro Leu Gln Arg Lys Ala Leu Glu Asp Ala Asn Val Ala Glu Ala
                245                 250                 255 gag gtc cgc gag gcc aag gcg tcg ctg ctg ccg caa ctg aac ctg gag    816
Glu Val Arg Glu Ala Lys Ala Ser Leu Leu Pro Gln Leu Asn Leu Glu
            260                 265                 270 gcc agc gcg ctg cgc cgg gag atc ggc ggg cat ccg gaa agc gac tcg    864
Ala Ser Ala Leu Arg Arg Glu Ile Gly Gly His Pro Glu Ser Asp Ser
        275                 280                 285 gtg gta tcc ctg cgc ttc cgc atg gac acc ttc cag ggg ctt tcc aac    912
Val Val Ser Leu Arg Phe Arg Met Asp Thr Phe Gln Gly Leu Ser Asn
    290                 295                 300 ttc cgc cgg ccg acc gcc gcg cag cag cgc ctg gag tcg gcg aaa tgg    960
Phe Arg Arg Pro Thr Ala Ala Gln Gln Arg Leu Glu Ser Ala Lys Trp
305                 310                 315                 320 agc gcc gac gcg atg cag cgc gac atc cgc cgg caa ctg cag aac ctc   1008
Ser Ala Asp Ala Met Gln Arg Asp Ile Arg Arg Gln Leu Gln Asn Leu
                325                 330                 335 ttc gac aac ggc gac acg ctg cgc tgg cgg gaa cag tcg ctg acc cag   1056
Phe Asp Asn Gly Asp Thr Leu Arg Trp Arg Glu Gln Ser Leu Thr Gln
            340                 345                 350 cag gtg acc gag tcg gag cag gtc ggc gag ttg tat cgc gaa cag ttc   1104
Gln Val Thr Glu Ser Glu Gln Val Gly Glu Leu Tyr Arg Glu Gln Phe
        355                 360                 365 gag gtt ggc cgg cgc gac gtg atc gac ctc ctc aac gtg cag cgc gag   1152
Glu Val Gly Arg Arg Asp Val Ile Asp Leu Leu Asn Val Gln Arg Glu
    370                 375                 380 cgg ttc gag gca gag cgg caa ctg atc aac ctg cgg atc gaa cgc aag   1200
Arg Phe Glu Ala Glu Arg Gln Leu Ile Asn Leu Arg Ile Glu Arg Lys
385                 390                 395                 400 cgc atc gag tat cgg gcg gcc gcg caa gtc ggc ctg ttg ggt ccg cta   1248
Arg Ile Glu Tyr Arg Ala Ala Ala Gln Val Gly Leu Leu Gly Pro Leu
                405                 410                 415 ttg gag aac cgg ctg aat cat gga agc tga                           1278
Leu Glu Asn Arg Leu Asn His Gly Ser *
            420                 425
```

| | | | | | | | | | | | | | | | | |
|---|---|---|---|---|---|---|---|---|---|---|---|---|---|---|---|---|
| atg | gaa | gct | gag | aaa | acc | ccg | gat | aac | gtc | gtg | atc | ctc | aac | cac | gac | 48 |
| Met | Glu | Ala | Glu | Lys | Thr | Pro | Asp | Asn | Val | Val | Ile | Leu | Asn | His | Asp | |
| 1 | | | | 5 | | | | | 10 | | | | | 15 | | |

| ccc | atc | gtc | gac | ccg | ttg | cgc | cag | ggc | ttg | ttg | ctg | ctc | tgc | cgg | cag | 96 |
| Pro | Ile | Val | Asp | Pro | Leu | Arg | Gln | Gly | Leu | Leu | Leu | Leu | Cys | Arg | Gln | |
| | | | 20 | | | | | 25 | | | | | 30 | | | |

| ctt | ggc | cga | ccg | ctc | ggc | gac | gcc | gaa | ctg | gtg | gac | ggc | atg | ccg | ctg | 144 |
| Leu | Gly | Arg | Pro | Leu | Gly | Asp | Ala | Glu | Leu | Val | Asp | Gly | Met | Pro | Leu | |
| | | 35 | | | | | 40 | | | | | 45 | | | | |

| gag | cac | ggt | cgc | ctg | ccg | ttg | cac | ctg | gtg | gcc | cgc | gcg | ttg | cgc | cgc | 192 |
| Glu | His | Gly | Arg | Leu | Pro | Leu | His | Leu | Val | Ala | Arg | Ala | Leu | Arg | Arg | |
| | 50 | | | | | 55 | | | | | 60 | | | | | |

| gcc | gac | atc | acc | gcc | cag | gtc | acc | cgc | cag | ccg | ttg | cgc | cgg | atc | gat | 240 |
| Ala | Asp | Ile | Thr | Ala | Gln | Val | Thr | Arg | Gln | Pro | Leu | Arg | Arg | Ile | Asp | |
| 65 | | | | | 70 | | | | | 75 | | | | | 80 | |

| cgc | tac | ctg | ctg | ccg | gcc | ctg | ctg | ctc | gac | gac | ggc | cgc | gcc | ctg | | 288 |
| Arg | Tyr | Leu | Leu | Pro | Ala | Leu | Leu | Leu | Asp | Asp | Gly | Arg | Ala | Leu | | |
| | | | | 85 | | | | | 90 | | | | | 95 | | |

| gtg | ctg | gtg | ggc | aac | gac | ggc | gag | cac | gcc | gag | gtg | ctg | gta | ccg | cag | 336 |
| Val | Leu | Val | Gly | Asn | Asp | Gly | Glu | His | Ala | Glu | Val | Leu | Val | Pro | Gln | |
| | | | 100 | | | | | 105 | | | | | 110 | | | |

| agc | gac | ggc | gga | agc | cag | agg | atg | ccg | ctg | gcc | gag | ctg | gaa | gcg | ctg | 384 |
| Ser | Asp | Gly | Gly | Ser | Gln | Arg | Met | Pro | Leu | Ala | Glu | Leu | Glu | Ala | Leu | |
| | | 115 | | | | | 120 | | | | | 125 | | | | |

| tac | agc | ggc | acg | gcg | gtc | ttc | gcc | aag | tgc | cgc | tac | cgc | ccg | gac | ggg | 432 |
| Tyr | Ser | Gly | Thr | Ala | Val | Phe | Ala | Lys | Cys | Arg | Tyr | Arg | Pro | Asp | Gly | |
| | 130 | | | | | 135 | | | | | 140 | | | | | |

| cgg | gtc | ggc | gac | tac | gcc | agc | gcc | ttg | ccc | gaa | cac | tgg | ttc | ttc | ggc | 480 |
| Arg | Val | Gly | Asp | Tyr | Ala | Ser | Ala | Leu | Pro | Glu | His | Trp | Phe | Phe | Gly | |
| 145 | | | | | 150 | | | | | 155 | | | | | 160 | |

| ccg | ctc | aag | cgg | ctc | tgg | cgt | tcc | tac | gcc | gag | gtc | acc | gcc | gcg | gcg | 528 |
| Pro | Leu | Lys | Arg | Leu | Trp | Arg | Ser | Tyr | Ala | Glu | Val | Thr | Ala | Ala | Ala | |
| | | | | 165 | | | | | 170 | | | | | 175 | | |

| ttg | gtg | gcc | aac | gtc | ctg | gcg | gtc | gcc | tcg | gca | ctg | ttc | gcc | atg | cag | 576 |
| Leu | Val | Ala | Asn | Val | Leu | Ala | Val | Ala | Ser | Ala | Leu | Phe | Ala | Met | Gln | |
| | | | 180 | | | | | 185 | | | | | 190 | | | |

| gtc | tac | gac | cgc | gtg | gtg | ccc | aac | gcg | gcg | ttc | gac | acc | ctg | tgg | atc | 624 |
| Val | Tyr | Asp | Arg | Val | Val | Pro | Asn | Ala | Ala | Phe | Asp | Thr | Leu | Trp | Ile | |
| | | 195 | | | | | 200 | | | | | 205 | | | | |

| ctc | gcc | agc | ggc | gtg | gcc | ctg | gcg | atc | gtc | ctc | gac | ggt | gtc | ctg | cgg | 672 |
| Leu | Ala | Ser | Gly | Val | Ala | Leu | Ala | Ile | Val | Leu | Asp | Gly | Val | Leu | Arg | |
| | 210 | | | | | 215 | | | | | 220 | | | | | |

FIG. 9A

```
atc atg cgc ggc cac ctg ctc aac gtg ctc ggc aag cgc ctc gac ctg    720
Ile Met Arg Gly His Leu Leu Asn Val Leu Gly Lys Arg Leu Asp Leu
225             230                 235                 240 caa ctc tcg acc ctg ctg ttc tcc cgc gtg ctg agc acc cgg gtc gcc    768
Gln Leu Ser Thr Leu Leu Phe Ser Arg Val Leu Ser Thr Arg Val Ala
                245                 250                 255 gcc aag ccg gcg tcg atg ggc gcc ttc agt acc cag gtg cgg gag ttc    816
Ala Lys Pro Ala Ser Met Gly Ala Phe Ser Thr Gln Val Arg Glu Phe
            260                 265                 270 gag tcg gtg cgc gag ttc ttt acc tcg tcc agc gcg gcg ctg atc agc    864
Glu Ser Val Arg Glu Phe Phe Thr Ser Ser Ser Ala Ala Leu Ile Ser
        275                 280                 285 gac ctg ccg ttc gtg gcg atc ttc ctg atc atc gcc gtg atc ggc        912
Asp Leu Pro Phe Val Ala Ile Phe Leu Leu Ile Ile Ala Val Ile Gly
    290                 295                 300 ggc cat gtg gtc tgg gtg ccg ctg gtg gcc tgc gtg ctg atg atc ctg    960
Gly His Val Val Trp Val Pro Leu Val Ala Cys Val Leu Met Ile Leu
305             310                 315                 320 ccg ggg ctg ctg acc cag cgc ctg ctc ggc cac ctg tcg cgg cag aac    1008
Pro Gly Leu Leu Thr Gln Arg Leu Leu Gly His Leu Ser Arg Gln Asn
                325                 330                 335 ctg cgc gaa ggg gcg atg aag aac ggc gtg ctg ctg gaa gcc ttc gag    1056
Leu Arg Glu Gly Ala Met Lys Asn Gly Val Leu Leu Glu Ala Phe Glu
            340                 345                 350 cac ctg gag acg gtc aag gcg acc cgc gcc gaa ggc cgc tgc ctg cac    1104
His Leu Glu Thr Val Lys Ala Thr Arg Ala Glu Gly Arg Cys Leu His
        355                 360                 365 cag tgg gaa acc ctg acc ggc gaa ctg gcc ggt acg gcg atg aag acc    1152
Gln Trp Glu Thr Leu Thr Gly Glu Leu Ala Gly Thr Ala Met Lys Thr
    370                 375                 380 cat act ctg gcc tcg acc ctg agc tac tcg gcg agc atc gtc cag cag    1200
His Thr Leu Ala Ser Thr Leu Ser Tyr Ser Ala Ser Ile Val Gln Gln
385             390                 395                 400 ctc tgc tac gtc ggc gtg gtg gtc ttc ggc gtc tat cgg atc agc gag    1248
Leu Cys Tyr Val Gly Val Val Val Phe Gly Val Tyr Arg Ile Ser Glu
                405                 410                 415 ggc gcg atg acc gtc ggc ggc ctg gtg gcc tgc tcg atc ctc gcc tcg    1296
Gly Ala Met Thr Val Gly Gly Leu Val Ala Cys Ser Ile Leu Ala Ser
            420                 425                 430 cgg gcc atc gca ccg ctg tcg cag gcg gcc ggc atc ctc ggt cgc tgg    1344
Arg Ala Ile Ala Pro Leu Ser Gln Ala Ala Gly Ile Leu Gly Arg Trp
        435                 440                 445
```

FIG. 9B

```
cag cac acc aag gtg gcg atg gaa ggc ctc gac caa ctg atg agc gcc      1392
Gln His Thr Lys Val Ala Met Glu Gly Leu Asp Gln Leu Met Ser Ala
        450                 455                 460 gag cag gag cga ccc cag ggc aag cgc ttc gtg cac aag gag cgc ctg      1440
Glu Gln Glu Arg Pro Gln Gly Lys Arg Phe Val His Lys Glu Arg Leu
465                 470                 475                 480 cag gga cat tac cgc ctg gag ggc gtg cgc ctg gcc cac ggc gac agc      1488
Gln Gly His Tyr Arg Leu Glu Gly Val Arg Leu Ala His Gly Asp Ser
                485                 490                 495 ccg ccg gtg gtc gac gtg cag gcc ctg aac atc cgc gcc ggc gag cgg      1536
Pro Pro Val Val Asp Val Gln Ala Leu Asn Ile Arg Ala Gly Glu Arg
            500                 505                 510 gtg gcg ctg ctc ggc ggc aac ggc gcc ggc aag tcg acc ctg ctg cgc      1584
Val Ala Leu Leu Gly Gly Asn Gly Ala Gly Lys Ser Thr Leu Leu Arg
        515                 520                 525 ctg ctc agc ggc ctg ctc gac gcg cag gcg gga cgc ctg ctg ctg gac      1632
Leu Leu Ser Gly Leu Leu Asp Ala Gln Ala Gly Arg Leu Leu Leu Asp
    530                 535                 540 gac gtc agc ctg acc cag atc gac ccg gcc gac cgc cag cgc ggt atc      1680
Asp Val Ser Leu Thr Gln Ile Asp Pro Ala Asp Arg Gln Arg Gly Ile
545                 550                 555                 560 ggc tac ctg ccg cag gac gtg gcg ctg ttc cat ggc agc ctg cgc gac      1728
Gly Tyr Leu Pro Gln Asp Val Ala Leu Phe His Gly Ser Leu Arg Asp
                565                 570                 575 aac ctc aac ctg gag aac gcc gcg ctg ggc gac gag gaa ctg ctg gag      1776
Asn Leu Asn Leu Glu Asn Ala Ala Leu Gly Asp Glu Glu Leu Leu Glu
            580                 585                 590 acc ctc gac ggg gtc ggc ctg ggc gcc ttc gtc cgc ggc cac ccg ctg      1824
Thr Leu Asp Gly Val Gly Leu Gly Ala Phe Val Arg Gly His Pro Leu
        595                 600                 605 ggg ctg gac atg ccg atc cag ggc aac gcc agc ctg tcc ggc ggc caa      1872
Gly Leu Asp Met Pro Ile Gln Gly Asn Ala Ser Leu Ser Gly Gly Gln
    610                 615                 620 cgc cag gcc gtc ggg ctg gcc cgg gtg ctg cta cag gac cct ccg atc      1920
Arg Gln Ala Val Gly Leu Ala Arg Val Leu Leu Gln Asp Pro Pro Ile
625                 630                 635                 640 ctg ctc ctc gac gag ccg acc gcg gcc ttc gac cag ggc agc gag aaa      1968
Leu Leu Leu Asp Glu Pro Thr Ala Ala Phe Asp Gln Gly Ser Glu Lys
                645                 650                 655 cag gtc atc gac tac ctg cag caa tgg ttg ggc aag cgc acc ctg gtc      2016
Gln Val Ile Asp Tyr Leu Gln Gln Trp Leu Gly Lys Arg Thr Leu Val
            660                 665                 670
```

FIG. 9C

```
atc acc acc cac aag aaa agc atg ctc gcc ctg gtc gag cgt gcg gtg    2064
Ile Thr Thr His Lys Lys Ser Met Leu Ala Leu Val Glu Arg Ala Val
        675                 680                 685 gtc ctg cgc cag ggc agg gtg atc atg gac ggc ccg ctg gag cag gtg    2112
Val Leu Arg Gln Gly Arg Val Ile Met Asp Gly Pro Leu Glu Gln Val
        690                 695                 700 gtg cag ggc aac cag gta cag gca ccg cag gcc gcc gaa gga ggc aac    2160
Val Gln Gly Asn Gln Val Gln Ala Pro Gln Ala Ala Glu Gly Gly Asn
705                 710                 715                 720 cat gga ctc tga                                                    2172
His Gly Leu  *
```

| | | | | | | | | | | | | | | | | |
|---|---|---|---|---|---|---|---|---|---|---|---|---|---|---|---|---|
| atg | gac | tct | gac | cgc | gac | gcc | gcc | gcc | ctg | cgc | cgg | caa | ctg | gcc | gac | 48 |
| Met | Asp | Ser | Asp | Arg | Asp | Ala | Ala | Ala | Leu | Arg | Arg | Gln | Leu | Ala | Asp | |
| 1 | | | | 5 | | | | | 10 | | | | | 15 | | |

| ccg | ttg | ctg | gcg | gct | acc | cac | ccg | gtc | tac | cgg | ccg | ctg | ctc | tgg | acc | 96 |
|---|---|---|---|---|---|---|---|---|---|---|---|---|---|---|---|---|
| Pro | Leu | Leu | Ala | Ala | Thr | His | Pro | Val | Tyr | Arg | Pro | Leu | Leu | Trp | Thr | |
| | | | 20 | | | | | 25 | | | | | 30 | | | |

| ctg | ctc | ggt | tgc | gtg | ctg | ctg | ttc | atc | ggc | tgg | gcg | gcc | tgg | gcg | caa | 144 |
|---|---|---|---|---|---|---|---|---|---|---|---|---|---|---|---|---|
| Leu | Leu | Gly | Cys | Val | Leu | Leu | Phe | Ile | Gly | Trp | Ala | Ala | Trp | Ala | Gln | |
| | | 35 | | | | | 40 | | | | | 45 | | | | |

| ctg | gac | gag | gtg | acc | cgc | ggc | gac | ggt | cgg | gtc | gtg | ccg | ttc | agc | cgc | 192 |
|---|---|---|---|---|---|---|---|---|---|---|---|---|---|---|---|---|
| Leu | Asp | Glu | Val | Thr | Arg | Gly | Asp | Gly | Arg | Val | Val | Pro | Phe | Ser | Arg | |
| | | 50 | | | | | 55 | | | | | 60 | | | | |

| atc | cag | aag | atc | cag | agc | ctg | gag | ggc | ggc | atc | ctc | gac | cgc | ctg | ctg | 240 |
|---|---|---|---|---|---|---|---|---|---|---|---|---|---|---|---|---|
| Ile | Gln | Lys | Ile | Gln | Ser | Leu | Glu | Gly | Gly | Ile | Leu | Asp | Arg | Leu | Leu | |
| 65 | | | | | 70 | | | | | 75 | | | | | 80 | |

| gtg | aag | gag | ggc | gac | ctg | gtg | gaa | gtc | ggc | cag | ccg | ctg | gtg | cgc | ctc | 288 |
|---|---|---|---|---|---|---|---|---|---|---|---|---|---|---|---|---|
| Val | Lys | Glu | Gly | Asp | Leu | Val | Glu | Val | Gly | Gln | Pro | Leu | Val | Arg | Leu | |
| | | | | 85 | | | | | 90 | | | | | 95 | | |

| gac | gag | acg | cgc | ttc | ctc | acc | aac | ttc | cag | gag | tcg | gcg | aac | cag | gcc | 336 |
|---|---|---|---|---|---|---|---|---|---|---|---|---|---|---|---|---|
| Asp | Glu | Thr | Arg | Phe | Leu | Thr | Asn | Phe | Gln | Glu | Ser | Ala | Asn | Gln | Ala | |
| | | | 100 | | | | | 105 | | | | | 110 | | | |

| agc | gtg | ctg | cgc | gcg | gcc | att | gcc | cgg | ctc | gac | gcc | gag | gtg | cta | ggc | 384 |
|---|---|---|---|---|---|---|---|---|---|---|---|---|---|---|---|---|
| Ser | Val | Leu | Arg | Ala | Ala | Ile | Ala | Arg | Leu | Asp | Ala | Glu | Val | Leu | Gly | |
| | | | 115 | | | | | 120 | | | | | 125 | | | |

| aag | aag | agc | atc | gag | ttc | ccg | ccg | gac | gtc | gat | ccc | gag | ggg | ccg | ctg | 432 |
|---|---|---|---|---|---|---|---|---|---|---|---|---|---|---|---|---|
| Lys | Lys | Ser | Ile | Glu | Phe | Pro | Pro | Asp | Val | Asp | Pro | Glu | Gly | Pro | Leu | |
| | 130 | | | | | 135 | | | | | 140 | | | | | |

| gcg | cgt | tcc | gaa | cgc | gag | ctg | ttc | aag | tcg | cgc | cgc | gac | aaa | ctg | gtg | 480 |
|---|---|---|---|---|---|---|---|---|---|---|---|---|---|---|---|---|
| Ala | Arg | Ser | Glu | Arg | Glu | Leu | Phe | Lys | Ser | Arg | Arg | Asp | Lys | Leu | Val | |
| 145 | | | | | 150 | | | | | 155 | | | | | 160 | |

| gag | ggc | acc | cag | gcg | atc | cag | cgg | cag | atc | cac | ctg | gcg | cag | agc | cag | 528 |
|---|---|---|---|---|---|---|---|---|---|---|---|---|---|---|---|---|
| Glu | Gly | Thr | Gln | Ala | Ile | Gln | Arg | Gln | Ile | His | Leu | Ala | Gln | Ser | Gln | |
| | | | | 165 | | | | | 170 | | | | | 175 | | |

| ctc | gac | ctg | gtt | cgc | ccg | ctg | gtg | gcc | aag | cgt | gcg | gtg | agc | cag | atg | 576 |
|---|---|---|---|---|---|---|---|---|---|---|---|---|---|---|---|---|
| Leu | Asp | Leu | Val | Arg | Pro | Leu | Val | Ala | Lys | Arg | Ala | Val | Ser | Gln | Met | |
| | | | 180 | | | | | 185 | | | | | 190 | | | |

| gag | gcg | ctc | aag | ctg | agc | cag | gac | atc | gcc | acc | ctc | agc | ggc | aag | ctg | 624 |
|---|---|---|---|---|---|---|---|---|---|---|---|---|---|---|---|---|
| Glu | Ala | Leu | Lys | Leu | Ser | Gln | Asp | Ile | Ala | Thr | Leu | Ser | Gly | Lys | Leu | |
| | | 195 | | | | | 200 | | | | | 205 | | | | |

| acc | gag | ctg | aaa | agc | acc | tat | ttc | cag | gat | gcc | tat | acc | gag | cgc | gcc | 672 |
|---|---|---|---|---|---|---|---|---|---|---|---|---|---|---|---|---|
| Thr | Glu | Leu | Lys | Ser | Thr | Tyr | Phe | Gln | Asp | Ala | Tyr | Thr | Glu | Arg | Ala | |
| | | 210 | | | | | 215 | | | | | 220 | | | | |

FIG. 10A

```
cag cgc aag gcc gat ctc agc gcc ctg gaa ccg atc gtc cag cag cgc    720
Gln Arg Lys Ala Asp Leu Ser Ala Leu Glu Pro Ile Val Gln Gln Arg
225             230                 235                 240 cag gac cag ttg cgc cgc acc gag atc ctg tcg cca gtg cgc ggg cgg    768
Gln Asp Gln Leu Arg Arg Thr Glu Ile Leu Ser Pro Val Arg Gly Arg
                245                 250                 255 gtg aac acc gtg ctg atc aac acc cgc ggc ggg gtg atc cag ccc ggc    816
Val Asn Thr Val Leu Ile Asn Thr Arg Gly Gly Val Ile Gln Pro Gly
            260                 265                 270 gag ccg atc atg gaa gtg atc ccg gta gag gag cgt ctg ctg gtg gag    864
Glu Pro Ile Met Glu Val Ile Pro Val Glu Glu Arg Leu Leu Val Glu
        275                 280                 285 gcg aag atc aag ccg cgc gac gtg gcc ttc ctg gtt ccc ggc atg ccg    912
Ala Lys Ile Lys Pro Arg Asp Val Ala Phe Leu Val Pro Gly Met Pro
    290                 295                 300 gcc aag gtg aag atc acc gcc tac gac tac acc atc tac ggc gac ctc    960
Ala Lys Val Lys Ile Thr Ala Tyr Asp Tyr Thr Ile Tyr Gly Asp Leu
305                 310                 315                 320 aag ggc acc ctg gag cag atc agt gcc gac acc atc gag gag gac acc   1008
Lys Gly Thr Leu Glu Gln Ile Ser Ala Asp Thr Ile Glu Glu Asp Thr
                325                 330                 335 ccg cat ggc aag gag tcc tac tac cag gtg ctg atc aag acc gat ggc   1056
Pro His Gly Lys Glu Ser Tyr Tyr Gln Val Leu Ile Lys Thr Asp Gly
            340                 345                 350 agc cag ttg aag cgc ggc gag gag gta ttg ccg atc att ccg ggg atg   1104
Ser Gln Leu Lys Arg Gly Glu Glu Val Leu Pro Ile Ile Pro Gly Met
        355                 360                 365 gtc gcc gag gtg gac atc ctc agc ggc aag cgc agc gtg ctc aac tac   1152
Val Ala Glu Val Asp Ile Leu Ser Gly Lys Arg Ser Val Leu Asn Tyr
    370                 375                 380 ctg ctg cgg ccg ctg atc aag gcg cgc ctt tac tga                   1188
Leu Leu Arg Pro Leu Ile Lys Ala Arg Leu Tyr  *
385                 390                 395
```

Peptide Sequence
MFRQEALDAQHAGGLGEIVLIRPVSFTFLTLLAAAMALLVVGFFLFGSYTKRSTVSGQLV
PASGQVKVHAPQAGIVLRKFVQEGQAVRRGERLMVLSSERYGSDAGPVQAGISRRLEQRR
DSLRDELEKLRRLQDDERDSLTSKVASLQRELTTLAAQTDSQQRLLALASDAAARYQGLM
DKGYISMDQLQQRQAELLGQRQTLQGLERERTSLRQQLTERRNELAGLSARQANQLAETR
RQLSAVEQDLAESEAKRTLLVTAPESGIATAVLAEAGQTVDSSRPLLSIVPADTPLQAEL
YAPSKSIGFIRPGDAVLIRYQAYPYQKFGQYHGKVQSISRASVSYAELSSMVGGVPGLGQ
DGEQLYRLRVTLDDQAVTAYGQPRPLQSGMLLDADILQDTRRLYEWVLEPLYSLTGKL

Nucleotide Sequence
ATGTTTCGCCAGGAAGCCCTCGACGCCCAGCATGCCGGCGGCCTGGGCGAGATCGTGCTG
ATCCGCCCGGTCTCCTTCACTTTTCTCACCCTGCTGGCCGCGGCGATGGCGCTGCTGGTG
GTGGGCTTCTTCCTGTTCGGCAGCTACACCAAGCGCAGCACCGTCAGCGGCCAATTGGTG
CCCGCCAGCGGCCAGGTCAAGGTGCACGCGCCGCAGGCCGGCATCGTGCTGCGCAAGTTC
GTCCAGGAAGGCCAGGCGGTACGACGTGGCGAGCGCCTGATGGTGCTTTCCAGCGAACGC
TACGGCAGCGATGCCGGGCCGGTGCAGGCCGGCATCAGCAGGCGCCTGGAACAACGCCGC
GACTCCCTGCGCGACGAACTGGAAAAGCTTCGCCGCCTGCAAGACGACGAGCGCGACAGC
CTGACCAGCAAGGTCGCCAGCCTGCAGCGCGAACTCACCACCCTCGCCGCCCAGACCGAC
AGCCAGCAACGCCTGCTGGCGCTGGCCAGCGACGCCGCCGCGCGCTACCAGGGGCTGATG
GACAAGGGCTACATCTCCATGGACCAGTTGCAGCAGCGCCAGGCCGAGCTGCTCGGCCAG
CGCCAGACCCTGCAAGGCCTGGAGCGCGAACGCACGTCGCTGCGGCAGCAGTTGACCGAG
CGCCGCAACGAACTCGCCGGGCTTTCCGCGCGCCAGGCCAACCAGCTCGCGGAAACCCGC
CGCCAGCTCAGCGCGGTGGAGCAGGACCTGGCCGAAAGCGAAGCCAAGCGCACCTTGCTG
GTCACCGCGCCGGAGAGCGGCATCGCCACCGCCGTGCTCGCCGAAGCCGGGCAGACCGTC
GACAGCTCGCGTCCGCTGCTGAGCATCGTTCCCGCCGACACCCCGTTGCAGGCCGAACTC
TACGCGCCGAGCAAGTCCATCGGTTTCATCCGGCCGGGCGACGCGGTGCTGATCCGCTAC
CAGGCCTATCCGTACCAGAAGTTCGGCCAGTACCACGGCAAGGTGCAGTCGATCTCCCGC
GCCAGCGTCTCCTATGCCGAGCTTTCCAGCATGGTCGGCGGCGTACCGGGGCTCGGCCAG
GATGGCGAGCAGCTGTACCGGCTGCGGGTAACCCTCGACGACCAGGCGGTGACCGCCTAC
GGCCAGCCGCGTCCGCTGCAGAGCGGCATGCTGCTGGACGCCGACATCCTCCAGGACACC
CGGCGCCTCTACGAATGGGTGCTGGAACCGCTCTACAGCCTGACCGGCAAACTCTAG

Peptide Sequence
MAFLDALALRLGRRLPLVLQTEATECGLACLAMIAGYHGHHTGLMELRRRFSVSLKGISL
KQLIQTAHRLGLGTRAVKLDLGDLGKLKLPCVLHWNFNHFVVLKAVDGRGAVLHDPAHGQ
RRLGLEEVSRSFTGVALELWPESGFEKQEAPPRIKLLGMLGKVTGLYRSLAQVLLLAGAL
EVFSLISPFFLQWTIDNVIVSEDRDLLSTLAIGFGLLLLMQQAVSGVRAWVMMHMSTLLG
VQWQANVFSHLLRLPAQYFEKRHLGDVVSRFGAVNSIQQTLTAAFLSAVLDGLMTVATLG
MMLLYSPPLAAIAIAAMSLYALGRWIWYRPLRNATEEQIVHAARQQSHFLETVRGIRPLK
LFQRQDERRSVWLGLLVEQINAGLRTQKLQLFYQQLNGLLFGVENLLVIWLGATMVMDGQ
FSVGILMAFNAYKSQFDSRVGSLIDKFFELRMLQLQGERLADIVLQAPEVSHGDILPENL
REREASIEIQGLRYRYAEQEPWVLDGLDLRIAGGESVAIVGPSGCGKSTLFNVLLGILPP
VEGQIRMAGLDLAQLGLDGLRELVGTVLQDDVLFAGSLSDNISFFDPQPDMPWLLQCAQM
AAIHDDIQAMPMGYNTLVGDMGTVLSGGQKQRVMLARALYKKPRILFLDEATSHLDVHCE
QRVNAAIRALRITRIMVAHRPETIASADRVIVLGQGKVSLDESTARLAERQAAAAREQA

Nucleotide Sequence
ATGGCCTTTCTCGACGCTCTCGCCCTGCGCCTGGGCCGCCGCCTGCCGCTGGTGCTGCAG
ACCGAAGCCACCGAATGCGGCCTGGCCTGCCTGGCGATGATCGCCGGCTACCACGGCCAC
CATACCGGCCTGATGGAACTGCGCCGGCGCTTCTCCGTATCGCTCAAGGGCATCTCCCTC
AAGCAACTGATCCAGACCGCCCACCGCCTCGGCCTGGGTACCCGCGCGGTGAAGCTCGAC
CTCGGCGACCTCGGCAAGCTCAAGCTGCCCTGCGTGCTGCACTGGAACTTCAACCACTTC
GTCGTGCTCAAGGCGGTCGACGGGCGCGGCGCGGTGCTCCACGACCCCGCCCACGGCCAG
CGCCGGCTGGGCCTGGAGGAAGTCTCGCGGAGCTTCACCGGGGTAGCCCTGGAACTCTGG
CCGGAGAGCGGCTTCGAGAAACAGGAGGCGCCGCCGCGGATCAAGCTGCTGGGCATGCTC
GGCAAGGTCACCGGGCTGTACCGCTCGCTGGCCCAGGTGCTGCTGCTCGCCGGCGCGCTG
GAAGTGTTCTCGCTGATCAGTCCGTTCTTCCTGCAATGGACCATCGACAACGTCATCGTC
AGCGAAGACCGTGACCTGCTCAGCACCCTGGCCATCGGCTTCGGCCTGTTGCTGCTGATG
CAGCAGGCGGTCAGCGGGGTGCGCGCCTGGGTGATGATGCACATGAGCACCCTGCTCGGC
GTGCAGTGGCAGGCCAACGTCTTCAGCCACCTGCTGCGGCTGCCCGCGCAGTATTTCGAG
AAGCGCCACCTGGGCGACGTGGTGTCGCGCTTCGGCGCGGTGAACAGCATCCAGCAGACC
CTCACCGCGGCCTTCCTCTCGGCGGTGCTGGACGGCCTGATGACCGTCGCCACCCTCGGC
ATGATGCTGCTCTACAGTCCGCCACTGGCGGCCATCGCCATCGCCGCCATGAGCCTCTAC
GCCCTCGGCCGCTGGATCTGGTACCGGCCGTTGCGCAACGCCACCGAGGAGCAGATCGTC
CACGCCGCGCGCCAGCAGAGCCACTTCCTCGAGACGGTGCGCGGCATCCGCCCGCTGAAG
CTGTTCCAGCGCCAGGACGAGCGCCGCTCGGTATGGCTCGGCCTGCTGGTGGAACAGATC
AACGCCGGCCTGCGTACGCAGAAGCTGCAACTGTTCTACCAGCAGCTCAACGGCCTGCTG
TTCGGCGTGGAGAACCTGCTGGTGATCTGGCTCGGCGCGACCATGGTGATGGACGGCCAG
TTCAGCGTCGGCATCCTGATGGCCTTCAACGCCTACAAGTCGCAGTTCGACAGCCGCGTC
GGCAGCCTGATCGACAAGTTCTTCGAGCTGCGCATGCTCCAGTTGCAGGGCGAGCGCCTG
GCCGACATCGTGCTCCAGGCCCCGGAGGTCAGCCACGGCGACATCCTCCCGGAGAACCTC
CGCGAGCGCGAGGCGAGCATCGAGATCCAGGGCCTGCGCTACCGCTACGCGGAACAGGAG
CCCTGGGTCCTCGACGGCCTCGACCTGCGCATCGCCGGCGGCGAGTCGGTGGCCATCGTC
GGCCCCTCGGGCTGCGGCAAGAGCACCCTGTTCAACGTCCTGCTGGGCATCCTCCCGCCA
GTGGAGGGACAGATCCGCATGGCCGGCCTGGACCTTGCGCAACTGGGCCTGGACGGCCTG
CGCGAACTGGTCGGCACGGTGCTGCAGGACGACGTGCTGTTCGCCGGTTCGCTCAGCGAC
AACATCAGTTTCTTCGACCCGCAACCGGACATGCCCTGGCTGCTGCAGTGCGCGCAGATG
GCTGCCATCCACGATGACATCCAGGCCATGCCGATGGGCTACAACACCCTGGTCGGCGAC
ATGGGCACGGTGCTCTCCGGCGGCCAGAAGCAGCGGGTGATGCTGGCCCGGGCGCTGTAC
AAGAAGCCGCGCATCCTGTTCCTCGACGAAGCCACCAGCCACCTCGACGTACACTGCGAA
CAGCGGGTCAACGCCGCCATTCGAGCGCTGCGCATCACCCGCATCATGGTCGCCCATCGG
CCCGAGACCATCGCCTCGGCGGACCGCGTGATAGTCCTCGGCCAGGGCAAGGTAAGCCTC
GACGAAAGCACCGCGCGCCTGGCCGAACGCCAGGCCGCCGCGGCGCGGGAGCAGGCCTGA

Peptide Sequence

MRALAGLLCGLLGLVPGAAAYEPDVFGTTGQVAGQAVYDLGGSGLPCRGGPPPTELSLEE
AIERILCHDPQTRLAWANAKAQAAQVGIGKSAYLPRLDGRLDASRGYSDMDYRDAPYLSG
DGHRHRRGASLQLSWVLFDFGRRSAALRNAQQLLLAANASQDATLQNTFALAAQAYYDAL
AAQRSLAASRQVAELAAQNLEAADAKYRAGAAALSDRLQAQTALSQASLAQVRDEGALSN
ALGVIALRMGLAPDTPLRLSGELEAQPDTGFVKAIDEMLAEARREHPALLAAQARLKAAA
ASVEESRAAGRPSLALSANLARSHSDQAMAFNGDTRERDRSIGLQLNIPLFEGFERTYQV
RNALARREASEAELADTEQQVSLEVWNNYQSLSVETRSLARTRELVEQSRQSLEVVQGRY
RSGVGSMIELLNALTAYASAEDQHIRALGNWQTSRLRLAASLGRLGFWSLR

Nucleotide Sequence

ATGCGTGCCCTCGCCGGCCTGTTGTGCGGCCTGCTCGGCCTGGTTCCCGGCGCCGCCGCC
TACGAGCCGGACGTGTTCGGCACCACCGGCCAGGTCGCCGGCCAGGCGGTCTACGACCTC
GGCGGCAGCGGTTTGCCCTGCCGCGGCGGGCCGCCACCGACCGAGCTGAGCCTGGAGGAA
GCCATCGAGCGGATCCTCTGCCACGACCCGCAGACCCGCCTCGCCTGGGCCAATGCCAAG
GCCCAGGCGGCCCAGGTCGGGATCGGCAAGTCCGCCTACCTGCCGCGCCTGGACGGCCGT
CTCGACGCCAGTCGCGGCTACAGCGACATGGATTATCGCGATGCCCCTACCTCTCCGGC
GACGGCCATCGCCACCGGCGCGGCGCCAGCCTCCAATTGAGCTGGGTGCTGTTCGACTTC
GGCCGCCGCAGCGCCGCCCTGCGCAACGCCCAGCAGTTGCTGCTGGCGGCCAACGCCAGC
CAGGACGCGACCCTGCAGAACACCTTCGCCCTCGCCGCCCAGGCCTACTACGACGCCCTC
GCCGCCCAGCGCAGCCTGGCCGCCTCGCGGCAGGTCGCGGAGCTGGCGGCGCAGAACCTG
GAAGCCGCCGACGCCAAGTACCGGGCCGGCGCCGCCGCCCTTTCCGATCGCCTGCAGGCG
CAGACCGCGCTGTCCCAGGCGAGCCTCGCCCAGGTCCGCGACGAAGGCGCCCTGAGCAAC
GCCCTCGGCGTCATCGCCCTGCGCATGGGCCTGGCGCCGGATACCCCGCTGCGCCTCTCC
GGCGAGCTGGAGGCGCAACCCGACACCGGCTTCGTCAAGGCCATCGACGAGATGCTCGCC
GAAGCCCGCCGCGAGCATCCGGCGCTGCTCGCCGCCCAGGCGCGGCTGAAAGCCGCCGCC
GCCTCGGTGGAGGAAAGCCGCGCCGCCGGCCGGCCGAGCCTGGCGCTGAGCGCCAACCTG
GCACGCAGCCATAGCGACCAGGCGATGGCGTTCAACGGCGATACCCGCGAACGCGACCGC
AGCATCGGCCTGCAACTGAACATCCCGTTGTTCGAAGGCTTCGAACGCACCTACCAGGTC
CGCAACGCCCTGGCCCGCCGCGAAGCCAGCGAAGCGGAGCTGGCCGACACCGAGCAGCAG
GTTTCGCTGGAGGTGTGGAACAACTACCAGTCGCTCAGCGTCGAGACCCGCAGCCTGGCG
CGCACCCGCGAACTGGTCGAACAGTCGCGGCAAAGCCTGGAGGTGGTGCAGGGCCGCTAC
CGCTCAGGGGTCGGCAGCATGATCGAGCTGCTCAACGCCCTGACCGCCTACGCCAGCGCC
GAGGACCAGCACATCCGCGCCCTCGGCAACTGGCAGACCTCGCGCCTGCGACTGGCGGCG
AGCCTCGGTCGCCTGGGTTTCTGGAGCCTGCGCTGA

Peptide Sequence

MRRTRSTRRALLVAVCLSPLIALAAWQAYPFRSNNFDTVSVSRGSIESSVSALGTLQPRR
YVDVGAQASGQIRKLHVEAGDDVTEGQLLVEIDPSTQQAKVDAGRYSIEMLKAQLAEQRA
QYTLARQQYQRQQRLAAGGATRTEDVQSAQAQMLATQARIEMYQAQIRQAQASLRSDEAE
LGYTRIYAPMSGTVVAVDAREGQTLNAQQQTPLILRIAKLSPMTVWAQVSEADIGRVKPG
MPAYFTTLSGEGRRWTGKVRQILPVPPKPLDQSNQGGGSPTSGSGGQSGSGRVVLYTVLV
DVDNGDHQLMAEMTAQVFFVAATAENILTAPVAAIHDDGKGGQVAWVVGSNGKPQSRQIR
TGISDRLRVQVLAGLEEGDRLLMAAPDGSDS

Nucleotide Sequence

ATGAGACGAACCCGTAGTACTCGTCGCGCACTGCTCGTCGCAGTCTGCCTCAGCCCCCTG
ATCGCCCTGGCCGCCTGGCAGGCCTATCCGTTCCGCAGCAACAACTTCGATACCGTGAGC
GTCAGCCGCGGCAGCATCGAGAGCAGCGTCTCGGCGCTCGGCACCCTGCAACCGCGGCGC
TACGTCGACGTCGGCGCCCAGGCCTCCGGGCAGATCCGCAAGTTGCACGTCGAGGCCGGG
GACGATGTGACGGAAGGCCAGTTGCTGGTCGAGATCGACCCCTCCACCCAGCAGGCCAAG
GTCGATGCCGGCCGCTATTCGATCGAGATGCTCAAGGCCCAACTGGCCGAGCAACGTGCC
CAGTACACCCTCGCCCGCCAGCAGTACCAGCGCCAGCAGCGGCTGGCCGCCGGCGGCGCA
ACGCGTACCGAGGACGTGCAGAGCGCCCAGGCGCAGATGCTCGCCACCCAGGCGCGGATC
GAGATGTACCAGGCGCAGATCCGCCAGGCCCAGGCCTCGTTGCGCAGCGACGAAGCCGAA
CTCGGCTATACCCGCATCTACGCGCCGATGTCCGGCACGGTGGTGGCGGTCGATGCGCGC
GAAGGCCAGACCCTCAATGCCCAGCAGCAGACCCCGTTGATCCTGCGGATCGCCAAATTG
TCGCCGATGACCGTCTGGGCCCAGGTTTCGGAAGCCGACATCGGCCGGGTCAAGCCCGGC
ATGCCGGCCTACTTCACGACCCTCAGCGGCGAAGGCCGGCGCTGGACCGGCAAGGTCCGG
CAGATCCTCCCGGTGCCGCCCAAGCCGCTGGACCAGAGCAACCAGGGCGGCGGCAGCCCC
ACCAGCGGCAGCGGCGGGCAGAGCGGCAGCGGCCGGGTGGTGCTGTATACCGTGCTGGTC
GACGTGGACAACGGCGACCACCAACTGATGGCGGAAATGACCGCCCAGGTGTTCTTCGTC
GCCGCCACCGCAGAAAACATCCTCACCGCGCCGGTCGCCGCCATCCACGACGACGGCAAG
GGCGGCCAGGTCGCCTGGGTGGTCGGCAGCAACGGCAAGCCGCAGAGCCGCCAGATCAGG
ACCGGCATCAGCGACCGCCTGCGGGTACAGGTGCTTGCCGGCCTGGAGGAAGGCGACCGC
CTGTTGATGGCCGCTCCCGACGGCAGCGACAGCTGA

Peptide Sequence
MENATQPVPLIELRDIRKRYGGNGTPEVEVLKGVSLSIHAGEFVAIVGASGSGKSTLMNI
LGCLDRPSSGSYHFAGHDVAELDSDEQAWLRREAFGVFQGYHLIPSASAQENVEMPAIY
AGIPASERHTRARALLERLGLAERTANRPHQLSGGQQQRVSIARALMNGGHIILADEPTG
ALDSHSGAEVMALLDELASQGHVVILITHDRDVAARAKRIIEVRDGEIVSDSANDERPAH
PSAGVERHLQADDLSQRLAEGSSEPSGAWRAELLEAVRAAWRVMWINRFRTALTLLGIII
GVASVVVMLAVGEGSKRQVMAQMGAFGSNIIYLSGYSPNPRAPMGIVSSDDVAAIATLPQ
VKKVMPVNGGELVVRYGNIDYHAYVGGNNTDFPEILNWPVAEGSYFTERDEDAATTVAVI
GYKVRKKLFGSANPIGRYILIENVPFQVIGVLAEKGSSSGDKDADNRIAIPYSAASIRLF
GTRNPEYVIIAAADAQRVHQAERAIDQLMLRLHRGQRDYELTNNAAMIQAEAKTQNTLSL
MLGSIAAISLLVGGIGVMNIMLMTVRERTREIGIRMATGARQGDILRQFLTEAAMLSVVG
GLAGIALALCIGGVLLLGQVAVAFSLSAIVGAFSCALVTGLVFGFMPARKAAQLDPVAAL
ASQ

Nucleotide Sequence
ATGGAAAACGCCACGCAACCCGTCCCCCTGATCGAACTGCGCGACATCCGCAAGCGCTAC
GGCGGCAATGGCACCCCGGAAGTCGAGGTACTCAAGGGCGTATCGCTGTCGATCCACGCC
GGCGAGTTCGTCGCCATCGTCGGCGCCTCCGGCTCCGGCAAGTCGACCCTGATGAACATC
CTCGGCTGCCTCGACCGGCCCAGCTCCGGCAGCTACCACTTCGCCGGCCACGACGTCGCC
GAACTGGACAGCGACGAGCAGGCCTGGCTGCGCCGCGAGGCATTCGGCTTCGTGTTCCAG
GGCTATCACCTGATCCCCTCCGCCTCGGCCCAGGAAAACGTCGAGATGCCGGCGATCTAC
GCCGGCATCCCGGCGAGCGAGCGGCACACCCGCGCGCGGGCCCTGCTCGAACGCCTGGGC
CTGGCCGAGCGCACCGCCAACCGTCCGCACCAGTTGTCCGGCGGCCAGCAGCAGCGGGTG
TCGATCGCCCGCGCGCTGATGAACGGCGGCCATATCATCCTCGCCGACGAACCCACCGGC
GCCCTCGACAGCCACAGCGGCGCGGAAGTCATGGCGCTGCTCGACGAGCTGGCCAGCCAG
GGCCACGTGGTGATCCTGATCACCCACGACCGCGACGTCGCCGCCCGCGCCAAGCGCATC
ATCGAGGTGCGCGACGGCGAGATCGTCAGCGACAGCGCCAACGACGAGCGCCCGGCGCAC
CCGAGCGCCGGCGTCGAGCGCCACCTGCAGGCCGACGATCTCAGCCAGCGCCTCGCCGAG
GGCAGCAGCGAACCCTCGGGGGCCTGGCGCGCCGAACTGCTGGAGGCGGTGCGCGCCGCC
TGGCGGGTGATGTGGATCAATCGGTTCCGCACCGCGCTGACCCTGCTCGGGATCATCATC
GGCGTCGCCTCGGTGGTGGTCATGCTCGCCGTCGGCGAGGGCAGCAAGCGCCAGGTGATG
GCGCAGATGGGCGCGTTCGGCTCGAACATCATCTATCTCAGCGGCTACTCGCCGAACCCG
CGCGCGCCGATGGGCATCGTCAGCAGCGACGACGTCGCCGCCATCGCCACCCTGCCCCAG
GTGAAGAAGGTCATGCCGGTGAACGGCGGCGAGCTGGTGGTGCGCTACGGGAACATCGAC
TACCACGCCTACGTCGGCGGCAACAACACCGACTTCCCGGAAATCCTCAACTGGCCGGTG
GCCGAGGGCAGCTACTTCACCGAGCGCGACGAAGACGCCGCCACCACGGTCGCGGTGATC
GGCTACAAGGTGCGCAAGAAGCTGTTCGGCAGCGCCAACCCGATCGGCCGCTACATCCTC
ATCGAGAACGTGCCGTTCCAGGTCATCGGCGTGCTCGCCGAGAAAGGCTCCAGCTCCGGC
GACAAGGATGCCGACAACCGCATCGCCATCCCCTACTCCGCTGCCAGCATCCGCCTGTTC
GGCACGCGCAACCCCGAGTACGTGATCATCGCCGCCGCCGACGCCCAGCGCGTGCACCAG
GCCGAACGCGCCATCGACCAGTTGATGCTGCGCCTGCACCGCGGCCAGCGCGACTACGAG
CTGACCAACAACGCGGCGATGATCCAGGCCGAGGCGAAGACCCAGAACACCCTGTCGCTG
ATGCTCGGCTCGATCGCCGCGATCTCCCTGCTGGTAGGCGGGATCGGCGTGATGAACATC
ATGCTCATGACCGTGCGCGAACGCACCCGCGAGATCGGCATCCGCATGGCCACTGGCGCC
CGCCAGGGCGATATCCTCCGCCAGTTCCTCACCGAGGCGGCGATGCTCTCGGTGGTCGGC
GGCCTGGCCGGGATCGCCCTGGCCCTGTGCATCGGCGGCGTGCTGCTGCTCGGCCAGGTC
GCGGTGGCCTTTTCCCTGTCGGCCATCGTCGGCGCCTTCAGTTGCGCGCTGGTCACCGGC
CTGGTGTTCGGCTTCATGCCGGCGCGCAAGGCCGCCCAGCTGGACCCGGTGGCCGCCCTG
GCCAGCCAATGA

Peptide Sequence
MSMKNLSLISACLLLGACGSTPAPLDSGLAAPSQWRYLAAGRSDASDIRQWWKAFGAPEL
DSLLQRALLNSQDLGAAVARVRQAQASAVIAGAPLLPELNATLGASRQKLLRDSGYSGTD
ATSDNDAVDSFSAGLSASYEVDFWGGRQAAYRSALESLKASEYDRATVELTLLSGVANSY
LQVLALREQQRIARLNLDNAEHVLRLVETRHAAGSATALEVAQQSSLVASQRKQLPLLEQ
QAHEALITLATLIGEPVQALQVAERPFDSLRWPETGAGLPSELLSRRPDIANAEAQLAAA
QADVQVARAALFPKLTLSASLSSGANRAADTFRNPYYNLGANLLAPIFNHGRLRAERDRS
LARQEELLETYRKAILTAFADTERSLNSIDGLDRQLHWQQQELEQAQRAFDLSDSRYQAG
AETLLTVLETQRTLYAAQDAAVQLRLARLQASVGLYKALGGGWQSDRQGLARKD

Nucleotide Sequence
ATGTCCATGAAGAATCTCTCCCTGATTTCCGCCTGCCTGCTGCTCGGCGCCTGCGGCAGC
ACGCCGGCGCCCCTCGACAGCGGCCTGGCCGCGCCCAGCCAGTGGCGCTACCTGGCGGCC
GGGCGCAGCGATGCCAGCGACATCCGCCAGTGGTGGAAGGCCTTCGGCGCGCCGGAACTG
GACAGCCTGCTGCAACGCGCCCTGCTGAACAGCCAGGACCTCGGCGCGGCGGTGGCCCGC
GTACGCCAGGCCCAGGCCTCGGCGGTGATCGCCGGCGCGCCGTTGCTGCCGGAGCTGAAT
GCGACGCTCGGCGCCAGCCGGCAGAAACTCCTGCGCGACTCGGGCTACAGCGGTACCGAC
GCGACCTCCGACAACGATGCCGTCGACTCCTTCTCCGCCGGCCTCAGCGCCAGCTACGAA
GTGGACTTCTGGGGCGGTCGCCAGGCTGCCTACCGCAGCGCCCTGGAAAGCCTCAAGGCC
AGCGAGTACGACCGCGCCACGGTAGAGCTGACCCTGCTCTCCGGCGTCGCCAACAGCTAC
CTGCAGGTATTGGCGCTGCGCGAACAGCAGCGCATCGCCAGGCTCAACCTGGACAACGCC
GAGCACGTCCTGCGCCTGGTGGAGACCCGCCATGCCGCGGGCTCGGCCACCGCCCTGGAG
GTCGCCCAACAGAGCAGCCTGGTCGCCAGCCAGCGCAAGCAGCTGCCGCTGCTCGAGCAG
CAGGCCCATGAGGCGCTGATTACCCTGGCCACCCTGATCGGCGAGCCGGTGCAGGCGCTA
CAGGTGGCCGAGCGGCCTTTCGACAGCCTGCGCTGGCCGGAGACCGGAGCGGGCCTGCCG
AGCGAACTGCTCAGCCGCCGTCCCGATATCGCCAACGCCGAAGCGCAACTGGCCGCGGCC
CAGGCCGACGTGCAGGTGGCGCGCGCGGCGCTGTTCCCCAAGCTGACCCTGAGCGCCTCG
CTGTCGTCCGGCGCCAACCGCGCCGCCGACACTTTCCGCAACCCCTATTACAACCTGGGC
GCCAACCTGCTCGCCCCGATCTTCAACCACGGCCGCCTGCGCGCCGAGCGCGACCGCAGC
CTGGCGCGCCAGGAAGAACTGCTGGAAACCTACCGCAAGGCGATCCTCACCGCCTTTGCC
GACACCGAACGCTCGCTGAACAGCATCGACGGCCTCGACCGCCAGCTGCACTGGCAACAG
CAGGAGCTGGAGCAGGCGCAGCGCGCCTTCGATCTCTCCGACAGCCGCTACCAGGCCGGC
GCGGAAACCCTGCTGACGGTCCTCGAAACGCAACGCACGCTGTACGCGGCGCAGGATGCC
GCCGTGCAACTGCGACTGGCCCGCCTGCAGGCCTCGGTCGGCCTGTACAAGGCCCTCGGC
GGCGGCTGGCAGAGCGACCGCCAGGGTCTCGCGCGGAAAGACTGA

FIG. 16

Promoter sequence 500 bp upstream of PA1874

P. aeruginosa nucleotides 2035941 - 2036441

```
GGTCGCTCGCGGGAGAGGATCGGTTGGATAACTTGGCATCGTGACGATGACGCTTTGATT
GCAGGACGATGAAGGCCGCTTCGCGGGATGCCCGGCGATGCTTTCCGTTGGAACTGTCGG
GGTCGTCTTGCCGTCGCCTCGCGCCGACGAACTACGAGGTGCCGGGAAGTGCTATTTCAT
TTCTCCCGGTTTTTTATGAAATACGCATCGTAGAGTTCTGATATTTGCCCGCTGGGTTAT
TTAGTCGATTTGCCGTGCCAGGTGATGGGGGTTGTTTATAAAGTATTATAACTTTTTGAT
TATATATTGTTTATCAATTAGATAGGCGTGTGATGGCTAAATGGCTGCATGTTTTCCAGG
GGTTATCTAAATTGAATTTTTCATGGGGGTTTTCTTAGTCGTTATATATAAAGTCAGACT
CGCCTTTTATTTAAAAGCTGCTATTTCTGGATTACATGGTGCGGCCGTTCGGTCGCTGCT
TGACAAGAGGAATGTCGGAAA
```

FIG. 17

Promoter sequence: 500 bp upstream of PA4142

P. aeruginosa nucleotides 4632372 - 4632872

```
AGCCCATGAAAAACCGCTAATCCTGGCAGTTCATCCCACTCTTTCGGATTAGTACCATTG
AATGGCTTTCCAGACTCATGGGAAGCCTAAAGGAGATATATGAAATGAAAGAACTCAATG
ACATTGAAGTCACCTGCGTTTCGGGTGGAACTCTTTCCGGCATGATCGTAGGCGCCGTCG
ACGGCGCCGCGACGGGCATGGCAATCGGCGGGAAATGGGGCGGTGCCGGCGGCTTCGGCT
TCGGCGCTCTTTCCCAGTTGGTCGGCCTGATCGTGCCAACCGCAATGGGCGCTATTGCCG
GGGGCACGGTCGGTCTCTTCACCAATGCAGAGACGGCTGTCGGTTACTTGGGCCAATACC
GGGAAAACTTCGGTCCCGGTGATGTAGGCCGCACCACCATCTAATTAGAAAAGTCGCACT
CCGGCACTTCATGCGTTTGAACTTTCGCAAGGGTGTCGGAGTGTCATGCAAGTATTATTC
GAATCCAGGATCCAGCCACCA
```

FIG. 18

Promoter sequence: 500 bp upstream of PA2389

P. aeruginosa nucleotides 2641631 - 2642131

```
CAACGTGGTAGTCACCGTCACCGAGGGCTCGGTGAAGGTCCGCAGCGAAGGCTCGGGCAA
CGACAGCAGCCTGACTCCCGGCATGCAGGCCAGCTACTATCCGGGCCTGCTGCAACCGTT
GGTCGAGGCCGTGGATACCCGCCAGACGCTAGCCTGGCGCGAGGGCCGCCTGGTACTCGA
CGACCTGCCCCTGTCCAAGGCCCTGCCGCTGATCAACCGCTACCTCGACGCTCCGCTGGT
CCTGGGCGACAGGAGCGCTGCGAAACTGCGCATTGGCGGGATCTACAGCACCCGCGACAT
CCGCAGCCTGGTCGACGCCCTGCCGAAAGTCCTGCCCGTGGACCTGGAACATCGCGAGGA
CGGCAGCATCCGCATCAGCAGCCGTTACGCCCAGCTCTGAACCCAGGTTAAATTTAGCCG
CCCTGGCCTCGTATATCTGGCAGTGCCCAGCCTGCCGATCCAGCGGCGGCGGTCTCTCCA
CGCACCGGCCGGATTCCCGAA
```

FIG. 19

Promoter sequence: 500 bp upstream of PA1163

P. aeruginosa nucleotides 1260057 - 1260557

```
TGCTCCGGGTGGTCGGCGACGAAGCGCTCGACGGCGACGATCATCGACGC
CAGGCTGCCTTTCATGTCCGCCGCGCCGCGCCCGCAGAGCATGCCCTGGT
CGTCGATCAGGGCGTCGAAGGGTTGGTGCTGCCAGGCCTGCAGCGGGCCG
GTGGGGACCACGTCGGTGTGCCCGGCGAAGCACAGCACCGGGCCGTCGCC
GCCGCGCCGTGCCCAGAAGTTGTCCACCTCCTCGATGCGCATCGGCTCCA
GGGCGAAGCCGGCGGCTTCCAGGCGGCGCATCATCAGGGCCTGGCAGTCG
GCGTCGAGCGGCGTGACGGAGGGCGGCGGATCAACTCGCAGGCGAGTTC
GAGGGTCGGCGAGAGACTCGGCGAAGAGGCGGTCATGGGGAGGGCATCCT
GAGCGGGTCGAGCGGAAAGGGGGAATCTTAAAGCATAAACGTGGGCGAAG
GGACGCCGTTTAGGCGAGCGGGGCCGGCCGTCCCGACGCCTCGCCCGACC
T
```

FIG. 20

```
  1 mrvvaavlll vsalhaglwg vlrdkepapd frgllpsvsy apfegsahpd idniptveki
 61 radlktlstm trairlysst ggvelvpaia aefglkvtvg awidkdkdrn ereikaaiel
121 arknsnvvgv vvgneviyrg eqkvedlidm ikkvkgsvrv pvttgeiwmi wrdnpdlasn
181 vdfiaahvlp ywenfrsdqa vdqavdrynl lrnlfpgkri viaefgwpsq gynlrnadpg
241 pfgqaltlrn fvsraeaigm eyniveaidq pwkffeggvg pywgilnasr epkfawtgpv
301 enpdywklmt iallvglls lpilrlqqpt akqafllsat angvgawaat vfafwnghyf
361 ifgsafaltl gmillvplvl iamarideia avafgrppqr llakskpven vpenyypkvs
421 ihipayfepv emlkqtldal srlnypnyec vviinntpdp afwqpigdhc ralgerfkfi
481 naekvqgfka galriamdrt avdaeiigil dadyvvdpdw lkdlvpafad prvglvqapq
541 ehrdgdlsim hyimngeyag ffdigmvqrn eanaiivhgt mclirraamd maggwssdti
601 cedsdiglai qelgwvthyt nhryggqllp dtyeafkkqr hrwaygglqi vkkhwrhflp
661 grsrltpdqk reyglgwlnw lgaeslgvvv alnlvwvpi vafadiaipd kiltlpiiga
721 fvvslahfls myrarvaikp ggmlgamiaa msvtvdgvar gragtdhrah rlrahlggrp
781 vqdvdrvpgv lggrdrrpap drrradrlq qfpadhrdlh lrragaakp avpgrgrhrh
841 praqphqlvp vlarqrdphr radwpapgrp adprrhaasr aerggargel tagwllgage
901 tsappshrqr sewiagrqsg
```

FIG. 22

```
  1 myfsaegdvq svlyvnltia igailfaila dprkmvdrla fsiimllslg vyivwratdt
 61 lpplefslet lwcytyftfe lisvlyamgs ilillrrtdw savadqgeay lagnphaplv
121 dvfictynep lnvleksiia aqamdyprlr vfvcddtrra evrtyceavg vnyvtrpdnk
181 hakagnlnna llhtnaleev sdfimvldad fapqanflrr vtglfsdpkv avvqtpqfyf
241 nsdpiqhnlg idksfvddqr vffdvfqpak davgcafcvg tsfvvrraav ngiggfpsda
301 lsedmlltyr lmergyvtrw lneklsvgls aegvpeyitq rtrwclgtiq igllrtgplw
361 rgnftltqrl hylhglfcwl skpfilclll apsiywltgv salqadelmf mklglsslal
421 fwtystwisg krtlplftev thaltavpit itlfqairkp fgrpfkvtek ggdrsqvrvh
481 lptaiffafv tlssavsivl avygldapse lssrdclnli wsavamviaf tsficcielp
541 rfgkeemigv dfrgqlrsas strpvritgl stenitlaav pssdvtdvf vpeagwmris
601 paehaqnsgk fdihpsdeqr rsilrllfrk apenvaeggd lmksmrilla rafg
```

FIG. 23

```
atgtcttcacgtaaattcggcctgaacctggtagtggtgctggcc
 M  S  S  R  K  F  G  L  N  L  V  V  V  L  A
atcgccgcactgttcaccgggttctgggcactgatcaaccgcccg
 I  A  A  L  F  T  G  F  W  A  L  I  N  R  P
gtctccgccccgcctggccagaacagatctctggcttttcgtat
 V  S  A  P  A  W  P  E  Q  I  S  G  F  S  Y
tcgccgttccgcctgggcgaaagcccacagaagggtcagtacccc
 S  P  F  R  L  G  E  S  P  Q  K  G  Q  Y  P
actgacgacgaaatgcgccaggacctggagcaactgagcaaactg
 T  D  D  E  M  R  Q  D  L  E  Q  L  S  K  L
accgacagcatccgtatctataccgtggaaggcacccaggccgac
 T  D  S  I  R  I  Y  T  V  E  G  T  Q  A  D
gtcccgcgcctggccgaggagttcggcctgcgggtgacgctgggg
 V  P  R  L  A  E  E  F  G  L  R  V  T  L  G
atatggatcagcccggacctggagcgcaacgagcgcgaaattgcc
 I  W  I  S  P  D  L  E  R  N  E  R  E  I  A
acggccatccagctggccaacacgtcgcgcagcgtggtgcgggtg
 T  A  I  Q  L  A  N  T  S  R  S  V  V  R  V
gtggtcggcaacgaggcgctgttccgtgaagaagtcacaccggaa
 V  V  G  N  E  A  L  F  R  E  E  V  T  P  E
aacctgatcaaatacctggaccgcgtacgcgcagccgtgaaggtg
 N  L  I  K  Y  L  D  R  V  R  A  A  V  K  V
cccgtgaccaccagtgaacagtggcacatctggaaggaacatcct
 P  V  T  T  S  E  Q  W  H  I  W  K  E  H  P
gagctggccaggcacgtcgacctgattgccgcgcacatcctgccc
 E  L  A  R  H  V  D  L  I  A  A  H  I  L  P
tactgggagttcgtgccgatgaaggattcggtcgagttcgtcctc
 Y  W  E  F  V  P  M  K  D  S  V  E  F  V  L
gagcgcgcccgtgaactgaagcaccagttcccgcgcaaacctctg
 E  R  A  R  E  L  K  H  Q  F  P  R  K  P  L
ctgctgtcggaagtcggctggccgagcaacggccgcatgcgcggt
 L  L  S  E  V  G  W  P  S  N  G  R  M  R  G
ggtgccgatgccacacaggccgaccaggccatctacttgcgcacc
 G  A  D  A  T  Q  A  D  Q  A  I  Y  L  R  T
ctggtcaataccctcaaccgccgtggctacaactactttgtcatt
 L  V  N  T  L  N  R  R  G  Y  N  Y  F  V  I
gaagcctatgaccaaccctggaaggccagcgacgaaggatcggta
 E  A  Y  D  Q  P  W  K  A  S  D  E  G  S  V
ggcgcctactggggcgtctacaacgccgagcgccagcagaagttc
 G  A  Y  W  G  V  Y  N  A  E  R  Q  Q  K  F
aacttcgacggccccgtggtggcgatcccgcagtggcgggccctg
 N  F  D  G  P  V  V  A  I  P  Q  W  R  A  L
gcagtggcgtcggtggtgctggcaatgatcgccttgatggtgctg
 A  V  A  S  V  V  L  A  M  I  A  L  M  V  L
ttcatcgatggctcggccctgcgccagcgtggccgtaccttcctg
 F  I  D  G  S  A  L  R  Q  R  G  R  T  F  L
acgttcatcaccttcctgtgcgggtcggtgctggtgtggatcgcc
 T  F  I  T  F  L  C  G  S  V  L  V  W  I  A
tacgactacagccagcaatacagcacctggttcagcctgaccgtg
 Y  D  Y  S  Q  Q  Y  S  T  W  F  S  L  T  V
ggcgtgctgctggccctcggcgcgctgggtgtgttcatcgtgctg
 G  V  L  L  A  L  G  A  L  G  V  F  I  V  L
```

FIG. 24A

```
ctcaccgaggcccacgaactggccgaggcggtctggatacacaag
L   T   E   A   H   E   L   A   E   A   V   W   I   H   K
cgccgccgcgagttcctgcccgtgcaggccgacactgcctaccgg
R   R   R   E   F   L   P   V   Q   A   D   T   A   Y   R
cccaaggtgtcggtgcatgtgccgtgctacaacgagccacctgag
P   K   V   S   V   H   V   P   C   Y   N   E   P   P   E
atggtgaaacagaccctggacgccctggccgccctggactacccc
M   V   K   Q   T   L   D   A   L   A   A   L   D   Y   P
gactacgaagtgctggtgatcgacaacaacaccaaggacccggcc
D   Y   E   V   L   V   I   D   N   N   T   K   D   P   A
gtgtgggagccgctcaaggcccactgcgaaaagcttggcgagcgc
V   W   E   P   L   K   A   H   C   E   K   L   G   E   R
ttcaagttcttccacgtcgcgccactggccggcttcaagggtggc
F   K   F   F   H   V   A   P   L   A   G   F   K   G   G
gcgctgaattacctgatcccgcacacggcaaaggacgccgaagtg
A   L   N   Y   L   I   P   H   T   A   K   D   A   E   V
atcgcggtaatcgactcggactactgcgtcgaccgcaactggctc
I   A   V   I   D   S   D   Y   C   V   D   R   N   W   L
aagcacatggtgccgcacttcgccgacccgaaaattgccgtggtg
K   H   M   V   P   H   F   A   D   P   K   I   A   V   V
cagtcaccgcaggattaccgtgaccagcacgaaagcgccttcaag
Q   S   P   Q   D   Y   R   D   Q   H   E   S   A   F   K
aagctgtgctacagcgaatacaagggcttcttccacatcggtatg
K   L   C   Y   S   E   Y   K   G   F   F   H   I   G   M
gtcacccgcaacgaccgtgacgcgatcatccagcacggcaccatg
V   T   R   N   D   R   D   A   I   I   Q   H   G   T   M
accatgacccggcgcagtgtgctggaagaactgggctgggccgag
T   M   T   R   R   S   V   L   E   E   L   G   W   A   E
tggtgcatctgcgaggacgccgaactgggcctgcgcgtgttcgag
W   C   I   C   E   D   A   E   L   G   L   R   V   F   E
aaaggcctgtccgccgcctacgcccacaacagctacggcaagggc
K   G   L   S   A   A   Y   A   H   N   S   Y   G   K   G
ctgatgcccgacaccttcatcgacttcaagaagcaacgcttccgc
L   M   P   D   T   F   I   D   F   K   K   Q   R   F   R
tgggcctacggcgccatccagatcatcaagcaccacgccggcgcg
W   A   Y   G   A   I   Q   I   I   K   H   H   A   G   A
ctgctgcgcggcaaaggcagccagctgacccgtggccagcgctac
L   L   R   G   K   G   S   Q   L   T   R   G   Q   R   Y
cacttcctggccggctggctaccgtggatcgccgatggcatgaac
H   F   L   A   G   W   L   P   W   I   A   D   G   M   N
atcttcttcaccatcggcgcgctgttgtggtcggcggcgatgatc
I   F   F   T   I   G   A   L   L   W   S   A   A   M   I
atcgtgccgcatcgggtcgatccgcccctgatgatcttcgccatc
I   V   P   H   R   V   D   P   P   L   M   I   F   A   I
ccgccgctggcgctgttcttcttcaaggtcggcaagatcatcttc
P   P   L   A   L   F   F   F   K   V   G   K   I   I   F
ctgtaccgccgagcggtggggtgaacctcaaggatgccttcgca
L   Y   R   R   A   V   G   V   N   L   K   D   A   F   A
Gctgcgctggccgggctggcactgtcgcacaccatcgccaaggcg
```

FIG. 24B

```
A  A  L  A  G  L  A  L  S  H  T  I  A  K  A
gtactgtatggttttcttcaccagcagcatgccgttcttccgcacg
V  L  Y  G  F  F  T  S  S  M  P  F  F  R  T
ccgaagaacgctgacagccatgggttgctggtggcgatttccgaa
P  K  N  A  D  S  H  G  L  L  V  A  I  S  E
gcccgtgaagagctgttcatcatggtgctgctgtggggcgcggcg
A  R  E  E  L  F  I  M  V  L  L  W  G  A  A
ttgggtatctacctggtgcaggggctgccgagttcggacatgcgc
L  G  I  Y  L  V  Q  G  L  P  S  S  D  M  R
ttctgggtggcgatgttgctggtgcagtcgttgccttatgtggca
F  W  V  A  M  L  L  V  Q  S  L  P  Y  V  A
gcgctggtgatggcgttcctgtcgtcgctgcccaagcccgcagaa
A  L  V  M  A  F  L  S  S  L  P  K  P  A  E
aaggctgcccaagcgcagcaggcttga
K  A  A  Q  A  Q  Q  A  *
```

FIG. 24C

```
atgtcgatataccgcatggagcacagtttagacatgaataaaaaa
 M  S  I  Y  R  M  E  H  S  L  D  M  N  K  K
atatcagacgctccaatctggccggtcaactcattcaaatccgtc
 I  S  D  A  P  I  W  P  V  N  S  F  K  S  V
gtgaccaaagtcccggactggcctgacagcatctcgggccttgcc
 V  T  K  V  P  D  W  P  D  S  I  S  G  L  A
tataaccccttcgtcccggacaaagtccctacaagcacatctat
 Y  N  P  F  R  P  G  Q  S  P  Y  K  H  I  Y
ccgacccgcgagcaaatcaaagaagacttgctgctgatccgccg
 P  T  R  E  Q  I  K  E  D  L  L  L  I  R  P
ttgactcgacatgtaagaacctactcggtcgagcagacgctggcc
 L  T  R  H  V  R  T  Y  S  V  E  Q  T  L  A
tgtattcccgaaatagccgaagaactcggcatgagtgtcacactc
 C  I  P  E  I  A  E  E  L  G  M  S  V  T  L
ggcatatggataggctgggacgaaaaacgcaatgatcgggaactg
 G  I  W  I  G  W  D  E  K  R  N  D  R  E  L
atcgagggcgtgaagcttgccaatcagtatcccagcgtccggcgt
 I  E  G  V  K  L  A  N  Q  Y  P  S  V  R  R
ctgatcatcggaaatgaaacattactgcgcaatgacgtcaccgtc
 L  I  I  G  N  E  T  L  L  R  N  D  V  T  V
agccaactgatcgattacatgcaaacggcacgacaaggtgtcaac
 S  Q  L  I  D  Y  M  Q  T  A  R  Q  G  V  N
gttccgatttcaacctcagagggatggcaacagtggcacgatacg
 V  P  I  S  T  S  E  G  W  Q  Q  W  H  D  T
ccggaactggctgatcacgcagacttcatcgcggcgcatgtcttg
 P  E  L  A  D  H  A  D  F  I  A  A  H  V  L
ccattcagggagttcgttccagtcacccaggcaggctctgcagtt
 P  F  R  E  F  V  P  V  T  Q  A  G  S  A  V
ctcgcacgggcgaacgaattgaggctgatgtttcccgaaaaaccg
 L  A  R  A  N  E  L  R  L  M  F  P  E  K  P
ctgatactttccgagattggctggccagacaaaggcaacttcaga
 L  I  L  S  E  I  G  W  P  D  K  G  N  F  R
agacgcaccaccgcctacgtcgccgaacagtcaatttacctgcgc
 R  R  T  T  A  Y  V  A  E  Q  S  I  Y  L  R
agccagctcgcgctgttgaaccagagtggcctcgactactttgtc
 S  Q  L  A  L  L  N  Q  S  G  L  D  Y  F  V
agggaggcatttgatcaacaatggaaaactgaggaagggttgccg
 R  E  A  F  D  Q  Q  W  K  T  E  E  G  L  P
gggcctcactggggcctgttcgatgcccagcgaaagataaagtta
 G  P  H  W  G  L  F  D  A  Q  R  K  I  K  L
ccactgcaaggcccagtgaaaatacgggccagctggcgatcagaa
 P  L  Q  G  P  V  K  I  R  A  S  W  R  S  E
gttccgagattggtcgccgattggcagcccgacaactggcgaaca
 V  P  R  L  V  A  D  W  Q  P  D  N  W  R  T
accgtattgattttctgctgcgttgtacacattattggtaggcgtt
 T  V  L  I  F  A  A  L  Y  T  L  L  V  G  V
ggcataagttacgcacagcccttatcgatgtgggtggctttgccc
 G  I  S  Y  A  Q  P  L  S  M  W  V  A  L  P
```

FIG. 25A

```
atcgccttggtgtgggtgaccagcttactgatcggcacggggata
 I  A  L  V  W  V  T  S  L  L  I  G  T  G  I
cagggttacgagttcctcgaatcatgctggggaccggagaaaccg
 Q  G  Y  E  F  L  E  S  C  W  G  P  E  K  P
cgatcttttcctccgttaagagcttacccggggccgttacccaaa
 R  S  F  P  P  L  R  A  Y  P  G  P  L  P  K
gtgtccatacacgtaccgtgctacaacgaacctcccgacatggtg
 V  S  I  H  V  P  C  Y  N  E  P  P  D  M  V
aagctgacgctcgacgcattacaacgcctggactatccgaacttt
 K  L  T  L  D  A  L  Q  R  L  D  Y  P  N  F
gaggttctgatcatcgacaacaacactcaagacccggaagtctgg
 E  V  L  I  I  D  N  N  T  Q  D  P  E  V  W
gagcccattgagcagtactgcaggcaactgggacctcgcttccgg
 E  P  I  E  Q  Y  C  R  Q  L  G  P  R  F  R
ctctttcatgtcaatccacttagcgggttcaagtcgggcgcactg
 L  F  H  V  N  P  L  S  G  F  K  S  G  A  L
aactacctgctggactacaccgccaaggatgccgaaatagtagcg
 N  Y  L  L  D  Y  T  A  K  D  A  E  I  V  A
gcgatcgatgctgattattgcgtgcaccggcattggctcaagcat
 A  I  D  A  D  Y  C  V  H  R  H  W  L  K  H
atggccccctatttgcgtgcccggatatagcggttatccaagta
 M  A  P  Y  F  A  C  P  D  I  A  V  I  Q  V
ccgcaagactaccgtgatggcgacgacagcctgttcaaacgttgc
 P  Q  D  Y  R  D  G  D  D  S  L  F  K  R  C
tgccaggccgagtatcgcgttttttcaatattggcatggtcatc
 C  Q  A  E  Y  R  V  F  F  N  I  G  M  V  I
cgcaacgaccacgacgcaatcattcagcacggcaccatgaccctg
 R  N  D  H  D  A  I  I  Q  H  G  T  M  T  L
attcgcaattcggtgttgcagcgactgcgctgggcagaatggagc
 I  R  N  S  V  L  Q  R  L  R  W  A  E  W  S
atctgcgaagatgccgagctcggactgcggatactggagaacggt
 I  C  E  D  A  E  L  G  L  R  I  L  E  N  G
ttttccaccggctatgtcgccatcagctatggcaagggactgatc
 F  S  T  G  Y  V  A  I  S  Y  G  K  G  L  I
ccggatacattcatggacttcaagaaacaacggtatcgctgggct
 P  D  T  F  M  D  F  K  K  Q  R  Y  R  W  A
tacggtgtcatccagatactcaaacgacatactggaagcctgatc
 Y  G  V  I  Q  I  L  K  R  H  T  G  S  L  I
gcaggtacgtgcgaggccttgacgccaatacagcgctatcacttc
 A  G  T  C  E  A  L  T  P  I  Q  R  Y  H  F
attgccggctggatgccttggattgcaggggggaataaattacttt
 I  A  G  W  M  P  W  I  A  G  G  I  N  Y  F
ctggctatcgctgtgcttctctggtcaatggcaatgatcattcaa
 L  A  I  A  V  L  L  W  S  M  A  M  I  I  Q
cccgacacactcgaacctgtgccgtggatatttcatcctcatta
 P  D  T  L  E  P  V  P  W  I  F  S  S  S  L
ctgttgatgtttgttctgggcgtttgcaaagcgatcagcctttat
 L  L  M  F  V  L  G  V  C  K  A  I  S  L  Y
caacgattggccagcaccgacatcaaagacgccttcgcagccata
 Q  R  L  A  S  T  D  I  K  D  A  F  A  A  I
```

FIG. 25B

```
attgcgagcatggcgctgtactcggttgtaggcaaggccgtgctt
 I  A  S  M  A  L  Y  S  V  V  G  K  A  V  L
tcatcggcattcacctcaggattaccgttctttcgcactcccaag
 S  S  A  F  T  S  G  L  P  F  F  R  T  P  K
cagacctctggcagcgggctcggcaaggccctgctggacgtccgg
 Q  T  S  G  S  G  L  G  K  A  L  L  D  V  R
gaagatctgtacatggccgtggtctggtgggtcatgacggtatcg
 E  D  L  Y  M  A  V  V  W  W  V  M  T  V  S
ctgtgcttccgaaaagaagctatcggtccggaccttggattctgg
 L  C  F  R  K  E  A  I  G  P  D  L  G  F  W
gtggcgataatgttcgcccagtcattgccttacgtagccgccatg
 V  A  I  M  F  A  Q  S  L  P  Y  V  A  A  M
atcatggcaatactgtcggctctcgcaaaccgcccttcacgctcc
 I  M  A  I  L  S  A  L  A  N  R  P  S  R  S
acaacctga
 T  T  *
```

FIG. 25C

BACTERIAL GLYCOSYLTRANSFERASE POLYPEPTIDES INVOLVED IN ANTIBIOTIC RESISTANCE

REFERENCE TO RELATED APPLICATIONS

This application claims priority from U.S. Provisional Application No. 60/323,241, filed Sep. 18, 2001, the entirety of which is incorporated by reference.

BACKGROUND OF THE INVENTION

Biofilms are complex communities of microorganisms, comprised either of a single or multiple species. Over the past few decades, there has been a growing realization that bacteria in most environments are not found in a unicellular, planktonic existence such as those typically studied in the laboratory, but exist predominantly in multi-cellular surface attached communities called biofilms. This realization has spurred much research into the physical and chemical properties of biofilms, their morphology, and the mechanism of their development.

The transition from the planktonic mode of existence to a biofilm is a regulated developmental process. This biofilm community has a number of distinct characteristics including the production of exopolysaccharides, the formation of chemical and pH gradients, a marked degree of structural heterogeneity, and the development of high level resistance to a variety of antimicrobial agents.

It has been shown that biofilm grown cells can become 10–1000× more resistant to the effects of antimicrobial agents than their planktonic counterparts. This characteristic of biofilms makes them extremely difficult to control in both medical and industrial settings. Traditional antibiotic therapies can eliminate planktonic bacteria, but organisms growing in a biofilm survive treatment and can eventually regrow once antibiotics are discontinued. The levels of antibiotic required to eliminate biofilm bacteria often cannot be achieved in the patient or are toxic. Therefore, biofilm-based infections can become chronic with the only recourse being removal of the contaminated surface.

The formation of biofilms can have serious negative consequences in medical, industrial, and natural settings, resulting in high costs both in human health and economic terms. Biofilm-associated infections extend hospital stays an average of about three days and it is estimated that up to 65% of nosocomial infections are biofilm-based with an associated treatment cost in excess of a billion dollars per year. In clinical settings, biofilms can form on a variety of surfaces. Biofilms formed on indwelling medical devices serve as a reservoir of bacteria that can be shed into the body, leading to a chronic systemic infection. Indeed, up to 82% of nosocomial bacteremias are the result of bacterial contamination of intravascular catheterizations. Examples of biofilms include oral microbes on teeth, chronic *Pseudomonas aeruginosa* infections in the lungs of cystic fibrosis patients and bacterial contaminants on medical devices such as pacemakers and catheters. Biofilms can form in almost any hydrated environment that has the proper nutrient conditions, and can develop on a wide variety of abiotic (both hydrophobic and hydrophilic) and biotic (e.g., eukaryotic cells) surfaces.

The formation of biofilms is an important aspect of normal development for many microbial species. The mechanisms responsible for the increased biofilm resistance, however, are not well understood. It has been suggested that the exopolysaccharide matrix that surrounds the cells in the biofilm prevent diffusion of antimicrobial agents through the biofilm, thus preventing access of the agent to the cells. While this may be the case for some antimicrobial agents, for many others it has been shown that antimicrobial agents can penetrate the biofilm matrix but are still unable to kill cells in the biofilm. It has also been suggested that cells within the biofilm grow slowly in response to nutrient deprivation and perhaps some form of stress. Therefore, antimicrobial agents that only act on actively dividing bacterial cells would be non-functional in this sort of environment. While a number of studies support the idea that slowed growth rate can explain some aspects of biofilm-related resistance, other studies have suggested that the full extent of resistance cannot be accounted for by this mechanism. Finally, while it has been suggested that quorum sensing is involved in resistance to antimicrobial agents, it is not clear what role, if any, this system plays in biofilm-related antimicrobial resistance. To date, none of the models put forward adequately explain the level of resistance to biocides attained by cells in a biofilm.

There is emerging evidence that the transition from planktonically growing bacteria to life in a biofilm requires a genetic program that responds to a variety of environmental cues. It is possible that the development of biofilm-related antibiotic resistance is also a regulated event, and taken together with the marked biochemical and physiological heterogeneity of biofilms, the induction of a biofilm-related resistance phenotype may occur within distinct regions of the biofilm. The subset of biocide-resistant cells in the biofilm is referred to as "persistors". The term persistor refers to the fact that not all of the cells within the biofilm resist killing by antimicrobial agents resulting in the survival of a small population of very resistant cells after antibiotic treatment.

There exists a strong need to discover methods and compositions that will inhibit biofilm formation and overcome their resistance mechanisms.

SUMMARY OF THE INVENTION

The invention features method for identifying compounds that can alter, e.g., reduce the resistance of microbial cells growing in a biofilm to antimicrobial agents. Certain of the compounds may also be used reduce resistance to antimicrobial agents associated with other physiological states as well as resistance caused by genetic changes. The invention also features methods for identifying genes that play a role in biofilm resistance as well as certain such genes and the proteins they encode.

A compound or compounds that are identified by the invention as modulating biofilm resistance to an antimicrobial agent can be further analyzed in the context of a flow cell assay and a colony biofilm assay. Using the flow cell assay, a biofilm, allowed to form in the flow cell, can be monitored in the presence of an antimicrobial agent and a compound. The antimicrobial agent and the compound can be quickly removed and the effect of the treatment on biofilm viability can be determined using standard techniques.

A colony biofilm assay can also be utilized to test the effect of biofilm resistance to antimicrobial agents in the presence of compounds identified by the invention. Microorganisms are allowed to form a biofilm on a polycarbonate filter then transferred to solid media. The biofilm is exposed to an antimicrobial agent and a compound and tested for viability after a pre-determined amount of time. A biofilm treated with a compound identified by the invention will demonstrate reduced viability and/or increased sensitivity when exposed to the antimicrobial agent after or during exposure to the compound. These techniques are described in more detail below.

The invention features a method of identifying a candidate compound for altering the sensitivity of a microorganism to an antimicrobial agent, the method comprising: a) providing a sample comprising an efflux pump selected from the group consisting of: i) an efflux pump comprising a polypeptide comprising SEQ ID NO:4 (gene PA1874), ii) an efflux pump comprising a polypeptide comprising SEQ ID NO: 12 (gene PA4142), iii) an efflux pump comprising a polypeptide comprising SEQ ID NO:18 (gene PA2389), b) contacting the sample with a test compound; and c) measuring activity of the efflux pump, wherein a change in the activity of the efflux pump in the presence of the test compound relative to the activity of the efflux pump in a control sample in the absence of the test compound, indicates that the compound is a candidate compound for altering the sensitivity of a microorganism to an antimicrobial agent.

In various embodiments: the efflux pump comprising a polypeptide comprising SEQ ID NO:4 (gene PA1874), further comprises at least one of: a polypeptide comprising SEQ ID NO:6 (gene PA1875), a polypeptide comprising SEQ ID NO:8 (gene PA1876), and a polypeptide comprising SEQ ID NO:10 (gene PA1877); the efflux pump comprising a polypeptide comprising SEQ ID NO:12 (gene PA4142), further comprises at least one of: a polypeptide comprising SEQ ID NO:14 (gene PA4143), and a polypeptide comprising SEQ ID NO:16 (gene PA4144); and the efflux pump comprising a polypeptide comprising SEQ ID NO:18 (gene PA2389), further comprises at least one of: a polypeptide comprising SEQ ID NO:20 (gene PA2390), and a polypeptide comprising SEQ ID NO:22 (gene PA2391).

The invention also features a method of identifying a candidate compound for altering the sensitivity of a microorganism to an antimicrobial agent, the method comprising:

a) providing a sample comprising a polypeptide selected from the group consisting of: i) a polypeptide comprising SEQ ID NO:8 (gene PA1876), ii) an efflux pump comprising a polypeptide comprising SEQ ID NO: 14 (gene PA4143), iii) an efflux pump comprising a polypeptide comprising SEQ ID NO:20 (gene PA2390), b) contacting the sample with a test compound; and c) measuring the ATPase activity of the polypeptide, wherein a change in the ATPase activity of the polypeptide in the presence of the test compound relative to the activity of the polypeptide in a control sample in the absence of the test compound, indicates that the compound is a candidate compound for altering the sensitivity of a microorganism to an antimicrobial agent.

In various embodiments: the sample comprises cells expressing the polypeptide, the sample comprises cells harboring an expression vector encoding the polypeptide. The cells are grown in a biofilm, the cells are grown planktonically, the sample comprises vesicles containing the efflux pump or a membrane system containing the efflux pump; the method comprises measuring the activity of two or more efflux pumps selected from the group consisting of: i) an efflux pump comprising a polypeptide comprising SEQ ID NO:4 (gene PA1874), ii) an efflux pump comprising a polypeptide comprising SEQ ID NO: 12 (gene PA4142), and iii) an efflux pump comprising a polypeptide comprising SEQ ID NO:18 (gene PA2389).

The invention further features: a method of identifying a candidate compound for altering the sensitivity of a microorganism to an antimicrobial agent, the method comprising:

a) providing a sample comprising a glucosyltransferase polypeptide selected from the group consisting of: i) a polypeptide comprising SEQ ID NO:2 (gene PA1163), ii) a polypeptide comprising SEQ ID NO:27, iii) a polypeptide comprising SEQ ID NO:28, iv) a polypeptide comprising SEQ ID NO:29, and v) a polypeptide comprising SEQ ID NO:32, b) contacting the sample with a test compound; and c) measuring activity of the glucosyltransferase polypeptide, wherein a change in the activity of the glucosyltransferase polypeptide in the presence of the test compound relative to the activity of the glucosyltransferase polypeptide in a control sample in the absence of the test compound, indicates that the compound is a candidate compound for altering the sensitivity of a microorganism to an antimicrobial agent.

In various embodiments: the glucosyltransferase polypeptide is contacted with the test compound in the presence of an antimicrobial agent; the sample comprises cells expressing the glucosyltransferase polypeptide; sample comprises cells harboring an expression vector encoding the glucosyltransferase polypeptide; the cells are grown as a biofilm; the cells are grown planktonically; and activity is measured by measuring cyclic-b-(1,3)-glucan formation.

The invetion further features: a method of identifying a candidate compound for altering the sensitivity of a microorganism to an antimicrobial agent, the method comprising:

a) providing a sample comprising cells expressing a gene encoding a glucosyltransferase polypeptide selected from the group consisting of: i) a polypeptide comprising SEQ ID NO:2 (gene PA1163), ii) a polypeptide comprising SEQ ID NO:27, iii) a polypeptide comprising SEQ ID NO:28, iv) a polypeptide comprising SEQ ID NO:29, and v) a polypeptide comprising SEQ ID NO:32, b) contacting the sample with a test compound; and c) measuring the expression of a gene encoding a glucosyltransferase polypeptide in the cells, wherein a change in the expression of the gene encoding the glucosyltransferase polypeptide in the presence of the test compound relative to the expression of the gene encoding the glucosyltransferase polypeptide in a control sample in the absence of the test compound, indicates that the compound is a candidate compound for altering the sensitivity of a microorganism to an antimicrobial agent.

In various embodiments: the cells are contacted with the test compound in the presence of an antimicrobial agent; the expression of the gene is measured by measuring mRNA expression; expression of the gene is measured by measuring polypeptide expression; and the cells contacted with the test compound are growing as a biofilm.

The invention also features: A method of identifying a candidate compound for altering the sensitivity of a microorganism to an antimicrobial agent, the method comprising:

a) providing a sample of cells expressing an efflux pump selected from the group consisting of: i) an efflux pump comprising a polypeptide comprising SEQ ID NO: 4 (gene PA1874), ii) an efflux pump comprising a polypeptide comprising SEQ ID NO: 12 (gene PA4142), iii) an efflux pump comprising a polypeptide comprising SEQ ID NO: 18 (gene PA2389), b) contacting the cells with a test compound; and c) measuring expression of the efflux pump in the cells wherein a change in the expression of the efflux pump in the presence of the test compound relative to the expression of the efflux pump in a control sample in the absence of the test compound, indicates that the test compound is a candidate compound for altering the sensitivity of a microorganism to an antimicrobial agent.

In various embodiments: the efflux pump comprising a polypeptide comprising SEQ ID NO: 4 (gene PA1874), further comprises at least one of: a polypeptide comprising SEQ ID NO:6 (gene PA1875), a polypeptide comprising SEQ ID NO:8 (gene PA1876), and a polypeptide comprising SEQ ID NO:10 (gene PA1877); the efflux pump comprising a polypeptide comprising SEQ ID NO:12 (gene PA4142), further comprises at least one of: a polypeptide comprising SEQ ID NO:14 (gene PA4143), and a polypeptide comprising SEQ ID NO:16 (gene PA4144); the efflux pump comprising a polypeptide comprising SEQ ID NO:18 (gene PA2389), further comprises at least one of: a polypeptide comprising SEQ ID NO:20 (gene PA2390), and a polypeptide comprising SEQ ID NO:22 (gene PA2391); the cells are contacted with the test compound in the presence of an antimicrobial agent; expression is measured by measuring polypeptide expression; expression is measured by measuring mRNA expression; the cells are grown as a biofilm; and the cells are grown planktonically.

The invention also features: a purified polypeptide comprising an amino acid sequence selected from the group consisting of: SEQ ID NO:4 (gene PA1874), SEQ ID NO:6 (gene PA1875), SEQ ID NO:8 (gene PA1876), SEQ ID NO:10 (gene PA1877), SEQ ID NO:12 (gene PA4142), SEQ ID NO:14 (gene PA4143), SEQ ID NO:16 (gene PA4144), SEQ ID NO:18 (gene PA2389), SEQ ID NO:20 (gene PA2390), SEQ ID NO:22 (gene PA2391) and a purified polypeptide comprising the amino acid sequence selected from the group consisting of: SEQ ID NO:2 (gene PA1163), SEQ ID NO:27, SEQ ID NO:28, SEQ ID NO:29 and SEQ ID NO:31.

The invention includes a method of identifying a gene that functions in biofilm-related resistance to an antimicrobial agent, the method comprising:

(a) providing a library of clones of a selected microbial strain that have been subjected to mutagenesis;

(b) growing each of a plurality of clones from the library as a biofilm;

(c) identifying a clone having altered biofilm-related resistance to the antimicrobial agent relative the to biofilm-related resistance of the selected microbial stain;

(d) isolating from the identified clone a gene having a mutation.

In various embodiments: the antimicrobial agent is an antibiotic; the mutagenesis comprises random mutagenesis; the selected strain exhibits at least a two-fold change in resistance to the anti-microbial agent; the microorganism is a bacterial microorganism; the microorganism is a fungal microorganism; the mutagenesis comprises chemical mutagenesis.

The invention includes: a method of identifying a compound that increases the sensitivity of a microorganism to a selected antimicrobial agent, the method comprising:

(a) providing a sample comprising a microorganism in a biofilm;

(b) contacting the sample with a test compound and the selected antimicrobial agent; and (c) measuring the sensitivity of the microorganism in the sample to the selected antimicrobial agent, wherein an increase in the sensitivity of the microorganism to the selected antimicrobial agent relative to the sensitivity of the microorganism in a biofilm to the selected antimicrobial agent in the absence of the test compound indicates that the test compound is a compound that increases the sensitivity of microorganism in a biofilm to the selected antimicrobial agent.

In various embodiments: the antimicrobial agent is selected from the group consisting of aminoglycosides, macrolides, tetracyclines, penicillins, β-lactam antibiotics (including cephalosporins, β-lactam/β-lactamase combinations), quinolones (including fluoroquinolones), glycopeptides, sulfonamides, sulfones, oxazolidinones, streptogramins; the microorganism is selected from the group consisting of *Pseudomonas fluorescens, Pseudomonas aeruginosa, Pseudomonas acidovorans, Pseudomonas alcaligenes, Pseudomonas putida, Pseudomonas syringae, Pseudomonas aureofaciens, Pseudomonas fragi, Fusobacterium nucleatum, Treponema denticola, Porphyromonas gingivalis, Moraxella catarrhalis, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudo tuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Pasteurella multocida, Pasteurella haemolytica, Helicobacter pylori, Campylobacter fetus, Campylobacter jejuni, Campylobacter coli, Borrelia burgdorferi, Vibrio cholerae, Vibrio paramaemolyticus, Legionella pneumophila, Listeria monocytogenes, Neisseria gonorrhoeae, Neisseria meningitidis, Gardnerella vaginalis,* Bacteroides spp., *Clostridium difficile, Mycobacterium tuberculosis, Mycobacterium avium, Mycobacterium intracellulare, Mycobacterium leprae, Corynebacterium diphtheriae, Corynebacterium ulcerans,* Streptococcus spp., Enterococcus spp., Desulfvibrio spp., Actinomyces spp., Erwinia spp., Xanthomonas spp., Xylella spp., Clavibacter spp., Desulfomonas spp., Desulfovibrio spp., Desulfococcus spp., Desulfobacter spp., Desulfobulbus spp., Desulfosarcina spp., Deslfuromonas spp., Bacillus spp., Streptomyces spp., Clostridium spp., Rhodococcus spp., Thermatoga spp., Sphingomonas spp., Zymomonas spp., Micrococcus spp., Azotobacter spp., Norcardia spp., Brevibacterium spp., Alcaligenes spp., Microbispora spp., Micromonospora spp., *Methylobacterium organophilum, Pseudomonas reptilivora, Pseudomonas carragienovora, Pseudomonas dentificans,* Corynebacterium spp., Propionibacterium spp., Xanothomonas spp., Methylobacterium spp., Chromobacterium spp., Saccharopolyspora spp., Actinobacillus spp., Alteromonas spp., Aeronomonas spp., *Agrobacterium tumefaciens, Staphylococcus aureus, Staphylococcus epidermidis, Staphylococcus hominis, Staphylococcus haemolyticus, Staphylococcus warneri, Staphylococcus cohnii, Staphylococcus saprophyticus, Staphylococcus capitis, Staphylococcus lugdunensis, Staphlyococcus intermedius, Staphylococcus hyicus, Staphylococcus saccharolyticus* and Rhizobium spp; the biofilm is associated with an abiotic surface; the biofilm is associated with a biotic surface; the biofilm is not associated with a surface; the microorganism has a mutation that reduces the expression or activity of a polypeptide selected from the group consisting of: SEQ ID NO:4 (gene PA1874), SEQ ID NO:6

(gene PA1875), SEQ ID NO:8 (gene PA1876), SEQ ID NO:10 (gene PA 1877), SEQ ID NO:12 (gene PA4142), SEQ ID NO:14 (gene PA4143), SEQ ID NO:16 (gene PA4144), SEQ ID NO:18 (gene PA2389), SEQ ID NO:20 (gene PA2390), SEQ ID NO:22 (gene PA2391); and the microorganism has a mutation that reduces the expression or activity of a polypeptide selected from the group consisting of: SEQ ID NO:2 (gene PA1163), SEQ ID NO:27, SEQ ID NO:28, SEQ ID NO:29 and SEQ ID NO:31 (e.g., a deletion mutation or an insertion mutation).

The invention features a method of identifying a candidate compound for altering the sensitivity of a microorganism to an antimicrobial agent, the method comprising:

a) providing a sample comprising cells harboring a reporter gene comprising a nucleotide sequence encoding a detectable protein operably linked to an expression control sequence comprising a nucleotide sequence selected from the group consisting of: i) SEQ ID NO:23 (expression control for PA1874), ii) SEQ ID NO:24 (expression control for PA4242), iii) SEQ ID NO:25 (expression control for PA2389), and iv) SEQ ID NO:26 (expression control for PA1163), b) measuring the expression of the reporter gene in the cells in the presence of a test compound, wherein a change in the expression of the reporter gene in the presence of the test compound relative to the expression of the reporter gene in a control sample in the absence of the test compound, indicates that the compound is a candidate compound for altering the sensitivity of a microorganism to an antimicrobial agent.

In certain embodiments expression of the reporter gene is measured by measuring the expression of the detectable protein.

The invention includes: a method of identifying a candidate compound for inhibiting the growth of a microorganism, the method comprising:

a) providing a sample comprising an efflux pump selected from the group consisting of: i) an efflux pump comprising a polypeptide comprising an amino acid sequence at least 70% identical to SEQ ID NO:4 (gene PA1874), ii) an efflux pump comprising a polypeptide comprising an amino acid sequence at least 70% identical to SEQ ID NO: 12 (gene PA4142), iii) an efflux pump comprising a polypeptide comprising SEQ ID NO:18 (gene PA2389), b) contacting the sample with a test compound; and c) measuring activity of the efflux pump, wherein a change in the activity of the efflux pump in the presence of the test compound relative to the activity of the efflux pump in a control sample in the absence of the test compound, indicates that the compound is a candidate compound for inhibiting the growth of a microorganism.

In certain embodiments: the efflux pump comprising a polypeptide comprising SEQ ID NO:4 (gene PA1874), further comprises at least one of: a polypeptide comprising SEQ ID NO:6 (gene PA1875), a polypeptide comprising SEQ ID NO:8 (gene PA1876), and a polypeptide comprising SEQ ID NO:10 (gene PA1877); the efflux pump comprising a polypeptide comprising SEQ ID NO:12 (gene PA4142), further comprises at least one of: a polypeptide comprising SEQ ID NO:14 (gene PA4143), and a polypeptide comprising SEQ ID NO:16 (gene PA4144).; the efflux pump comprising a polypeptide comprising SEQ ID NO:18 (gene PA2389), further comprises at least one of: a polypeptide comprising SEQ ID NO:20 (gene PA2390), and a polypeptide comprising SEQ ID NO:22 (gene PA2391); the sample comprises cells expressing the polypeptide; the cells are grown in a biofilm; and the cells are grown planktonially.

The invention features: a method of identifying a candidate compound that inhibits growth of a microorganism, the method comprising:

a) providing a sample comprising a glucosyltransferase polypeptide selected from the group consisting of: i) a polypeptide comprising SEQ ID NO:2 (gene PA1163), ii) a polypeptide comprising SEQ ID NO:27, iii) a polypeptide comprising SEQ ID NO:28, iv) a polypeptide comprising SEQ ID NO:29, and v) a polypeptide comprising SEQ ID NO:32, b) contacting the sample with a test compound; and c) measuring activity of the glucosyltransferase polypeptide, wherein a change in the activity of the glucosyltransferase polypeptide in the presence of the test compound relative to the activity of the glucosyltransferase polypeptide in a control sample in the absence of the test compound, indicates that the compound is a candidate compound inhibiting the growth of a microorganism.

"Naturally-occurring" as used herein, as applied to an object, refers to the fact that an object can be found in nature. For example, a polypeptide or polynucleotide sequence that is present in an organism (including viruses) that can be isolated from a source in nature is naturally-occurring.

By "compound," "test compound," or "candidate compound" we mean any substance or chemical. Encompassed within this definition are, for example, compound analogs, naturally occurring, synthetic and recombinant pharmaceuticals, hormones, or antimicrobials, antibiotics, nucleic acid molecules, polypeptides, and peptide nucleic acids.

By "test sample" we mean one or more of the components of a sample and a test compound.

By "control sample" we mean a test sample lacking a test compound. Therefore, the control sample has all of the characteristics of the test sample except for the presence of a test compound in the test sample.

By "cell component" we mean a protein, carbohydrate, lipid, nucleic acid molecule, ion, or any other constituent contained within or secreted by an organism.

By "biological activity" we mean a protein having structural, regulatory, or biochemical functions of a naturally occurring molecule.

By "efflux pump" we mean a protein assembly which exports substrate molecules, compounds, or antimicrobial agents from the cytoplasm or periplasm of a cell, in an energy dependent fashion. Thus an efflux pump will typically be located in the cytoplasmic membrane of the cell (spanning the cytoplasmic membrane). For example, in Gram-negative bacteria the pump may span the periplasmic space and there may also be portion of the efflux pump which spans the outer membrane.

"Expression cassette" refers to a recombinantly produced nucleic acid molecule which is capable of directing the expression of one or more proteins. The expression cassette must include a promoter capable of directing the expression of said protein(s), and a sequence encoding one or more proteins. Optionally, the expression cassette may include transcription termination, splice recognition, and polyadenylation addition sites. Desired promoters include the TK, CMV, MMTV, MoMLV, $P_{tac}$, $P_{lac}$, $P_{ara}$, $P_{xyl}$, and $P_{T7}$ promoters. In addition, the expression cassette may contain a selectable marker, for example, Neo, SV2 Neo, hygromycin, phleomycin, histidinol, DHFR, tetracycline, carbenecillin, gentamycin, kanamycin, and ampicillin; a chemiluminescent marker, for example, luciferase and green fluorescent protein; or an enzymatic marker, for example, chloramphenicol acetyltransferase.

"Reporter gene" means a gene that encodes a detectable protein, e.g., reporter enzyme, such as they are known in the art or are later developed, such as reporter enzyme activity. A reporter gene may be a component of an expression cassette. "Reporter enzyme" means an enzyme that encode a reporter enzyme that has a detectable read-out, such as beta-lactamase, beta-galactosidase, or luciferase (for beta-lactamase, see WO 96/30540 to Tsien, published Oct. 3, 1996). Desirably, reporter enzymes localize in the cytosol of a cell, such as cytosolic beta-lactamase. Reporter enzymes can be detected using methods known in the art, such as the use of chromogenic or fluorogenic substrates for reporter enzymes as such substrates are known in the art. Such substrates are desirably membrane permeant. Chromogenic or fluorogenic readouts can be detected using, for example, optical methods such as absorbance or fluorescence. A reporter gene can be part of a reporter gene construct, such as a plasmid or viral vector, such as a retrovirus or adeno-associated virus. A reporter gene can also be extra-chromosomal or be integrated into the genome of a host cell. The expression of the reporter gene can be under the control of exogenous expression control sequences or expression control sequences within the genome of the host cell. Under the latter configuration, the reporter gene is desirably integrated into the genome of the host cell.

"Polypeptide" means any chain of amino acids, regardless of length or post-translational modification (e.g., glycosylation or phosphorylation). By the use of "precursor" we mean that a polypeptide can be encoded by a full length gene sequence or by any portion of the coding sequence so long as the enzymatic activity is retained.

"Substantially pure polypeptide" means a polypeptide which has been separated from components which naturally accompany it. Typically, the polypeptide is substantially pure when it is at least 60%, by weight, free from the proteins and naturally-occurring organic molecules with which it is naturally associated. It is desirable for the preparation to be at least 75%, more desirably at least 90%, and even more desirably 95%, and most desirably 99%, by weight the desired protein. A substantially pure polypeptide may be obtained, for example, by extraction from a natural source (e.g., a bacterial cell); by expression of a recombinant nucleic acid molecule encoding the polypeptide; or by chemically synthesizing the protein. Purification of polypeptides may be by techniques known in the art, for example, differential extraction, salt fractionation, chromatography on ion exchange resins, affinity chromatography, centrifugation, and the like. See, for example, Methods in Enzymology for a variety of methods for purifying proteins. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus a protein which is chemically synthesized or produced in a cellular system different from the cell from which it naturally originates will be substantially free from its naturally associated components. Accordingly, substantially pure polypeptides include those derived from prokaryotic organisms, but synthesized in other prokaryotes or eukaryotes.

"Substantially pure DNA" means DNA that is free of the genes which, in the naturally occurring genome of the organism from which the DNA of the invention is derived, flank the gene. The term therefore includes, for example, a recombinant DNA which is incorporated into a vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

By "antimicrobial agent" we mean an agent, e.g., a compound which reduces the rate of growth of an organism compared to the rate of growth of the organism in the absence of the composition. A reduction in the rate of growth of an organism may be by at least 5%, more desirably, by at least 10%, even more desirably, by at least 20%, 50%, or 75%, and most desirably, by 90% or more. The definition also extends to compositions which affect the viability, virulence, or pathogenicity of an organism. An antimicrobial agent can be natural (e.g., derived from bacteria), synthetic, or recombinant. An antimicrobial agent can be bacteriostatic, bactericidal or both. An antimicrobial agent is bacteriostatic if it inhibits cell division without affecting the viability of the inhibited cell. An antimicrobial agent is bactericidal if it causes cell death. Cell death is commonly detected by the absence of cell growth in liquid growth medium (e.g., absence of turbidity) or on a solid surface (e.g., absence of colony formation on agar). Those of skill in the art know that a composition which is bacteriostatic at a given concentration may be bactericidal at a higher concentration. Certain bacteriostatic compositions are not bactericidal at any concentration.

Encompassed within the definition of antimicrobial agents are compound analogs, naturally occurring, synthetic and recombinant pharmaceuticals, antibiotics, etc.

As used herein, the term "antimicrobial" refers to the ability of compounds to prevent, inhibit or destroy the growth or viability of microbes such as bacteria, fungi, protozoa, and viruses. The term may also refer to the ability of compounds to prevent, reduce, or inhibit the virulence, cytotoxicity, reactogenicity, or pathogenicity of microbes such as bacteria, fungi, protozoa, and viruses.

"MBC" means minimal bacteriocidal concentration defined as the lowest concentration of an antimicrobial compound that kills 99.9% of the original inoculum of a microganism, or more stringently as the lowest concentration of an antimicrobial compound that kills all of the mircroorganisms of the original inoculum.

"MIC" means minimal inhibitory concentration defined as the lowest concentration of an antimicrobial agent that results in inhibition of visible growth of a microorganism (i.e., colonies on a plate or turbidity in broth culture) under standard conditions known in the art.

The term "bacteria," and "bacterial" refer to all prokaryotic organisms, including those within all of the phyla in the Kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. Also included within this term are prokaryotic organisms which are gram negative or gram positive. "Gram negative" and "gram positive" refer to staining patterns with the Gram-staining process which is well known in the art (Finegold and Martin, Diagnostic Microbiology, 6th Ed. (1982), C. V. Mosby St. Louis, pp 13–15). "Gram positive bacteria" are bacteria which retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red. A bacterial organism can be one selected from the group consisting of, but not limited to, *Pseudomonas fluorescens, Pseudomonas aeruginosa, Pseudomonas acidovorans, Pseudomonas alcaligenes, Pseudomonas putida, Pseudomonas syringae, Pseudomonas aureofaciens, Pseudomonas fragi, Fusobacterium nucleatum, Treponema denticola, Porphyromonas gingivalis, Moraxella catarrhalis, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter calcoaceticus, Acinetobacter haemolyticus, Yersinia enterocolitica, Yersinia pestis, Yersinia pseudo tuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Pasteurella multocida, Pasteurella haemolytica, Helicobacter pylori, Campylobacter fetus, Campylobacter jejuni, Campylobacter coli, Borrelia burgdorferi, Vibrio cholerae, Vibrio paramaemolyticus, Legionella pneumophila, Listeria monocytogenes, Neisseria gonorrhoeae, Neisseria meningitidis, Gardnerella vaginalis,* Bacteroides spp., *Clostridium difficile, Mycobacterium tuberculosis, Mycobacterium avium, Mycobacterium intracellulare, Mycrobacterium leprae, Corynebacterium diphtheriae, Corynebacterium ulcerans,* Streptococcus spp., Enterococcus spp., Desulfvibrio spp., Actinomyces spp., Erwinia spp., Xanthomonas spp., Xylella spp., Clavibacter spp., Desulfomonas spp., Desulfovibrio spp., Desulfococcus spp., Desulfobacter spp., Desulfobulbus spp., Desulfosarcina spp., Deslfuromonas spp., Bacillus spp., Streptomyces spp., Clostridium spp., Rhodococcus spp., Thermatoga spp., Sphingomonas spp., Zymomonas spp., Micrococcus spp., Azotobacter spp., Norcardia spp., Brevibacterium spp., Alcaligenes spp., Microbispora spp., Micromonospora spp., *Methylobacterium organophilum, Pseudomonas reptilivora, Pseudomonas carragienovora, Pseudomonas dentificans,* Corynebacterium spp., Propionibacterium spp., Xanothomonas spp., Methylobacterium spp., Chromobacterium spp., Saccharopolyspora spp., Actinobacillus spp., Alteromonas spp., Aeronomonas spp., *Agrobacterium tumefaciens, Staphylococcus aureus, Staphylococcus epidermidis, Staphylococcus hominis, Staphylococcus haemolyticus, Staphylococcus warneri, Staphylococcus cohnii, Staphylococcus saprophyticus, Staphylococcus capitis, Staphylococcus lugdunensis, Staphlyococcus intermedius, Staphylococcus hyicus, Staphylococcus saccharolyticus* and Rhizobium spp.

"Fungi," "Fungal," "Fungus," or "Fungal Organism" is intended to mean a eukaryotic cell having a nuclear membrane and cell wall. The subject fungi may grow as single cells (e.g., yeasts), chains (e.g., hyphae), aggregates, rafts and the like, and are not plant or mammalian cells. A fungal organism can be one selected from the group consisting of, but not limited to, Absidia spp., *Actinomadura madurae,* Actinomyces spp., *Allescheria boydii,* Altemaria spp., *Anthopsis deltoidea,* Aphanomyces spp., *Apophysomyces eleqans,* Armillaria spp., *Arnium leoporinum,* Aspergillus spp., *Aureobasidium pullulans, Basidiobolus ranarum,* Bipolaris spp., *Blastomyces dermatitidis,* Botrytis spp., Candida spp., Centrospora spp., Cephalosporium spp., Cerato- cystis spp., Chaetoconidium spp., Chaetomium spp., Cladosporium spp., *Coccidioides immitis,* Colletotrichum spp, Conidiobolus spp., *Corynebacterium tenuis,* Cryptoporiopsis spp., Cylindrocladium spp., Cryptococcus spp., *Cunninghamella bertholletiae,* Curvularia spp., Dactylaria spp., Diplodia spp., Epidermophyton spp., *Epidermophyton floccosum,* Exserophilum spp., Exophiala spp., Fonsecaea spp., Fulvia spp., Fusarium spp., Geotrichum spp., Guignardia spp., Helminthosporium spp., Histoplasma spp., Lecythophora spp., Macrophomina spp., Madurella spp., Magnaporthe spp., *Malassezia furfur,* Microsporum spp., Monilinia spp., Mucor spp., *Mycocentrospora acerina,* Nectria spp., Nocardia spp., Oospora spp., Ophiobolus spp., Paecilomyces spp., *Paracoccidioides brasiliensis,* Penicillium spp., *Phaeosclera dematioides,* Phaeoannellomyces spp., *Phialemonium obovatum,* Phialophora spp., Phlyctaena spp., Phoma spp., Phomopsis spp., Phymatotrichum spp., Phytophthora spp., Pythium spp., *Piedraia hortai, Pneumocystis carinii,* Puccinia spp., *Pythium insidiosum, Rhinocladiella aquaspersa, Rhizomucor pusillus,* Rhizoctonia spp., Rhizopus spp., Saccharomyces spp., *Saksenaea vasiformis, Sarcinomyces phaeomuriformis,* Scerotium spp., Sclerotinia spp., Sphaerotheca spp., *Sporothrix schenckii, Syncephalastrum racemosum, Taeniolella boppii,* Taphrina spp., Thielaviopsis spp., Torulopsosis spp., Trichophyton spp., Trichosporon spp., *Ulocladium chartarum,* Ustilago spp., Venturia spp., Verticillium spp., *Wangiella dermatitidis,* Whetxelinia spp., Xylohypha spp., and their synonyms.

By "exponential" is meant the phase of microbial growth during which the microbial population is growing at a constant and maximum rate, dividing and doubling at regular intervals (i.e., log phase growth, actively growing cells).

By "glucosyltransferase activity" we mean the enzymatic activity which promotes the synthesis of complex oligosaccharides by catalyzing the addition or conformation of sugar residues, for example, the formation of cyclic-$\beta$-(1,3)-glucans.

By "glucan synthesis" we mean the formation of saccharide molecules, for example cyclic-$\beta$-(1,3)-glucan, through natural or recombinant means.

By "inhibitor" we mean a compound that is able to reduce the expression of a gene encoding a polypeptide and/or the expression of the polypeptide, or the biological activity of a polypeptide, e.g., a polypeptide that functions as an efflux pump or a glucosyltransferase, by at least 5%, more desirably, by at least 10%, even more desirably, by at least 25%, 50%, or 75%, and most desirably, by 90% or more.

By "binding" we mean a non-covalent or covalent interaction between components. By "component" we mean a protein, a nucleic acid molecule, a glucan, or a compound. The binding components interact with a binding constant (Kd) equal to less than 1 uM, more desirably less that 100 nM, and most desirably less than 10 nM.

"Transformed cell" means a cell into which (or into an ancestor of which) has been introduced, by means of recombinant DNA techniques, a DNA molecule encoding (as used herein) a polypeptide described herein (for example, an NvdB polypeptide).

"Operably linked" means that a gene and a regulatory sequence(s) are connected in such a way as to permit gene expression when the appropriate molecules (e.g., transcriptional activator proteins) are bound to the regulatory sequence(s).

"Transgene" means any piece of DNA which is inserted by artifice into a cell, and becomes part of the genome of the organism which develops from that cell. Such a transgene may include a gene which is partly or entirely heterologous (i.e., foreign) to the transgenic organism, or may represent a gene homologous to an endogenous gene of the organism.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

"Promoter" means minimal sequence sufficient to direct transcription. Also included in the invention are those promoter elements which are sufficient to render promoter-dependent gene expression controllable for cell-type specific, tissue-specific or inducible by external signals or agents; such elements may be located in the $_5$' or 3' regions of the native gene.

"Positioned for expression" means that the DNA molecule is positioned adjacent to a DNA sequence which directs transcription and translation of the sequence (i.e., facilitates the production of, e.g., an NdvB polypeptide, a recombinant protein or a RNA molecule).

By "biofilm" is meant a population of microorganisms comprised of a single species or multiple species that form at an interface, e.g., on a biotic or abiotic surface exposed to liquid, and have increased resistance to antimicrobial agents relative to planktonic cells growing in the expotential phase. The population of cells may also have one or more of the following characteristics: a) produce or are enclosed by an extracellular matrix, b) adhere to a surface, c) form a complex architecture, d) have a gene and/or protein expression profile different from planktonic cells growing in the exponential phase under similar conditions.

By "biological activity" is meant an activity associated with a microbial organism, including the formation, development, and dissolution of biofilms.

By "culture system" is meant a fluid containing single-celled organisms living independently or as part of a multi-cellular community or colony. The major groups of microorganisms include archaea, bacteria, fungi, protozoa, and algae.

By "expose" is meant to allow contact between a substance, including a compound, culture supernatant, or extract thereof, and a microorganism or target organism.

By "environment" is meant the habitat or living conditions of a population of microorganisms, such as source microorganisms or target organisms.

By "extract" is meant a product obtained from treating supernatant from a culture system to at least one purification step of any kind. In a desired embodiment, the purification is designed to isolate or increase the concentration of a biofilm modulating compound or remove undesirable elements within the supernatant.

By "microorganism," "microbial organism," "microbe," or "microbial" is meant a microscopic, single-celled organism that may either live independently or as part of a multi-cellular community or colony. The major groups of microorganisms include archaca, bacteria, fungi, protozoa, and algae.

By "resistant" is meant a increase greater than 5% in the MBC or MIC for at least one selected antimicrobial agent, or an decreased killing under a selected growth condition in the presence of at least one antimicrobial agent compared to a control microorganism grown under the same conditions. This term may refer to the ability of a microorganism to the ability of a microorganism to maintain viability, virulence or pathogenicity in the presence of at least one antimicrobial agent compared to a control mircroorganism grown under the same conditions.

By "sensitive" is meant a decrease greater than 5% in the MBC or MIC for at least one selected antimicrobial agent, or an increased killing under a selected growth condition in the presence of at least one antimicrobial agent compared to a control microorganism grown under the same conditions. This term may refer to the ability of a microorganism to the ability of a microorganism to maintain viability, virulence or pathogenicity in the presence of at least one antimicrobial agent compared to a control mircroorganism grown under the same conditions By "modulating" is meant changing, by increase, decrease or otherwise. The change may be in amount, timing, or any other parameter. A decrease or increase in, for example, cell growth, viability, virulence, or pathogenicty, may be by at least 5%, more desirably at least 10%, even more desirably at least 25%, most desirably by 50% or more.

"Modulation" refers to the capacity to either enhance or inhibit a functional property of a biological activity or process (e.g., enzyme activity, receptor binding, cell growth, viability, virulence, or pathogenicty). Such enhancement or inhibition may be contingent on the occurrence of a specific event, such as activation of a signal transduction pathway, and/or may be manifest only in particular cell types.

BRIEF DESCRIPTION OF THE DRAWINGS

FIGS. 6A–6E presents the nucleotide (SEQ ID NO:1) and amino acid (SEQ ID NO:2) sequence of NdvB (PA1163).

FIGS. 7A–7K presents the nucleotide (SEQ ID NO:3) and amino acid (SEQ ID NO:4) sequence of PA1874.

FIGS. 8A–8B presents the nucleotide (SEQ ID NO:5) and amino acid (SEQ ID NO:6) sequence of PA1875.

FIGS. 9A–9D presents the nucleotide (SEQ ID NO:7) and amino acid (SEQ ID NO:8) sequence of PA1876.

FIGS. 10A–10B presents the nucleotide (SEQ ID NO:9) and amino acid (SEQ ID NO:10) sequence of PA1877.

FIG. 11 presents the nucleotide (SEQ ID NO:11) and amino acid (SEQ ID NO:12) sequence of PA4142.

FIG. 12 presents the nucleotide (SEQ ID NO:13) and amino acid (SEQ ID NO:14) sequence of PA4143.

FIG. 13 presents the nucleotide (SEQ ID NO:15) and amino acid (SEQ ID NO:16) sequence of PA4144.

FIG. 14 presents the nucleotide (SEQ ID NO:17) and amino acid (SEQ ID NO:18) sequence of PA2389.

FIG. 15 presents the nucleotide (SEQ ID NO:19) and amino acid (SEQ ID NO:20) sequence of PA2390.

FIG. 16 presents the nucleotide (SEQ ID NO:21) and amino acid (SEQ ID NO:22) sequence of PA2391.

FIG. 17 presents the nucleotide sequence of a putative expression control sequence (SEQ ID NO:23) located upstream of PA1874.

FIG. 18 presents the nucleotide sequence of a putative expression control sequence (SEQ ID NO:24) located upstream of PA4142.

FIG. 19 presents the nucleotide sequence of a putative expression control sequence (SEQ ID NO:25) located upstream of PA2389.

FIG. 20 presents the nucleotide sequence of a putative expression control sequence (SEQ ID NO:26) located upstream of PA1163.

FIG. 22 presents the amino acid sequence (SEQ ID NO:27) of *B. japonicum* ndvB (GenBank Accession No. AAC62210).

FIG. 23 presents the amino acid sequence (SEQ ID NO:28) of an *Agrobacterium tumefaciens* protein (GenBank Accession No. NP 357541).

FIGS. 24A–24C presents the nucleotide (SEQ ID NO:29) and amino acid SEQ ID NO:30) sequence of *Pseudomonas putida* KT2440.

FIGS. 25A–25C presents the nucleotide (SEQ ID NO:31) and amino acid (SEQ ID NO:32) sequence of a *Pseudomonas syringae* gene.

DETAILED DESCRIPTION OF THE INVENTION

Figure 1:
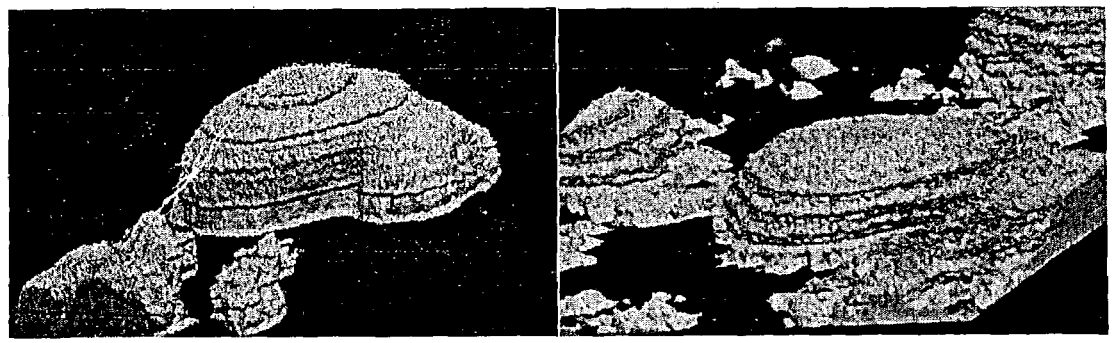
FIG. 1 is a comparison of wild type (left panel) ad 45E7 (right panel) biofilm architecture. Flow cell grown strains are shown after 3 days of growth. Both strains exhibit the typical macrocolonies and channels characteristic of these biofilms formed by P. aeruginosa. These images are reconstructed from XZ slices through the biofilm ~35 μm in height) using the Volocity software package.

We posit that biofilm resistance to antimicrobial agents is part of a regulated developmental process and thus would require an identifiable set of genetic determinants. Based upon this hypothesis, a screen was designed to identify genes which, when mutated, would affect the ability of biofilm cells to resist the effects of an antimicrobial agent, while having no substantial effect on the sensitivity of planktonic cells growing in the exponential phase cells to the same antimicrobial agent. This screen was based on a modification of the microtiter plate assay that yielded surface attachment mutants (sad) of *Pseudomonas aeruginosa* and *P. fluorescens* (O'Toole, G. A., and R. Kolter. *Mol. Microbiol.* 30(2):295–304, 1998; O'Toole, G. A., and R. Kolter, *Mol. Microbiol.* 28:449–461, 1998). In the present studies, bacteria were cultured on the same minimal M63 medium expect arginine (0.4%) was used as the sole source of carbon and energy, and cultures were incubated for 24 hours. Other screens and techniques for generating mutations in cell components that function in biofilm resistance to antimicrobial agents are well known in the art, for example, the use of transposon insertion and chemical mutagenesis.

The microtiter plate assay was modified to measure the increase in resistance developed by the wild type strain when growing in a biofilm. The wells of the microtiter dish are inoculated with bacteria and biofilms are allowed to form on the walls of the wells for 24 hrs in the absence of any shear force. After the biofilms had formed on the wells of the microtiter dish, the spent medium was replaced with the same media containing an antimicrobial agent. In this case, we used the aminoglycoside antibiotic tobramycin (Tb), an antibiotic that targets protein synthesis. Tb was selected because it is the primary antibiotic used to treat cystic fibrosis patients with chronic *P. aeruginosa* lung infections (Banerjee, D., and D. Stableforth, *Drugs*, 60(5):1053–64, 2000; Bonsignore, C. L., *Pediatr Nurs*. 24(3):258–9, 1998; Ratjen, F, *Int J Antimicrob Agents* 17(2):93–6, 2001). After exposing the biofilms to Tb for 24 hours, the antibiotic-containing medium is removed and replaced with fresh antibiotic-free medium. Any bacteria surviving in the biofilm outgrow and repopulate the planktonic phase of the wells. Viable cells were detected by plating on rich medium. Using this assay, we determined that the minimal bacteriocidal concentration (MBC) of Tb for the wt biofilm grown cells is 0.4 mg/ml. The MBC of planktonic cells was determined by adding the antibiotic to cells at the time they were inoculated into the microtiter dish, incubating the cells in the presence of antibiotic for 24 hrs, and assessing cell viability by plating on rich medium. Using this assay, the planktonic MBC was shown to be 0.008 mg/ml, a 50-fold decrease relative to the biofilm-grown bacteria.

Using the assay for biofilm-related antibiotic resistance described above, a library of random *P. aeruginosa* PA14 transposon insertion mutants was screened for the inability to develop characteristic increase in resistance of biofilm-grown cells. The concentration of Tb used in the screen was 0.2 mg/ml, a concentration 25-fold greater than the planktonic MBC, but still below the concentration that will kill biofilm grown cells. From a library of 4,320 transposon mutants, forty-three putative mutants defective in biofilm-related Tb resistance were identified.

The goal of the screen was to identify mutants with a biofilm-related defect in the development of antimicrobial agent resistance. Therefore, the 43 candidate mutants were subjected to a series of secondary tests to confirm the biofilm-related phenotype. Of the original 43 candidate mutants from the initial screen, two mutants grew as well as the wild type in liquid culture, formed a wild-type biofilm in the microtiter plates, and had a planktonic MBC indistinguishable from the parent strain. These mutants, designated 45E7 and 30 B1, were characterized further.

Characterization of the 45E7 Mutant.

In addition to the decrease in sensitivity to Tb, we determined the MBC of biofilm and planktonic cells growing in the expotential phase for gentamycin (Gm) and ciprofloxacin (Cip). Gm, like Tb, is an aminoglycoside protein synthesis inhibitor while Cip is a fluoroquinolone that targets DNA gyrase. Table 1 shows the results of these studies. For all antibiotics, there was no difference in the MBC of planktonic cells growing in the exponential phase between the wild type and 45E7 mutant. The MCB of biofilm grown 45E7 was lower for all three antibiotics when compared to the wt: Tb (16-fold), Gm (8-fold) and Cip (8-fold).

TABLE 1

Biofilm and planktonic (exponential phase) resistance of the wild type and 45E7 mutant.

| Strain | Tb | | Gm | | Cip | |
|---|---|---|---|---|---|---|
| | MBC-P | MBC-B | MBC-P | MBC-B | MBC-P | MBC-B |
| Wild-type | 0.008 | 0.4 | 0.04 | 0.5 | 0.004 | 0.05 |
| 45E7 | 0.008 | 0.025 | 0.04 | 0.06 | 0.004 | 0.006 |

Notes: MBC-P, MBC of planktonically grown cells; MBC-B, MBC of biofilm grown cells. All antibiotic concentrations are in mg/ml.

One of the characteristics of biofilm grown bacteria is their distinctive architecture. Currently, it is not clear what relationship, if any, exists between the architecture of the biofilm and resistance to antimicrobial agents. Early studies of biofilm grown cells suggested that inhibition of antibiotic diffusion through the biofilm could account for the increased resistance of these communities (Costerton et al., Microbial biofilms, p. 711–745. In L. N. Omston, A. Balows, and E. P. Greenberg (ed.), *Annu. Rev. Microbiol.*, vol. 49. Annual Reviews, Inc., Palo Alto, Calif., 1995). Therefore, it was possible that altering biofilm architecture could increase diffusion of Tb through the biofilm, thereby increasing sensitivity to this agent. In support of this idea, a quorum-sensing mutant of *P. aeruginosa* that exhibited altered architecture was reported to be abnormally sensitive to SDS (Davies et al., *Science* 280(5361):295–298, 1998). However, the same mutant was as resistant to killing by the antibiotic ofloxacin as the wild type biofilm cells (Brooun et al., *Antimicrob Agents Chemother.* 44(3):640–6, 2000).

We utilized flow cells to analyze the architecture of the wild type and mutant strains. A flow cell allows a continuous supply of fresh medium to be delivered to a biofilm that is formed on the walls of a small, enclosed chamber. One side of this chamber is a glass cover slip, and the chamber can be mounted on to a microscope to allow for the non-destructive imaging of the biofilm. GFP-tagged wild type and 45E7 strains were inoculated into different chambers of a flow cell and the architecture of the biofilms produced by these strains was analyzed by epifluorescence microscopy. The reconstructed architecture of the wild-type and 45E7 mutant is shown in FIG. 1. This analysis showed that is no discernible difference in the architecture of these strains.

Currently, there are no standard methods for determining biofilm resistance to antimicrobial agents. Thus, we utilized two other assays of biofilm antibiotic resistance to demonstrate that the phenotype observed in the microtiter plate was robust and could be observed across a number of experimental models. We chose to analyze this mutant in flow cell and colony biofilm assays.

Figure 2:
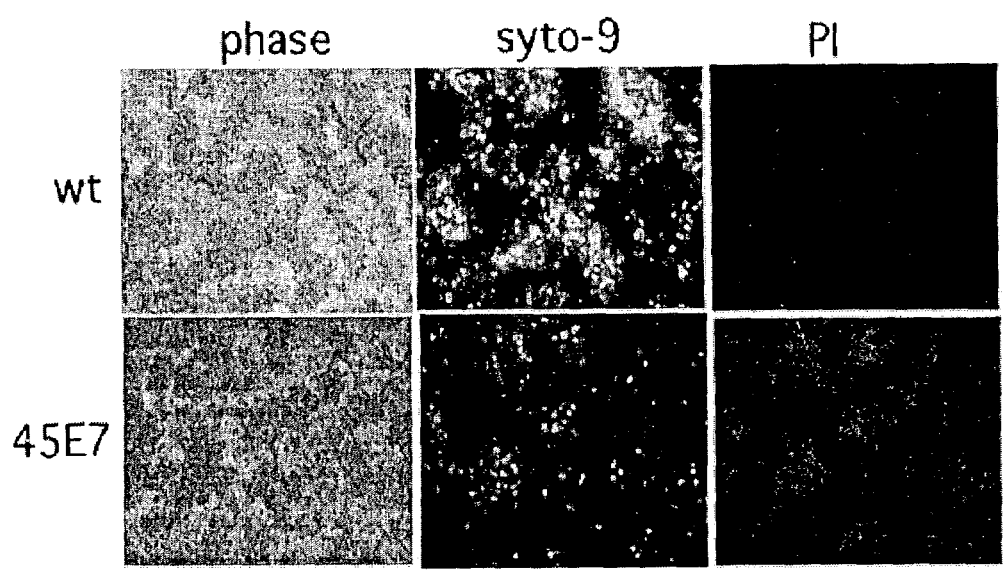
FIG. 2 presents the results of the flow cell assay for antibiotic resistance with 45E7. The left most panels (phase-contrast micrographs) show the architecture of the 24 hr old biofilm. The syto-9 panels indicate viable cells and the PI (propidium iodide) panels indicate dead cells.

In order to document the sensitivity phenotype of the biofilms in the flow cell, the biofilm of the wild type and 45E7 strains were allowed to form. After the biofilm had developed for 24 hrs 0.2 mg/ml Tb was added to the medium. After 24 hours of exposure to Tb, flow through the cell was stopped and the BacLight viability stain was injected into the flow chambers. BacLight differentiates between cells with intact membranes (considered "live") and those with damaged membranes (considered "dead"). After 15 minutes of staining, flow through the chamber was resumed and following a 15 minute wash the cells were examined by epifluorescent microscopy (FIG. 2). The left-hand panels show phase contrast images—there was no difference in biofilm architecture between these strains (see also FIG. 1). The center and right panel shows that there were more live than dead cells in the Tb-treated biofilm of the wild type strain. Conversely, there were more dead cells than live ones in the Tb-treated biofilm of the 45E7 mutant strain. This result confirmed the drug sensitivity phenotype first observed in the microtiter plate assay.

Figure 3:
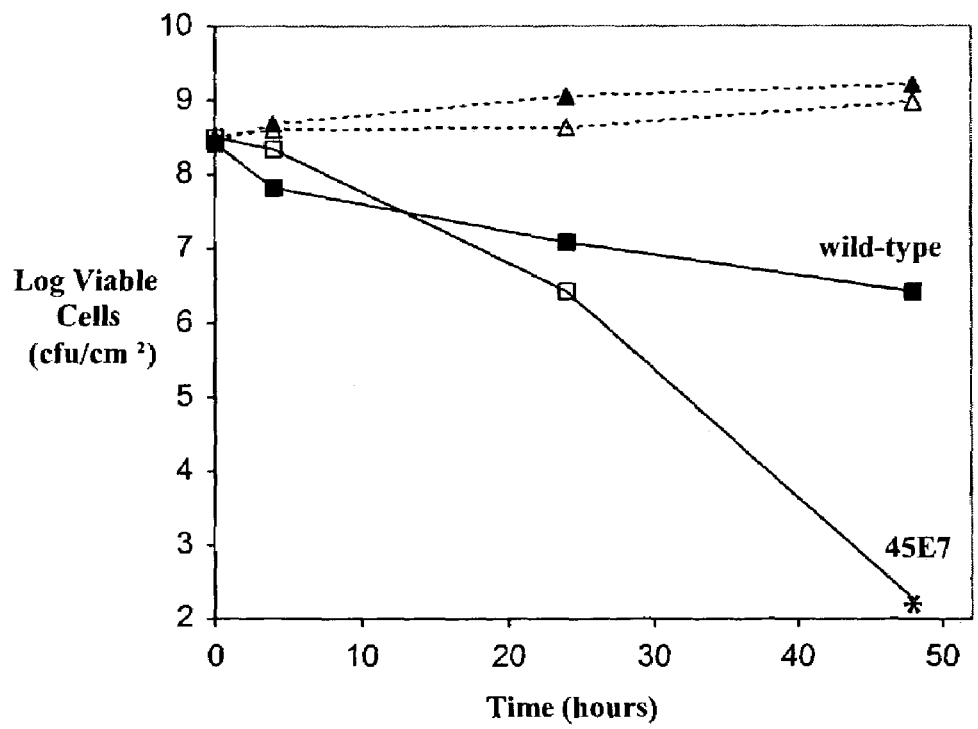
FIG. 3 presents the results of the colony biofilm assay with 45E7. Colonies of the wild type (filled symbols) and the 45E7 mutant (open symbols) were transferred to solid medium without (triangles) or with 0.2 mg/ml Tb (squares). The viability of the wild-type drops ~100-fold over 48 hrs with Tb treatment, while the 45E7 mutant drops below detection (indicated by the asterisk). In the absence of antibiotic, there is no difference in viability between the two strains.

We also used the quantitative colony biofilm assay to document the 45E7 mutant phenotype. It has been reported that bacterial colonies develop some of the properties associated with biofilms, including increased resistance to biocides (Anderl et al., *Antimicrob Agents Chemother.* 44(7): 1818–24, 2000; Stewart, P. S., *Biotechnol Bioeng.* 59(3): 261–72, 1998). Colony biofilms were formed on polycarbonate filters for 48 hrs then transferred to solid media containing Tb. Viable cell numbers in the colony was determined after 4, 24 and 48 hours of exposure to Tb (FIG. 3). The 45E7 biofilm cells remained as resistant to the effects of Tb as the wild type at the first two time points assayed. However, at 48 hours, while the wild type biofilm cell viability was only reduced by 100-fold, no viable cells were detected for the 45E7 mutant. In the absence of Tb, there was difference in viability between the two strains tested. Taken together with the data presented above, we concluded that the 45E7 mutant is less resistant to the antimicrobial effects of Tb when growing in a biofilm.

The 45E7 Mutation is in PA1163, a Putative Glucosyltransferase

The transposon insertion carried by the 45E7 strain was cloned and the DNA flanking the transposon sequenced and compared to the published sequence of *P. aeruginosa* PAO1. The gene disrupted in 45E7, PA1163 is 58% identical to a *Bradyrhizobium japonicum* gene ndvB. The ndvB gene of *Bradyrhizobium japonicum* codes for a glucosyltransferase that is required for the syntheis of cyclic-$\beta$-(1,3), $\beta$-(1,6)-glucans (Bhagwat et al., *J Bacteriol.* 178(15):4635–42, 1996). Located in the periplasm and extrcellular media, cyclic glucans have been shown to play a role in growth in low osmotic media and in plant infection (Breedveld, M. W., and K. J. Miller, *Microbiol Rev.* 58(2):145–61, 1994). In *B. japonicum*, another gene, ndvC acts in concert with ndvB to form the $\beta$-(1,3), $\beta$-(1,6) linkages. ndvC mutants produce glucans with only $\beta$-(1,3) linkages (Bhagwat et al., *Plant Physiol*. 119(3):1057–64, 1999). Furthermore, in *Sinorhizobium melioloti*, the ndvA gene product is thought to be required for the export of cyclic glucans from the periplasm to the extracellular medium (Breedveld, M. W., and K. J. Miller. *Microbiol Rev.* 58(2):145–61, 1994). Upon investigation of the *P. aeruginosa genome*, we noticed that there is no ndvC homolog present, but there are three genes with ~50% homology to *S. melioti* ndvA. Thus, it seemed likely that *P. aeruginosa* produces periplasmic and extracellular $\beta$-(1,3)-glucans. To confirm that cyclic glucans were made by the wild type strain and that these glucans were altered or not present in the ndvB PA1163 mutant we characterized the periplasmic and extracellular polysaccharides produced by these strains. Ethanol extracts from both the periplasm and the extracellular medium of these strains were fractionated by gel filtration chromatography to estimate the molecular weight of the material (Wang et al., *J Bacteriol.* 181(15):

4576–83, 1999). Fractons were assayed for polysaccharides using the colorometric anthrone-sulfuric acid method. The anthrone assay measures the total concentration of carbohydrate, or monosaccharide equivalents, in a sample (Loewus, F. A., Anal. Chem. 24:219, 1952). Anthrone-positive extracellular material from the wild type eluted from the sizing column in fractions that corresponded to a molecular weight (MW) of approximately 1500, while the mutant produced no anthrone positive fraction in the 100 MW range. In contrast, anthrone-positive material from the 45E7 mutant extracts eluted in the column void volume, indicates a MW of greater than 80,000, possibly indicating an aggregate of polysaccharides.

Figure 4:
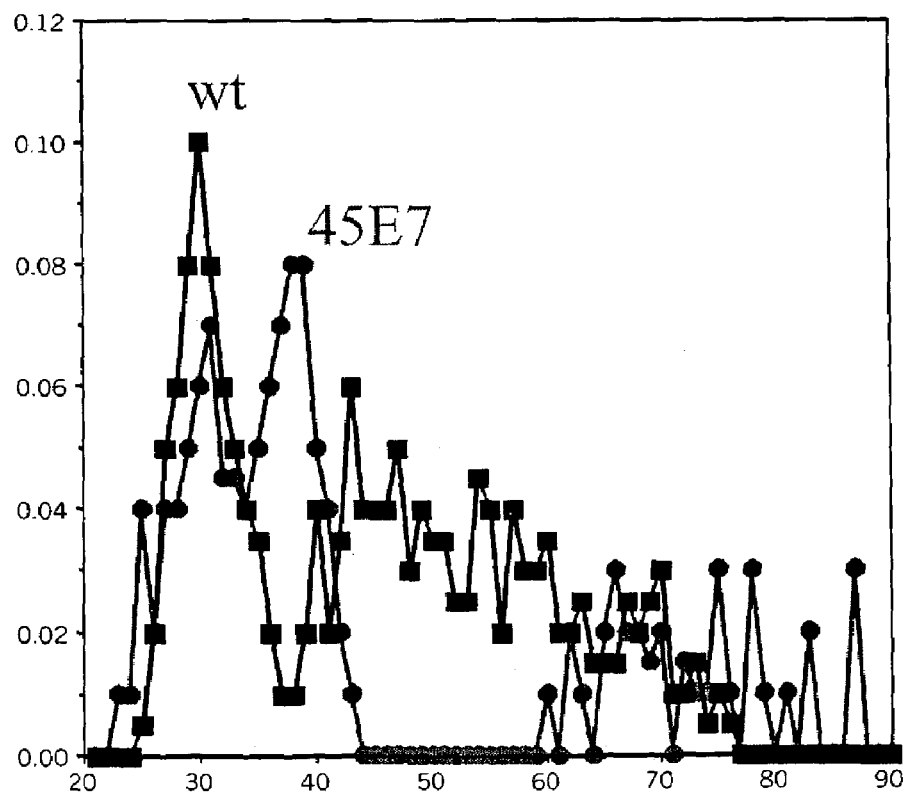
FIG. 4 demonstrates the difference between wild type and 45E7 fractiontation characteristics of periplasmic glucans. The elution profiles of periplasmic extracts of the wild type (squares) and 45E7 mutant (circle) on a G75 column are shown. Fractions 45–60 have anthrone positive material in periplasmic extracts from the wild type strain. This anthrone positive material is absent from the periplasmic extracts of the 45E7 mutant. Work in other organisms has shown that cyclic glucans typically elute in this size range. The Y-axis is a measure of absorbance at 620 nm.

The material extracted from the periplasm was also fractionated by gel filtration chromatography and it was found that the anthrone-positive material produced by the wild type and mutant strains also differed (FIG. 4). While the wild type strain produced material that eluted across the molecular weight range of the column, the mutant strain lacked anthrone-positive material in fractions where cyclic glucans typically elute (Wang et al., J Bacteriol. 181(15): 4576–83, 1999).

Based on the current understanding of the roles of cyclic glucans in B. japonicum, S. meliloti and Agrobacterium tumefaciens, we envisioned three possible models to describe the role of these molecules in the development of resistance in biofilm populations. Cyclic glucans may be required to: i) maintain the osmotic balance within biofilms, ii) sequester antimicrobial agents in biofilm-grown cells, or iii) act as signaling molecules required for the development of resistance to antimicrobial agents.

To test the hypothesis that cyclic glucans are important for hypo-osmotic adaptation, we examined the wild type and -PA1163 strains for their ability to survive and grow in low osmotic strength medium. As a first step, we diluted overnight cultures into water and monitored the survival of the wild type and mutant strains over 24 hrs. There was no difference in the survival of these strains in water. We assessed the growth of both strains in liquid 1/10 strength minimal salts M63 medium (a hypo-osmotic medium compared to full strength M63) and on solid GYM media with no salt. The ndvB mutant of S. meliloti grows very slowly on GYM media, while the wild type shows no growth defect (Bhagwat et al., FEMS Microbiol Lett. 114(2): 139–44, 1993; Cangelosi et al., J Bacteriol. 172(4):2172–4, 1990; Ielpi et al., J Biol Chem. 265(5):2843–5 1990). There was no difference in the growth of the wild type and PA1163 mutant of P. aeruginosa on these media, suggesting that PA1163 may not be involved in hypo-osmotic adaptation in P. aeruginosa.

A number of reports suggest that cyclic glucans can bind or sequester a range of chemically unrelated compounds [reviewed in (Breedveld, M. W., and K. J. Miller. Microbiol Rev. 58(2):145–61, 1994)]. This suggested the possibility that glucans in the extracellular and/or periplasmic space might sequester antimicrobial agents and thus prevent them from entering into the cytoplasm of the bacterial cell. To test this idea, we utilized the putative cyclic glucan fractions isolated by gel filtration chromatography from the periplasm of the wild-type strain (see above). This material was incubated in the presence of Tb, then spotted on a filter disk placed on a freshly spread lawn of E. coli. Filter disks spotted with Tb alone, glucans alone, and water were also included as controls. Preliminary studies with the disk-diffusion assay indicated that glucan-treated Tb was decreased in its zone of killing as compared to Tb alone. Glucans had no antimicrobial activity at the concentrations used in these assays. These data indicate that the presence of cyclic glucans can decrease the antimicrobial activity of Tb, and is consistent with a role for glucans in the sequestering of antimicrobial agents.

PA1163 mRNA is Expressed in Biofilm Grown Cells, but not in Planktonic Cells

In order to investigate the expression pattern of PA1163 we used a continuous flow system to grow planktonic and biofilm bacteria. Total mRNA was harvested from both biofilm and planktonic cells and RT-PCR used to detect the presence of PA1163 transcript. In this study expression of rplU, a gene known to be expressed in both planktonic cells and biofilm grown cells, was used as a control. Chromosomal DNA was used to identify the expected size of the PA1163 mRNA. This study revealed that PA1163mRNA is expressed in biofilm grown cells and is undetectable in planktonic cells. These data indicate that PA1163 may be poorly expressed (or not expressed at all) under planktonic conditions. The fact that PA1163 appears to be expressed only in biofilm-grown cells is consistent with our model that PA1163 plays a role in biofilm-related antibiotic resistance.

*P. aeruginosa* PA1163 can Complement a ndvB *S. meliloti* Mutant

The Rm8519 ndvB mutant of *S. meliloti* exhibits a hypo-osmotic growth phenotype. In order to investigate whether *P. aeruginosa* PA1163 can complement this mutant, and is thus likely to encode a glucosyltransferase, we introduced a vector pSMC654 containing the *P. aeruginosa* PA1163 gene into the ndvB mutant of *S. meliloti*. As a control, wild type strain and the ndvB mutant of *S. meliloti* were transformed with empty vector pSW213 alone. The PA1163 containing vector (but not the empty vector) complemented the ndvB mutant of *S. meliloti* for its hypo-osmotic growth phenotype. Therefore, the PA 1163 gene of *P. aeruginosa* can functionally substitute for *S. meliloti* ndvB, strongly suggesting that *P. aeruginosa* PA1163 protein is a glucosyltransferase.

Wild-Type *P. aeruginosa*, but not PA1163 Mutants Produce Glucans.

We compared carbohydrates produced by wild-type *P. aeruginosa* to purified cyclic glucan from *S. meliloti* using chromatographic analysis. This analysis revealed that glucans produced by wild-type *P. aeruginosa* elute in same fractions as purified cyclic glucan from *S. meliloti*. Similarly eluting material was not detectable in carbohydrates produced by a *P. aeruginosa* PA1163 mutant. Moreover, analysis of the pooled glucan-containing fractions from the wild-type *P. aeruginosa* strain showed that glucose is the predominate sugar as judged by a glucose standard and consistent with their identification as glucans. The same fractions from the PA1163 mutant did not contain glucose.

Glucans Interact with Tb in vitro

If periplasmic glucans were indeed sequestering Tb, we predicted that these molecules should interact in vitro. To test this possibility, we examined in vitro interactions of purified glucans with Tb. Tb was loaded onto a C18 column and its elution profile was monitored by a bioassay on a lawn of sensitive bacteria. A zone of clearing indicated the presence of Tb in a fraction. Tb was detected in the column flow-through and first water wash, but not in any subsequent fractions. In contrast, when a crude periplasmic carbohydrate extracted from the wild type strain was pre-loaded onto the column, a portion of the Tb was retained on the column and eluted with 25% acetonitrile. Thus, the presence of the wild type extract on the column retarded the elution of Tb, suggesting that periplasmic glucans interacted with Tb.

To determine which components of the crude extract were responsible for the Tb retention on the C18 column, we performed the same experiment as above except the C-18 column was pre-loaded with partially pure glucan-containing fractions from a G-75 gel filtration sizing column. Tb was retained on the column pre-loaded with material from the wild type extract and eluted from the column with 25% acetonitrile. In contrast, no Tb activity was present in the 25% acetonitrile fraction from the column preloaded with the corresponding fractions isolated from the *P. aeruginosa* PA1163 mutant. Only the material present in glucan-containing fractions derived from the wild type interacted with and changed the chromatographic behavior of Tb.

Characterization of the 30B1 Mutant.

A second mutant strain defective in biofilm specific Tb resistance, designated 30B1, was isolated and characterized. Like 45E7, this strain grew as well as the wild type in liquid culture, formed a wild-type biofilm in the microtiter plates, and had an exponential phase planktonic MBC indistinguishable from the parent strain. This mutant is also less resistant to the antibiotics Gm and Cip. In all cases, the decrease in resistance of this mutant is less than the decrease observed for the 45E7 mutant. These results suggest that the functions disrupted in this strain debilitate biofilm-related antibiotic resistance via a different mechanism.

TABLE 2

Bioflim and planktonic resistance of the wild type and 45E7 mutant.

| Strain | Tb | | Gm | | Cip | |
|---|---|---|---|---|---|---|
| | MBC-P | MBC-B | MBC-P | MBC-B | MBC-P | MBC-B |
| Wild-type | 0.008 | 0.4 | 0.04 | 0.5 | 0.004 | 0.05 |
| 30B1 | 0.008 | 0.1 | 0.04 | 0.25 | 0.004 | 0.0125 |

Notes: MBC-P, MBC of planktonically grown cells; MBC-B, MBC of bioflim grown cells. All antibiotic concentrations are in mg/ml.

We also examined the architecture of this mutant and showed that it was identical to the wild-type strain as judged by the flow cell assay and analysis of the biofilms by fluorescence microscopy (data not shown).

Figure 5:
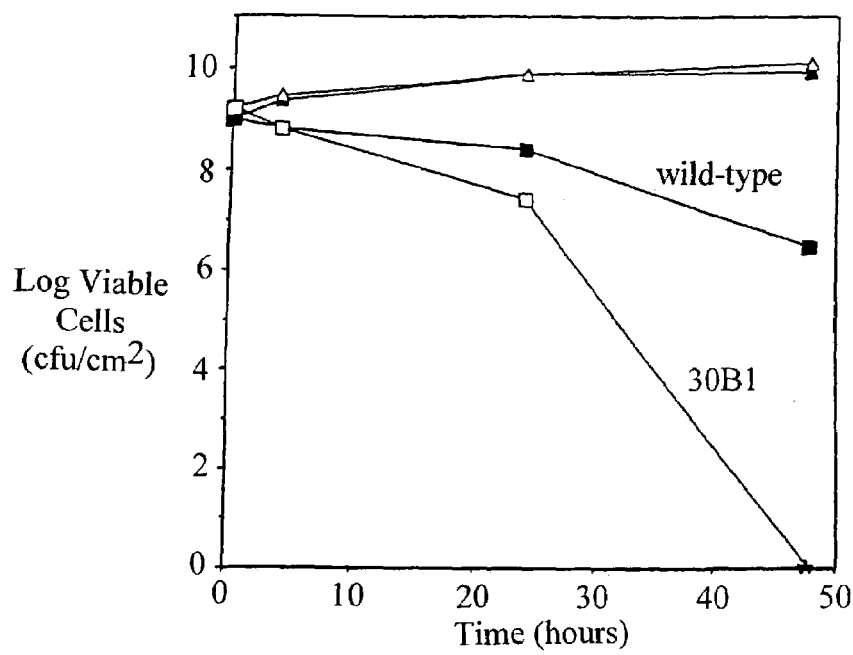
FIG. 5 presents the results of the colony biofilm assay with 30B 1. The viable cell count for the wt (filled symbols) and 30B1 mutant (open symbols) either untreated (triangles) or treated with Tb (squares) are shown over 48 hrs. There is no difference in viable counts between these strains when grown in the absence of antibiotics. The wild type decreases 100-fold in the presence of Tb, while the viable count of the 30B1 mutant is below detection at 48 hrs (indicated by the asterisk).

The colony biofilm assay was also utilized to assess the antibiotic resistance of the 30B1 mutant strain as described above. As was observed for the 45E7 mutant, the 30B1 strain showed a marked decrease in resistance to Tb as compared to the wild-type strain (FIG. 5). After 48 hrs of exposure to Tb, the viability of the wild type had dropped ~100-fold, while there were no viable cells detected for the 30B1 mutant (a drop in viable count of ~$10^9$). This experiment confirms the results obtained in the microtiter dish assay.

The 30B1 Mutation is in PA1874

The transposon insertion carried by the 30B1 strain was cloned and the DNA flanking the transposon was sequenced and compared to the published sequence of *P. aeruginosa* PAO1. The open reading frame (ORF) disrupted by the transposon, PA1874, encodes a predicted outer membrane protein with sequence similarity to LapA of *P. putida* (42% similarity) and Bap of *Staphylococcus aureus* (46% similarity). Both of these proteins are important for biofilm development. LapA is required for the colonization of seeds by *P. putida* and Bap was identified in a screen for mutants unable to make a biofilm (Cucarella et al., *J Bacteriol.* 183(9):2888–2896, 2001; Espinosa-Urgel et al., *J Bacteriol.* 182(9):2363–2369, 2000).

In *P. aeruginosa*, PA1874 is the first gene in a predicted four gene operon that, in addition to PA1874, includes: PA1875, an OprN-like outer membrane protein that bears some similarity to outer membrane proteins in the RND family; PA1876, a protein that is similar to an ABC family ATPase; and PA1877, a protein that appears to be a ABC family membrane fusion protein.

As noted above, PA1875 is similar to OprN. The OprN protein is part of the MexEF-OprN multidrug efflux pump, a RND-type efflux pump which is involved in fluoroquinolone resistance (Nikaido, H. 1994. Prevention of drug access to bacterial targets: permeability barriers and active efflux. Science. 264(5157):382–8; Piddock, L. J. 1999. Mechanisms of fluoroquinolone resistance: an update 1994–1998. Drugs. 58(Suppl 2):11–8. Thus, the PA1874-PA1877 operon encodes components of both multi-drug efflux pumps and ABC transporters. Although other RND efflux pumps include an outer membrane protein and a membrane fusion protein, they do not typically include a ABC family cytoplasmic membrane-located ATPase and they do not typically require two outer membrane proteins (Poole, K., J Mol Microbiol Biotechnol. 3(2):255–64, 2001). Thus, the PA1874-PA1877 operon appears to encode anew type of hybrid efflux pump that combines features of a RND multidrug efflux pumps and ABC transporters.

Identification of Additional Hybrid Efflux Pumps

We analyzed the sequence of the *P. aeruginosa* genome in a effort to identify other genetic loci that resemble PA1874-PA1877. We identified two other genetic loci, PA4142-PA4143 and PA2389-PA2391, that are similar to the PA1874-PA1877 operon in both sequence and organization. Each of these loci appears to encode three, rather than four polypeptides. These loci encode putative hybrid efflux pumps that are predicted to play a role in biofilm resistance.

Table 3 summarizes information for each of the proteins in the three identified hybrid efflux pump operons. Putative expression control sequences upstream of PA1874,PA4142, and 2389 are shown in FIGS. 17, 18 and 19 respectively.

TABLE 3

Summary of Hybrid Efflux Pump Genes

| Name | Proposed Function | Nucleotide and Protein Sequence | Nucleic Acid SEQ ID NO. | Protein SEQ ID NO. |
|---|---|---|---|---|
| PA1874 | OMP | FIG. 7 | SEQ ID NO:3 | SEQ ID NO:4 |
| PA1875 | OprN-like OMP (similar to RND family OMP) | FIG. 8 | SEQ ID NO:5 | SEQ ID NO:6 |
| PA1876 | ABC family ATPase | FIG. 9 | SEQ ID NO:7 | SEQ ID NO:8 |
| PA1877 | MFP | FIG. 10 | SEQ ID NO:9 | SEQ ID NO:10 |
| PA4142 | MFP | FIG. 11 | SEQ ID NO:11 | SEQ ID NO:12 |
| PA4143 | ABC family ATPase | FIG. 12 | SEQ ID NO:13 | SEQ ID NO:14 |
| PA4144 | OprM-like OMP efflux pump protein (similar to RND family OMP) | FIG. 13 | SEQ ID NO:15 | SEQ ID NO:16 |
| PA2389 | MFP | FIG. 14 | SEQ ID NO:17 | SEQ ID NO:18 |
| PA2390 | ABC family ATPase | FIG. 15 | SEQ ID NO:19 | SEQ ID NO:20 |
| PA2391 | | FIG. 16 | SEQ ID NO:21 | SEQ ID NO:22 |

The putative Hybrid Efflux Pump Encoded by PA4144-PA4146 Appears to Play a Role in Biofilm Resistance In order to determine whether the putative hybrid efflux pump encoded by PA4144-PA4146) plays a role antibiotic resistance, we inserted a nucleotide sequence that includes PA4144-PA4146 into a medium copy plasmid pSMC32 and used the resulting vector pSMC51 to transform *P. aerugi*- nosa strain PA14. Neither the PA4144-PA4146 encoding vector nor the parent plasmid had any effect on the resistance of planktonic *P. aeruginosa* to Tb.

Figure 21:
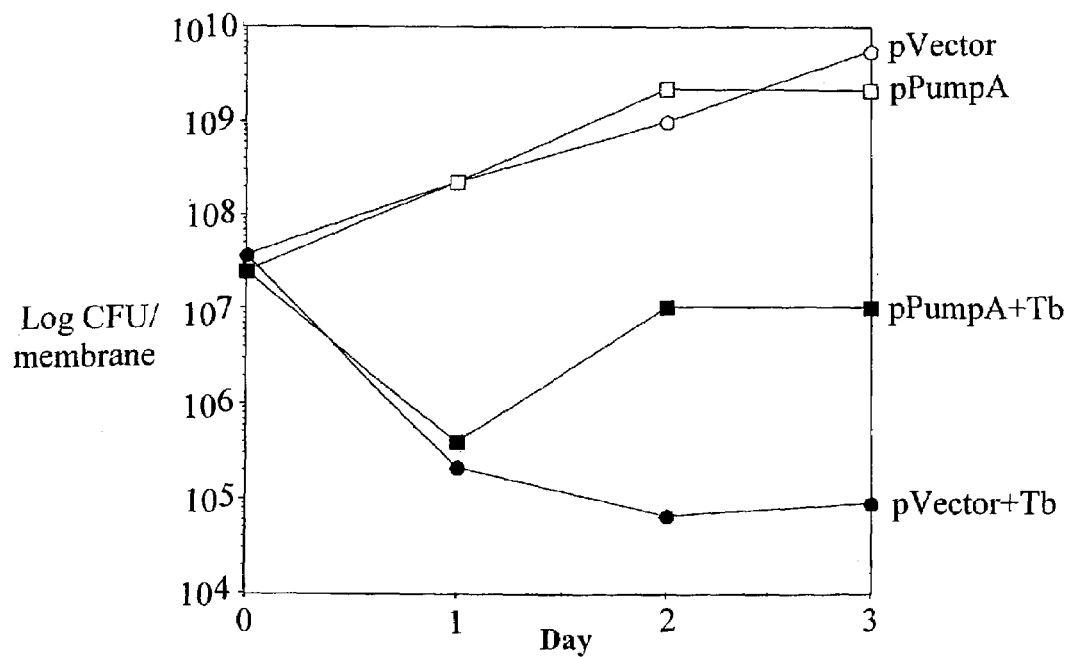
FIG. 21 presents the results the results of colony biofilm assay. The viable cell count for vector only (circles) or vector encoding PA4142-PA4144 (squares) was determined over 3 days in the presence (filled symbols) or absence (open symbols) of Tb.

We also investigated the resistance of the transformed cells to Tb when grown as a biofilm. Interestingly, wild-type *P. aeruginosa* carrying the PA4144-PA4146 encoding vector became hypersensitive to antibiotics in the colony biofilm assay for reasons that are not clear, but may be due to the increased metabolic burden of carrying a plasmid (see FIG. 21). Therefore, we created a "synthetic sensitivity" to antibiotics by having the wild type *P. aeruginosa* strain carry a parent plasmid (no PA4144-PA4146 encoding sequences). As shown in FIG. 21, a *P. aeruginosa* strain carrying both this parent plasmid and the PA4144-PA4146 encoding vector regained a level of antibiotic resistance similar to the of an untransformed strain (no parent plasmid and no PA4144-PA4146 encoding vector). These indirect data suggest that the hybrid efflux pump encoded by PA4144-PA4146 has the ability to confer antibiotic resistance in biofilm-grown bacteria and supports our hypothesis that these novel, hybrid efflux pumps play a role in biofilm-related antibiotic resistance.

Identification of Additional Proteins Resembling PA1163

We used sequence homology searching to identify genes encoding proteins that are likely homologs. The proteins encoded by these genes, like ndvB, are expected to play a role in biofilm resistance. The genes are: *B. japonicum* ndvB (GenBank Accession No. AAC62210; FIG. 22; SEQ ID NO:27); *Agrobacterium tumefaciens* unannotated sequence (GenBank Accession No. NP 357541; FIG. 23; SEQ ID NO:28); *Pseudomonas putida* KT2440 (FIGS. 24A–24C; SEQ ID Nos:29 and 30); and a *Pseudomonas syringae* gene (FIGS. 25A–25C; SEQ ID Nos:31 and 32).

Uses of the Identified Genes

The data described herein suggest two novel mechanisms for biofilm-related antimicrobial resistance. We have shown that a mutant unable to acquire biofilm-related resistance to the antibiotic Tb is defective in glucan synthesis. The *P. aeruginosa* ndvB mutant had increased biofilm-related sensitivity to Gm and Cip. We propose that these glucans sequester Tb and thereby prevent access of this antibiotic to the cytoplasm of the bacteria. This observation is consistent with previous reports that glucans can bind a range of chemically distinct molecules (Breedveld, M. W., and K. J. Miller. *Microbiol Rev.* 58(2):145–61, 1994). The ability to bind a range of biocides is also consistent with the reported ability of biofilms to develop broad resistance to antimicrobial agents [reviewed in (Mah, T.-F., and G. A. O'Toole. *TIMS* 9:34–39,2001)].

Based on our data, we submit that compounds that modulate the expression of ndvB or the function of an NdvB polypeptide, such that there is a decrease in ndvB gene transcription, ndvB mRNA translation, or NdvB polypeptide function, are expected to promote a decrease in microbial resistance to antimicrobial agents, possibly due to the loss of, or lower levels of, glucan synthesis. Compounds which alter the activity of PA1163 can be identified using an assay for ndvB activity, e.g., the assay described by Bhagwat et al. (*J. Bact.* 178:4635–42, 1994). Compounds that modulate function of the identified homologs of ndvB are also expected to promote a decrease in microbial resistance to antimicrobial agents, possibly due to the loss of, or lower levels of, glucan synthesis. This decrease in resistance is predicted to occur in biofilms, but may also occur in other physiological states as well as in cells having genetic changes leading to increased resistance.

We have also identified a novel efflux pump that is required for full biofilm-related antibiotic resistance. This pump appears to be a hybrid between known efflux pumps of the RND superfamily and ABC transporters. Efflux pumps typically have broad substrate specificity, which is consistent with the decrease in resistance of the 30B1 mutant to Tb, Gm and Cip.

Compounds that decrease either the expression of PA1874 or one or more of the following: PA1875, PA1876, and PA1877, or the function of the corresponding polypeptides, such that there is a decrease in gene transcription, mRNA translation, or polypeptide function of one or more of PA1874, PA1875, PA1876, or PA1877 are expected to promote a decrease in microbial resistance to antimicrobial agents. Similarly, compounds that decrease either the expression of any of PA4142-PA4144 and PA2389-PA2391, or the function of the corresponding polypeptides, such that there is a decrease in gene transcription, mRNA translation, or polypeptide function of one or more of PA4142-PA4144 and PA2389-PA2391 are expected to promote a decrease in microbial resistance to antimicrobial agents. This decrease in resistance is predicted to occur in biofilms, but may also occur in other physiological states as well as in cells having genetic changes leading to increased resistance.

Compounds which alter the expression of one or more of the hybrid efflux pump genes described herein can be identified using a reporter construct in which a reporter gene is operably linked to an expression control region located upstream of PA1873, PA4142 or PA2389 (see Table 3). The reporter construct is introduced into a cell, e.g., bacterial cell such as a *P. aeruginosa* cell. The cell is exposed to a test compound and the expression of the reporter gene is monitored.

One method to further examine the function of the novel efflux pumps is to express the components of the efflux pump in a variety of cell types, prokaryotic and eukaryotic, and use it to screen for compounds which overcome (inhibit) the action of the efflux pump. Bacteria have developed several different mechanisms to overcome the action of antibiotics. These mechanisms of resistance can be specific for a molecule or a family of antibiotics, or can be non-specific and be involved in resistance to unrelated antibiotics. Several mechanisms of resistance can exist in a single bacterial strain, and those mechanisms may act independently or they may act synergistically to overcome the action of an antibiotic or a combination of antibiotics. Specific mechanisms include degradation of the drug, inactivation of the drug by enzymatic modification, and alteration of the drug target (B. G. Spratt, Science 264:388 (1994)). There are, however, more general mechanisms of drug resistance, in which access of the antibiotic to the target is prevented or reduced by decreasing the transport of the antibiotic into the cell or by increasing the efflux of the drug from the cell to the outside medium. Both mechanisms can lower the concentration of drug at the target site and allow bacterial survival in the presence of one or more antibiotics which would otherwise inhibit or kill the bacterial cells. Some bacteria utilize both mechanisms, combining a low permeability of the cell wall (including membranes) with an active efflux of antibiotics. (H. Nikaido, Science 264:382–388 (1994)).

Different pumps can efflux specifically a drug or group of drugs, such as the NorA system that transports quinolones, or Tet A that transports tetracyclines, or they can efflux a large variety of molecules, such as certain efflux pumps of *P. aeruginosa*. In general, efflux pumps have a cytoplasmic component and energy is required to transport molecules out of the cell. Some efflux pumps have a second cytoplasmic membrane protein that extends into the periplasm. At least some efflux pumps of P. aeruginosa have a third protein located in the outer membrane.

Efflux pumps are involved in antibiotic resistance since, in some cases, they can remove a significant fraction of the antibiotic molecules which manage to enter the cells, thereby maintaining a very low intracellular antibiotic concentration. To illustrate, P. aeruginosa laboratory-derived mutant strain 799/61 which does not produce any measurable amounts of efflux pump is 8 to 10 fold more susceptible to tetracycline and ciprofloxacin than the parent strain P. aeruginosa 799, which synthesizes efflux pumps. Also, null mutants of mexA, the cytoplasmic component of a P. aeruginosa efflux pump, are more susceptible to antibiotics than the wild type.

The physiological role of efflux pumps has not been clearly defined yet. They are involved in drug resistance but they also are involved in the normal physiology of the bacterial cell. The efflux pump coded in the mexA operon of P. aeruginosa has been shown to be regulated by the iron content of the medium, and it is co-regulated with the synthesis of the receptors of siderophores. Siderophores are molecules that are needed for bacterial growth under iron starvation conditions, such as during infection of an animal. They are synthesized in the cytoplasm and exported when the bacterial cell needs iron. Siderophores scavenge iron within the infected animal and return the iron to the microbe to be used for essential microbial processes. Since there is essentially no free iron in the bodies of animals, including the human body, the production of siderophores by infecting bacteria is an important virulence factor for the progress of the infection.

One aspect of this invention concerns the identification of compounds that are inhibitors of a hybrid efflux pump described herein. Such efflux pumps export substrate molecules from the cytoplasm in an energy-dependent manner, and the exported substrate molecules can include antibacterial agents or other antimicrobial agents. Such efflux pump inhibitors are useful, for example, for treating microbial infections by reducing the export of a co-administered antimicrobial agent or by preventing the export of a compound synthesized by microbes (e.g., bacteria) to allow or improve their growth. An example of reducing the export of such a compound is inhibiting iron availability for the microbe by reducing the export of siderophores. Thus, this invention provides methods to identify compounds that are efflux pump inhibitors.

One recent hypothesis to explain biofilm-related antibiotic resistance invoked the development of "persistors", or a subset of bacteria that develop high level resistance to antimicrobial agents. As is the case for the development of biofilm architecture we propose that entry into this persistent state requires a specific set of genes and their gene products. The isolation of mutants defective in biofilm-related resistance, such as PA1163, supports the hypothesis that there is a distinct genetic basis for this biofilm-related resistance and our approach has begun to identify these components.

The resistance of biofilms to traditional antibiotic therapy in the clinical setting is an ongoing problem. Our invention, however, provides new strategies to block the development of this resistance by identifying the genes and gene products responsible for resistance. In addition to providing a means for inhibiting biofilms, we provide a co-therapeutic approach where traditional antibiotics are combined with a drug that interferes with biofilm-related resistance to render biofilms, and possibly related physiological states, more susceptible to treatment.

What is claimed is:

1. A purified polypeptide comprising the amino acid sequence of SEQ ID NO:30 or SEQ ID NO:32.

* * * * *

SEQUENCE LISTING

<160> NUMBER OF SEQ ID NOS: 32

<210> SEQ ID NO 1
<211> LENGTH: 2610
<212> TYPE: DNA
<213> ORGANISM: Pseudomonas aeruginosa
<220> FEATURE:
<221> NAME/KEY: CDS
<222> LOCATION: (1)...(2607)

<400> SEQUENCE: 1

```
atg tct tca cgc aag atc ggg ctc aac ctg gtg gtc atc gtc gcc ctg      48
Met Ser Ser Arg Lys Ile Gly Leu Asn Leu Val Val Ile Val Ala Leu
 1               5                  10                  15 gcc gcc ctc ttc acc ggc atc tgg gcc ctg tac aac cgt ccg gtc agc      96
Ala Ala Leu Phe Thr Gly Ile Trp Ala Leu Tyr Asn Arg Pro Val Ser
             20                  25                  30 gta ccg gac tgg ccg gaa cgc atc tcc ggc ttc tcc ttc tcg ccg ttc     144
Val Pro Asp Trp Pro Glu Arg Ile Ser Gly Phe Ser Phe Ser Pro Phe
         35                  40                  45 cgc ctc aac cag aac ccg cag agc ggc cgc tac ccc agc gcc gaa cag     192
Arg Leu Asn Gln Asn Pro Gln Ser Gly Arg Tyr Pro Ser Ala Glu Gln
     50                  55                  60 atg cgc acc gac ctg gaa ctg gtc gcc cgg cac acc cac agc atc cgc     240
Met Arg Thr Asp Leu Glu Leu Val Ala Arg His Thr His Ser Ile Arg
 65                  70                  75                  80
```

-continued

```
acc tat tcg gtc cag ggc gcg ctc ggc gac atc ccg gcg ctg gcc gag      288
Thr Tyr Ser Val Gln Gly Ala Leu Gly Asp Ile Pro Ala Leu Ala Glu
             85                  90                  95 gcg ttc ggc ctg cgc gtc agc ctg ggc atc tgg ctc ggc ccg gac ctg      336
Ala Phe Gly Leu Arg Val Ser Leu Gly Ile Trp Leu Gly Pro Asp Leu
        100                 105                 110 gcc agc aac gag gcc gag atc gcc cgc gcc atc cgc atc gcc aac gag      384
Ala Ser Asn Glu Ala Glu Ile Ala Arg Ala Ile Arg Ile Ala Asn Glu
            115                 120                 125 tcg ccg agc gtg gtg cga gtg ata gtc ggc aac gag gcg ctg ttc cgc      432
Ser Pro Ser Val Val Arg Val Ile Val Gly Asn Glu Ala Leu Phe Arg
130                 135                 140 cgc gag gtg acg gcg gaa cag ttg atc gcc tac ctc gac cgg gtc cgc      480
Arg Glu Val Thr Ala Glu Gln Leu Ile Ala Tyr Leu Asp Arg Val Arg
145                 150                 155                 160 gcg gcg gtc aag gtt ccg gtg acc acc gcc gaa cag tgg cac gtc tac      528
Ala Ala Val Lys Val Pro Val Thr Thr Ala Glu Gln Trp His Val Tyr
                165                 170                 175 cgc gaa cac ccg gaa ctg gcg caa cac gtc gac ctg atc gcc gcc cac      576
Arg Glu His Pro Glu Leu Ala Gln His Val Asp Leu Ile Ala Ala His
            180                 185                 190 gtc ctg ccc tac tgg gag gcc acg ccg gtg gcc gac gcg gtg gac ttc      624
Val Leu Pro Tyr Trp Glu Ala Thr Pro Val Ala Asp Ala Val Asp Phe
        195                 200                 205 gtg ctc gaa cgc gcg cgc gaa ctc aag gcc gcc ttc ccg agg aag ccg      672
Val Leu Glu Arg Ala Arg Glu Leu Lys Ala Ala Phe Pro Arg Lys Pro
    210                 215                 220 ctg ctg ctc gcc gag gtc ggc tgg ccg agc aac ggg cgc atg cgc ggc      720
Leu Leu Leu Ala Glu Val Gly Trp Pro Ser Asn Gly Arg Met Arg Gly
225                 230                 235                 240 agc gcc gag gcg aca ccc gcg gac cag gcc atc tac ctg cgg cgc ctg      768
Ser Ala Glu Ala Thr Pro Ala Asp Gln Ala Ile Tyr Leu Arg Arg Leu
                245                 250                 255 acc aac gcg ctc aac ggc gaa ggc tac agc tac ttc gtc atc gaa gcc      816
Thr Asn Ala Leu Asn Gly Glu Gly Tyr Ser Tyr Phe Val Ile Glu Ala
            260                 265                 270 ttc gac cag ccc tgg aag gtc agc gcc gaa ggc tcg gtg ggc gcc tac      864
Phe Asp Gln Pro Trp Lys Val Ser Ala Glu Gly Ser Val Gly Ala Tyr
        275                 280                 285 tgg ggc gtc tac aac gcc gac cgc aag gcc aag ttc aac ttc acc ggg      912
Trp Gly Val Tyr Asn Ala Asp Arg Lys Ala Lys Phe Asn Phe Thr Gly
    290                 295                 300 ccg gtg gtg ccg att ccc aag tgg cgc gcc ctg gcc atc gcc tcg gcg      960
Pro Val Val Pro Ile Pro Lys Trp Arg Ala Leu Ala Ile Ala Ser Ala
305                 310                 315                 320 gta ctc gcg gta ctc gcc ttc acc ctg ctg ctg atc gac agt tcc tcg     1008
Val Leu Ala Val Leu Ala Phe Thr Leu Leu Leu Ile Asp Ser Ser Ser
                325                 330                 335 ctg cgc cag cgc ggg agg acc ttc ctc gcc gtg gtc tcg ttc gcc tgc     1056
Leu Arg Gln Arg Gly Arg Thr Phe Leu Ala Val Val Ser Phe Ala Cys
            340                 345                 350 gcc tcg gtg ctg gtg tgg atc gcc tac gac tac agc cag cag tac agc     1104
Ala Ser Val Leu Val Trp Ile Ala Tyr Asp Tyr Ser Gln Gln Tyr Ser
        355                 360                 365 acc tgg ttc agc ctg acc gtc ggc gcg ttg ctg ggc gtc ggc gcg cta     1152
Thr Trp Phe Ser Leu Thr Val Gly Ala Leu Leu Gly Val Gly Ala Leu
    370                 375                 380 ggg gtg gtc atc gtg ctg ttc acc gag gcc cac gag ctg gcc gag gcg     1200
Gly Val Val Ile Val Leu Phe Thr Glu Ala His Glu Leu Ala Glu Ala
```

```
                385                 390                 395                 400
gtc tgg acg cgc aag cgg cgc cgg cca ttc ctg ccg atc acc gcc gcg         1248
Val Trp Thr Arg Lys Arg Arg Arg Pro Phe Leu Pro Ile Thr Ala Ala
                    405                 410                 415 cgg gcc tat cgg ccc aag gtg tcg atc cac gtg ccc tgc tac aac gag         1296
Arg Ala Tyr Arg Pro Lys Val Ser Ile His Val Pro Cys Tyr Asn Glu
                420                 425                 430 ccg ccg gaa ctg ctg aag cag acc ctc gac gcc ctt gcc cgc ctc gac         1344
Pro Pro Glu Leu Leu Lys Gln Thr Leu Asp Ala Leu Ala Arg Leu Asp
            435                 440                 445 tac ccg gac tac gaa gtc ctg gtg atc gac aac aac acc cgc gac ccg         1392
Tyr Pro Asp Tyr Glu Val Leu Val Ile Asp Asn Asn Thr Arg Asp Pro
        450                 455                 460 gcc gtc tgg cag ccg gtc gag gcg cac tgc gcg cgc ctg ggc gag cgc         1440
Ala Val Trp Gln Pro Val Glu Ala His Cys Ala Arg Leu Gly Glu Arg
465                 470                 475                 480 ttc cgc ttc ttc cac gtt gcc ccg ctg gaa ggc ttc aag gcc ggc gcg         1488
Phe Arg Phe Phe His Val Ala Pro Leu Glu Gly Phe Lys Ala Gly Ala
                    485                 490                 495 ctg aac ttc gcc ctg ggc cac gtg gcg gcg gac gtc gag gtg gtc gcg         1536
Leu Asn Phe Ala Leu Gly His Val Ala Ala Asp Val Glu Val Val Ala
                500                 505                 510 gtg atc gac gcc gac tac tgc gtc gac ccc gac tgg ctc agg cac atg         1584
Val Ile Asp Ala Asp Tyr Cys Val Asp Pro Asp Trp Leu Arg His Met
            515                 520                 525 gtg ccg cac ttc ggc gac ccg cgg atc gcc gtg gtg cag tcg ccg cag         1632
Val Pro His Phe Gly Asp Pro Arg Ile Ala Val Val Gln Ser Pro Gln
        530                 535                 540 gac tac cgc gac cag cac gag agc gcc ttc aag cgg ctc tgc tac gcc         1680
Asp Tyr Arg Asp Gln His Glu Ser Ala Phe Lys Arg Leu Cys Tyr Ala
545                 550                 555                 560 gag tac aag ggc ttc ttc cac atc ggc atg gtc acc cgc aac gac cgc         1728
Glu Tyr Lys Gly Phe Phe His Ile Gly Met Val Thr Arg Asn Asp Arg
                    565                 570                 575 gac gcg atc atc gag cac ggc acc atg acc atg atc cgg cgc agc gtg         1776
Asp Ala Ile Ile Glu His Gly Thr Met Thr Met Ile Arg Arg Ser Val
                580                 585                 590 ctg gac gag ctg aga tgg ccg gaa tgg tgc atc acc gag gac gcc gag         1824
Leu Asp Glu Leu Arg Trp Pro Glu Trp Cys Ile Thr Glu Asp Ala Glu
            595                 600                 605 ctg ggc ctg cgg gtg ttc gag aag ggc ctg tcg gcc gcc tac ttc gag         1872
Leu Gly Leu Arg Val Phe Glu Lys Gly Leu Ser Ala Ala Tyr Phe Glu
        610                 615                 620 cgc agc tac ggc aag ggg gtg atg ccc gat acc ttc atc gat ttc aag         1920
Arg Ser Tyr Gly Lys Gly Val Met Pro Asp Thr Phe Ile Asp Phe Lys
625                 630                 635                 640 aag cag cgc ttc cgc tgg gcc tac ggc gcg atc cag atc atg aag cgg         1968
Lys Gln Arg Phe Arg Trp Ala Tyr Gly Ala Ile Gln Ile Met Lys Arg
                    645                 650                 655 cat acc gac gcc ctg ctg cgc ggc cgc ggt ccc gac ggc agc cgc ctg         2016
His Thr Asp Ala Leu Leu Arg Gly Arg Gly Pro Asp Gly Ser Arg Leu
                660                 665                 670 acc cgc ggc cag cgc tac cac ttc gtg gcc ggc tgg ctg ccg tgg atc         2064
Thr Arg Gly Gln Arg Tyr His Phe Val Ala Gly Trp Leu Pro Trp Ile
            675                 680                 685 gcc gac ggc ctg aac atc ttc ttc acc ctc ggc gcg ctg ctc tgg tcg         2112
Ala Asp Gly Leu Asn Ile Phe Phe Thr Leu Gly Ala Leu Leu Trp Ser
        690                 695                 700 gcg gcg atg atc atc gtg ccc aag cgc gtc gac ccg ccg ctg ctg atc         2160
```

```
Ala Ala Met Ile Ile Val Pro Lys Arg Val Asp Pro Pro Leu Leu Ile
705                 710                 715                 720 ttc gcg atc ctg ccg ctg gcc ctg ttc gtc ttc aag gtc ggc aag atc         2208
Phe Ala Ile Leu Pro Leu Ala Leu Phe Val Phe Lys Val Gly Lys Ile
                725                 730                 735 ctc ttc ctc tac cgg cgc acc gtc ggc gtc gac ctg cgc gac tcg ttc         2256
Leu Phe Leu Tyr Arg Arg Thr Val Gly Val Asp Leu Arg Asp Ser Phe
            740                 745                 750 ttc gcc gcc ctc gcc ggc ctg tcg ctc tcg cac acc att gcc aag gcg         2304
Phe Ala Ala Leu Ala Gly Leu Ser Leu Ser His Thr Ile Ala Lys Ala
            755                 760                 765 gtg ctg tac ggc ttc gtc acc cgc ggc atc ccg ttc ttc cgc acg ccg         2352
Val Leu Tyr Gly Phe Val Thr Arg Gly Ile Pro Phe Phe Arg Thr Pro
        770                 775                 780 aag atg cgc tcc agc cac ggc ctg ctg gtg gcc ctg gcg gag gcc cgc         2400
Lys Met Arg Ser Ser His Gly Leu Leu Val Ala Leu Ala Glu Ala Arg
785                 790                 795                 800 gag gaa gtc ttc gtg atg ctc ctg ctg tgg ggc gcg gcg gcc ggc atc         2448
Glu Glu Val Phe Val Met Leu Leu Leu Trp Gly Ala Ala Ala Gly Ile
                805                 810                 815 gtg gcg gtt cag ggc gtg ccg agc cgc gac ctg ctg atc tgg gtc gcc         2496
Val Ala Val Gln Gly Val Pro Ser Arg Asp Leu Leu Ile Trp Val Ala
            820                 825                 830 atg ctc ctg gtg caa tcg ctg ccc tac ctg gcg gcg ctg gtc atg gcc         2544
Met Leu Leu Val Gln Ser Leu Pro Tyr Leu Ala Ala Leu Val Met Ala
            835                 840                 845 ttg ctc tcg tcg ctg ccg aaa ccg cgc gag gaa ctg gcc ggc ggc gcc         2592
Leu Leu Ser Ser Leu Pro Lys Pro Arg Glu Glu Leu Ala Gly Gly Ala
850                 855                 860 gag cag atc ggc ggt tga                                                 2610
Glu Gln Ile Gly Gly
865

<210> SEQ ID NO 2
<211> LENGTH: 869
<212> TYPE: PRT
<213> ORGANISM: Pseudomonas aeruginosa

<400> SEQUENCE: 2

Met Ser Ser Arg Lys Ile Gly Leu Asn Leu Val Ile Val Ala Leu
 1               5                  10                  15

Ala Ala Leu Phe Thr Gly Ile Trp Ala Leu Tyr Asn Arg Pro Val Ser
                20                  25                  30

Val Pro Asp Trp Pro Glu Arg Ile Ser Gly Phe Ser Phe Ser Pro Phe
            35                  40                  45

Arg Leu Asn Gln Asn Pro Gln Ser Gly Arg Tyr Pro Ser Ala Glu Gln
        50                  55                  60

Met Arg Thr Asp Leu Glu Leu Val Ala Arg His Thr His Ser Ile Arg
65                  70                  75                  80

Thr Tyr Ser Val Gln Gly Ala Leu Gly Asp Ile Pro Ala Leu Ala Glu
                85                  90                  95

Ala Phe Gly Leu Arg Val Ser Leu Gly Ile Trp Leu Gly Pro Asp Leu
            100                 105                 110

Ala Ser Asn Glu Ala Glu Ile Ala Arg Ala Ile Arg Ile Ala Asn Glu
        115                 120                 125

Ser Pro Ser Val Val Arg Val Ile Val Gly Asn Glu Ala Leu Phe Arg
    130                 135                 140

Arg Glu Val Thr Ala Glu Gln Leu Ile Ala Tyr Leu Asp Arg Val Arg
```

```
           145                 150                 155                 160
     Ala Ala Val Lys Val Pro Val Thr Thr Ala Glu Gln Trp His Val Tyr
                     165                 170                 175
     Arg Glu His Pro Glu Leu Ala Gln His Val Asp Leu Ile Ala Ala His
                 180                 185                 190
     Val Leu Pro Tyr Trp Glu Ala Thr Pro Val Ala Asp Val Asp Phe
             195                 200                 205
     Val Leu Glu Arg Ala Arg Glu Leu Lys Ala Ala Phe Pro Arg Lys Pro
         210                 215                 220
     Leu Leu Leu Ala Glu Val Gly Trp Pro Ser Asn Gly Arg Met Arg Gly
     225                 230                 235                 240
     Ser Ala Glu Ala Thr Pro Ala Asp Gln Ala Ile Tyr Leu Arg Arg Leu
                     245                 250                 255
     Thr Asn Ala Leu Asn Gly Glu Gly Tyr Ser Tyr Phe Val Ile Glu Ala
                 260                 265                 270
     Phe Asp Gln Pro Trp Lys Val Ser Ala Glu Gly Ser Val Gly Ala Tyr
             275                 280                 285
     Trp Gly Val Tyr Asn Ala Asp Arg Lys Ala Lys Phe Asn Phe Thr Gly
         290                 295                 300
     Pro Val Val Pro Ile Pro Lys Trp Arg Ala Leu Ala Ile Ala Ser Ala
     305                 310                 315                 320
     Val Leu Ala Val Leu Ala Phe Thr Leu Leu Leu Ile Asp Ser Ser Ser
                     325                 330                 335
     Leu Arg Gln Arg Gly Arg Thr Phe Leu Ala Val Val Ser Phe Ala Cys
                 340                 345                 350
     Ala Ser Val Leu Val Trp Ile Ala Tyr Asp Tyr Ser Gln Gln Tyr Ser
             355                 360                 365
     Thr Trp Phe Ser Leu Thr Val Gly Ala Leu Leu Gly Val Gly Ala Leu
         370                 375                 380
     Gly Val Val Ile Val Leu Phe Thr Glu Ala His Glu Leu Ala Glu Ala
     385                 390                 395                 400
     Val Trp Thr Arg Lys Arg Arg Arg Pro Phe Leu Pro Ile Thr Ala Ala
                     405                 410                 415
     Arg Ala Tyr Arg Pro Lys Val Ser Ile His Val Pro Cys Tyr Asn Glu
                 420                 425                 430
     Pro Pro Glu Leu Leu Lys Gln Thr Leu Asp Ala Leu Ala Arg Leu Asp
             435                 440                 445
     Tyr Pro Asp Tyr Glu Val Leu Val Ile Asp Asn Asn Thr Arg Asp Pro
         450                 455                 460
     Ala Val Trp Gln Pro Val Glu Ala His Cys Ala Arg Leu Gly Glu Arg
     465                 470                 475                 480
     Phe Arg Phe Phe His Val Ala Pro Leu Glu Gly Phe Lys Ala Gly Ala
                     485                 490                 495
     Leu Asn Phe Ala Leu Gly His Val Ala Ala Asp Val Glu Val Val Ala
                 500                 505                 510
     Val Ile Asp Ala Asp Tyr Cys Val Asp Pro Asp Trp Leu Arg His Met
             515                 520                 525
     Val Pro His Phe Gly Asp Pro Arg Ile Ala Val Val Gln Ser Pro Gln
         530                 535                 540
     Asp Tyr Arg Asp Gln His Glu Ser Ala Phe Lys Arg Leu Cys Tyr Ala
     545                 550                 555                 560
     Glu Tyr Lys Gly Phe Phe His Ile Gly Met Val Thr Arg Asn Asp Arg
                     565                 570                 575
```

```
Asp Ala Ile Ile Glu His Gly Thr Met Thr Met Ile Arg Arg Ser Val
            580                 585                 590

Leu Asp Glu Leu Arg Trp Pro Glu Trp Cys Ile Thr Glu Asp Ala Glu
        595                 600                 605

Leu Gly Leu Arg Val Phe Glu Lys Gly Leu Ser Ala Ala Tyr Phe Glu
        610                 615                 620

Arg Ser Tyr Gly Lys Gly Val Met Pro Asp Thr Phe Ile Asp Phe Lys
625                 630                 635                 640

Lys Gln Arg Phe Arg Trp Ala Tyr Gly Ala Ile Gln Ile Met Lys Arg
                645                 650                 655

His Thr Asp Ala Leu Leu Arg Gly Arg Gly Pro Asp Gly Ser Arg Leu
            660                 665                 670

Thr Arg Gly Gln Arg Tyr His Phe Val Ala Gly Trp Leu Pro Trp Ile
        675                 680                 685

Ala Asp Gly Leu Asn Ile Phe Phe Thr Leu Gly Ala Leu Leu Trp Ser
        690                 695                 700

Ala Ala Met Ile Ile Val Pro Lys Arg Val Asp Pro Pro Leu Leu Ile
705                 710                 715                 720

Phe Ala Ile Leu Pro Leu Ala Leu Phe Val Phe Lys Val Gly Lys Ile
                725                 730                 735

Leu Phe Leu Tyr Arg Arg Thr Val Gly Val Asp Leu Arg Asp Ser Phe
            740                 745                 750

Phe Ala Ala Leu Ala Gly Leu Ser Leu Ser His Thr Ile Ala Lys Ala
        755                 760                 765

Val Leu Tyr Gly Phe Val Thr Arg Gly Ile Pro Phe Phe Arg Thr Pro
        770                 775                 780

Lys Met Arg Ser Ser His Gly Leu Leu Val Ala Leu Ala Glu Ala Arg
785                 790                 795                 800

Glu Glu Val Phe Val Met Leu Leu Leu Trp Gly Ala Ala Ala Gly Ile
                805                 810                 815

Val Ala Val Gln Gly Val Pro Ser Arg Asp Leu Leu Ile Trp Val Ala
            820                 825                 830

Met Leu Leu Val Gln Ser Leu Pro Tyr Leu Ala Ala Leu Val Met Ala
        835                 840                 845

Leu Leu Ser Ser Leu Pro Lys Pro Arg Glu Glu Leu Ala Gly Gly Ala
        850                 855                 860

Glu Gln Ile Gly Gly
865

<210> SEQ ID NO 3
<211> LENGTH: 7407
<212> TYPE: DNA
<213> ORGANISM: Pseudomonas aeruginosa
<220> FEATURE:
<221> NAME/KEY: CDS
<222> LOCATION: (1)...(7404)

<400> SEQUENCE: 3 atg tcg atc cag gcg aaa gtt acc cct atc gat cag agt att tct tct    48
Met Ser Ile Gln Ala Lys Val Thr Pro Ile Asp Gln Ser Ile Ser Ser
 1               5                  10                  15 gcg gct gcc gtc gag gtt ccg gaa aac ggg ata ctc aaa ctc tcc cag    96
Ala Ala Ala Val Glu Val Pro Glu Asn Gly Ile Leu Lys Leu Ser Gln
            20                  25                  30 agc agt aat gtc gcg ctc gat gtc gca ccg gag tcg gtg gcg gga tac   144
Ser Ser Asn Val Ala Leu Asp Val Ala Pro Glu Ser Val Ala Gly Tyr
```

-continued

```
              35                  40                  45
tcg aag agc ggt tcg gac ctg atc gtc cag ctg aag acc ggg gaa agc      192
Ser Lys Ser Gly Ser Asp Leu Ile Val Gln Leu Lys Thr Gly Glu Ser
    50                  55                  60 gtc cgg atc gcc aac ttc tat gcg gaa ggc cag cct tcc agc caa ctg      240
Val Arg Ile Ala Asn Phe Tyr Ala Glu Gly Gln Pro Ser Ser Gln Leu
65                  70                  75                  80 ttc ctg gcc gac aag gac aag ctg gtg gcg gta gat ctg ccg ccg gtc      288
Phe Leu Ala Asp Lys Asp Lys Leu Val Ala Val Asp Leu Pro Pro Val
                85                  90                  95 gct gcc gac ggg ccg ctg atg gcc ggc tac atc ccg cag gaa agc ctg      336
Ala Ala Asp Gly Pro Leu Met Ala Gly Tyr Ile Pro Gln Glu Ser Leu
            100                 105                 110 gcc ggt ttc gag tcg ctg acc ggc gcc ggt gtg ctc ggt ggc atg agc      384
Ala Gly Phe Glu Ser Leu Thr Gly Ala Gly Val Leu Gly Gly Met Ser
        115                 120                 125 gca ggg act gcg ctg ctg gtc ggt gcg gcg gcc atc ggc gcc ggg gtg      432
Ala Gly Thr Ala Leu Leu Val Gly Ala Ala Ala Ile Gly Ala Gly Val
    130                 135                 140 gcg att tcc aac agc agc ggc ggt ggc ggc ggc ggt tct tcg gtg          480
Ala Ile Ser Asn Ser Ser Gly Gly Gly Gly Gly Gly Ser Ser Val
145                 150                 155                 160 ccc ccg gac acc act ccg ccg aag gcg gcc agc ggc ctg aag ata gcg      528
Pro Pro Asp Thr Thr Pro Pro Lys Ala Ala Ser Gly Leu Lys Ile Ala
                165                 170                 175 cct gac ggc agc agc atc agc ggc cag gcc gag gcc ggc gcg agc gtc      576
Pro Asp Gly Ser Ser Ile Ser Gly Gln Ala Glu Ala Gly Ala Ser Val
            180                 185                 190 ggc atc gat acc aat ggc gac ggc aag ccg gac ctc acc gtg atc gcc      624
Gly Ile Asp Thr Asn Gly Asp Gly Lys Pro Asp Leu Thr Val Ile Ala
        195                 200                 205 gat gcc aac ggc aat ttc acc gct ccg ctg aac ccg ccg ctg acc aat      672
Asp Ala Asn Gly Asn Phe Thr Ala Pro Leu Asn Pro Pro Leu Thr Asn
    210                 215                 220 ggc cag acg gtc acc gtg gtg gtc acc gac ccg gct ggc aac gcc agc      720
Gly Gln Thr Val Thr Val Val Val Thr Asp Pro Ala Gly Asn Ala Ser
225                 230                 235                 240 ccg ccg gcc cag gtc acc gct ccg gac act acc gcc ccg gcg ccg gct      768
Pro Pro Ala Gln Val Thr Ala Pro Asp Thr Thr Ala Pro Ala Pro Ala
                245                 250                 255 acc gac gtg cag gtg gcg ccg gac ggc agc agc gtc acc ggc aag gcc      816
Thr Asp Val Gln Val Ala Pro Asp Gly Ser Ser Val Thr Gly Lys Ala
            260                 265                 270 gaa ccc ggc tcg acg gtg ggc gtc gat acc gac ggc gac ggc cag ccg      864
Glu Pro Gly Ser Thr Val Gly Val Asp Thr Asp Gly Asp Gly Gln Pro
        275                 280                 285 gac acc acc gtg gtg gtc ggc ccc ggc ggc agc ttc gag gtt ccg ctg      912
Asp Thr Thr Val Val Val Gly Pro Gly Gly Ser Phe Glu Val Pro Leu
    290                 295                 300 aac ccg ccg ctg acc aat ggc gag acg gtg acg gtg atc gtt acc gac      960
Asn Pro Pro Leu Thr Asn Gly Glu Thr Val Thr Val Ile Val Thr Asp
305                 310                 315                 320 ccg gcc ggc aac aac agc acc ccg gtg acc gtc gag gcg ccg gac acc     1008
Pro Ala Gly Asn Asn Ser Thr Pro Val Thr Val Glu Ala Pro Asp Thr
                325                 330                 335 acc gcc ccg gcg ccg gcc acc gac gtg cag gtg gcg ccg gac ggc agc     1056
Thr Ala Pro Ala Pro Ala Thr Asp Val Gln Val Ala Pro Asp Gly Ser
            340                 345                 350 agc gtc acc ggc aac gca gag ccg ggc gcc acc gtc ggt gtc gac acc     1104
```

```
                                                     -continued

Ser Val Thr Gly Asn Ala Glu Pro Gly Ala Thr Val Gly Val Asp Thr
        355                 360                 365 gat ggc gac ggc cag ccg gac acc acc gtg gtg gtc ggt ccc ggc ggc       1152
Asp Gly Asp Gly Gln Pro Asp Thr Thr Val Val Val Gly Pro Gly Gly
370                 375                 380 agc ttc gag gtt ccg ctg aac ccg ccg ctg acc aat ggc gag acg gtg       1200
Ser Phe Glu Val Pro Leu Asn Pro Pro Leu Thr Asn Gly Glu Thr Val
385                 390                 395                 400 acg gtg atc gtt acc gac ccg gcc ggc aac agc agc acc ccg gtc acc       1248
Thr Val Ile Val Thr Asp Pro Ala Gly Asn Ser Ser Thr Pro Val Thr
                    405                 410                 415 gcc gaa gcc ccc gac ttc ccc gac gcg ccc cag gtc aat gcc agc aac       1296
Ala Glu Ala Pro Asp Phe Pro Asp Ala Pro Gln Val Asn Ala Ser Asn
                420                 425                 430 ggc agc gtc ctc agt ggt acg gcg gaa gcg ggc gtg acc atc gtg atc       1344
Gly Ser Val Leu Ser Gly Thr Ala Glu Ala Gly Val Thr Ile Val Ile
            435                 440                 445 acc gac ggc aac ggc aat ccg atc ggc cag acc agc gcc gat gcc aac       1392
Thr Asp Gly Asn Gly Asn Pro Ile Gly Gln Thr Ser Ala Asp Ala Asn
        450                 455                 460 ggc aac tgg agc ttc acc ccc ggt agc caa ctg ccg gat ggc acc gtg       1440
Gly Asn Trp Ser Phe Thr Pro Gly Ser Gln Leu Pro Asp Gly Thr Val
465                 470                 475                 480 gtc aat gtg gtg gcc agg gac gcc gcc ggc aac agc agc ccg gcg acc       1488
Val Asn Val Val Ala Arg Asp Ala Ala Gly Asn Ser Ser Pro Ala Thr
                    485                 490                 495 tcc atc acc gtc gac ggc gtg gcg ccg aac gcg ccg gtg gtc gag ccg       1536
Ser Ile Thr Val Asp Gly Val Ala Pro Asn Ala Pro Val Val Glu Pro
                500                 505                 510 agc aac ggc agc gaa ctc agc ggg act gcc gaa ccg ggc agc agc gtg       1584
Ser Asn Gly Ser Glu Leu Ser Gly Thr Ala Glu Pro Gly Ser Ser Val
            515                 520                 525 acc ctg acc gac ggc aat ggc aat ccg atc ggc cag acc acc gcc gat       1632
Thr Leu Thr Asp Gly Asn Gly Asn Pro Ile Gly Gln Thr Thr Ala Asp
        530                 535                 540 gcc aac ggc aac tgg tct ttc acg ccg tcc acc ccg ttg ccg gac ggt       1680
Ala Asn Gly Asn Trp Ser Phe Thr Pro Ser Thr Pro Leu Pro Asp Gly
545                 550                 555                 560 acc gtg gtc aac gtg gtg gcc agg gat gcc gcc ggc aac agc agt ccg       1728
Thr Val Val Asn Val Val Ala Arg Asp Ala Ala Gly Asn Ser Ser Pro
                    565                 570                 575 ccg gcc agc gtt acc gtg gat gcc gtc gcg ccg gcc acg ccc acc gtc       1776
Pro Ala Ser Val Thr Val Asp Ala Val Ala Pro Ala Thr Pro Thr Val
                580                 585                 590 gat ccg agc aac ggt acg acc ctc agc ggc acc gcc gag ccg ggc agt       1824
Asp Pro Ser Asn Gly Thr Thr Leu Ser Gly Thr Ala Glu Pro Gly Ser
            595                 600                 605 agc gtg acc ctg acc gac ggc aac ggt aac ccg ata ggg cag gtc acc       1872
Ser Val Thr Leu Thr Asp Gly Asn Gly Asn Pro Ile Gly Gln Val Thr
        610                 615                 620 gcc gac ggc agc ggc aac tgg acc ttc acc ccg agc acg ccg ttg ccc       1920
Ala Asp Gly Ser Gly Asn Trp Thr Phe Thr Pro Ser Thr Pro Leu Pro
625                 630                 635                 640 aac ggc acg gtg gtc aac gcc acg gct acc gac ccg tcc ggc aac gcc       1968
Asn Gly Thr Val Val Asn Ala Thr Ala Thr Asp Pro Ser Gly Asn Ala
                    645                 650                 655 agt tcg ccg gcc agc gtc acc gtg gac gcc gtg gca ccg gcc acg cca       2016
Ser Ser Pro Ala Ser Val Thr Val Asp Ala Val Ala Pro Ala Thr Pro
                660                 665                 670
```

-continued

```
gtg gtc aac ccg agc aac ggc acc acg ctc agc ggc acc gcc gag ccg      2064
Val Val Asn Pro Ser Asn Gly Thr Thr Leu Ser Gly Thr Ala Glu Pro
            675                 680                 685 ggc gcc acc gtg acc ctg acc gat ggc aac ggc aat ccc atc ggg cag      2112
Gly Ala Thr Val Thr Leu Thr Asp Gly Asn Gly Asn Pro Ile Gly Gln
    690                 695                 700 gtc acc gcc gat ggc agc ggc aac tgg agc ttc act ccg acc acg ccg      2160
Val Thr Ala Asp Gly Ser Gly Asn Trp Ser Phe Thr Pro Thr Thr Pro
705                 710                 715                 720 ttg ccc aac ggc acc gtg gtc aac gcc acg gcc acc gac gcc tcc ggc      2208
Leu Pro Asn Gly Thr Val Val Asn Ala Thr Ala Thr Asp Ala Ser Gly
                725                 730                 735 aac acc agt gcg ggc agc agt gtc acc gtg gac tcg gta gcc ccg gcc      2256
Asn Thr Ser Ala Gly Ser Ser Val Thr Val Asp Ser Val Ala Pro Ala
            740                 745                 750 acg cca gtg atc aac ccc agc aac ggc acc acg ctc agc ggc acc gcc      2304
Thr Pro Val Ile Asn Pro Ser Asn Gly Thr Thr Leu Ser Gly Thr Ala
            755                 760                 765 gag ccg ggc agc agc gtg act ctg acc gat ggc aac ggc aac ccg att      2352
Glu Pro Gly Ser Ser Val Thr Leu Thr Asp Gly Asn Gly Asn Pro Ile
    770                 775                 780 ggc cag gtc acc gcc gac ggc agc ggc aac tgg agc ttc acc ccg tcc      2400
Gly Gln Val Thr Ala Asp Gly Ser Gly Asn Trp Ser Phe Thr Pro Ser
785                 790                 795                 800 acg ccg ctg gcg gat gga acc gtg gtc aac gcc acg gcc acc gat ccg      2448
Thr Pro Leu Ala Asp Gly Thr Val Val Asn Ala Thr Ala Thr Asp Pro
                805                 810                 815 gcg ggc aac acc agc ggc cag ggc agc acc acc gtc gat ggc gtg gcg      2496
Ala Gly Asn Thr Ser Gly Gln Gly Ser Thr Thr Val Asp Gly Val Ala
            820                 825                 830 ccg acc acg ccg acc gtc aac ctg agc aac ggc agc agc ctc agc ggc      2544
Pro Thr Thr Pro Thr Val Asn Leu Ser Asn Gly Ser Ser Leu Ser Gly
            835                 840                 845 act gcg gaa ccg ggc agc acg gtg atc ctc acc gac ggc aac ggc aat      2592
Thr Ala Glu Pro Gly Ser Thr Val Ile Leu Thr Asp Gly Asn Gly Asn
    850                 855                 860 ccg atc gcc gag gtc acc gcc gac ggc agc ggc aac tgg acc tac acc      2640
Pro Ile Ala Glu Val Thr Ala Asp Gly Ser Gly Asn Trp Thr Tyr Thr
865                 870                 875                 880 ccg tcc acg ccg atc gcc aac ggc acc gtg gtc aac gtg gtg gcc cag      2688
Pro Ser Thr Pro Ile Ala Asn Gly Thr Val Val Asn Val Val Ala Gln
                885                 890                 895 gac gcc gcc ggc aat agc agc ccg ggc gcc agc gtc acc gtg gac tcg      2736
Asp Ala Ala Gly Asn Ser Ser Pro Gly Ala Ser Val Thr Val Asp Ser
            900                 905                 910 cag gcc ccg gcg gct ccg gtg gtc aac ccg agc aac ggc act acg ctc      2784
Gln Ala Pro Ala Ala Pro Val Val Asn Pro Ser Asn Gly Thr Thr Leu
    915                 920                 925 agc ggc acc gcc gag ccg ggc gct acc gtg acc ctg acc gac ggc aac      2832
Ser Gly Thr Ala Glu Pro Gly Ala Thr Val Thr Leu Thr Asp Gly Asn
930                 935                 940 ggc aac ccg att ggc cag gtc acc gcc gac ggc agc ggc aac tgg agc      2880
Gly Asn Pro Ile Gly Gln Val Thr Ala Asp Gly Ser Gly Asn Trp Ser
945                 950                 955                 960 ttc aca ccg ggc acg ccg ctg gcc aac ggc acc gtg gtc aac gcc acg      2928
Phe Thr Pro Gly Thr Pro Leu Ala Asn Gly Thr Val Val Asn Ala Thr
                965                 970                 975 gcc agc gac ccg acc ggc aat acc agc gct ccg gcc agc acc acc gtg      2976
Ala Ser Asp Pro Thr Gly Asn Thr Ser Ala Pro Ala Ser Thr Thr Val
            980                 985                 990
```

```
gac tcg gtg gcg ccg gcc gcg ccg gtg gtc aat ccg agc aac ggc gcg    3024
Asp Ser Val Ala Pro Ala Ala Pro Val Val Asn Pro Ser Asn Gly Ala
        995                 1000                1005 gag atc agc ggc acc gcc gaa ccg ggc gcc acc gtg acc ctg acc gat    3072
Glu Ile Ser Gly Thr Ala Glu Pro Gly Ala Thr Val Thr Leu Thr Asp
    1010                1015                1020 ggc agc ggc aat ccg atc ggg cag gtc acc gcc gac ggc agc ggc aac    3120
Gly Ser Gly Asn Pro Ile Gly Gln Val Thr Ala Asp Gly Ser Gly Asn
1025                1030                1035                1040 tgg agc ttc acc ccg tcc acg ccg ctg gcg gat gga acc gtg gtc aac    3168
Trp Ser Phe Thr Pro Ser Thr Pro Leu Ala Asp Gly Thr Val Val Asn
                1045                1050                1055 gcc acc gct acc gac ccg gcc ggc aat acc ggc ggc cag ggc agc acc    3216
Ala Thr Ala Thr Asp Pro Ala Gly Asn Thr Gly Gly Gln Gly Ser Thr
            1060                1065                1070 acc gtg gac gcc atc gcg ccg gcc acg ccg acc gtc aac ctg agc aat    3264
Thr Val Asp Ala Ile Ala Pro Ala Thr Pro Thr Val Asn Leu Ser Asn
        1075                1080                1085 ggc agc agc ctc agc ggc acc gcc gag ccg ggc agc acg gtg att ctc    3312
Gly Ser Ser Leu Ser Gly Thr Ala Glu Pro Gly Ser Thr Val Ile Leu
    1090                1095                1100 acc gac ggc aac ggc aat ccg atc gcc gag gtc acc gcc gac ggc agc    3360
Thr Asp Gly Asn Gly Asn Pro Ile Ala Glu Val Thr Ala Asp Gly Ser
1105                1110                1115                1120 ggc aac tgg acc tac acc ccg tcc acg ccg atc gcc aac ggt act gtg    3408
Gly Asn Trp Thr Tyr Thr Pro Ser Thr Pro Ile Ala Asn Gly Thr Val
                1125                1130                1135 gtc aac gtg gtg gcc cag gac gcc tcc ggt aac agc agc ccg ccg gcg    3456
Val Asn Val Val Ala Gln Asp Ala Ser Gly Asn Ser Ser Pro Pro Ala
            1140                1145                1150 acg gtg acc gtc gat tcc agc gcg ccg ccg gcg ccg gtg atc aac ccg    3504
Thr Val Thr Val Asp Ser Ser Ala Pro Pro Ala Pro Val Ile Asn Pro
        1155                1160                1165 agc aac ggc gtc gtc atc agc ggc acc gcc gag gcc ggt gcc acg gtg    3552
Ser Asn Gly Val Val Ile Ser Gly Thr Ala Glu Ala Gly Ala Thr Val
    1170                1175                1180 acc ctc acc gat gcc ggc ggc aac ccg ata ggg cag gtc acc gcc gac    3600
Thr Leu Thr Asp Ala Gly Gly Asn Pro Ile Gly Gln Val Thr Ala Asp
1185                1190                1195                1200 ggc agc ggc aac tgg agc ttc acg ccg ggc acc ccg ctg gcc aac ggc    3648
Gly Ser Gly Asn Trp Ser Phe Thr Pro Gly Thr Pro Leu Ala Asn Gly
                1205                1210                1215 acg gtg atc gtc gcc acg gcc acc gac ccg acc ggc aat acc ggc ccg    3696
Thr Val Ile Val Ala Thr Ala Thr Asp Pro Thr Gly Asn Thr Gly Pro
            1220                1225                1230 cag gcc gcc acc acg gtg gac gcg gtg gcg ccg ccg gcg ccg gtg atc    3744
Gln Ala Ala Thr Thr Val Asp Ala Val Ala Pro Pro Ala Pro Val Ile
        1235                1240                1245 gat ccg agc aac ggc acg acc atc agc ggc acc gcg gag gcc ggg gcc    3792
Asp Pro Ser Asn Gly Thr Thr Ile Ser Gly Thr Ala Glu Ala Gly Ala
    1250                1255                1260 aag gtg atc ctc acc gac ggc aac ggc aac ccg atc ggc gaa acc acc    3840
Lys Val Ile Leu Thr Asp Gly Asn Gly Asn Pro Ile Gly Glu Thr Thr
1265                1270                1275                1280 gcc gac ggc agc ggc aac tgg agc ttc acg ccc ggc acg ccg ctg gcc    3888
Ala Asp Gly Ser Gly Asn Trp Ser Phe Thr Pro Gly Thr Pro Leu Ala
                1285                1290                1295 aac ggc acg gtg gtc aac gcc gtg gcc cag gac cct gcg ggc aat acc    3936
Asn Gly Thr Val Val Asn Ala Val Ala Gln Asp Pro Ala Gly Asn Thr
```

-continued

```
              1300              1305              1310
ggc ccg cag ggc agc act acc gtg gac gcg gtg gcg ccg aac acg cct       3984
Gly Pro Gln Gly Ser Thr Thr Val Asp Ala Val Ala Pro Asn Thr Pro
        1315              1320              1325 gtg gtc aat ccg agc aac ggc aac ctc ctc aac ggt acc gcc gag ccg       4032
Val Val Asn Pro Ser Asn Gly Asn Leu Leu Asn Gly Thr Ala Glu Pro
1330              1335              1340 ggc agc acc gtg acc ttg acc gac ggc aac ggc aac ccg atc ggc cag       4080
Gly Ser Thr Val Thr Leu Thr Asp Gly Asn Gly Asn Pro Ile Gly Gln
    1345              1350              1355              1360 acc acc gcc gat ggc agc ggc aac tgg agc ttc acg ccc ggc tcg caa       4128
Thr Thr Ala Asp Gly Ser Gly Asn Trp Ser Phe Thr Pro Gly Ser Gln
            1365              1370              1375 ctg ccc aac ggc acc gtg gtc aac gtg acc gcg agc gac gcc gcc ggc       4176
Leu Pro Asn Gly Thr Val Val Asn Val Thr Ala Ser Asp Ala Ala Gly
                1380              1385              1390 aat acc agc ctt ccc gct acc acg acg gtg gat tcc tcg ctg ccg tcg       4224
Asn Thr Ser Leu Pro Ala Thr Thr Thr Val Asp Ser Ser Leu Pro Ser
        1395              1400              1405 atc ccg cag gtg gat ccg agc aac ggt tcg gtg atc agc ggc acc gcg       4272
Ile Pro Gln Val Asp Pro Ser Asn Gly Ser Val Ile Ser Gly Thr Ala
    1410              1415              1420 gac gcc ggc aac acc atc atc atc acc gat ggc aac ggc aac ccg att       4320
Asp Ala Gly Asn Thr Ile Ile Ile Thr Asp Gly Asn Gly Asn Pro Ile
1425              1430              1435              1440 ggc cag gtc acc gcc gac ggc agc ggc aac tgg tcc ttc act cca ggc       4368
Gly Gln Val Thr Ala Asp Gly Ser Gly Asn Trp Ser Phe Thr Pro Gly
            1445              1450              1455 atc ccg ctg ccg gat ggc acg gtg gtc aac gtg gtg gcg cgc agc cca       4416
Ile Pro Leu Pro Asp Gly Thr Val Val Asn Val Val Ala Arg Ser Pro
                1460              1465              1470 agc aat gtc gac agt gcg ccg gcg gtg atc act gtg gat ggc gtg gcc       4464
Ser Asn Val Asp Ser Ala Pro Ala Val Ile Thr Val Asp Gly Val Ala
        1475              1480              1485 ccg gcg gcg ccg gtg atc gat ccg agc aac ggc acc gag ata agc ggt       4512
Pro Ala Ala Pro Val Ile Asp Pro Ser Asn Gly Thr Glu Ile Ser Gly
    1490              1495              1500 acc gcg gag gcc ggc gcg acg gtg atc ctc acc gat ggc ggc ggc aac       4560
Thr Ala Glu Ala Gly Ala Thr Val Ile Leu Thr Asp Gly Gly Gly Asn
1505              1510              1515              1520 ccg atc ggc cag gcc acc gcc gac ggc agc ggc aac tgg acg ttc acc       4608
Pro Ile Gly Gln Ala Thr Ala Asp Gly Ser Gly Asn Trp Thr Phe Thr
            1525              1530              1535 ccg agc acc ccg ctg gcc aac ggc acc gtg atc aac gcc gtg gcc cag       4656
Pro Ser Thr Pro Leu Ala Asn Gly Thr Val Ile Asn Ala Val Ala Gln
                1540              1545              1550 gac ccg gcc ggc aat acc agc ggt ccg gcc agc gtc acc gtc gat gcc       4704
Asp Pro Ala Gly Asn Thr Ser Gly Pro Ala Ser Val Thr Val Asp Ala
        1555              1560              1565 atc gcc ccg ccg gcg ccg gtg atc aat ccg agc aat gga gtc gtc atc       4752
Ile Ala Pro Pro Ala Pro Val Ile Asn Pro Ser Asn Gly Val Val Ile
    1570              1575              1580 agc ggt acg gcg gaa gcc ggg gcc acg gtg atc ctc acc gac ggc aac       4800
Ser Gly Thr Ala Glu Ala Gly Ala Thr Val Ile Leu Thr Asp Gly Asn
1585              1590              1595              1600 ggc aac ccg atc ggc cag gtc acc gcc gac ggc agc ggc aac tgg agc       4848
Gly Asn Pro Ile Gly Gln Val Thr Ala Asp Gly Ser Gly Asn Trp Ser
            1605              1610              1615 ttc acg ccc ggc acg ccg ctg gcc aac ggc tcg gtg atc aat gcg ctg       4896
```

```
                                                          -continued
Phe Thr Pro Gly Thr Pro Leu Ala Asn Gly Ser Val Ile Asn Ala Leu
        1620                1625                1630 gcc cag gac gcc gcc ggc aac aac agc agt ccc acc agc gcc acc gtc    4944
Ala Gln Asp Ala Ala Gly Asn Asn Ser Ser Pro Thr Ser Ala Thr Val
    1635                1640                1645 gac tcg ctg gcg cca gca gcc ccg gtg atc gat ccg agc aac ggt agc    4992
Asp Ser Leu Ala Pro Ala Ala Pro Val Ile Asp Pro Ser Asn Gly Ser
1650                1655                1660 gtg atc gcc ggt acc gcc gag gct ggt gcc acg gtg atc ctc acc gac    5040
Val Ile Ala Gly Thr Ala Glu Ala Gly Ala Thr Val Ile Leu Thr Asp
1665                1670                1675                1680 ggc aac ggc aac ccg atc ggc cag gtc acc gcc gat ggc agc ggc aac    5088
Gly Asn Gly Asn Pro Ile Gly Gln Val Thr Ala Asp Gly Ser Gly Asn
                1685                1690                1695 tgg agc ttc acg ccc ggc acg ccg ctg tcc aat ggc acg gtg gtc aat    5136
Trp Ser Phe Thr Pro Gly Thr Pro Leu Ser Asn Gly Thr Val Val Asn
        1700                1705                1710 gcg gtg gcc cag gac gct gcc ggc aac acc agc ggc ccg gtc agc acc    5184
Ala Val Ala Gln Asp Ala Ala Gly Asn Thr Ser Gly Pro Val Ser Thr
    1715                1720                1725 acg gtg gac gcg gtg gcc ccg gcc acc ccg gtg atc gac ccg agc aac    5232
Thr Val Asp Ala Val Ala Pro Ala Thr Pro Val Ile Asp Pro Ser Asn
1730                1735                1740 ggt gtc gaa ctc agc ggc acc gcc gaa ccc ggc gtc cgg gtg atc ctc    5280
Gly Val Glu Leu Ser Gly Thr Ala Glu Pro Gly Val Arg Val Ile Leu
1745                1750                1755                1760 acc gat ggc aat ggc aat ccg atc ggc cag acc ctt gcc gac ggc agc    5328
Thr Asp Gly Asn Gly Asn Pro Ile Gly Gln Thr Leu Ala Asp Gly Ser
                1765                1770                1775 ggc aac tgg agc ttc acg ccg ggc acg ccg ctg gcc aac ggc acg gtg    5376
Gly Asn Trp Ser Phe Thr Pro Gly Thr Pro Leu Ala Asn Gly Thr Val
        1780                1785                1790 gtc aat gcc gtg gcc cag gac ccg gcc ggc aat acc agc ggc ccg gcc    5424
Val Asn Ala Val Ala Gln Asp Pro Ala Gly Asn Thr Ser Gly Pro Ala
    1795                1800                1805 agc acc acg gtg gac acg gtg gct ccg gcc acg ccg gtg atc aat ccc    5472
Ser Thr Thr Val Asp Thr Val Ala Pro Ala Thr Pro Val Ile Asn Pro
1810                1815                1820 agc aac ggc agc gtg atc acc ggc acc gcc gag gtc ggc gcc aag gtg    5520
Ser Asn Gly Ser Val Ile Thr Gly Thr Ala Glu Val Gly Ala Lys Val
1825                1830                1835                1840 atc ctc acc gat ggc aac ggc aac ccg atc ggc gag acc acc gcc gac    5568
Ile Leu Thr Asp Gly Asn Gly Asn Pro Ile Gly Glu Thr Thr Ala Asp
                1845                1850                1855 ggc agt ggt aac tgg acc ttc acc ccc ggc acg ccg ctg gcc aac ggt    5616
Gly Ser Gly Asn Trp Thr Phe Thr Pro Gly Thr Pro Leu Ala Asn Gly
        1860                1865                1870 acg gtg atc aac gcc gtc gcc gag gac gcc gcg ggc aac gcc agc ggt    5664
Thr Val Ile Asn Ala Val Ala Glu Asp Ala Ala Gly Asn Ala Ser Gly
    1875                1880                1885 ccg gcc agc acc acg gtg gac tcg gtg gcg ccg tcc gct ccg ctg ctg    5712
Pro Ala Ser Thr Thr Val Asp Ser Val Ala Pro Ser Ala Pro Leu Leu
1890                1895                1900 agc atc agc gcc gac ggc gcg ctg ctg acc ggc acc gcc gag ccg aac    5760
Ser Ile Ser Ala Asp Gly Ala Leu Leu Thr Gly Thr Ala Glu Pro Asn
1905                1910                1915                1920 agc cag gtg cgc atc gtg gtc aac ggc gac acc gcc aac ccg atc acg    5808
Ser Gln Val Arg Ile Val Val Asn Gly Asp Thr Ala Asn Pro Ile Thr
                1925                1930                1935
```

```
gtc acc gtc gac ggc gcc ggc aac ttc agc ctg ccg ttc gcg ccg ccg    5856
Val Thr Val Asp Gly Ala Gly Asn Phe Ser Leu Pro Phe Ala Pro Pro
            1940                1945                1950 ctg atc acc ggc gag ctg atc gcc ggg gtc gcc gtc gac gcc gcc ggc    5904
Leu Ile Thr Gly Glu Leu Ile Ala Gly Val Ala Val Asp Ala Ala Gly
    1955                1960                1965 aac gtc agc ggg ccg gcc acc atc aac gcc ccg gac ctg gcg ccg ccg    5952
Asn Val Ser Gly Pro Ala Thr Ile Asn Ala Pro Asp Leu Ala Pro Pro
1970                1975                1980 acc atc agc gtg ccg gaa gcc gcc gat acc tgg atc aat gcc gcg gag    6000
Thr Ile Ser Val Pro Glu Ala Ala Asp Thr Trp Ile Asn Ala Ala Glu
1985                1990                1995                2000 atc ggc gac ggt atc cag gtc gat gtg acg gtc cgt ccg acc atg cag    6048
Ile Gly Asp Gly Ile Gln Val Asp Val Thr Val Arg Pro Thr Met Gln
        2005                2010                2015 gtc ggc cag gtg gtc acg gtc aag ttc gcc ggg cag aac ggc tac gag    6096
Val Gly Gln Val Val Thr Val Lys Phe Ala Gly Gln Asn Gly Tyr Glu
    2020                2025                2030 gcc gag gtc agc cat acc ctc acc gcc ggc gac atc gcc gcc ggc aac    6144
Ala Glu Val Ser His Thr Leu Thr Ala Gly Asp Ile Ala Ala Gly Asn
2035                2040                2045 ctg acc ctg acc ctg acg cct ccc ggc ggc atg ggc ccg ttc ccg gag    6192
Leu Thr Leu Thr Leu Thr Pro Pro Gly Gly Met Gly Pro Phe Pro Glu
    2050                2055                2060 ggt gcc tcg acc gtc acc gcc gac atc aac ggc ggc acc gcg tcg acc    6240
Gly Ala Ser Thr Val Thr Ala Asp Ile Asn Gly Gly Thr Ala Ser Thr
2065                2070                2075                2080 ccg gtg ccg ttc acc atc gac acc att ccg ccg gcg acc ccg gtg ctg    6288
Pro Val Pro Phe Thr Ile Asp Thr Ile Pro Pro Ala Thr Pro Val Leu
            2085                2090                2095 tcc ctg gtc ggc aac atc ctg acc atc tcg gcg gag cca ggg acc gag    6336
Ser Leu Val Gly Asn Ile Leu Thr Ile Ser Ala Glu Pro Gly Thr Glu
        2100                2105                2110 ttg acg gtg acc gtc gac gtc ggc ggg gtg acc gcc acc gcc acg gtg    6384
Leu Thr Val Thr Val Asp Val Gly Gly Val Thr Ala Thr Ala Thr Val
    2115                2120                2125 acc gcc gac aac agc ggg ctg gcg tcg ctg aac ctg ctc acc gac ctg    6432
Thr Ala Asp Asn Ser Gly Leu Ala Ser Leu Asn Leu Leu Thr Asp Leu
2130                2135                2140 gac atc gac ttc agt tgg gac cag ttg ctc aat gcc cag gtg tcg gtg    6480
Asp Ile Asp Phe Ser Trp Asp Gln Leu Leu Asn Ala Gln Val Ser Val
2145                2150                2155                2160 gtc gga cgc gac ccg gcc ggc aac ccg agc aac acg gcg agc atc ggc    6528
Val Gly Arg Asp Pro Ala Gly Asn Pro Ser Asn Thr Ala Ser Ile Gly
            2165                2170                2175 gtc ggc acc agc atc gag caa ccg gtg acc atc ggc aac ttc ggc ctc    6576
Val Gly Thr Ser Ile Glu Gln Pro Val Thr Ile Gly Asn Phe Gly Leu
        2180                2185                2190 gac gtc agc ctc aac ccg ctg aac ccg cgt ttc ggt ttc agc gga acc    6624
Asp Val Ser Leu Asn Pro Leu Asn Pro Arg Phe Gly Phe Ser Gly Thr
    2195                2200                2205 acc gag cct gac tcc agc gtg gtg atc cgg gtc atc acc ccg gcg ttg    6672
Thr Glu Pro Asp Ser Ser Val Val Ile Arg Val Ile Thr Pro Ala Leu
2210                2215                2220 aac gtc gaa ttg ctg ccg atc cag gcg gat tcg tcc gga aac ttc tcg    6720
Asn Val Glu Leu Leu Pro Ile Gln Ala Asp Ser Ser Gly Asn Phe Ser
2225                2230                2235                2240 ctg aac ctg ctg agc ccg acc atc ctc acc cag ttg ggg ctg aac atc    6768
Leu Asn Leu Leu Ser Pro Thr Ile Leu Thr Gln Leu Gly Leu Asn Ile
            2245                2250                2255
```

```
acc gac atc ctc aac ctc ggc tcg cag atc tcg ttc aac ctg gtg tcc      6816
Thr Asp Ile Leu Asn Leu Gly Ser Gln Ile Ser Phe Asn Leu Val Ser
            2260                2265                2270 acc gac tcc aat ggc aac gac agc gcc gcc tac ggg atc acc ctg acc      6864
Thr Asp Ser Asn Gly Asn Asp Ser Ala Ala Tyr Gly Ile Thr Leu Thr
        2275                2280                2285 ccc aac gga ctg tcg ctc aat atc ggc cag atc gat gtc aac ggt act      6912
Pro Asn Gly Leu Ser Leu Asn Ile Gly Gln Ile Asp Val Asn Gly Thr
    2290                2295                2300 tcc ggc gac gac gtg ctg tcc ggc gcc aac ggc agt tcg gag cac atc      6960
Ser Gly Asp Asp Val Leu Ser Gly Ala Asn Gly Ser Ser Glu His Ile
2305                2310                2315                2320 aac ggc ggc gac ggc agc gac ctg atc ttc aac gtg ggc acc ggc gat      7008
Asn Gly Gly Asp Gly Ser Asp Leu Ile Phe Asn Val Gly Thr Gly Asp
            2325                2330                2335 cac gtg gtg gcc ggc aac ggc aac gac acc atc cag atc acc gcg acc      7056
His Val Val Ala Gly Asn Gly Asn Asp Thr Ile Gln Ile Thr Ala Thr
        2340                2345                2350 gat ttc gtc agc atc gat ggc ggc gcc ggg ttc gac acc ctg gtc ctg      7104
Asp Phe Val Ser Ile Asp Gly Gly Ala Gly Phe Asp Thr Leu Val Leu
    2355                2360                2365 gcc aac ggc atc gac ctc gac tac aac gcc gtc ggc gtc ggc acg ctc      7152
Ala Asn Gly Ile Asp Leu Asp Tyr Asn Ala Val Gly Val Gly Thr Leu
2370                2375                2380 agc aac ctc gag cgc atc gac ctc ggc aag ggc gat tcg ggt agc gtg      7200
Ser Asn Leu Glu Arg Ile Asp Leu Gly Lys Gly Asp Ser Gly Ser Val
2385                2390                2395                2400 ctg acc ctg acc gcg gcg gag gtg gat gcc atc acc gat gcc aac aac      7248
Leu Thr Leu Thr Ala Ala Glu Val Asp Ala Ile Thr Asp Ala Asn Asn
            2405                2410                2415 acg ttg cag atc acc ggc gag aac aac gac acc ctg aac gtg gtg ggc      7296
Thr Leu Gln Ile Thr Gly Glu Asn Asn Asp Thr Leu Asn Val Val Gly
        2420                2425                2430 gcg gtg aat acc ggt acc acg caa ctg atc aac ggc att acc tac gac      7344
Ala Val Asn Thr Gly Thr Thr Gln Leu Ile Asn Gly Ile Thr Tyr Asp
    2435                2440                2445 gtc tac acc ttc ggc agt acc acc ctg ctg atc gag gac aac acg gta      7392
Val Tyr Thr Phe Gly Ser Thr Thr Leu Leu Ile Glu Asp Asn Thr Val
2450                2455                2460 cag gtc gtg gtc tga                                                  7407
Gln Val Val Val
2465

<210> SEQ ID NO 4
<211> LENGTH: 2468
<212> TYPE: PRT
<213> ORGANISM: Pseudomonas aeruginosa

<400> SEQUENCE: 4

Met Ser Ile Gln Ala Lys Val Thr Pro Ile Asp Gln Ser Ile Ser Ser
1               5                   10                  15

Ala Ala Ala Val Glu Val Pro Glu Asn Gly Ile Leu Lys Leu Ser Gln
            20                  25                  30

Ser Ser Asn Val Ala Leu Asp Val Ala Pro Glu Ser Val Ala Gly Tyr
        35                  40                  45

Ser Lys Ser Gly Ser Asp Leu Ile Val Gln Leu Lys Thr Gly Glu Ser
    50                  55                  60

Val Arg Ile Ala Asn Phe Tyr Ala Glu Gly Gln Pro Ser Ser Gln Leu
65                  70                  75                  80
```

```
Phe Leu Ala Asp Lys Asp Lys Leu Val Ala Val Asp Leu Pro Pro Val
                 85                  90                  95

Ala Ala Asp Gly Pro Leu Met Ala Gly Tyr Ile Pro Gln Glu Ser Leu
            100                 105                 110

Ala Gly Phe Glu Ser Leu Thr Gly Ala Gly Val Leu Gly Gly Met Ser
        115                 120                 125

Ala Gly Thr Ala Leu Leu Val Gly Ala Ala Ile Gly Ala Gly Val
    130                 135                 140

Ala Ile Ser Asn Ser Ser Gly Gly Gly Gly Gly Gly Ser Ser Val
145                 150                 155                 160

Pro Pro Asp Thr Thr Pro Pro Lys Ala Ala Ser Gly Leu Lys Ile Ala
                165                 170                 175

Pro Asp Gly Ser Ser Ile Ser Gly Gln Ala Glu Ala Gly Ala Ser Val
            180                 185                 190

Gly Ile Asp Thr Asn Gly Asp Gly Lys Pro Asp Leu Thr Val Ile Ala
        195                 200                 205

Asp Ala Asn Gly Asn Phe Thr Ala Pro Leu Asn Pro Pro Leu Thr Asn
    210                 215                 220

Gly Gln Thr Val Thr Val Val Thr Asp Pro Ala Gly Asn Ala Ser
225                 230                 235                 240

Pro Pro Ala Gln Val Thr Ala Pro Asp Thr Thr Ala Pro Ala Pro Ala
                245                 250                 255

Thr Asp Val Gln Val Ala Pro Asp Gly Ser Ser Val Thr Gly Lys Ala
            260                 265                 270

Glu Pro Gly Ser Thr Val Gly Val Asp Thr Asp Gly Asp Gly Gln Pro
        275                 280                 285

Asp Thr Thr Val Val Val Gly Pro Gly Gly Ser Phe Glu Val Pro Leu
    290                 295                 300

Asn Pro Pro Leu Thr Asn Gly Glu Thr Val Thr Val Ile Val Thr Asp
305                 310                 315                 320

Pro Ala Gly Asn Asn Ser Thr Pro Val Thr Val Glu Ala Pro Asp Thr
                325                 330                 335

Thr Ala Pro Ala Pro Ala Thr Asp Val Gln Val Ala Pro Asp Gly Ser
            340                 345                 350

Ser Val Thr Gly Asn Ala Glu Pro Gly Ala Thr Val Gly Val Asp Thr
        355                 360                 365

Asp Gly Asp Gly Gln Pro Asp Thr Thr Val Val Val Gly Pro Gly Gly
    370                 375                 380

Ser Phe Glu Val Pro Leu Asn Pro Pro Leu Thr Asn Gly Glu Thr Val
385                 390                 395                 400

Thr Val Ile Val Thr Asp Pro Ala Gly Asn Ser Ser Thr Pro Val Thr
                405                 410                 415

Ala Glu Ala Pro Asp Phe Pro Asp Ala Pro Gln Val Asn Ala Ser Asn
            420                 425                 430

Gly Ser Val Leu Ser Gly Thr Ala Glu Ala Gly Val Thr Ile Val Ile
        435                 440                 445

Thr Asp Gly Asn Gly Asn Pro Ile Gly Gln Thr Ser Ala Asp Ala Asn
    450                 455                 460

Gly Asn Trp Ser Phe Thr Pro Gly Ser Gln Leu Pro Asp Gly Thr Val
465                 470                 475                 480

Val Asn Val Val Ala Arg Asp Ala Ala Gly Asn Ser Ser Pro Ala Thr
                485                 490                 495
```

```
Ser Ile Thr Val Asp Gly Val Ala Pro Asn Ala Pro Val Val Glu Pro
            500                 505                 510

Ser Asn Gly Ser Glu Leu Ser Gly Thr Ala Glu Pro Gly Ser Ser Val
            515                 520                 525

Thr Leu Thr Asp Gly Asn Gly Asn Pro Ile Gly Gln Thr Thr Ala Asp
            530                 535                 540

Ala Asn Gly Asn Trp Ser Phe Thr Pro Ser Thr Pro Leu Pro Asp Gly
545                 550                 555                 560

Thr Val Val Asn Val Val Ala Arg Asp Ala Ala Gly Asn Ser Ser Pro
                565                 570                 575

Pro Ala Ser Val Thr Val Asp Ala Val Ala Pro Ala Thr Pro Thr Val
            580                 585                 590

Asp Pro Ser Asn Gly Thr Thr Leu Ser Gly Thr Ala Glu Pro Gly Ser
            595                 600                 605

Ser Val Thr Leu Thr Asp Gly Asn Gly Asn Pro Ile Gly Gln Val Thr
            610                 615                 620

Ala Asp Gly Ser Gly Asn Trp Thr Phe Thr Pro Ser Thr Pro Leu Pro
625                 630                 635                 640

Asn Gly Thr Val Val Asn Ala Thr Ala Thr Asp Pro Ser Gly Asn Ala
                645                 650                 655

Ser Ser Pro Ala Ser Val Thr Val Asp Ala Val Ala Pro Ala Thr Pro
            660                 665                 670

Val Val Asn Pro Ser Asn Gly Thr Thr Leu Ser Gly Thr Ala Glu Pro
            675                 680                 685

Gly Ala Thr Val Thr Leu Thr Asp Gly Asn Gly Asn Pro Ile Gly Gln
            690                 695                 700

Val Thr Ala Asp Gly Ser Gly Asn Trp Ser Phe Thr Pro Thr Pro
705                 710                 715                 720

Leu Pro Asn Gly Thr Val Val Asn Ala Thr Ala Thr Asp Ala Ser Gly
            725                 730                 735

Asn Thr Ser Ala Gly Ser Ser Val Thr Val Asp Ser Val Ala Pro Ala
            740                 745                 750

Thr Pro Val Ile Asn Pro Ser Asn Gly Thr Thr Leu Ser Gly Thr Ala
            755                 760                 765

Glu Pro Gly Ser Ser Val Thr Leu Thr Asp Gly Asn Gly Asn Pro Ile
            770                 775                 780

Gly Gln Val Thr Ala Asp Gly Ser Gly Asn Trp Ser Phe Thr Pro Ser
785                 790                 795                 800

Thr Pro Leu Ala Asp Gly Thr Val Val Asn Ala Thr Ala Thr Asp Pro
            805                 810                 815

Ala Gly Asn Thr Ser Gly Gln Gly Ser Thr Thr Val Asp Gly Val Ala
            820                 825                 830

Pro Thr Thr Pro Thr Val Asn Leu Ser Asn Gly Ser Ser Leu Ser Gly
            835                 840                 845

Thr Ala Glu Pro Gly Ser Thr Val Ile Leu Thr Asp Gly Asn Gly Asn
            850                 855                 860

Pro Ile Ala Glu Val Thr Ala Asp Gly Ser Gly Asn Trp Thr Tyr Thr
865                 870                 875                 880

Pro Ser Thr Pro Ile Ala Asn Gly Thr Val Val Asn Val Val Ala Gln
            885                 890                 895

Asp Ala Ala Gly Asn Ser Ser Pro Gly Ala Ser Val Thr Val Asp Ser
            900                 905                 910

Gln Ala Pro Ala Ala Pro Val Val Asn Pro Ser Asn Gly Thr Thr Leu
```

```
                915                 920                 925
Ser Gly Thr Ala Glu Pro Gly Ala Thr Val Thr Leu Thr Asp Gly Asn
    930                 935                 940
Gly Asn Pro Ile Gly Gln Val Thr Ala Asp Gly Ser Gly Asn Trp Ser
945                 950                 955                 960
Phe Thr Pro Gly Thr Pro Leu Ala Asn Gly Thr Val Val Asn Ala Thr
                965                 970                 975
Ala Ser Asp Pro Thr Gly Asn Thr Ser Ala Pro Ala Ser Thr Thr Val
            980                 985                 990
Asp Ser Val Ala Pro Ala Pro Val Val Asn Pro Ser Asn Gly Ala
        995                 1000                1005
Glu Ile Ser Gly Thr Ala Glu Pro Gly Ala Thr Val Thr Leu Thr Asp
    1010                1015                1020
Gly Ser Gly Asn Pro Ile Gly Gln Val Thr Ala Asp Gly Ser Gly Asn
1025                1030                1035                1040
Trp Ser Phe Thr Pro Ser Thr Pro Leu Ala Asp Gly Thr Val Val Asn
                1045                1050                1055
Ala Thr Ala Thr Asp Pro Ala Gly Asn Thr Gly Gly Gln Gly Ser Thr
        1060                1065                1070
Thr Val Asp Ala Ile Ala Pro Ala Thr Pro Thr Val Asn Leu Ser Asn
    1075                1080                1085
Gly Ser Ser Leu Ser Gly Thr Ala Glu Pro Gly Ser Thr Val Ile Leu
    1090                1095                1100
Thr Asp Gly Asn Gly Asn Pro Ile Ala Glu Val Thr Ala Asp Gly Ser
1105                1110                1115                1120
Gly Asn Trp Thr Tyr Thr Pro Ser Thr Pro Ile Ala Asn Gly Thr Val
                1125                1130                1135
Val Asn Val Val Ala Gln Asp Ala Ser Gly Asn Ser Ser Pro Pro Ala
            1140                1145                1150
Thr Val Thr Val Asp Ser Ser Ala Pro Pro Ala Pro Val Ile Asn Pro
        1155                1160                1165
Ser Asn Gly Val Val Ile Ser Gly Thr Ala Glu Ala Gly Ala Thr Val
    1170                1175                1180
Thr Leu Thr Asp Ala Gly Gly Asn Pro Ile Gly Gln Val Thr Ala Asp
1185                1190                1195                1200
Gly Ser Gly Asn Trp Ser Phe Thr Pro Gly Thr Pro Leu Ala Asn Gly
                1205                1210                1215
Thr Val Ile Val Ala Thr Ala Thr Asp Pro Thr Gly Asn Thr Gly Pro
        1220                1225                1230
Gln Ala Ala Thr Thr Val Asp Ala Val Ala Pro Pro Ala Pro Val Ile
        1235                1240                1245
Asp Pro Ser Asn Gly Thr Thr Ile Ser Gly Thr Ala Glu Ala Gly Ala
    1250                1255                1260
Lys Val Ile Leu Thr Asp Gly Asn Gly Asn Pro Ile Gly Glu Thr Thr
1265                1270                1275                1280
Ala Asp Gly Ser Gly Asn Trp Ser Phe Thr Pro Gly Thr Pro Leu Ala
                1285                1290                1295
Asn Gly Thr Val Val Asn Ala Val Ala Gln Asp Pro Ala Gly Asn Thr
            1300                1305                1310
Gly Pro Gln Gly Ser Thr Thr Val Asp Ala Val Ala Pro Asn Thr Pro
        1315                1320                1325
Val Val Asn Pro Ser Asn Gly Asn Leu Leu Asn Gly Thr Ala Glu Pro
    1330                1335                1340
```

-continued

Gly Ser Thr Val Thr Leu Thr Asp Gly Asn Gly Asn Pro Ile Gly Gln
1345                1350                1355                1360

Thr Thr Ala Asp Gly Ser Gly Asn Trp Ser Phe Thr Pro Gly Ser Gln
            1365                1370                1375

Leu Pro Asn Gly Thr Val Val Asn Val Thr Ala Ser Asp Ala Ala Gly
        1380                1385                1390

Asn Thr Ser Leu Pro Ala Thr Thr Val Asp Ser Ser Leu Pro Ser
    1395                1400                1405

Ile Pro Gln Val Asp Pro Ser Asn Gly Ser Val Ile Ser Gly Thr Ala
        1410                1415                1420

Asp Ala Gly Asn Thr Ile Ile Ile Thr Asp Gly Asn Gly Asn Pro Ile
1425                1430                1435                1440

Gly Gln Val Thr Ala Asp Gly Ser Gly Asn Trp Ser Phe Thr Pro Gly
                1445                1450                1455

Ile Pro Leu Pro Asp Gly Thr Val Val Asn Val Ala Arg Ser Pro
        1460                1465                1470

Ser Asn Val Asp Ser Ala Pro Ala Val Ile Thr Val Asp Gly Val Ala
    1475                1480                1485

Pro Ala Ala Pro Val Ile Asp Pro Ser Asn Gly Thr Glu Ile Ser Gly
        1490                1495                1500

Thr Ala Glu Ala Gly Ala Thr Val Ile Leu Thr Asp Gly Gly Asn
1505                1510                1515                1520

Pro Ile Gly Gln Ala Thr Ala Asp Gly Ser Gly Asn Trp Thr Phe Thr
                1525                1530                1535

Pro Ser Thr Pro Leu Ala Asn Gly Thr Val Ile Asn Ala Val Ala Gln
        1540                1545                1550

Asp Pro Ala Gly Asn Thr Ser Gly Pro Ala Ser Val Thr Val Asp Ala
        1555                1560                1565

Ile Ala Pro Pro Ala Pro Val Ile Asn Pro Ser Asn Gly Val Val Ile
1570                1575                1580

Ser Gly Thr Ala Glu Ala Gly Ala Thr Val Ile Leu Thr Asp Gly Asn
1585                1590                1595                1600

Gly Asn Pro Ile Gly Gln Val Thr Ala Asp Gly Ser Gly Asn Trp Ser
            1605                1610                1615

Phe Thr Pro Gly Thr Pro Leu Ala Asn Gly Ser Val Ile Asn Ala Leu
        1620                1625                1630

Ala Gln Asp Ala Ala Gly Asn Asn Ser Ser Pro Thr Ser Ala Thr Val
        1635                1640                1645

Asp Ser Leu Ala Pro Ala Ala Pro Val Ile Asp Pro Ser Asn Gly Ser
    1650                1655                1660

Val Ile Ala Gly Thr Ala Glu Ala Gly Ala Thr Val Ile Leu Thr Asp
1665                1670                1675                1680

Gly Asn Gly Asn Pro Ile Gly Gln Val Thr Ala Asp Gly Ser Gly Asn
            1685                1690                1695

Trp Ser Phe Thr Pro Gly Thr Pro Leu Ser Asn Gly Thr Val Val Asn
            1700                1705                1710

Ala Val Ala Gln Asp Ala Ala Gly Asn Thr Ser Gly Pro Val Ser Thr
        1715                1720                1725

Thr Val Asp Ala Val Ala Pro Ala Thr Pro Val Ile Asp Pro Ser Asn
        1730                1735                1740

Gly Val Glu Leu Ser Gly Thr Ala Glu Pro Gly Val Arg Val Ile Leu
1745                1750                1755                1760

-continued

Thr Asp Gly Asn Gly Asn Pro Ile Gly Gln Thr Leu Ala Asp Gly Ser
            1765                1770                1775

Gly Asn Trp Ser Phe Thr Pro Gly Thr Pro Leu Ala Asn Gly Thr Val
        1780                1785                1790

Val Asn Ala Val Ala Gln Asp Pro Ala Gly Asn Thr Ser Gly Pro Ala
    1795                1800                1805

Ser Thr Thr Val Asp Thr Val Ala Pro Ala Thr Pro Val Ile Asn Pro
    1810                1815                1820

Ser Asn Gly Ser Val Ile Thr Gly Thr Ala Glu Val Gly Ala Lys Val
1825                1830                1835                1840

Ile Leu Thr Asp Gly Asn Gly Asn Pro Ile Gly Glu Thr Thr Ala Asp
            1845                1850                1855

Gly Ser Gly Asn Trp Thr Phe Thr Pro Gly Thr Pro Leu Ala Asn Gly
            1860                1865                1870

Thr Val Ile Asn Ala Val Ala Glu Asp Ala Ala Gly Asn Ala Ser Gly
        1875                1880                1885

Pro Ala Ser Thr Thr Val Asp Ser Val Ala Pro Ser Ala Pro Leu Leu
    1890                1895                1900

Ser Ile Ser Ala Asp Gly Ala Leu Leu Thr Gly Thr Ala Glu Pro Asn
1905                1910                1915                1920

Ser Gln Val Arg Ile Val Val Asn Gly Asp Thr Ala Asn Pro Ile Thr
            1925                1930                1935

Val Thr Val Asp Gly Ala Gly Asn Phe Ser Leu Pro Phe Ala Pro Pro
            1940                1945                1950

Leu Ile Thr Gly Glu Leu Ile Ala Gly Val Ala Val Asp Ala Ala Gly
        1955                1960                1965

Asn Val Ser Gly Pro Ala Thr Ile Asn Ala Pro Asp Leu Ala Pro Pro
    1970                1975                1980

Thr Ile Ser Val Pro Glu Ala Ala Asp Thr Trp Ile Asn Ala Ala Glu
1985                1990                1995                2000

Ile Gly Asp Gly Ile Gln Val Asp Val Thr Val Arg Pro Thr Met Gln
            2005                2010                2015

Val Gly Gln Val Val Thr Val Lys Phe Ala Gly Gln Asn Gly Tyr Glu
        2020                2025                2030

Ala Glu Val Ser His Thr Leu Thr Ala Gly Asp Ile Ala Ala Gly Asn
        2035                2040                2045

Leu Thr Leu Thr Leu Thr Pro Pro Gly Gly Met Gly Pro Phe Pro Glu
    2050                2055                2060

Gly Ala Ser Thr Val Thr Ala Asp Ile Asn Gly Gly Thr Ala Ser Thr
2065                2070                2075                2080

Pro Val Pro Phe Thr Ile Asp Thr Ile Pro Pro Ala Thr Pro Val Leu
            2085                2090                2095

Ser Leu Val Gly Asn Ile Leu Thr Ile Ser Ala Glu Pro Gly Thr Glu
            2100                2105                2110

Leu Thr Val Thr Val Asp Val Gly Gly Val Thr Ala Thr Ala Thr Val
        2115                2120                2125

Thr Ala Asp Asn Ser Gly Leu Ala Ser Leu Asn Leu Leu Thr Asp Leu
    2130                2135                2140

Asp Ile Asp Phe Ser Trp Asp Gln Leu Leu Asn Ala Gln Val Ser Val
2145                2150                2155                2160

Val Gly Arg Asp Pro Ala Gly Asn Pro Ser Asn Thr Ala Ser Ile Gly
            2165                2170                2175

Val Gly Thr Ser Ile Glu Gln Pro Val Thr Ile Gly Asn Phe Gly Leu

-continued

```
                    2180                2185                2190
Asp Val Ser Leu Asn Pro Leu Asn Pro Arg Phe Gly Phe Ser Gly Thr
    2195                2200                2205

Thr Glu Pro Asp Ser Ser Val Val Ile Arg Val Ile Thr Pro Ala Leu
    2210                2215                2220

Asn Val Glu Leu Leu Pro Ile Gln Ala Asp Ser Ser Gly Asn Phe Ser
2225                2230                2235                2240

Leu Asn Leu Leu Ser Pro Thr Ile Leu Thr Gln Leu Gly Leu Asn Ile
                2245                2250                2255

Thr Asp Ile Leu Asn Leu Gly Ser Gln Ile Ser Phe Asn Leu Val Ser
                2260                2265                2270

Thr Asp Ser Asn Gly Asn Asp Ser Ala Ala Tyr Gly Ile Thr Leu Thr
                2275                2280                2285

Pro Asn Gly Leu Ser Leu Asn Ile Gly Gln Ile Asp Val Asn Gly Thr
    2290                2295                2300

Ser Gly Asp Asp Val Leu Ser Gly Ala Asn Gly Ser Ser Glu His Ile
2305                2310                2315                2320

Asn Gly Gly Asp Gly Ser Asp Leu Ile Phe Asn Val Gly Thr Gly Asp
                2325                2330                2335

His Val Val Ala Gly Asn Gly Asn Asp Thr Ile Gln Ile Thr Ala Thr
                2340                2345                2350

Asp Phe Val Ser Ile Asp Gly Gly Ala Gly Phe Asp Thr Leu Val Leu
                2355                2360                2365

Ala Asn Gly Ile Asp Leu Asp Tyr Asn Ala Val Gly Val Gly Thr Leu
    2370                2375                2380

Ser Asn Leu Glu Arg Ile Asp Leu Gly Lys Gly Asp Ser Gly Ser Val
2385                2390                2395                2400

Leu Thr Leu Thr Ala Ala Glu Val Asp Ala Ile Thr Asp Ala Asn Asn
                2405                2410                2415

Thr Leu Gln Ile Thr Gly Glu Asn Asn Asp Thr Leu Asn Val Val Gly
                2420                2425                2430

Ala Val Asn Thr Gly Thr Thr Gln Leu Ile Asn Gly Ile Thr Tyr Asp
    2435                2440                2445

Val Tyr Thr Phe Gly Ser Thr Thr Leu Leu Ile Glu Asp Asn Thr Val
    2450                2455                2460

Gln Val Val Val
2465

<210> SEQ ID NO 5
<211> LENGTH: 1278
<212> TYPE: DNA
<213> ORGANISM: Pseudomonas aeruginosa
<220> FEATURE:
<221> NAME/KEY: CDS
<222> LOCATION: (1)...(1275)

<400> SEQUENCE: 5 atg cgc ggg cgc agg cag tac gcg cgc aag gga cgg cgg cat ggg aag      48
Met Arg Gly Arg Arg Gln Tyr Ala Arg Lys Gly Arg Arg His Gly Lys
 1               5                  10                  15 gga gcc atc tgg ctc ctt tcc ctg ggt ctg ccg atg ttc gcg tcg gcc      96
Gly Ala Ile Trp Leu Leu Ser Leu Gly Leu Pro Met Phe Ala Ser Ala
             20                  25                  30 atg ccc ctc gac cag gcg gtc agg gca ggg ctg gcg atc cac ccg gaa     144
Met Pro Leu Asp Gln Ala Val Arg Ala Gly Leu Ala Ile His Pro Glu
         35                  40                  45
```

-continued

| | | |
|---|---|---|
| gta cga tcc gcg atg gcc gaa gcg gac cgt gca ggc acc gag gtg gag<br>Val Arg Ser Ala Met Ala Glu Ala Asp Arg Ala Gly Thr Glu Val Glu<br>50                        55                       60 | 192 |
| atg gcc aaa ggg ggg tac tac ccc tcc gtg acg atg tcc ggg ggg ccg<br>Met Ala Lys Gly Gly Tyr Tyr Pro Ser Val Thr Met Ser Gly Gly Pro<br>65                        70                       75                 80 | 240 |
| cag gag ttc gac ttc ggc gag atc gtc tac gat ctc acc gcg tcg cag<br>Gln Glu Phe Asp Phe Gly Glu Ile Val Tyr Asp Leu Thr Ala Ser Gln<br>                       85                       90                       95 | 288 |
| atg ctg tac gac tgg ggt cgg gtg acg agc aag gtc gac agc gcc agc<br>Met Leu Tyr Asp Trp Gly Arg Val Thr Ser Lys Val Asp Ser Ala Ser<br>                 100                     105                    110 | 336 |
| gcg acc cag cgc aag ctg tcc gag gcg gtg ctg gtg gcg cgc gac gat<br>Ala Thr Gln Arg Lys Leu Ser Glu Ala Val Leu Val Ala Arg Asp Asp<br>                 115                     120                    125 | 384 |
| gcg gcg ctg gat atc gtc gag acc tac ctc gat gtg ctt gcc tcg gag<br>Ala Ala Leu Asp Ile Val Glu Thr Tyr Leu Asp Val Leu Ala Ser Glu<br>130                       135                     140 | 432 |
| cgc cgg gtg gag gcg gtg cgc gaa cac atc cag cgc ctc gac ggc atc<br>Arg Arg Val Glu Ala Val Arg Glu His Ile Gln Arg Leu Asp Gly Ile<br>145                       150                     155                    160 | 480 |
| cgc gag atg acc cag gcg cgc ggc ggc gac ggc tac gcc gac cgc agc<br>Arg Glu Met Thr Gln Ala Arg Gly Gly Asp Gly Tyr Ala Asp Arg Ser<br>                 165                     170                    175 | 528 |
| gag ctg gat cgc gcc aat ctg gaa ctg tcg cgg gcc cag gag cag ttg<br>Glu Leu Asp Arg Ala Asn Leu Glu Leu Ser Arg Ala Gln Glu Gln Leu<br>                 180                     185                    190 | 576 |
| tcg ctg gag aag ggc aac ctg cag gac gcg cgc aac cag tac gcg atc<br>Ser Leu Glu Lys Gly Asn Leu Gln Asp Ala Arg Asn Gln Tyr Ala Ile<br>                 195                     200                    205 | 624 |
| ctg gtc ggc cag gag ccc gcc gac ctg gtg gag ccc gag ccg atg tcg<br>Leu Val Gly Gln Glu Pro Ala Asp Leu Val Glu Pro Glu Pro Met Ser<br>210                       215                     220 | 672 |
| ctg caa cgc tac ctg gcg gcc agc gat atg gcg cgg gtg atc cgc gaa<br>Leu Gln Arg Tyr Leu Ala Ala Ser Asp Met Ala Arg Val Ile Arg Glu<br>225                       230                     235                    240 | 720 |
| tcg cct ttg cag cgc aag gcc ctg gag gac gcc aat gtc gcc gag gcc<br>Ser Pro Leu Gln Arg Lys Ala Leu Glu Asp Ala Asn Val Ala Glu Ala<br>                 245                     250                    255 | 768 |
| gag gtc cgc gag gcc aag gcg tcg ctg ctg ccg caa ctg aac ctg gag<br>Glu Val Arg Glu Ala Lys Ala Ser Leu Leu Pro Gln Leu Asn Leu Glu<br>                 260                     265                    270 | 816 |
| gcc agc gcg ctg cgc cgg gag atc ggg ggg cat ccg gaa agc gac tcg<br>Ala Ser Ala Leu Arg Arg Glu Ile Gly Gly His Pro Glu Ser Asp Ser<br>                 275                     280                    285 | 864 |
| gtg gta tcc ctg cgc ttc cgc atg gac acc ttc cag ggg ctt tcc aac<br>Val Val Ser Leu Arg Phe Arg Met Asp Thr Phe Gln Gly Leu Ser Asn<br>290                       295                     300 | 912 |
| ttc cgc cgg ccg acc gcc gcg cag cag cgc ctg gag tcg gcg aaa tgg<br>Phe Arg Arg Pro Thr Ala Ala Gln Gln Arg Leu Glu Ser Ala Lys Trp<br>305                       310                     315                    320 | 960 |
| agc gcc gac gcg atg cag cgc gac atc cgc cgg caa ctg cag aac ctc<br>Ser Ala Asp Ala Met Gln Arg Asp Ile Arg Arg Gln Leu Gln Asn Leu<br>                 325                     330                    335 | 1008 |
| ttc gac aac ggc gac acg ctg cgc tgg cgg gaa cag tcg ctg acc cag<br>Phe Asp Asn Gly Asp Thr Leu Arg Trp Arg Glu Gln Ser Leu Thr Gln<br>                 340                     345                    350 | 1056 |
| cag gtg acc gag tcg gag cag gtc ggc gag ttg tat cgc gaa cag ttc<br>Gln Val Thr Glu Ser Glu Gln Val Gly Glu Leu Tyr Arg Glu Gln Phe<br>                 355                     360                    365 | 1104 |

```
gag gtt ggc cgg cgc gac gtg atc gac ctg ctc aac gtg cag cgc gag      1152
Glu Val Gly Arg Arg Asp Val Ile Asp Leu Leu Asn Val Gln Arg Glu
    370                 375                 380 cgg ttc gag gca gag cgg caa ctg atc aac ctg cgg atc gaa cgc aag      1200
Arg Phe Glu Ala Glu Arg Gln Leu Ile Asn Leu Arg Ile Glu Arg Lys
385                 390                 395                 400 cgc atc gag tat cgg gcg gcc gcg caa gtc ggc ctg ttg ggt ccg cta      1248
Arg Ile Glu Tyr Arg Ala Ala Ala Gln Val Gly Leu Leu Gly Pro Leu
                405                 410                 415 ttg gag aac cgg ctg aat cat gga agc tga                              1278
Leu Glu Asn Arg Leu Asn His Gly Ser
            420                 425

<210> SEQ ID NO 6
<211> LENGTH: 425
<212> TYPE: PRT
<213> ORGANISM: Pseudomonas aeruginosa

<400> SEQUENCE: 6

Met Arg Gly Arg Gln Tyr Ala Arg Lys Gly Arg Arg His Gly Lys
 1               5                  10                  15

Gly Ala Ile Trp Leu Leu Ser Leu Gly Leu Pro Met Phe Ala Ser Ala
                20                  25                  30

Met Pro Leu Asp Gln Ala Val Arg Ala Gly Leu Ala Ile His Pro Glu
            35                  40                  45

Val Arg Ser Ala Met Ala Glu Ala Asp Arg Ala Gly Thr Glu Val Glu
    50                  55                  60

Met Ala Lys Gly Gly Tyr Tyr Pro Ser Val Thr Met Ser Gly Gly Pro
65                  70                  75                  80

Gln Glu Phe Asp Phe Gly Glu Ile Val Tyr Asp Leu Thr Ala Ser Gln
                85                  90                  95

Met Leu Tyr Asp Trp Gly Arg Val Thr Ser Lys Val Asp Ser Ala Ser
            100                 105                 110

Ala Thr Gln Arg Lys Leu Ser Glu Ala Val Leu Val Ala Arg Asp Asp
    115                 120                 125

Ala Ala Leu Asp Ile Val Glu Thr Tyr Leu Asp Val Leu Ala Ser Glu
130                 135                 140

Arg Arg Val Glu Ala Val Arg Glu His Ile Gln Arg Leu Asp Gly Ile
145                 150                 155                 160

Arg Glu Met Thr Gln Ala Arg Gly Gly Asp Gly Tyr Ala Asp Arg Ser
                165                 170                 175

Glu Leu Asp Arg Ala Asn Leu Glu Leu Ser Arg Ala Gln Glu Gln Leu
            180                 185                 190

Ser Leu Glu Lys Gly Asn Leu Gln Asp Ala Arg Asn Gln Tyr Ala Ile
    195                 200                 205

Leu Val Gly Gln Glu Pro Ala Asp Leu Val Glu Pro Glu Pro Met Ser
210                 215                 220

Leu Gln Arg Tyr Leu Ala Ala Ser Asp Met Ala Arg Val Ile Arg Glu
225                 230                 235                 240

Ser Pro Leu Gln Arg Lys Ala Leu Glu Asp Ala Asn Val Ala Glu Ala
                245                 250                 255

Glu Val Arg Glu Ala Lys Ala Ser Leu Leu Pro Gln Leu Asn Leu Glu
            260                 265                 270

Ala Ser Ala Leu Arg Arg Glu Ile Gly Gly His Pro Glu Ser Asp Ser
    275                 280                 285
```

```
Val Val Ser Leu Arg Phe Arg Met Asp Thr Phe Gln Gly Leu Ser Asn
    290                 295                 300

Phe Arg Arg Pro Thr Ala Ala Gln Gln Arg Leu Glu Ser Ala Lys Trp
305                 310                 315                 320

Ser Ala Asp Ala Met Gln Arg Asp Ile Arg Arg Gln Leu Gln Asn Leu
                    325                 330                 335

Phe Asp Asn Gly Asp Thr Leu Arg Trp Arg Glu Gln Ser Leu Thr Gln
                340                 345                 350

Gln Val Thr Glu Ser Glu Gln Val Gly Glu Leu Tyr Arg Glu Gln Phe
            355                 360                 365

Glu Val Gly Arg Arg Asp Val Ile Asp Leu Leu Asn Val Gln Arg Glu
370                 375                 380

Arg Phe Glu Ala Glu Arg Gln Leu Ile Asn Leu Arg Ile Glu Arg Lys
385                 390                 395                 400

Arg Ile Glu Tyr Arg Ala Ala Gln Val Gly Leu Leu Gly Pro Leu
                405                 410                 415

Leu Glu Asn Arg Leu Asn His Gly Ser
            420                 425

<210> SEQ ID NO 7
<211> LENGTH: 2172
<212> TYPE: DNA
<213> ORGANISM: Pseudomonas aeruginosa
<220> FEATURE:
<221> NAME/KEY: CDS
<222> LOCATION: (1)...(2169)

<400> SEQUENCE: 7 atg gaa gct gag aaa acc ccg gat aac gtc gtg atc ctc aac cac gac      48
Met Glu Ala Glu Lys Thr Pro Asp Asn Val Val Ile Leu Asn His Asp
1               5                   10                  15 ccc atc gtc gac ccg ttg cgc cag ggc ttg ttg ctg ctc tgc cgg cag      96
Pro Ile Val Asp Pro Leu Arg Gln Gly Leu Leu Leu Leu Cys Arg Gln
                20                  25                  30 ctt ggc cga ccg ctc ggc gac gcc gaa ctg gtg gac ggc atg ccg ctg      144
Leu Gly Arg Pro Leu Gly Asp Ala Glu Leu Val Asp Gly Met Pro Leu
            35                  40                  45 gag cac ggt cgc ctg ccg ttg cac ctg gtg gcc cgc gcg ttg cgc cgc      192
Glu His Gly Arg Leu Pro Leu His Leu Val Ala Arg Ala Leu Arg Arg
    50                  55                  60 gcc gac atc acc gcc cag gtc acc cgc cag ccg ttg cgc cgg atc gat      240
Ala Asp Ile Thr Ala Gln Val Thr Arg Gln Pro Leu Arg Arg Ile Asp
65                  70                  75                  80 cgc tac ctg ctg ccg gcc ctg ctg ctc gac gac ggc cgc gcc ctg           288
Arg Tyr Leu Leu Pro Ala Leu Leu Leu Asp Asp Gly Arg Ala Leu
                85                  90                  95 gtg ctg gtg ggc aac gac ggc gag cac gcc gag gtg ctg gta ccg cag      336
Val Leu Val Gly Asn Asp Gly Glu His Ala Glu Val Leu Val Pro Gln
            100                 105                 110 agc gac ggc gga agc cag agg atg ccg ctg gcc gag ctg gaa gcg ctg      384
Ser Asp Gly Gly Ser Gln Arg Met Pro Leu Ala Glu Leu Glu Ala Leu
        115                 120                 125 tac agc ggc acg gcg gtc ttc gcc aag tgc cgc tac cgc ccg gac ggg      432
Tyr Ser Gly Thr Ala Val Phe Ala Lys Cys Arg Tyr Arg Pro Asp Gly
    130                 135                 140 cgg gtc ggc gac tac gcc agc gcc ttg ccc gaa cac tgg ttc ttc ggc      480
Arg Val Gly Asp Tyr Ala Ser Ala Leu Pro Glu His Trp Phe Phe Gly
145                 150                 155                 160 ccg ctc aag cgg ctc tgg cgt tcc tac gcc gag gtc acc gcc gcg gcg      528
Pro Leu Lys Arg Leu Trp Arg Ser Tyr Ala Glu Val Thr Ala Ala Ala
```

-continued

```
                165                 170                 175
ttg gtg gcc aac gtc ctg gcg gtc gcc tcg gca ctg ttc gcc atg cag        576
Leu Val Ala Asn Val Leu Ala Val Ala Ser Ala Leu Phe Ala Met Gln
            180                 185                 190 gtc tac gac cgc gtg gtg ccc aac gcg gcg ttc gac acc ctg tgg atc        624
Val Tyr Asp Arg Val Val Pro Asn Ala Ala Phe Asp Thr Leu Trp Ile
            195                 200                 205 ctc gcc agc ggc gtg gcc ctg gcg atc gtc ctc gac ggt gtc ctg cgg        672
Leu Ala Ser Gly Val Ala Leu Ala Ile Val Leu Asp Gly Val Leu Arg
            210                 215                 220 atc atg cgc ggc cac ctg ctc aac gtg ctc ggc aag cgc ctc gac ctg        720
Ile Met Arg Gly His Leu Leu Asn Val Leu Gly Lys Arg Leu Asp Leu
225                 230                 235                 240 caa ctc tcg acc ctg ctg ttc tcc cgc gtg ctg agc acc cgg gtc gcc        768
Gln Leu Ser Thr Leu Leu Phe Ser Arg Val Leu Ser Thr Arg Val Ala
                245                 250                 255 gcc aag ccg gcg tcg atg ggc gcc ttc agt acc cag gtg cgg gag ttc        816
Ala Lys Pro Ala Ser Met Gly Ala Phe Ser Thr Gln Val Arg Glu Phe
            260                 265                 270 gag tcg gtg cgc gag ttc ttt acc tcg tcc agc gcg gcg ctg atc agc        864
Glu Ser Val Arg Glu Phe Phe Thr Ser Ser Ser Ala Ala Leu Ile Ser
            275                 280                 285 gac ctg ccg ttc gtg gcg atc ttc ctg ctg atc atc gcc gtg atc ggc        912
Asp Leu Pro Phe Val Ala Ile Phe Leu Leu Ile Ile Ala Val Ile Gly
            290                 295                 300 ggc cat gtg gtc tgg gtg ccg ctg gtg gcc tgc gtg ctg atg atc ctg        960
Gly His Val Val Trp Val Pro Leu Val Ala Cys Val Leu Met Ile Leu
305                 310                 315                 320 ccg ggg ctg ctg acc cag cgc ctg ctc ggc cac ctg tcg cgg cag aac       1008
Pro Gly Leu Leu Thr Gln Arg Leu Leu Gly His Leu Ser Arg Gln Asn
                325                 330                 335 ctg cgc gaa ggg gcg atg aag aac ggc gtg ctg ctg gaa gcc ttc gag       1056
Leu Arg Glu Gly Ala Met Lys Asn Gly Val Leu Leu Glu Ala Phe Glu
            340                 345                 350 cac ctg gag acg gtc aag gcg acc cgc gcc gaa ggc cgc tgc ctg cac       1104
His Leu Glu Thr Val Lys Ala Thr Arg Ala Glu Gly Arg Cys Leu His
            355                 360                 365 cag tgg gaa acc ctg acc ggc gaa ctg gcc ggt acg gcg atg aag acc       1152
Gln Trp Glu Thr Leu Thr Gly Glu Leu Ala Gly Thr Ala Met Lys Thr
            370                 375                 380 cat act ctg gcc tcg acc ctg agc tac tcg gcg agc atc gtc cag cag       1200
His Thr Leu Ala Ser Thr Leu Ser Tyr Ser Ala Ser Ile Val Gln Gln
385                 390                 395                 400 ctc tgc tac gtc ggc gtg gtg gtc ttc ggc gtc tat cgg atc agc gag       1248
Leu Cys Tyr Val Gly Val Val Val Phe Gly Val Tyr Arg Ile Ser Glu
                405                 410                 415 ggc gcg atg acc gtc ggc ggc ctg gtg gcc tgc tcg atc ctc gcc tcg       1296
Gly Ala Met Thr Val Gly Gly Leu Val Ala Cys Ser Ile Leu Ala Ser
            420                 425                 430 cgg gcc atc gca ccg ctg tcg cag gcg gcc ggc atc ctc ggt cgc tgg       1344
Arg Ala Ile Ala Pro Leu Ser Gln Ala Ala Gly Ile Leu Gly Arg Trp
            435                 440                 445 cag cac acc aag gtg gcg atg gaa ggc ctc gac caa ctg atg agc gcc       1392
Gln His Thr Lys Val Ala Met Glu Gly Leu Asp Gln Leu Met Ser Ala
450                 455                 460 gag cag gag cga ccc cag ggc aag cgc ttc gtg cac aag gag cgc ctg       1440
Glu Gln Glu Arg Pro Gln Gly Lys Arg Phe Val His Lys Glu Arg Leu
465                 470                 475                 480 cag gga cat tac cgc ctg gag ggc gtg cgc ctg gcc cac ggc gac agc       1488
Gln Gly His Tyr Arg Leu Glu Gly Val Arg Leu Ala His Gly Asp Ser
```

```
Gln Gly His Tyr Arg Leu Glu Gly Val Arg Leu Ala His Gly Asp Ser
            485                 490                 495 ccg ccg gtg gtc gac gtg cag gcc ctg aac atc cgc gcc ggc gag cgg      1536
Pro Pro Val Val Asp Val Gln Ala Leu Asn Ile Arg Ala Gly Glu Arg
        500                 505                 510 gtg gcg ctg ctc ggc ggc aac ggc gcc ggc aag tcg acc ctg ctg cgc      1584
Val Ala Leu Leu Gly Gly Asn Gly Ala Gly Lys Ser Thr Leu Leu Arg
            515                 520                 525 ctg ctc agc ggc ctg ctc gac gcg cag gcg gga cgc ctg ctg ctg gac      1632
Leu Leu Ser Gly Leu Leu Asp Ala Gln Ala Gly Arg Leu Leu Leu Asp
        530                 535                 540 gac gtc agc ctg acc cag atc gac ccg gcc gac cgc cag cgc ggt atc      1680
Asp Val Ser Leu Thr Gln Ile Asp Pro Ala Asp Arg Gln Arg Gly Ile
545                 550                 555                 560 ggc tac ctg ccg cag gac gtg gcg ctg ttc cat ggc agc ctg cgc gac      1728
Gly Tyr Leu Pro Gln Asp Val Ala Leu Phe His Gly Ser Leu Arg Asp
                565                 570                 575 aac ctc aac ctg gag aac gcc gcg ctg ggc gac gag gaa ctg ctg gag      1776
Asn Leu Asn Leu Glu Asn Ala Ala Leu Gly Asp Glu Glu Leu Leu Glu
            580                 585                 590 acc ctc gac ggg gtc ggc ctg ggc gcc ttc gtc cgc ggc cac ccg ctg      1824
Thr Leu Asp Gly Val Gly Leu Gly Ala Phe Val Arg Gly His Pro Leu
        595                 600                 605 ggg ctg gac atg ccg atc cag ggc aac gcc agc ctg tcc ggc ggc caa      1872
Gly Leu Asp Met Pro Ile Gln Gly Asn Ala Ser Leu Ser Gly Gly Gln
    610                 615                 620 cgc cag gcc gtc ggg ctg gcc cgg gtg ctg cta cag gac cct ccg atc      1920
Arg Gln Ala Val Gly Leu Ala Arg Val Leu Leu Gln Asp Pro Pro Ile
625                 630                 635                 640 ctg ctg ctc gac gag ccg acc gcg gcc ttc gac cag ggc agc gag aaa      1968
Leu Leu Leu Asp Glu Pro Thr Ala Ala Phe Asp Gln Gly Ser Glu Lys
                645                 650                 655 cag gtc atc gac tac ctg cag caa tgg ttg ggc aag cgc acc ctg gtc      2016
Gln Val Ile Asp Tyr Leu Gln Gln Trp Leu Gly Lys Arg Thr Leu Val
            660                 665                 670 atc acc acc cac aag aaa agc atg ctc gcc ctg gtc gag cgt gcg gtg      2064
Ile Thr Thr His Lys Lys Ser Met Leu Ala Leu Val Glu Arg Ala Val
        675                 680                 685 gtc ctg cgc cag ggc agg gtg atc atg gac ggc ccg ctg gag cag gtg      2112
Val Leu Arg Gln Gly Arg Val Ile Met Asp Gly Pro Leu Glu Gln Val
    690                 695                 700 gtg cag ggc aac cag gta cag gca ccg cag gcc gcc gaa gga ggc aac      2160
Val Gln Gly Asn Gln Val Gln Ala Pro Gln Ala Ala Glu Gly Gly Asn
705                 710                 715                 720 cat gga ctc tga                                                      2172
His Gly Leu <210> SEQ ID NO 8
<211> LENGTH: 723
<212> TYPE: PRT
<213> ORGANISM: Pseudomonas aeruginosa

<400> SEQUENCE: 8

Met Glu Ala Glu Lys Thr Pro Asp Asn Val Ile Leu Asn His Asp
  1               5                  10                  15

Pro Ile Val Asp Pro Leu Arg Gln Gly Leu Leu Leu Cys Arg Gln
                 20                  25                  30

Leu Gly Arg Pro Leu Gly Asp Ala Glu Leu Val Asp Gly Met Pro Leu
             35                  40                  45
```

```
Glu His Gly Arg Leu Pro Leu His Leu Val Ala Arg Ala Leu Arg Arg
 50                  55                  60

Ala Asp Ile Thr Ala Gln Val Thr Arg Gln Pro Leu Arg Arg Ile Asp
 65                  70                  75                  80

Arg Tyr Leu Leu Pro Ala Leu Leu Leu Asp Asp Gly Arg Ala Leu
                 85                  90                  95

Val Leu Val Gly Asn Asp Gly Glu His Ala Glu Val Leu Val Pro Gln
                100                 105                 110

Ser Asp Gly Gly Ser Gln Arg Met Pro Leu Ala Glu Leu Glu Ala Leu
                115                 120                 125

Tyr Ser Gly Thr Ala Val Phe Ala Lys Cys Arg Tyr Arg Pro Asp Gly
    130                 135                 140

Arg Val Gly Asp Tyr Ala Ser Ala Leu Pro Glu His Trp Phe Phe Gly
145                 150                 155                 160

Pro Leu Lys Arg Leu Trp Arg Ser Tyr Ala Glu Val Thr Ala Ala Ala
                165                 170                 175

Leu Val Ala Asn Val Leu Ala Val Ala Ser Ala Leu Phe Ala Met Gln
                180                 185                 190

Val Tyr Asp Arg Val Pro Asn Ala Ala Phe Asp Thr Leu Trp Ile
                195                 200                 205

Leu Ala Ser Gly Val Ala Leu Ala Ile Val Leu Asp Gly Val Leu Arg
    210                 215                 220

Ile Met Arg Gly His Leu Leu Asn Val Leu Gly Lys Arg Leu Asp Leu
225                 230                 235                 240

Gln Leu Ser Thr Leu Leu Phe Ser Arg Val Leu Ser Thr Arg Val Ala
                245                 250                 255

Ala Lys Pro Ala Ser Met Gly Ala Phe Ser Thr Gln Val Arg Glu Phe
                260                 265                 270

Glu Ser Val Arg Glu Phe Phe Thr Ser Ser Ala Ala Leu Ile Ser
    275                 280                 285

Asp Leu Pro Phe Val Ala Ile Phe Leu Leu Ile Ile Ala Val Ile Gly
    290                 295                 300

Gly His Val Val Trp Val Pro Leu Val Ala Cys Val Leu Met Ile Leu
305                 310                 315                 320

Pro Gly Leu Leu Thr Gln Arg Leu Leu Gly His Leu Ser Arg Gln Asn
                325                 330                 335

Leu Arg Glu Gly Ala Met Lys Asn Gly Val Leu Leu Glu Ala Phe Glu
                340                 345                 350

His Leu Glu Thr Val Lys Ala Thr Arg Ala Glu Gly Arg Cys Leu His
    355                 360                 365

Gln Trp Glu Thr Leu Thr Gly Glu Leu Ala Gly Thr Ala Met Lys Thr
    370                 375                 380

His Thr Leu Ala Ser Thr Leu Ser Tyr Ser Ala Ser Ile Val Gln Gln
385                 390                 395                 400

Leu Cys Tyr Val Gly Val Val Phe Gly Val Tyr Arg Ile Ser Glu
                405                 410                 415

Gly Ala Met Thr Val Gly Gly Leu Val Ala Cys Ser Ile Leu Ala Ser
                420                 425                 430

Arg Ala Ile Ala Pro Leu Ser Gln Ala Ala Gly Ile Leu Gly Arg Trp
    435                 440                 445

Gln His Thr Lys Val Ala Met Glu Gly Leu Asp Gln Leu Met Ser Ala
    450                 455                 460

Glu Gln Glu Arg Pro Gln Gly Lys Arg Phe Val His Lys Glu Arg Leu
```

-continued

```
                465                 470                 475                 480
        Gln Gly His Tyr Arg Leu Glu Gly Val Arg Leu Ala His Gly Asp Ser
                        485                 490                 495
        Pro Pro Val Val Asp Val Gln Ala Leu Asn Ile Arg Ala Gly Glu Arg
                    500                 505                 510
        Val Ala Leu Leu Gly Gly Asn Gly Ala Gly Lys Ser Thr Leu Leu Arg
                    515                 520                 525
        Leu Leu Ser Gly Leu Leu Asp Ala Gln Ala Gly Arg Leu Leu Leu Asp
                    530                 535                 540
        Asp Val Ser Leu Thr Gln Ile Asp Pro Ala Asp Arg Gln Arg Gly Ile
        545                 550                 555                 560
        Gly Tyr Leu Pro Gln Asp Val Ala Leu Phe His Gly Ser Leu Arg Asp
                        565                 570                 575
        Asn Leu Asn Leu Glu Asn Ala Ala Leu Gly Asp Glu Leu Leu Glu
                    580                 585                 590
        Thr Leu Asp Gly Val Gly Leu Gly Ala Phe Val Arg Gly His Pro Leu
                    595                 600                 605
        Gly Leu Asp Met Pro Ile Gln Gly Asn Ala Ser Leu Ser Gly Gly Gln
                    610                 615                 620
        Arg Gln Ala Val Gly Leu Ala Arg Val Leu Leu Gln Asp Pro Pro Ile
        625                 630                 635                 640
        Leu Leu Leu Asp Glu Pro Thr Ala Ala Phe Asp Gln Gly Ser Glu Lys
                        645                 650                 655
        Gln Val Ile Asp Tyr Leu Gln Gln Trp Leu Gly Lys Arg Thr Leu Val
                        660                 665                 670
        Ile Thr Thr His Lys Lys Ser Met Leu Ala Leu Val Glu Arg Ala Val
                    675                 680                 685
        Val Leu Arg Gln Gly Arg Val Ile Met Asp Gly Pro Leu Glu Gln Val
                    690                 695                 700
        Val Gln Gly Asn Gln Val Gln Ala Pro Gln Ala Glu Gly Gly Asn
        705                 710                 715                 720
        His Gly Leu

<210> SEQ ID NO 9
<211> LENGTH: 1188
<212> TYPE: DNA
<213> ORGANISM: Pseudomonas aeruginosa
<220> FEATURE:
<221> NAME/KEY: CDS
<222> LOCATION: (1)...(1185)

<400> SEQUENCE: 9 atg gac tct gac cgc gac gcc gcc gcc ctg cgc cgg caa ctg gcc gac       48
Met Asp Ser Asp Arg Asp Ala Ala Ala Leu Arg Arg Gln Leu Ala Asp
 1               5                  10                  15 ccg ttg ctg gcg gct acc cac ccg gtc tac cgg ccg ctg ctc tgg acc       96
Pro Leu Leu Ala Ala Thr His Pro Val Tyr Arg Pro Leu Leu Trp Thr
                20                  25                  30 ctg ctc ggt tgc gtg ctg ctg ttc atc ggc tgg gcg gcc tgg gcg caa      144
Leu Leu Gly Cys Val Leu Leu Phe Ile Gly Trp Ala Ala Trp Ala Gln
            35                  40                  45 ctg gac gag gtg acc cgc ggc gac ggt cgg gtc gtg ccg ttc agc cgc      192
Leu Asp Glu Val Thr Arg Gly Asp Gly Arg Val Val Pro Phe Ser Arg
        50                  55                  60 atc cag aag atc cag agc ctg gag ggc ggc atc ctc gac cgc ctg ctg      240
Ile Gln Lys Ile Gln Ser Leu Glu Gly Gly Ile Leu Asp Arg Leu Leu
 65                  70                  75                  80
```

-continued

```
gtg aag gag ggc gac ctg gtg gaa gtc ggc cag ccg ctg gtg cgc ctc      288
Val Lys Glu Gly Asp Leu Val Glu Val Gly Gln Pro Leu Val Arg Leu
                85                  90                  95 gac gag acg cgc ttc ctc acc aac ttc cag gag tcg gcg aac cag gcc      336
Asp Glu Thr Arg Phe Leu Thr Asn Phe Gln Glu Ser Ala Asn Gln Ala
            100                 105                 110 agc gtg ctg cgc gcg gcc att gcc cgg ctc gac gcc gag gtg cta ggc      384
Ser Val Leu Arg Ala Ala Ile Ala Arg Leu Asp Ala Glu Val Leu Gly
        115                 120                 125 aag aag agc atc gag ttc ccg ccg gac gtc gat ccc gag ggg ccg ctg      432
Lys Lys Ser Ile Glu Phe Pro Pro Asp Val Asp Pro Glu Gly Pro Leu
    130                 135                 140 gcg cgt tcc gaa cgc gag ctg ttc aag tcg cgc cgc gac aaa ctg gtg      480
Ala Arg Ser Glu Arg Glu Leu Phe Lys Ser Arg Arg Asp Lys Leu Val
145                 150                 155                 160 gag ggc acc cag gcg atc cag cgg cag atc cac ctg gcg cag agc cag      528
Glu Gly Thr Gln Ala Ile Gln Arg Gln Ile His Leu Ala Gln Ser Gln
                165                 170                 175 ctc gac ctg gtt cgc ccg ctg gtg gcc aag cgt gcg gtg agc cag atg      576
Leu Asp Leu Val Arg Pro Leu Val Ala Lys Arg Ala Val Ser Gln Met
            180                 185                 190 gag gcg ctc aag ctg agc cag gac atc gcc acc ctc agc ggc aag ctg      624
Glu Ala Leu Lys Leu Ser Gln Asp Ile Ala Thr Leu Ser Gly Lys Leu
        195                 200                 205 acc gag ctg aaa agc acc tat ttc cag gat gcc tat acc gag cgc gcc      672
Thr Glu Leu Lys Ser Thr Tyr Phe Gln Asp Ala Tyr Thr Glu Arg Ala
    210                 215                 220 cag cgc aag gcc gat ctc agc gcc ctg gaa ccg atc gtc cag cag cgc      720
Gln Arg Lys Ala Asp Leu Ser Ala Leu Glu Pro Ile Val Gln Gln Arg
225                 230                 235                 240 cag gac cag ttg cgc cgc acc gag atc ctg tcg cca gtg cgc ggg cgg      768
Gln Asp Gln Leu Arg Arg Thr Glu Ile Leu Ser Pro Val Arg Gly Arg
                245                 250                 255 gtg aac acc gtg ctg atc aac acc cgc ggc ggg gtg atc cag ccc ggc      816
Val Asn Thr Val Leu Ile Asn Thr Arg Gly Gly Val Ile Gln Pro Gly
            260                 265                 270 gag ccg atc atg gaa gtg atc ccg gta gag gag cgt ctg ctg gtg gag      864
Glu Pro Ile Met Glu Val Ile Pro Val Glu Glu Arg Leu Leu Val Glu
        275                 280                 285 gcg aag atc aag ccg cgc gac gtg gcc ttc ctg gtt ccc ggc atg ccg      912
Ala Lys Ile Lys Pro Arg Asp Val Ala Phe Leu Val Pro Gly Met Pro
    290                 295                 300 gcc aag gtg aag atc acc gcc tac gac tac acc atc tac ggc gac ctc      960
Ala Lys Val Lys Ile Thr Ala Tyr Asp Tyr Thr Ile Tyr Gly Asp Leu
305                 310                 315                 320 aag ggc acc ctg gag cag atc agt gcc gac acc atc gag gag gac acc     1008
Lys Gly Thr Leu Glu Gln Ile Ser Ala Asp Thr Ile Glu Glu Asp Thr
                325                 330                 335 ccg cat ggc aag gag tcc tac tac cag gtg ctg atc aag acc gat ggc     1056
Pro His Gly Lys Glu Ser Tyr Tyr Gln Val Leu Ile Lys Thr Asp Gly
            340                 345                 350 agc cag ttg aag cgc ggc gag gag gta ttg ccg atc att ccg ggg atg     1104
Ser Gln Leu Lys Arg Gly Glu Glu Val Leu Pro Ile Ile Pro Gly Met
        355                 360                 365 gtc gcc gag gtg gac atc ctc agc ggc aag cgc agc gtg ctc aac tac     1152
Val Ala Glu Val Asp Ile Leu Ser Gly Lys Arg Ser Val Leu Asn Tyr
    370                 375                 380 ctg ctg cgg ccg ctg atc aag gcg cgc ctt tac tga                     1188
Leu Leu Arg Pro Leu Ile Lys Ala Arg Leu Tyr
```

385 390 395

<210> SEQ ID NO 10
<211> LENGTH: 395
<212> TYPE: PRT
<213> ORGANISM: Pseudomonas aeruginosa

<400> SEQUENCE: 10

Met Asp Ser Asp Arg Asp Ala Ala Leu Arg Arg Gln Leu Ala Asp
1               5                   10                  15

Pro Leu Ala Ala Thr His Pro Val Tyr Arg Pro Leu Leu Trp Thr
                20                  25                  30

Leu Leu Gly Cys Val Leu Leu Phe Ile Gly Trp Ala Ala Trp Ala Gln
            35                  40                  45

Leu Asp Glu Val Thr Arg Gly Asp Gly Arg Val Val Pro Phe Ser Arg
    50                  55                  60

Ile Gln Lys Ile Gln Ser Leu Glu Gly Gly Ile Leu Asp Arg Leu Leu
65                  70                  75                  80

Val Lys Glu Gly Asp Leu Val Glu Val Gly Gln Pro Leu Val Arg Leu
                85                  90                  95

Asp Glu Thr Arg Phe Leu Thr Asn Phe Gln Glu Ser Ala Asn Gln Ala
                100                 105                 110

Ser Val Leu Arg Ala Ala Ile Ala Arg Leu Asp Ala Glu Val Leu Gly
            115                 120                 125

Lys Lys Ser Ile Glu Phe Pro Pro Asp Val Asp Pro Glu Gly Pro Leu
130                 135                 140

Ala Arg Ser Glu Arg Glu Leu Phe Lys Ser Arg Arg Asp Lys Leu Val
145                 150                 155                 160

Glu Gly Thr Gln Ala Ile Gln Arg Gln Ile His Leu Ala Gln Ser Gln
                165                 170                 175

Leu Asp Leu Val Arg Pro Leu Val Ala Lys Arg Ala Val Ser Gln Met
            180                 185                 190

Glu Ala Leu Lys Leu Ser Gln Asp Ile Ala Thr Leu Ser Gly Lys Leu
            195                 200                 205

Thr Glu Leu Lys Ser Thr Tyr Phe Gln Asp Ala Tyr Thr Glu Arg Ala
210                 215                 220

Gln Arg Lys Ala Asp Leu Ser Ala Leu Glu Pro Ile Val Gln Gln Arg
225                 230                 235                 240

Gln Asp Gln Leu Arg Arg Thr Glu Ile Leu Ser Pro Val Arg Gly Arg
                245                 250                 255

Val Asn Thr Val Leu Ile Asn Thr Arg Gly Gly Val Ile Gln Pro Gly
            260                 265                 270

Glu Pro Ile Met Glu Val Ile Pro Val Glu Glu Arg Leu Leu Val Glu
            275                 280                 285

Ala Lys Ile Lys Pro Arg Asp Val Ala Phe Leu Val Pro Gly Met Pro
            290                 295                 300

Ala Lys Val Lys Ile Thr Ala Tyr Asp Tyr Thr Ile Tyr Gly Asp Leu
305                 310                 315                 320

Lys Gly Thr Leu Glu Gln Ile Ser Ala Asp Thr Ile Glu Glu Asp Thr
                325                 330                 335

Pro His Gly Lys Glu Ser Tyr Tyr Gln Val Leu Ile Lys Thr Asp Gly
            340                 345                 350

Ser Gln Leu Lys Arg Gly Glu Glu Val Leu Pro Ile Ile Pro Gly Met
            355                 360                 365

```
                    Val Ala Glu Val Asp Ile Leu Ser Gly Lys Arg Ser Val Leu Asn Tyr
                        370                 375                 380

Leu Leu Arg Pro Leu Ile Lys Ala Arg Leu Tyr
                    385                 390                 395

<210> SEQ ID NO 11
<211> LENGTH: 1257
<212> TYPE: DNA
<213> ORGANISM: Pseudomonas aeruginosa
<220> FEATURE:
<221> NAME/KEY: CDS
<222> LOCATION: (1)...(1254)

<400> SEQUENCE: 11 atg ttt cgc cag gaa gcc ctc gac gcc cag cat gcc ggc ggc ctg ggc        48
Met Phe Arg Gln Glu Ala Leu Asp Ala Gln His Ala Gly Gly Leu Gly
  1               5                  10                  15 gag atc gtg ctg atc cgc ccg gtc tcc ttc act ttt ctc acc ctg ctg        96
Glu Ile Val Leu Ile Arg Pro Val Ser Phe Thr Phe Leu Thr Leu Leu
                 20                  25                  30 gcc gcg gcg atg gcg ctg ctg gtg gtg ggc ttc ttc ctg ttc ggc agc       144
Ala Ala Ala Met Ala Leu Leu Val Val Gly Phe Phe Leu Phe Gly Ser
             35                  40                  45 tac acc aag cgc agc acc gtc agc ggc caa ttg gtg ccc gcc agc ggc       192
Tyr Thr Lys Arg Ser Thr Val Ser Gly Gln Leu Val Pro Ala Ser Gly
         50                  55                  60 cag gtc aag gtg cac gcg ccg cag gcc ggc atc gtg ctg cgc aag ttc       240
Gln Val Lys Val His Ala Pro Gln Ala Gly Ile Val Leu Arg Lys Phe
 65                  70                  75                  80 gtc cag gaa ggc cag gcg gta cga cgt ggc gag cgc ctg atg gtg ctt       288
Val Gln Glu Gly Gln Ala Val Arg Arg Gly Glu Arg Leu Met Val Leu
                 85                  90                  95 tcc agc gaa cgc tac ggc agc gat gcc ggg ccg gtg cag gcc ggc atc       336
Ser Ser Glu Arg Tyr Gly Ser Asp Ala Gly Pro Val Gln Ala Gly Ile
                100                 105                 110 agc agg cgc ctg gaa caa cgc cgc gac tcc ctg cgc gac gaa ctg gaa       384
Ser Arg Arg Leu Glu Gln Arg Arg Asp Ser Leu Arg Asp Glu Leu Glu
            115                 120                 125 aag ctt cgc cgc ctg caa gac gac gag cgc gac agc ctg acc agc aag       432
Lys Leu Arg Arg Leu Gln Asp Asp Glu Arg Asp Ser Leu Thr Ser Lys
        130                 135                 140 gtc gcc agc ctg cag cgc gaa ctc acc acc ctc gcc gcc cag acc gac       480
Val Ala Ser Leu Gln Arg Glu Leu Thr Thr Leu Ala Ala Gln Thr Asp
145                 150                 155                 160 agc cag caa cgc ctg ctg gcg ctg gcc agc gac gcc gcg cgc tac           528
Ser Gln Gln Arg Leu Leu Ala Leu Ala Ser Asp Ala Ala Arg Tyr
                165                 170                 175 cag ggg ctg atg gac aag ggc tac atc tcc atg gac cag ttg cag cag       576
Gln Gly Leu Met Asp Lys Gly Tyr Ile Ser Met Asp Gln Leu Gln Gln
            180                 185                 190 cgc cag gcc gag ctg ctc ggc cag cgc cag acc ctg caa ggc ctg gag       624
Arg Gln Ala Glu Leu Leu Gly Gln Arg Gln Thr Leu Gln Gly Leu Glu
        195                 200                 205 cgc gaa cgc acg tcg ctg cgg cag cag ttg acc gag cgc cgc aac gaa       672
Arg Glu Arg Thr Ser Leu Arg Gln Gln Leu Thr Glu Arg Arg Asn Glu
    210                 215                 220 ctc gcc ggg ctt tcc gcg cgc cag gcc aac cag ctc gcg gaa acc cgc       720
Leu Ala Gly Leu Ser Ala Arg Gln Ala Asn Gln Leu Ala Glu Thr Arg
225                 230                 235                 240 cgc cag ctc agc gcg gtg gag cag gac ctg gcc gaa agc gaa gcc aag       768
Arg Gln Leu Ser Ala Val Glu Gln Asp Leu Ala Glu Ser Glu Ala Lys
```

-continued

```
                  245                 250                 255
cgc acc ttg ctg gtc acc gcg ccg gag agc ggc atc gcc acc gcc gtg          816
Arg Thr Leu Leu Val Thr Ala Pro Glu Ser Gly Ile Ala Thr Ala Val
            260                 265                 270 ctc gcc gaa gcc ggg cag acc gtc gac agc tcg cgt ccg ctg ctg agc          864
Leu Ala Glu Ala Gly Gln Thr Val Asp Ser Ser Arg Pro Leu Leu Ser
        275                 280                 285 atc gtt ccc gcc gac acc ccg ttg cag gcc gaa ctc tac gcg ccg agc          912
Ile Val Pro Ala Asp Thr Pro Leu Gln Ala Glu Leu Tyr Ala Pro Ser
    290                 295                 300 aag tcc atc ggt ttc atc cgg ccg ggc gac gcg gtg ctg atc cgc tac          960
Lys Ser Ile Gly Phe Ile Arg Pro Gly Asp Ala Val Leu Ile Arg Tyr
305                 310                 315                 320 cag gcc tat ccg tac cag aag ttc ggc cag tac cac ggc aag gtg cag         1008
Gln Ala Tyr Pro Tyr Gln Lys Phe Gly Gln Tyr His Gly Lys Val Gln
                325                 330                 335 tcg atc tcc cgc gcc agc gtc tcc tat gcc gag ctt tcc agc atg gtc         1056
Ser Ile Ser Arg Ala Ser Val Ser Tyr Ala Glu Leu Ser Ser Met Val
            340                 345                 350 ggc ggc gta ccg ggg ctc ggc cag gat ggc gag cag ctg tac cgg ctg         1104
Gly Gly Val Pro Gly Leu Gly Gln Asp Gly Glu Gln Leu Tyr Arg Leu
        355                 360                 365 cgg gta acc ctc gac gac cag gcg gtg acc gcc tac ggc cag ccg cgt         1152
Arg Val Thr Leu Asp Asp Gln Ala Val Thr Ala Tyr Gly Gln Pro Arg
    370                 375                 380 ccg ctg cag agc ggc atg ctg ctg gac gcc gac atc ctc cag gac acc         1200
Pro Leu Gln Ser Gly Met Leu Leu Asp Ala Asp Ile Leu Gln Asp Thr
385                 390                 395                 400 cgg cgc ctc tac gaa tgg gtg ctg gaa ccg ctc tac agc ctg acc ggc         1248
Arg Arg Leu Tyr Glu Trp Val Leu Glu Pro Leu Tyr Ser Leu Thr Gly
                405                 410                 415 aaa ctc tag                                                             1257
Lys Leu
```

<210> SEQ ID NO 12
<211> LENGTH: 418
<212> TYPE: PRT
<213> ORGANISM: Pseudomonas aeruginosa

<400> SEQUENCE: 12

```
Met Phe Arg Gln Glu Ala Leu Asp Ala Gln His Ala Gly Gly Leu Gly
 1               5                  10                  15

Glu Ile Val Leu Ile Arg Pro Val Ser Phe Thr Phe Leu Thr Leu Leu
            20                  25                  30

Ala Ala Ala Met Ala Leu Leu Val Val Gly Phe Phe Leu Phe Gly Ser
        35                  40                  45

Tyr Thr Lys Arg Ser Thr Val Ser Gly Gln Leu Val Pro Ala Ser Gly
    50                  55                  60

Gln Val Lys Val His Ala Pro Gln Ala Gly Ile Val Leu Arg Lys Phe
65                  70                  75                  80

Val Gln Glu Gly Gln Ala Val Arg Arg Gly Glu Arg Leu Met Val Leu
                85                  90                  95

Ser Ser Glu Arg Tyr Gly Ser Asp Ala Gly Pro Val Gln Ala Gly Ile
            100                 105                 110

Ser Arg Arg Leu Glu Gln Arg Arg Asp Ser Leu Arg Asp Glu Leu Glu
        115                 120                 125

Lys Leu Arg Arg Leu Gln Asp Asp Glu Arg Asp Ser Leu Thr Ser Lys
    130                 135                 140
```

```
Val Ala Ser Leu Gln Arg Glu Leu Thr Thr Leu Ala Ala Gln Thr Asp
145                 150                 155                 160

Ser Gln Gln Arg Leu Leu Ala Leu Ala Ser Asp Ala Ala Arg Tyr
            165                 170                 175

Gln Gly Leu Met Asp Lys Gly Tyr Ile Ser Met Asp Gln Leu Gln Gln
            180                 185                 190

Arg Gln Ala Glu Leu Leu Gly Gln Arg Gln Thr Leu Gln Gly Leu Glu
            195                 200                 205

Arg Glu Arg Thr Ser Leu Arg Gln Gln Leu Thr Glu Arg Arg Asn Glu
            210                 215                 220

Leu Ala Gly Leu Ser Ala Arg Gln Ala Asn Gln Leu Ala Glu Thr Arg
225                 230                 235                 240

Arg Gln Leu Ser Ala Val Glu Gln Asp Leu Ala Glu Ser Glu Ala Lys
                245                 250                 255

Arg Thr Leu Leu Val Thr Ala Pro Glu Ser Gly Ile Ala Thr Ala Val
                260                 265                 270

Leu Ala Glu Ala Gly Gln Thr Val Asp Ser Ser Arg Pro Leu Leu Ser
            275                 280                 285

Ile Val Pro Ala Asp Thr Pro Leu Gln Ala Glu Leu Tyr Ala Pro Ser
290                 295                 300

Lys Ser Ile Gly Phe Ile Arg Pro Gly Asp Ala Val Leu Ile Arg Tyr
305                 310                 315                 320

Gln Ala Tyr Pro Tyr Gln Lys Phe Gly Gln Tyr His Gly Lys Val Gln
                325                 330                 335

Ser Ile Ser Arg Ala Ser Val Ser Tyr Ala Glu Leu Ser Ser Met Val
                340                 345                 350

Gly Gly Val Pro Gly Leu Gly Gln Asp Gly Glu Gln Leu Tyr Arg Leu
            355                 360                 365

Arg Val Thr Leu Asp Asp Gln Ala Val Thr Ala Tyr Gly Gln Pro Arg
            370                 375                 380

Pro Leu Gln Ser Gly Met Leu Leu Asp Ala Asp Ile Leu Gln Asp Thr
385                 390                 395                 400

Arg Arg Leu Tyr Glu Trp Val Leu Glu Pro Leu Tyr Ser Leu Thr Gly
                405                 410                 415

Lys Leu

<210> SEQ ID NO 13
<211> LENGTH: 2160
<212> TYPE: DNA
<213> ORGANISM: Pseudomonas aeruginosa
<220> FEATURE:
<221> NAME/KEY: CDS
<222> LOCATION: (1)...(2157)

<400> SEQUENCE: 13 atg gcc ttt ctc gac gct ctc gcc ctg cgc ctg ggc cgc cgc ctg ccg      48
Met Ala Phe Leu Asp Ala Leu Ala Leu Arg Leu Gly Arg Arg Leu Pro
1               5                   10                  15 ctg gtg ctg cag acc gaa gcc acc gaa tgc ggc ctg gcc tgc ctg gcg      96
Leu Val Leu Gln Thr Glu Ala Thr Glu Cys Gly Leu Ala Cys Leu Ala
            20                  25                  30 atg atc gcc ggc tac cac ggc cac cat acc ggc ctg atg gaa ctg cgc     144
Met Ile Ala Gly Tyr His Gly His His Thr Gly Leu Met Glu Leu Arg
        35                  40                  45 cgg cgc ttc tcc gta tcg ctc aag ggc atc tcc ctc aag caa ctg atc     192
Arg Arg Phe Ser Val Ser Leu Lys Gly Ile Ser Leu Lys Gln Leu Ile
```

```
                50                  55                  60
cag acc gcc cac cgc ctc ggc ctg ggt acc cgc gcg gtg aag ctc gac       240
Gln Thr Ala His Arg Leu Gly Leu Gly Thr Arg Ala Val Lys Leu Asp
 65                  70                  75                  80 ctc ggc gac ctc ggc aag ctc aag ctg ccc tgc gtg ctg cac tgg aac       288
Leu Gly Asp Leu Gly Lys Leu Lys Leu Pro Cys Val Leu His Trp Asn
                     85                  90                  95 ttc aac cac ttc gtc gtg ctc aag gcg gtc gac ggg cgc ggc gcg gtg       336
Phe Asn His Phe Val Val Leu Lys Ala Val Asp Gly Arg Gly Ala Val
                100                 105                 110 ctc cac gac ccc gcc cac ggc cag cgc cgg ctg ggc ctg gag gaa gtc       384
Leu His Asp Pro Ala His Gly Gln Arg Arg Leu Gly Leu Glu Glu Val
            115                 120                 125 tcg cgg agc ttc acc ggg gta gcc ctg gaa ctc tgg ccg gag agc ggc       432
Ser Arg Ser Phe Thr Gly Val Ala Leu Glu Leu Trp Pro Glu Ser Gly
        130                 135                 140 ttc gag aaa cag gag gcg ccg ccg cgg atc aag ctg ctg ggc atg ctc       480
Phe Glu Lys Gln Glu Ala Pro Pro Arg Ile Lys Leu Leu Gly Met Leu
145                 150                 155                 160 ggc aag gtc acc ggg ctg tac cgc tcg ctg gcc cag gtg ctg ctg ctc       528
Gly Lys Val Thr Gly Leu Tyr Arg Ser Leu Ala Gln Val Leu Leu Leu
                165                 170                 175 gcc ggc gcg ctg gaa gtg ttc tcg ctg atc agt ccg ttc ttc ctg caa       576
Ala Gly Ala Leu Glu Val Phe Ser Leu Ile Ser Pro Phe Phe Leu Gln
            180                 185                 190 tgg acc atc gac aac gtc atc gtc agc gaa gac cgt gac ctg ctc agc       624
Trp Thr Ile Asp Asn Val Ile Val Ser Glu Asp Arg Asp Leu Leu Ser
        195                 200                 205 acc ctg gcc atc ggc ttc ggc ctg ttg ctg ctg atg cag cag gcg gtc       672
Thr Leu Ala Ile Gly Phe Gly Leu Leu Leu Leu Met Gln Gln Ala Val
210                 215                 220 agc ggg gtg cgc gcc tgg gtg atg atg cac atg agc acc ctg ctc ggc       720
Ser Gly Val Arg Ala Trp Val Met Met His Met Ser Thr Leu Leu Gly
225                 230                 235                 240 gtg cag tgg cag gcc aac gtc ttc agc cac ctg ctg cgg ctg ccc gcg       768
Val Gln Trp Gln Ala Asn Val Phe Ser His Leu Leu Arg Leu Pro Ala
                245                 250                 255 cag tat ttc gag aag cgc cac ctg ggc gac gtg gtg tcg cgc ttc ggc       816
Gln Tyr Phe Glu Lys Arg His Leu Gly Asp Val Val Ser Arg Phe Gly
            260                 265                 270 gcg gtg aac agc atc cag cag acc ctc acc gcg gcc ttc ctc tcg gcg       864
Ala Val Asn Ser Ile Gln Gln Thr Leu Thr Ala Ala Phe Leu Ser Ala
        275                 280                 285 gtg ctg gac ggc ctg atg acc gtc gcc acc ctc ggc atg atg ctg ctc       912
Val Leu Asp Gly Leu Met Thr Val Ala Thr Leu Gly Met Met Leu Leu
290                 295                 300 tac agt ccg cca ctg gcg gcc atc gcc atc gcc gcc atg agc ctc tac       960
Tyr Ser Pro Pro Leu Ala Ala Ile Ala Ile Ala Ala Met Ser Leu Tyr
305                 310                 315                 320 gcc ctc ggc cgc tgg atc tgg tac cgg ccg ttg cgc aac gcc acc gag      1008
Ala Leu Gly Arg Trp Ile Trp Tyr Arg Pro Leu Arg Asn Ala Thr Glu
                325                 330                 335 gag cag atc gtc cac gcc gcg cgc cag cag agc cac ttc ctc gag acg      1056
Glu Gln Ile Val His Ala Ala Arg Gln Gln Ser His Phe Leu Glu Thr
            340                 345                 350 gtg cgc ggc atc cgc ccg ctg aag ctg ttc cag cgc cag gac gag cgc      1104
Val Arg Gly Ile Arg Pro Leu Lys Leu Phe Gln Arg Gln Asp Glu Arg
        355                 360                 365 cgc tcg gta tgg ctc ggc ctg ctg gtg gaa cag atc aac gcc ggc ctg      1152
```

```
                                                          -continued

Arg Ser Val Trp Leu Gly Leu Leu Val Glu Gln Ile Asn Ala Gly Leu
    370                 375                 380 cgt acg cag aag ctg caa ctg ttc tac cag cag ctc aac ggc ctg ctg    1200
Arg Thr Gln Lys Leu Gln Leu Phe Tyr Gln Gln Leu Asn Gly Leu Leu
385                 390                 395                 400 ttc ggc gtg gag aac ctg ctg gtg atc tgg ctc ggc gcg acc atg gtg    1248
Phe Gly Val Glu Asn Leu Leu Val Ile Trp Leu Gly Ala Thr Met Val
                405                 410                 415 atg gac ggc cag ttc agc gtc ggc atc ctg atg gcc ttc aac gcc tac    1296
Met Asp Gly Gln Phe Ser Val Gly Ile Leu Met Ala Phe Asn Ala Tyr
            420                 425                 430 aag tcg cag ttc gac agc cgc gtc ggc agc ctg atc gac aag ttc ttc    1344
Lys Ser Gln Phe Asp Ser Arg Val Gly Ser Leu Ile Asp Lys Phe Phe
        435                 440                 445 gag ctg cgc atg ctc cag ttg cag ggc gag cgc ctg gcc gac atc gtg    1392
Glu Leu Arg Met Leu Gln Leu Gln Gly Glu Arg Leu Ala Asp Ile Val
    450                 455                 460 ctc cag gcc ccg gag gtc agc cac ggc gac atc ctc ccg gag aac ctc    1440
Leu Gln Ala Pro Glu Val Ser His Gly Asp Ile Leu Pro Glu Asn Leu
465                 470                 475                 480 cgc gag cgc gag gcg agc atc gag atc cag ggc ctg cgc tac cgc tac    1488
Arg Glu Arg Glu Ala Ser Ile Glu Ile Gln Gly Leu Arg Tyr Arg Tyr
                485                 490                 495 gcg gaa cag gag ccc tgg gtc ctc gac ggc ctc gac ctg cgc atc gcc    1536
Ala Glu Gln Glu Pro Trp Val Leu Asp Gly Leu Asp Leu Arg Ile Ala
            500                 505                 510 ggc ggc gag tcg gtg gcc atc gtc ggc ccc tcg ggc tgc ggc aag agc    1584
Gly Gly Glu Ser Val Ala Ile Val Gly Pro Ser Gly Cys Gly Lys Ser
        515                 520                 525 acc ctg ttc aac gtc ctg ctg ggc atc ctc ccg cca gtg gag gga cag    1632
Thr Leu Phe Asn Val Leu Leu Gly Ile Leu Pro Pro Val Glu Gly Gln
    530                 535                 540 atc cgc atg gcc ggc ctg gac ctt gcg caa ctg ggc ctg gac ggc ctg    1680
Ile Arg Met Ala Gly Leu Asp Leu Ala Gln Leu Gly Leu Asp Gly Leu
545                 550                 555                 560 cgc gaa ctg gtc ggc acg gtg ctg cag gac gac gtg ctg ttc gcc ggt    1728
Arg Glu Leu Val Gly Thr Val Leu Gln Asp Asp Val Leu Phe Ala Gly
                565                 570                 575 tcg ctc agc gac aac atc agt ttc ttc gac ccg caa ccg gac atg ccc    1776
Ser Leu Ser Asp Asn Ile Ser Phe Phe Asp Pro Gln Pro Asp Met Pro
            580                 585                 590 tgg ctg ctg cag tgc gcg cag atg gct gcc atc cac gat gac atc cag    1824
Trp Leu Leu Gln Cys Ala Gln Met Ala Ala Ile His Asp Asp Ile Gln
        595                 600                 605 gcc atg ccg atg ggc tac aac acc ctg gtc ggc gac atg ggc acg gtg    1872
Ala Met Pro Met Gly Tyr Asn Thr Leu Val Gly Asp Met Gly Thr Val
    610                 615                 620 ctc tcc ggc ggc cag aag cag cgg gtg atg ctg gcc cgg gcg ctg tac    1920
Leu Ser Gly Gly Gln Lys Gln Arg Val Met Leu Ala Arg Ala Leu Tyr
625                 630                 635                 640 aag aag ccg cgc atc ctg ttc ctc gac gaa gcc acc agc cac ctc gac    1968
Lys Lys Pro Arg Ile Leu Phe Leu Asp Glu Ala Thr Ser His Leu Asp
                645                 650                 655 gta cac tgc gaa cag cgg gtc aac gcc gcc att cga gcg ctg cgc atc    2016
Val His Cys Glu Gln Arg Val Asn Ala Ala Ile Arg Ala Leu Arg Ile
            660                 665                 670 acc cgc atc atg gtc gcc cat cgg ccc gag acc atc gcc tcg gcg gac    2064
Thr Arg Ile Met Val Ala His Arg Pro Glu Thr Ile Ala Ser Ala Asp
        675                 680                 685
```

-continued

```
cgc gtg ata gtc ctc ggc cag ggc aag gta agc ctc gac gaa agc acc    2112
Arg Val Ile Val Leu Gly Gln Gly Lys Val Ser Leu Asp Glu Ser Thr
    690             695                 700 gcg cgc ctg gcc gaa cgc cag gcc gcc gcg gcg cgg gag cag gcc        2157
Ala Arg Leu Ala Glu Arg Gln Ala Ala Ala Ala Arg Glu Gln Ala
705                 710                 715 tga                                                                 2160
```

<210> SEQ ID NO 14
<211> LENGTH: 719
<212> TYPE: PRT
<213> ORGANISM: Pseudomonas aeruginosa

<400> SEQUENCE: 14

```
Met Ala Phe Leu Asp Ala Leu Ala Leu Arg Leu Gly Arg Arg Leu Pro
 1               5                  10                  15

Leu Val Leu Gln Thr Glu Ala Thr Glu Cys Gly Leu Ala Cys Leu Ala
            20                  25                  30

Met Ile Ala Gly Tyr His Gly His Thr Gly Leu Met Glu Leu Arg
        35                  40                  45

Arg Arg Phe Ser Val Ser Leu Lys Gly Ile Ser Leu Lys Gln Leu Ile
    50                  55                  60

Gln Thr Ala His Arg Leu Gly Leu Gly Thr Arg Ala Val Lys Leu Asp
65                  70                  75                  80

Leu Gly Asp Leu Gly Lys Leu Lys Leu Pro Cys Val Leu His Trp Asn
                85                  90                  95

Phe Asn His Phe Val Val Leu Lys Ala Val Asp Gly Arg Gly Ala Val
            100                 105                 110

Leu His Asp Pro Ala His Gly Gln Arg Arg Leu Gly Leu Glu Glu Val
        115                 120                 125

Ser Arg Ser Phe Thr Gly Val Ala Leu Glu Leu Trp Pro Glu Ser Gly
    130                 135                 140

Phe Glu Lys Gln Glu Ala Pro Pro Arg Ile Lys Leu Leu Gly Met Leu
145                 150                 155                 160

Gly Lys Val Thr Gly Leu Tyr Arg Ser Leu Ala Gln Val Leu Leu Leu
                165                 170                 175

Ala Gly Ala Leu Glu Val Phe Ser Leu Ile Ser Pro Phe Phe Leu Gln
            180                 185                 190

Trp Thr Ile Asp Asn Val Ile Val Ser Glu Asp Arg Asp Leu Leu Ser
        195                 200                 205

Thr Leu Ala Ile Gly Phe Gly Leu Leu Leu Met Gln Gln Ala Val
    210                 215                 220

Ser Gly Val Arg Ala Trp Val Met Met His Met Ser Thr Leu Leu Gly
225                 230                 235                 240

Val Gln Trp Gln Ala Asn Val Phe Ser His Leu Leu Arg Leu Pro Ala
                245                 250                 255

Gln Tyr Phe Glu Lys Arg His Leu Gly Asp Val Val Ser Arg Phe Gly
            260                 265                 270

Ala Val Asn Ser Ile Gln Gln Thr Leu Thr Ala Ala Phe Leu Ser Ala
        275                 280                 285

Val Leu Asp Gly Leu Met Thr Val Ala Thr Leu Gly Met Met Leu Leu
    290                 295                 300

Tyr Ser Pro Pro Leu Ala Ala Ile Ala Ile Ala Ala Met Ser Leu Tyr
305                 310                 315                 320

Ala Leu Gly Arg Trp Ile Trp Tyr Arg Pro Leu Arg Asn Ala Thr Glu
```

```
                     325                 330                 335
Glu Gln Ile Val His Ala Ala Arg Gln Gln Ser His Phe Leu Glu Thr
                340                 345                 350
Val Arg Gly Ile Arg Pro Leu Lys Leu Phe Gln Arg Gln Asp Glu Arg
            355                 360                 365
Arg Ser Val Trp Leu Gly Leu Val Glu Gln Ile Asn Ala Gly Leu
        370                 375                 380
Arg Thr Gln Lys Leu Gln Leu Phe Tyr Gln Gln Leu Asn Gly Leu Leu
385                 390                 395                 400
Phe Gly Val Glu Asn Leu Leu Val Ile Trp Leu Gly Ala Thr Met Val
                405                 410                 415
Met Asp Gly Gln Phe Ser Val Gly Ile Leu Met Ala Phe Asn Ala Tyr
                420                 425                 430
Lys Ser Gln Phe Asp Ser Arg Val Gly Ser Leu Ile Asp Lys Phe Phe
            435                 440                 445
Glu Leu Arg Met Leu Gln Leu Gln Gly Glu Arg Leu Ala Asp Ile Val
        450                 455                 460
Leu Gln Ala Pro Glu Val Ser His Gly Asp Ile Leu Pro Glu Asn Leu
465                 470                 475                 480
Arg Glu Arg Glu Ala Ser Ile Glu Ile Gln Gly Leu Arg Tyr Arg Tyr
                485                 490                 495
Ala Glu Gln Glu Pro Trp Val Leu Asp Gly Leu Asp Leu Arg Ile Ala
                500                 505                 510
Gly Gly Glu Ser Val Ala Ile Val Gly Pro Ser Gly Cys Gly Lys Ser
            515                 520                 525
Thr Leu Phe Asn Val Leu Leu Gly Ile Leu Pro Pro Val Glu Gly Gln
        530                 535                 540
Ile Arg Met Ala Gly Leu Asp Leu Ala Gln Leu Gly Leu Asp Gly Leu
545                 550                 555                 560
Arg Glu Leu Val Gly Thr Val Leu Gln Asp Asp Val Leu Phe Ala Gly
                565                 570                 575
Ser Leu Ser Asp Asn Ile Ser Phe Phe Asp Pro Gln Pro Asp Met Pro
                580                 585                 590
Trp Leu Leu Gln Cys Ala Gln Met Ala Ala Ile His Asp Asp Ile Gln
            595                 600                 605
Ala Met Pro Met Gly Tyr Asn Thr Leu Val Gly Asp Met Gly Thr Val
        610                 615                 620
Leu Ser Gly Gly Gln Lys Gln Arg Val Met Leu Ala Arg Ala Leu Tyr
625                 630                 635                 640
Lys Lys Pro Arg Ile Leu Phe Leu Asp Glu Ala Thr Ser His Leu Asp
                645                 650                 655
Val His Cys Glu Gln Arg Val Asn Ala Ala Ile Arg Ala Leu Arg Ile
                660                 665                 670
Thr Arg Ile Met Val Ala His Arg Pro Glu Thr Ile Ala Ser Ala Asp
            675                 680                 685
Arg Val Ile Val Leu Gly Gln Gly Lys Val Ser Leu Asp Glu Ser Thr
        690                 695                 700
Ala Arg Leu Ala Glu Arg Gln Ala Ala Ala Arg Glu Gln Ala
705                 710                 715
```

<210> SEQ ID NO 15
<211> LENGTH: 1416
<212> TYPE: DNA
<213> ORGANISM: Pseudomonas aeruginosa

```
<220> FEATURE:
<221> NAME/KEY: CDS
<222> LOCATION: (1)...(1413)

<400> SEQUENCE: 15 atg cgt gcc ctc gcc ggc ctg ttg tgc ggc ctg ctc ggc ctg gtt ccc        48
Met Arg Ala Leu Ala Gly Leu Leu Cys Gly Leu Leu Gly Leu Val Pro
1               5                   10                  15 ggc gcc gcc gcc tac gag ccg gac gtg ttc ggc acc acc ggc cag gtc        96
Gly Ala Ala Ala Tyr Glu Pro Asp Val Phe Gly Thr Thr Gly Gln Val
            20                  25                  30 gcc ggc cag gcg gtc tac gac ctc ggc ggc agc ggt ttg ccc tgc cgc        144
Ala Gly Gln Ala Val Tyr Asp Leu Gly Gly Ser Gly Leu Pro Cys Arg
        35                  40                  45 ggg ggg ccg cca ccg acc gag ctg agc ctg gag gaa gcc atc gag cgg        192
Gly Gly Pro Pro Pro Thr Glu Leu Ser Leu Glu Glu Ala Ile Glu Arg
50                  55                  60 atc ctc tgc cac gac ccg cag acc cgc ctc gcc tgg gcc aat gcc aag        240
Ile Leu Cys His Asp Pro Gln Thr Arg Leu Ala Trp Ala Asn Ala Lys
65                  70                  75                  80 gcc cag gcg gcc cag gtc ggg atc ggc aag tcc gcc tac ctg ccg cgc        288
Ala Gln Ala Ala Gln Val Gly Ile Gly Lys Ser Ala Tyr Leu Pro Arg
                85                  90                  95 ctg gac ggc cgt ctc gac gcc agt cgc ggc tac agc gac atg gat tat        336
Leu Asp Gly Arg Leu Asp Ala Ser Arg Gly Tyr Ser Asp Met Asp Tyr
            100                 105                 110 cgc gat gcc ccc tac ctc tcc ggc gac ggc cat cgc cac cgg cgc ggc        384
Arg Asp Ala Pro Tyr Leu Ser Gly Asp Gly His Arg His Arg Arg Gly
        115                 120                 125 gcc agc ctc caa ttg agc tgg gtg ctg ttc gac ttc ggc cgc cgc agc        432
Ala Ser Leu Gln Leu Ser Trp Val Leu Phe Asp Phe Gly Arg Arg Ser
130                 135                 140 gcc gcc ctg cgc aac gcc cag cag ttg ctg ctg gcg gcc aac gcc agc        480
Ala Ala Leu Arg Asn Ala Gln Gln Leu Leu Leu Ala Ala Asn Ala Ser
145                 150                 155                 160 cag gac gcg acc ctg cag aac acc ttc gcc ctc gcc gcc cag gcc tac        528
Gln Asp Ala Thr Leu Gln Asn Thr Phe Ala Leu Ala Ala Gln Ala Tyr
                165                 170                 175 tac gac gcc ctc gcc gcc cag cgc agc ctg gcc gcc tcg cgg cag gtc        576
Tyr Asp Ala Leu Ala Ala Gln Arg Ser Leu Ala Ala Ser Arg Gln Val
            180                 185                 190 gcg gag ctg gcg gcg cag aac ctg gaa gcc gcc gac gcc aag tac cgg        624
Ala Glu Leu Ala Ala Gln Asn Leu Glu Ala Ala Asp Ala Lys Tyr Arg
        195                 200                 205 gcc ggc gcc gcc gcc ctt tcc gat cgc ctg cag gcg cag acc gcg ctg        672
Ala Gly Ala Ala Ala Leu Ser Asp Arg Leu Gln Ala Gln Thr Ala Leu
210                 215                 220 tcc cag gcg agc ctc gcc cag gtc cgc gac gaa ggc gcc ctg agc aac        720
Ser Gln Ala Ser Leu Ala Gln Val Arg Asp Glu Gly Ala Leu Ser Asn
225                 230                 235                 240 gcc ctc ggc gtc atc gcc ctg cgc atg ggc ctg gcg ccg gat acc ccg        768
Ala Leu Gly Val Ile Ala Leu Arg Met Gly Leu Ala Pro Asp Thr Pro
                245                 250                 255 ctg cgc ctc tcc ggc gag ctg gag gcg caa ccc gac acc ggc ttc gtc        816
Leu Arg Leu Ser Gly Glu Leu Glu Ala Gln Pro Asp Thr Gly Phe Val
            260                 265                 270 aag gcc atc gac gag atg ctc gcc gaa gcc cgc cgc gag cat ccg gcg        864
Lys Ala Ile Asp Glu Met Leu Ala Glu Ala Arg Arg Glu His Pro Ala
        275                 280                 285 ctg ctc gcc gcc cag gcg cgg ctg aaa gcc gcc gcc gcc tcg gtg gag        912
```

```
      Leu Leu Ala Ala Gln Ala Arg Leu Lys Ala Ala Ala Ser Val Glu
          290                 295                 300 gaa agc cgc gcc gcc ggc cgg ccg agc ctg gcg ctg agc gcc aac ctg        960
Glu Ser Arg Ala Ala Gly Arg Pro Ser Leu Ala Leu Ser Ala Asn Leu
305                 310                 315                 320 gca cgc agc cat agc gac cag gcg atg gcg ttc aac ggc gat acc cgc       1008
Ala Arg Ser His Ser Asp Gln Ala Met Ala Phe Asn Gly Asp Thr Arg
                325                 330                 335 gaa cgc gac cgc agc atc ggc ctg caa ctg aac atc ccg ttg ttc gaa       1056
Glu Arg Asp Arg Ser Ile Gly Leu Gln Leu Asn Ile Pro Leu Phe Glu
            340                 345                 350 ggc ttc gaa cgc acc tac cag gtc cgc aac gcc ctg gcc cgc cgc gaa       1104
Gly Phe Glu Arg Thr Tyr Gln Val Arg Asn Ala Leu Ala Arg Arg Glu
        355                 360                 365 gcc agc gaa gcg gag ctg gcc gac acc gag cag cag gtt tcg ctg gag       1152
Ala Ser Glu Ala Glu Leu Ala Asp Thr Glu Gln Gln Val Ser Leu Glu
    370                 375                 380 gtg tgg aac aac tac cag tcg ctc agc gtc gag acc cgc agc ctg gcg       1200
Val Trp Asn Asn Tyr Gln Ser Leu Ser Val Glu Thr Arg Ser Leu Ala
385                 390                 395                 400 cgc acc cgc gaa ctg gtc gaa cag tcg cgg caa agc ctg gag gtg gtg       1248
Arg Thr Arg Glu Leu Val Glu Gln Ser Arg Gln Ser Leu Glu Val Val
                405                 410                 415 cag ggc cgc tac cgc tca ggg gtc ggc agc atg atc gag ctg ctc aac       1296
Gln Gly Arg Tyr Arg Ser Gly Val Gly Ser Met Ile Glu Leu Leu Asn
            420                 425                 430 gcc ctg acc gcc tac gcc agc gcc gag gac cag cac atc cgc gcc ctc       1344
Ala Leu Thr Ala Tyr Ala Ser Ala Glu Asp Gln His Ile Arg Ala Leu
        435                 440                 445 ggc aac tgg cag acc tcg cgc ctg cga ctg gcg gcg agc ctc ggt cgc       1392
Gly Asn Trp Gln Thr Ser Arg Leu Arg Leu Ala Ala Ser Leu Gly Arg
    450                 455                 460 ctg ggt ttc tgg agc ctg cgc tga                                       1416
Leu Gly Phe Trp Ser Leu Arg
465                 470

<210> SEQ ID NO 16
<211> LENGTH: 471
<212> TYPE: PRT
<213> ORGANISM: Pseudomonas aeruginosa

<400> SEQUENCE: 16

Met Arg Ala Leu Ala Gly Leu Cys Gly Leu Leu Gly Leu Val Pro
  1               5                  10                  15

Gly Ala Ala Ala Tyr Glu Pro Asp Val Phe Gly Thr Thr Gly Gln Val
                20                  25                  30

Ala Gly Gln Ala Val Tyr Asp Leu Gly Gly Ser Gly Leu Pro Cys Arg
            35                  40                  45

Gly Gly Pro Pro Thr Glu Leu Ser Leu Glu Glu Ala Ile Glu Arg
        50                  55                  60

Ile Leu Cys His Asp Pro Gln Thr Arg Leu Ala Trp Ala Asn Ala Lys
65                  70                  75                  80

Ala Gln Ala Ala Gln Val Gly Ile Gly Lys Ser Ala Tyr Leu Pro Arg
                85                  90                  95

Leu Asp Gly Arg Leu Asp Ala Ser Arg Gly Tyr Ser Asp Met Asp Tyr
            100                 105                 110

Arg Asp Ala Pro Tyr Leu Ser Gly Asp Gly His Arg His Arg Arg Gly
        115                 120                 125
```

```
Ala Ser Leu Gln Leu Ser Trp Val Leu Phe Asp Phe Gly Arg Arg Ser
    130                 135                 140

Ala Ala Leu Arg Asn Ala Gln Gln Leu Leu Leu Ala Ala Asn Ala Ser
145                 150                 155                 160

Gln Asp Ala Thr Leu Gln Asn Thr Phe Ala Leu Ala Ala Gln Ala Tyr
                165                 170                 175

Tyr Asp Ala Leu Ala Ala Gln Arg Ser Leu Ala Ala Ser Arg Gln Val
            180                 185                 190

Ala Glu Leu Ala Ala Gln Asn Leu Glu Ala Ala Asp Ala Lys Tyr Arg
        195                 200                 205

Ala Gly Ala Ala Ala Leu Ser Asp Arg Leu Gln Ala Gln Thr Ala Leu
    210                 215                 220

Ser Gln Ala Ser Leu Ala Gln Val Arg Asp Glu Gly Ala Leu Ser Asn
225                 230                 235                 240

Ala Leu Gly Val Ile Ala Leu Arg Met Gly Leu Ala Pro Asp Thr Pro
                245                 250                 255

Leu Arg Leu Ser Gly Glu Leu Glu Ala Gln Pro Asp Thr Gly Phe Val
            260                 265                 270

Lys Ala Ile Asp Glu Met Leu Ala Glu Ala Arg Arg Glu His Pro Ala
        275                 280                 285

Leu Leu Ala Ala Gln Ala Arg Leu Lys Ala Ala Ala Ser Val Glu
    290                 295                 300

Glu Ser Arg Ala Ala Gly Arg Pro Ser Leu Ala Leu Ser Ala Asn Leu
305                 310                 315                 320

Ala Arg Ser His Ser Asp Gln Ala Met Ala Phe Asn Gly Asp Thr Arg
                325                 330                 335

Glu Arg Asp Arg Ser Ile Gly Leu Gln Leu Asn Ile Pro Leu Phe Glu
            340                 345                 350

Gly Phe Glu Arg Thr Tyr Gln Val Arg Asn Ala Leu Ala Arg Arg Glu
        355                 360                 365

Ala Ser Glu Ala Glu Leu Ala Asp Thr Glu Gln Val Ser Leu Glu
    370                 375                 380

Val Trp Asn Asn Tyr Gln Ser Leu Ser Val Glu Thr Arg Ser Leu Ala
385                 390                 395                 400

Arg Thr Arg Glu Leu Val Glu Gln Ser Arg Gln Ser Leu Glu Val Val
                405                 410                 415

Gln Gly Arg Tyr Arg Ser Gly Val Gly Ser Met Ile Glu Leu Leu Asn
            420                 425                 430

Ala Leu Thr Ala Tyr Ala Ser Ala Glu Asp Gln His Ile Arg Ala Leu
        435                 440                 445

Gly Asn Trp Gln Thr Ser Arg Leu Arg Leu Ala Ala Ser Leu Gly Arg
    450                 455                 460

Leu Gly Phe Trp Ser Leu Arg
465                 470

<210> SEQ ID NO 17
<211> LENGTH: 1176
<212> TYPE: DNA
<213> ORGANISM: Pseudomonas aeruginosa
<220> FEATURE:
<221> NAME/KEY: CDS
<222> LOCATION: (1)...(1173)

<400> SEQUENCE: 17 atg aga cga acc cgt agt act cgt cgc gca ctg ctc gtc gca gtc tgc      48
Met Arg Arg Thr Arg Ser Thr Arg Arg Ala Leu Leu Val Ala Val Cys
```

-continued

| 1 | 5 | 10 | 15 | |
|---|---|---|---|---|
| ctc agc ccc ctg atc gcc ctg gcc gcc tgg cag gcc tat ccg ttc cgc | | | | 96 |
| Leu Ser Pro Leu Ile Ala Leu Ala Ala Trp Gln Ala Tyr Pro Phe Arg | | | | |
| | 20 | 25 | 30 | |
| agc aac aac ttc gat acc gtg agc gtc agc cgc ggc agc atc gag agc | | | | 144 |
| Ser Asn Asn Phe Asp Thr Val Ser Val Ser Arg Gly Ser Ile Glu Ser | | | | |
| | 35 | 40 | 45 | |
| agc gtc tcg gcg ctc ggc acc ctg caa ccg cgg cgc tac gtc gac gtc | | | | 192 |
| Ser Val Ser Ala Leu Gly Thr Leu Gln Pro Arg Arg Tyr Val Asp Val | | | | |
| 50 | 55 | 60 | | |
| ggc gcc cag gcc tcc ggg cag atc cgc aag ttg cac gtc gag gcc ggg | | | | 240 |
| Gly Ala Gln Ala Ser Gly Gln Ile Arg Lys Leu His Val Glu Ala Gly | | | | |
| 65 | 70 | 75 | 80 | |
| gac gat gtg acg gaa ggc cag ttg ctg gtc gag atc gac ccc tcc acc | | | | 288 |
| Asp Asp Val Thr Glu Gly Gln Leu Leu Val Glu Ile Asp Pro Ser Thr | | | | |
| | 85 | 90 | 95 | |
| cag cag gcc aag gtc gat gcc ggc cgc tat tcg atc gag atg ctc aag | | | | 336 |
| Gln Gln Ala Lys Val Asp Ala Gly Arg Tyr Ser Ile Glu Met Leu Lys | | | | |
| | 100 | 105 | 110 | |
| gcc caa ctg gcc gag caa cgt gcc cag tac acc ctc gcc cgc cag cag | | | | 384 |
| Ala Gln Leu Ala Glu Gln Arg Ala Gln Tyr Thr Leu Ala Arg Gln Gln | | | | |
| | 115 | 120 | 125 | |
| tac cag cgc cag cag cgg ctg gcc gcc ggc ggc gca acg cgt acc gag | | | | 432 |
| Tyr Gln Arg Gln Gln Arg Leu Ala Ala Gly Gly Ala Thr Arg Thr Glu | | | | |
| 130 | 135 | 140 | | |
| gac gtg cag agc gcc cag gcg cag atg ctc gcc acc cag gcg cgg atc | | | | 480 |
| Asp Val Gln Ser Ala Gln Ala Gln Met Leu Ala Thr Gln Ala Arg Ile | | | | |
| 145 | 150 | 155 | 160 | |
| gag atg tac cag gcg cag atc cgc cag gcc cag gcc tcg ttg cgc agc | | | | 528 |
| Glu Met Tyr Gln Ala Gln Ile Arg Gln Ala Gln Ala Ser Leu Arg Ser | | | | |
| | 165 | 170 | 175 | |
| gac gaa gcc gaa ctc ggc tat acc cgc atc tac gcg ccg atg tcc ggc | | | | 576 |
| Asp Glu Ala Glu Leu Gly Tyr Thr Arg Ile Tyr Ala Pro Met Ser Gly | | | | |
| | 180 | 185 | 190 | |
| acg gtg gtg gcg gtc gat gcg cgc gaa ggc cag acc ctc aat gcc cag | | | | 624 |
| Thr Val Val Ala Val Asp Ala Arg Glu Gly Gln Thr Leu Asn Ala Gln | | | | |
| | 195 | 200 | 205 | |
| cag cag acc ccg ttg atc ctg cgg atc gcc aaa ttg tcg ccg atg acc | | | | 672 |
| Gln Gln Thr Pro Leu Ile Leu Arg Ile Ala Lys Leu Ser Pro Met Thr | | | | |
| 210 | 215 | 220 | | |
| gtc tgg gcc cag gtt tcg gaa gcc gac atc ggc cgg gtc aag ccc ggc | | | | 720 |
| Val Trp Ala Gln Val Ser Glu Ala Asp Ile Gly Arg Val Lys Pro Gly | | | | |
| 225 | 230 | 235 | 240 | |
| atg ccg gcc tac ttc acg acc ctc agc ggc gaa ggc cgg cgc tgg acc | | | | 768 |
| Met Pro Ala Tyr Phe Thr Thr Leu Ser Gly Glu Gly Arg Arg Trp Thr | | | | |
| | 245 | 250 | 255 | |
| ggc aag gtc cgg cag atc ctc ccg gtg ccg ccc aag ccg ctg gac cag | | | | 816 |
| Gly Lys Val Arg Gln Ile Leu Pro Val Pro Pro Lys Pro Leu Asp Gln | | | | |
| | 260 | 265 | 270 | |
| agc aac cag ggc ggc ggc agc ccc acc agc ggc agc ggc ggg cag agc | | | | 864 |
| Ser Asn Gln Gly Gly Gly Ser Pro Thr Ser Gly Ser Gly Gly Gln Ser | | | | |
| | 275 | 280 | 285 | |
| ggc agc ggc cgg gtg gtg ctg tat acc gtg ctg gtc gac gtg gac aac | | | | 912 |
| Gly Ser Gly Arg Val Val Leu Tyr Thr Val Leu Val Asp Val Asp Asn | | | | |
| 290 | 295 | 300 | | |
| ggc gac cac caa ctg atg gcg gaa atg acc gcc cag gtg ttc ttc gtc | | | | 960 |
| Gly Asp His Gln Leu Met Ala Glu Met Thr Ala Gln Val Phe Phe Val | | | | |
| 305 | 310 | 315 | 320 | |
| gcc gcc acc gca gaa aac atc ctc acc gcg ccg gtc gcc gcc atc cac | | | | 1008 |

```
Ala Ala Thr Ala Glu Asn Ile Leu Thr Ala Pro Val Ala Ala Ile His
                325                 330                 335 gac gac ggc aag ggc ggc cag gtc gcc tgg gtg gtc ggc agc aac ggc       1056
Asp Asp Gly Lys Gly Gly Gln Val Ala Trp Val Val Gly Ser Asn Gly
            340                 345                 350 aag ccg cag agc cgc cag atc agg acc ggc atc agc gac cgc ctg cgg       1104
Lys Pro Gln Ser Arg Gln Ile Arg Thr Gly Ile Ser Asp Arg Leu Arg
        355                 360                 365 gta cag gtg ctt gcc ggc ctg gag gaa ggc gac cgc ctg ttg atg gcc       1152
Val Gln Val Leu Ala Gly Leu Glu Glu Gly Asp Arg Leu Leu Met Ala
    370                 375                 380 gct ccc gac ggc agc gac agc tga                                        1176
Ala Pro Asp Gly Ser Asp Ser
385                 390

<210> SEQ ID NO 18
<211> LENGTH: 391
<212> TYPE: PRT
<213> ORGANISM: Pseudomonas aeruginosa

<400> SEQUENCE: 18

Met Arg Arg Thr Arg Ser Thr Arg Arg Ala Leu Leu Val Ala Val Cys
  1               5                  10                  15

Leu Ser Pro Leu Ile Ala Leu Ala Ala Trp Gln Ala Tyr Pro Phe Arg
             20                  25                  30

Ser Asn Asn Phe Asp Thr Val Ser Val Ser Arg Gly Ser Ile Glu Ser
         35                  40                  45

Ser Val Ser Ala Leu Gly Thr Leu Gln Pro Arg Arg Tyr Val Asp Val
     50                  55                  60

Gly Ala Gln Ala Ser Gly Gln Ile Arg Lys Leu His Val Glu Ala Gly
 65                  70                  75                  80

Asp Asp Val Thr Glu Gly Gln Leu Leu Val Glu Ile Asp Pro Ser Thr
                 85                  90                  95

Gln Gln Ala Lys Val Asp Ala Gly Arg Tyr Ser Ile Glu Met Leu Lys
            100                 105                 110

Ala Gln Leu Ala Glu Gln Arg Ala Gln Tyr Thr Leu Ala Arg Gln Gln
        115                 120                 125

Tyr Gln Arg Gln Gln Arg Leu Ala Ala Gly Gly Ala Thr Arg Thr Glu
    130                 135                 140

Asp Val Gln Ser Ala Gln Ala Gln Met Leu Ala Thr Gln Ala Arg Ile
145                 150                 155                 160

Glu Met Tyr Gln Ala Gln Ile Arg Gln Ala Gln Ala Ser Leu Arg Ser
                165                 170                 175

Asp Glu Ala Glu Leu Gly Tyr Thr Arg Ile Tyr Ala Pro Met Ser Gly
            180                 185                 190

Thr Val Val Ala Val Asp Ala Arg Glu Gly Gln Thr Leu Asn Ala Gln
        195                 200                 205

Gln Gln Thr Pro Leu Ile Leu Arg Ile Ala Lys Leu Ser Pro Met Thr
    210                 215                 220

Val Trp Ala Gln Val Ser Glu Ala Asp Ile Gly Arg Val Lys Pro Gly
225                 230                 235                 240

Met Pro Ala Tyr Phe Thr Thr Leu Ser Gly Glu Gly Arg Arg Trp Thr
                245                 250                 255

Gly Lys Val Arg Gln Ile Leu Pro Val Pro Lys Pro Leu Asp Gln
            260                 265                 270
```

```
Ser Asn Gln Gly Gly Ser Pro Thr Ser Gly Ser Gly Gly Gln Ser
    275                 280                 285

Gly Ser Gly Arg Val Val Leu Tyr Thr Val Leu Val Asp Val Asp Asn
        290                 295                 300

Gly Asp His Gln Leu Met Ala Glu Met Thr Ala Gln Val Phe Phe Val
305                 310                 315                 320

Ala Ala Thr Ala Glu Asn Ile Leu Thr Ala Pro Val Ala Ala Ile His
                325                 330                 335

Asp Asp Gly Lys Gly Gly Gln Val Ala Trp Val Val Gly Ser Asn Gly
            340                 345                 350

Lys Pro Gln Ser Arg Gln Ile Arg Thr Gly Ile Ser Asp Arg Leu Arg
        355                 360                 365

Val Gln Val Leu Ala Gly Leu Glu Glu Gly Asp Arg Leu Leu Met Ala
    370                 375                 380

Ala Pro Asp Gly Ser Asp Ser
385                 390

<210> SEQ ID NO 19
<211> LENGTH: 1992
<212> TYPE: DNA
<213> ORGANISM: Pseudomonas aeruginosa
<220> FEATURE:
<221> NAME/KEY: CDS
<222> LOCATION: (1)...(1989)

<400> SEQUENCE: 19
```

| | | | | | | | | | | | | | | | | |
|---|---|---|---|---|---|---|---|---|---|---|---|---|---|---|---|---|
| atg | gaa | aac | gcc | acg | caa | ccc | gtc | ccc | ctg | atc | gaa | ctg | cgc | gac | atc | 48 |
| Met | Glu | Asn | Ala | Thr | Gln | Pro | Val | Pro | Leu | Ile | Glu | Leu | Arg | Asp | Ile | |
| 1 | | | | 5 | | | | | 10 | | | | | 15 | | |

```
cgc aag cgc tac ggc ggc aat ggc acc ccg gaa gtc gag gta ctc aag         96
Arg Lys Arg Tyr Gly Gly Asn Gly Thr Pro Glu Val Glu Val Leu Lys
                20                  25                  30 ggc gta tcg ctg tcg atc cac gcc ggc gag ttc gtc gcc atc gtc ggc        144
Gly Val Ser Leu Ser Ile His Ala Gly Glu Phe Val Ala Ile Val Gly
            35                  40                  45 gcc tcc ggc tcc ggc aag tcg acc ctg atg aac atc ctc ggc tgc ctc        192
Ala Ser Gly Ser Gly Lys Ser Thr Leu Met Asn Ile Leu Gly Cys Leu
    50                  55                  60 gac cgg ccc agc tcc ggc agc tac cac ttc gcc ggc cac gac gtc gcc        240
Asp Arg Pro Ser Ser Gly Ser Tyr His Phe Ala Gly His Asp Val Ala
65                  70                  75                  80 gaa ctg gac agc gac gag cag gcc tgg ctg cgc cgc gag gca ttc ggc        288
Glu Leu Asp Ser Asp Glu Gln Ala Trp Leu Arg Arg Glu Ala Phe Gly
                85                  90                  95 ttc gtg ttc cag ggc tat cac ctg atc ccc tcc gcc tcg gcc cag gaa        336
Phe Val Phe Gln Gly Tyr His Leu Ile Pro Ser Ala Ser Ala Gln Glu
                100                 105                 110 aac gtc gag atg ccg gcg atc tac gcc ggc atc ccg gcg agc gag cgg        384
Asn Val Glu Met Pro Ala Ile Tyr Ala Gly Ile Pro Ala Ser Glu Arg
            115                 120                 125 cac acc cgc gcg cgg gcc ctg ctc gaa cgc ctg ggc ctg gcc gag cgc        432
His Thr Arg Ala Arg Ala Leu Leu Glu Arg Leu Gly Leu Ala Glu Arg
    130                 135                 140 acc gcc aac cgt ccg cac cag ttg tcc ggc ggc cag cag cag cgg gtg        480
Thr Ala Asn Arg Pro His Gln Leu Ser Gly Gly Gln Gln Gln Arg Val
145                 150                 155                 160 tcg atc gcc cgc gcg ctg atg aac ggc ggc cat atc atc ctc gcc gac        528
Ser Ile Ala Arg Ala Leu Met Asn Gly Gly His Ile Ile Leu Ala Asp
                165                 170                 175
```

-continued

| | | |
|---|---|---|
| gaa ccc acc ggc gcc ctc gac agc cac agc ggc gcg gaa gtc atg gcg<br>Glu Pro Thr Gly Ala Leu Asp Ser His Ser Gly Ala Glu Val Met Ala<br>    180                 185                 190 | | 576 |
| ctg ctc gac gag ctg gcc agc cag ggc cac gtg gtg atc ctg atc acc<br>Leu Leu Asp Glu Leu Ala Ser Gln Gly His Val Val Ile Leu Ile Thr<br>195                 200                 205 | | 624 |
| cac gac cgc gac gtc gcc gcc cgc gcc aag cgc atc atc gag gtg cgc<br>His Asp Arg Asp Val Ala Ala Arg Ala Lys Arg Ile Ile Glu Val Arg<br>    210                 215                 220 | | 672 |
| gac ggc gag atc gtc agc gac agc gcc aac gac gag cgc ccg gcg cac<br>Asp Gly Glu Ile Val Ser Asp Ser Ala Asn Asp Glu Arg Pro Ala His<br>225                 230                 235                 240 | | 720 |
| ccg agc gcc ggc gtc gag cgc cac ctg cag gcc gac gat ctc agc cag<br>Pro Ser Ala Gly Val Glu Arg His Leu Gln Ala Asp Asp Leu Ser Gln<br>                245                 250                 255 | | 768 |
| cgc ctc gcc gag ggc agc agc gaa ccc tcg ggg gcc tgg cgc gcc gaa<br>Arg Leu Ala Glu Gly Ser Ser Glu Pro Ser Gly Ala Trp Arg Ala Glu<br>            260                 265                 270 | | 816 |
| ctg ctg gag gcg gtg cgc gcc gcc tgg cgg gtg atg tgg atc aat cgg<br>Leu Leu Glu Ala Val Arg Ala Ala Trp Arg Val Met Trp Ile Asn Arg<br>        275                 280                 285 | | 864 |
| ttc cgc acc gcg ctg acc ctc ctc ggg atc atc atc ggc gtc gcc tcg<br>Phe Arg Thr Ala Leu Thr Leu Leu Gly Ile Ile Ile Gly Val Ala Ser<br>    290                 295                 300 | | 912 |
| gtg gtg gtc atg ctc gcc gtc ggc gag ggc agc aag cgc cag gtg atg<br>Val Val Val Met Leu Ala Val Gly Glu Gly Ser Lys Arg Gln Val Met<br>305                 310                 315                 320 | | 960 |
| gcg cag atg ggc gcg ttc ggc tcg aac atc atc tat ctc agc ggc tac<br>Ala Gln Met Gly Ala Phe Gly Ser Asn Ile Ile Tyr Leu Ser Gly Tyr<br>                325                 330                 335 | | 1008 |
| tcg ccg aac ccg cgc gcg ccg atg ggc atc gtc agc agc gac gac gtc<br>Ser Pro Asn Pro Arg Ala Pro Met Gly Ile Val Ser Ser Asp Asp Val<br>            340                 345                 350 | | 1056 |
| gcc gcc atc gcc acc ctg ccc cag gtg aag aag gtc atg ccg gtg aac<br>Ala Ala Ile Ala Thr Leu Pro Gln Val Lys Lys Val Met Pro Val Asn<br>        355                 360                 365 | | 1104 |
| ggc ggc gag ctg gtg gtg cgc tac ggg aac atc gac tac cac gcc tac<br>Gly Gly Glu Leu Val Val Arg Tyr Gly Asn Ile Asp Tyr His Ala Tyr<br>    370                 375                 380 | | 1152 |
| gtc ggc ggc aac aac acc gac ttc ccg gaa atc ctc aac tgg ccg gtg<br>Val Gly Gly Asn Asn Thr Asp Phe Pro Glu Ile Leu Asn Trp Pro Val<br>385                 390                 395                 400 | | 1200 |
| gcc gag ggc agc tac ttc acc gag cgc gac gaa gac gcc gcc acc acg<br>Ala Glu Gly Ser Tyr Phe Thr Glu Arg Asp Glu Asp Ala Ala Thr Thr<br>                405                 410                 415 | | 1248 |
| gtc gcg gtg atc ggc tac aag gtg cgc aag aag ctg ttc ggc agc gcc<br>Val Ala Val Ile Gly Tyr Lys Val Arg Lys Lys Leu Phe Gly Ser Ala<br>            420                 425                 430 | | 1296 |
| aac ccg atc ggc cgc tac atc ctc atc gag aac gtg ccg ttc cag gtc<br>Asn Pro Ile Gly Arg Tyr Ile Leu Ile Glu Asn Val Pro Phe Gln Val<br>        435                 440                 445 | | 1344 |
| atc ggc gtg ctc gcc gag aaa ggc tcc agc tcc ggc gac aag gat gcc<br>Ile Gly Val Leu Ala Glu Lys Gly Ser Ser Ser Gly Asp Lys Asp Ala<br>    450                 455                 460 | | 1392 |
| gac aac cgc atc gcc atc ccc tac tcc gct gcc agc atc cgc ctg ttc<br>Asp Asn Arg Ile Ala Ile Pro Tyr Ser Ala Ala Ser Ile Arg Leu Phe<br>465                 470                 475                 480 | | 1440 |
| ggc acg cgc aac ccc gag tac gtg atc atc gcc gcc gcc gac gcc cag<br>Gly Thr Arg Asn Pro Glu Tyr Val Ile Ile Ala Ala Ala Asp Ala Gln<br>                485                 490                 495 | | 1488 |

```
cgc gtg cac cag gcc gaa cgc gcc atc gac cag ttg atg ctg cgc ctg      1536
Arg Val His Gln Ala Glu Arg Ala Ile Asp Gln Leu Met Leu Arg Leu
        500                 505                 510 cac cgc ggc cag cgc gac tac gag ctg acc aac aac gcg gcg atg atc      1584
His Arg Gly Gln Arg Asp Tyr Glu Leu Thr Asn Asn Ala Ala Met Ile
            515                 520                 525 cag gcc gag gcg aag acc cag aac acc ctg tcg ctg atg ctc ggc tcg      1632
Gln Ala Glu Ala Lys Thr Gln Asn Thr Leu Ser Leu Met Leu Gly Ser
530                 535                 540 atc gcc gcg atc tcc ctg ctg gta ggc ggg atc ggc gtg atg aac atc      1680
Ile Ala Ala Ile Ser Leu Leu Val Gly Gly Ile Gly Val Met Asn Ile
545                 550                 555                 560 atg ctc atg acc gtg cgc gaa cgc acc cgc gag atc ggc atc cgc atg      1728
Met Leu Met Thr Val Arg Glu Arg Thr Arg Glu Ile Gly Ile Arg Met
                565                 570                 575 gcc act ggc gcc cgc cag ggc gat atc ctc cgc cag ttc ctc acc gag      1776
Ala Thr Gly Ala Arg Gln Gly Asp Ile Leu Arg Gln Phe Leu Thr Glu
            580                 585                 590 gcg gcg atg ctc tcg gtg gtc ggc ggc ctg gcc ggg atc gcc ctg gcc      1824
Ala Ala Met Leu Ser Val Val Gly Gly Leu Ala Gly Ile Ala Leu Ala
        595                 600                 605 ctg tgc atc ggc ggc gtg ctg ctc ggc cag gtc gcg gtg gcc ttt          1872
Leu Cys Ile Gly Gly Val Leu Leu Gly Gln Val Ala Val Ala Phe
610                 615                 620 tcc ctg tcg gcc atc gtc ggc gcc ttc agt tgc gcg ctg gtc acc ggc      1920
Ser Leu Ser Ala Ile Val Gly Ala Phe Ser Cys Ala Leu Val Thr Gly
625                 630                 635                 640 ctg gtg ttc ggc ttc atg ccg gcg cgc aag gcc gcc cag ctg gac ccg      1968
Leu Val Phe Gly Phe Met Pro Ala Arg Lys Ala Ala Gln Leu Asp Pro
                645                 650                 655 gtg gcc gcc ctg gcc agc caa tga                                      1992
Val Ala Ala Leu Ala Ser Gln
            660
```

<210> SEQ ID NO 20
<211> LENGTH: 663
<212> TYPE: PRT
<213> ORGANISM: Pseudomonas aeruginosa

<400> SEQUENCE: 20

```
Met Glu Asn Ala Thr Gln Pro Val Pro Leu Ile Glu Leu Arg Asp Ile
1               5                   10                  15

Arg Lys Arg Tyr Gly Gly Asn Gly Thr Pro Glu Val Glu Val Leu Lys
            20                  25                  30

Gly Val Ser Leu Ser Ile His Ala Gly Glu Phe Val Ala Ile Val Gly
        35                  40                  45

Ala Ser Gly Ser Gly Lys Ser Thr Leu Met Asn Ile Leu Gly Cys Leu
    50                  55                  60

Asp Arg Pro Ser Ser Gly Ser Tyr His Phe Ala Gly His Asp Val Ala
65                  70                  75                  80

Glu Leu Asp Ser Asp Glu Gln Ala Trp Leu Arg Arg Glu Ala Phe Gly
                85                  90                  95

Phe Val Phe Gln Gly Tyr His Leu Ile Pro Ser Ala Ser Ala Gln Glu
            100                 105                 110

Asn Val Glu Met Pro Ala Ile Tyr Ala Gly Ile Pro Ala Ser Glu Arg
        115                 120                 125

His Thr Arg Ala Arg Ala Leu Leu Glu Arg Leu Gly Leu Ala Glu Arg
    130                 135                 140
```

-continued

```
Thr Ala Asn Arg Pro His Gln Leu Ser Gly Gly Gln Gln Arg Val
145                 150                 155                 160

Ser Ile Ala Arg Ala Leu Met Asn Gly Gly His Ile Ile Leu Ala Asp
            165                 170                 175

Glu Pro Thr Gly Ala Leu Asp Ser His Ser Gly Ala Glu Val Met Ala
                180                 185                 190

Leu Leu Asp Glu Leu Ala Ser Gln Gly His Val Val Ile Leu Ile Thr
            195                 200                 205

His Asp Arg Asp Val Ala Ala Arg Ala Lys Arg Ile Ile Glu Val Arg
    210                 215                 220

Asp Gly Glu Ile Val Ser Asp Ser Ala Asn Asp Glu Arg Pro Ala His
225                 230                 235                 240

Pro Ser Ala Gly Val Glu Arg His Leu Gln Ala Asp Asp Leu Ser Gln
                245                 250                 255

Arg Leu Ala Glu Gly Ser Ser Glu Pro Ser Gly Ala Trp Arg Ala Glu
            260                 265                 270

Leu Leu Glu Ala Val Arg Ala Ala Trp Arg Val Met Trp Ile Asn Arg
        275                 280                 285

Phe Arg Thr Ala Leu Thr Leu Leu Gly Ile Ile Ile Gly Val Ala Ser
    290                 295                 300

Val Val Val Met Leu Ala Val Gly Glu Gly Ser Lys Arg Gln Val Met
305                 310                 315                 320

Ala Gln Met Gly Ala Phe Gly Ser Asn Ile Ile Tyr Leu Ser Gly Tyr
                325                 330                 335

Ser Pro Asn Pro Arg Ala Pro Met Gly Ile Val Ser Ser Asp Asp Val
            340                 345                 350

Ala Ala Ile Ala Thr Leu Pro Gln Val Lys Lys Val Met Pro Val Asn
        355                 360                 365

Gly Gly Glu Leu Val Val Arg Tyr Gly Asn Ile Asp Tyr His Ala Tyr
    370                 375                 380

Val Gly Gly Asn Asn Thr Asp Phe Pro Glu Ile Leu Asn Trp Pro Val
385                 390                 395                 400

Ala Glu Gly Ser Tyr Phe Thr Glu Arg Asp Glu Asp Ala Ala Thr Thr
                405                 410                 415

Val Ala Val Ile Gly Tyr Lys Val Arg Lys Lys Leu Phe Gly Ser Ala
            420                 425                 430

Asn Pro Ile Gly Arg Tyr Ile Leu Ile Glu Asn Val Pro Phe Gln Val
        435                 440                 445

Ile Gly Val Leu Ala Glu Lys Gly Ser Ser Ser Gly Asp Lys Asp Ala
    450                 455                 460

Asp Asn Arg Ile Ala Ile Pro Tyr Ser Ala Ala Ser Ile Arg Leu Phe
465                 470                 475                 480

Gly Thr Arg Asn Pro Glu Tyr Val Ile Ile Ala Ala Asp Ala Gln
                485                 490                 495

Arg Val His Gln Ala Glu Arg Ala Ile Asp Gln Leu Met Leu Arg Leu
            500                 505                 510

His Arg Gly Gln Arg Asp Tyr Glu Leu Thr Asn Asn Ala Ala Met Ile
        515                 520                 525

Gln Ala Glu Ala Lys Thr Gln Asn Thr Leu Ser Leu Met Leu Gly Ser
    530                 535                 540

Ile Ala Ala Ile Ser Leu Leu Val Gly Ile Gly Val Met Asn Ile
545                 550                 555                 560
```

-continued

```
Met Leu Met Thr Val Arg Glu Arg Thr Arg Glu Ile Gly Ile Arg Met
                565                 570                 575

Ala Thr Gly Ala Arg Gln Gly Asp Ile Leu Arg Gln Phe Leu Thr Glu
            580                 585                 590

Ala Ala Met Leu Ser Val Val Gly Gly Leu Ala Gly Ile Ala Leu Ala
        595                 600                 605

Leu Cys Ile Gly Gly Val Leu Leu Leu Gly Gln Val Ala Val Ala Phe
    610                 615                 620

Ser Leu Ser Ala Ile Val Gly Ala Phe Ser Cys Ala Leu Val Thr Gly
625                 630                 635                 640

Leu Val Phe Gly Phe Met Pro Ala Arg Lys Ala Ala Gln Leu Asp Pro
                645                 650                 655

Val Ala Ala Leu Ala Ser Gln
            660

<210> SEQ ID NO 21
<211> LENGTH: 1425
<212> TYPE: DNA
<213> ORGANISM: Pseudomonas aeruginosa
<220> FEATURE:
<221> NAME/KEY: CDS
<222> LOCATION: (1)...(1422)

<400> SEQUENCE: 21 atg tcc atg aag aat ctc tcc ctg att tcc gcc tgc ctg ctg ctc ggc        48
Met Ser Met Lys Asn Leu Ser Leu Ile Ser Ala Cys Leu Leu Leu Gly
  1               5                  10                  15 gcc tgc ggc agc acg ccg gcg ccc ctc gac agc ggc ctg gcc gcg ccc        96
Ala Cys Gly Ser Thr Pro Ala Pro Leu Asp Ser Gly Leu Ala Ala Pro
             20                  25                  30 agc cag tgg cgc tac ctg gcg gcc ggg cgc agc gat gcc agc gac atc       144
Ser Gln Trp Arg Tyr Leu Ala Ala Gly Arg Ser Asp Ala Ser Asp Ile
         35                  40                  45 cgc cag tgg tgg aag gcc ttc ggc gcg ccg gaa ctg gac agc ctg ctg       192
Arg Gln Trp Trp Lys Ala Phe Gly Ala Pro Glu Leu Asp Ser Leu Leu
     50                  55                  60 caa cgc gcc ctg ctg aac agc cag gac ctc ggc gcg gcg gtg gcc cgc       240
Gln Arg Ala Leu Leu Asn Ser Gln Asp Leu Gly Ala Ala Val Ala Arg
 65                  70                  75                  80 gta cgc cag gcc cag gcc tcg gcg gtg atc gcc ggc gcg ccg ttg ctg       288
Val Arg Gln Ala Gln Ala Ser Ala Val Ile Ala Gly Ala Pro Leu Leu
                 85                  90                  95 ccg gag ctg aat gcg acg ctc ggc gcc agc cgg cag aaa ctc ctg cgc       336
Pro Glu Leu Asn Ala Thr Leu Gly Ala Ser Arg Gln Lys Leu Leu Arg
            100                 105                 110 gac tcg ggc tac agc ggt acc gac gcg acc tcc gac aac gat gcc gtc       384
Asp Ser Gly Tyr Ser Gly Thr Asp Ala Thr Ser Asp Asn Asp Ala Val
        115                 120                 125 gac tcc ttc tcc gcc ggc ctc agc gcc agc tac gaa gtg gac ttc tgg       432
Asp Ser Phe Ser Ala Gly Leu Ser Ala Ser Tyr Glu Val Asp Phe Trp
    130                 135                 140 ggc ggt cgc cag gct gcc tac cgc agc gcc ctg gaa agc ctc aag gcc       480
Gly Gly Arg Gln Ala Ala Tyr Arg Ser Ala Leu Glu Ser Leu Lys Ala
145                 150                 155                 160 agc gag tac gac cgc gcc acg gta gag ctg acc ctg ctc tcc ggc gtc       528
Ser Glu Tyr Asp Arg Ala Thr Val Glu Leu Thr Leu Leu Ser Gly Val
                165                 170                 175 gcc aac agc tac ctg cag gta ttg gcg ctg cgc gaa cag cag cgc atc       576
Ala Asn Ser Tyr Leu Gln Val Leu Ala Leu Arg Glu Gln Gln Arg Ile
            180                 185                 190
```

```
gcc agg ctc aac ctg gac aac gcc gag cac gtc ctg cgc ctg gtg gag      624
Ala Arg Leu Asn Leu Asp Asn Ala Glu His Val Leu Arg Leu Val Glu
        195                 200                 205 acc cgc cat gcc gcg ggc tcg gcc acc gcc ctg gag gtc gcc caa cag      672
Thr Arg His Ala Ala Gly Ser Ala Thr Ala Leu Glu Val Ala Gln Gln
    210                 215                 220 agc agc ctg gtc gcc agc cag cgc aag cag ctg ccg ctg ctc gag cag      720
Ser Ser Leu Val Ala Ser Gln Arg Lys Gln Leu Pro Leu Leu Glu Gln
225                 230                 235                 240 cag gcc cat gag gcg ctg att acc ctg gcc acc ctg atc ggc gag ccg      768
Gln Ala His Glu Ala Leu Ile Thr Leu Ala Thr Leu Ile Gly Glu Pro
                245                 250                 255 gtg cag gcg cta cag gtg gcc gag cgg cct ttc gac agc ctg cgc tgg      816
Val Gln Ala Leu Gln Val Ala Glu Arg Pro Phe Asp Ser Leu Arg Trp
        260                 265                 270 ccg gag acc gga gcg ggc ctg ccg agc gaa ctg ctc agc cgc cgt ccc      864
Pro Glu Thr Gly Ala Gly Leu Pro Ser Glu Leu Leu Ser Arg Arg Pro
    275                 280                 285 gat atc gcc aac gcc gaa gcg caa ctg gcc gcg gcc cag gcc gac gtg      912
Asp Ile Ala Asn Ala Glu Ala Gln Leu Ala Ala Ala Gln Ala Asp Val
290                 295                 300 cag gtg gcg cgc gcg gcg ctg ttc ccc aag ctg acc ctg agc gcc tcg      960
Gln Val Ala Arg Ala Ala Leu Phe Pro Lys Leu Thr Leu Ser Ala Ser
305                 310                 315                 320 ctg tcg tcc ggc gcc aac cgc gcc gcc gac act ttc cgc aac ccc tat     1008
Leu Ser Ser Gly Ala Asn Arg Ala Ala Asp Thr Phe Arg Asn Pro Tyr
                325                 330                 335 tac aac ctg ggc gcc aac ctg ctc gcc ccg atc ttc aac cac ggc cgc     1056
Tyr Asn Leu Gly Ala Asn Leu Leu Ala Pro Ile Phe Asn His Gly Arg
        340                 345                 350 ctg cgc gcc gag cgc gac cgc agc ctg gcg cgc cag gaa gaa ctg ctg     1104
Leu Arg Ala Glu Arg Asp Arg Ser Leu Ala Arg Gln Glu Glu Leu Leu
    355                 360                 365 gaa acc tac cgc aag gcg atc ctc acc gcc ttt gcc gac acc gaa cgc     1152
Glu Thr Tyr Arg Lys Ala Ile Leu Thr Ala Phe Ala Asp Thr Glu Arg
370                 375                 380 tcg ctg aac agc atc gac ggc ctc gac cgc cag ctg cac tgg caa cag     1200
Ser Leu Asn Ser Ile Asp Gly Leu Asp Arg Gln Leu His Trp Gln Gln
385                 390                 395                 400 cag gag ctg gag cag gcg cag cgc gcc ttc gat ctc tcc gac agc cgc     1248
Gln Glu Leu Glu Gln Ala Gln Arg Ala Phe Asp Leu Ser Asp Ser Arg
                405                 410                 415 tac cag gcc ggc gcg gaa acc ctg ctg acg gtc ctc gaa acg caa cgc     1296
Tyr Gln Ala Gly Ala Glu Thr Leu Leu Thr Val Leu Glu Thr Gln Arg
        420                 425                 430 acg ctg tac gcg gcg cag gat gcc gcc gtg caa ctg cga ctg gcc cgc     1344
Thr Leu Tyr Ala Ala Gln Asp Ala Ala Val Gln Leu Arg Leu Ala Arg
    435                 440                 445 ctg cag gcc tcg gtc ggc ctg tac aag gcc ctc ggc ggc ggc tgg cag     1392
Leu Gln Ala Ser Val Gly Leu Tyr Lys Ala Leu Gly Gly Gly Trp Gln
450                 455                 460 agc gac cgc cag ggt ctc gcg cgg aaa gac tga                         1425
Ser Asp Arg Gln Gly Leu Ala Arg Lys Asp
465                 470

<210> SEQ ID NO 22
<211> LENGTH: 474
<212> TYPE: PRT
<213> ORGANISM: Pseudomonas aeruginosa
```

```
<400> SEQUENCE: 22

Met Ser Met Lys Asn Leu Ser Leu Ile Ser Ala Cys Leu Leu Leu Gly
 1               5                  10                  15

Ala Cys Gly Ser Thr Pro Ala Pro Leu Asp Ser Gly Leu Ala Ala Pro
            20                  25                  30

Ser Gln Trp Arg Tyr Leu Ala Ala Gly Arg Ser Asp Ala Ser Asp Ile
        35                  40                  45

Arg Gln Trp Trp Lys Ala Phe Gly Ala Pro Glu Leu Asp Ser Leu Leu
    50                  55                  60

Gln Arg Ala Leu Leu Asn Ser Gln Asp Leu Gly Ala Ala Val Ala Arg
65                  70                  75                  80

Val Arg Gln Ala Gln Ala Ser Ala Val Ile Ala Gly Ala Pro Leu Leu
                85                  90                  95

Pro Glu Leu Asn Ala Thr Leu Gly Ala Ser Arg Gln Lys Leu Leu Arg
            100                 105                 110

Asp Ser Gly Tyr Ser Gly Thr Asp Ala Thr Ser Asp Asn Asp Ala Val
        115                 120                 125

Asp Ser Phe Ser Ala Gly Leu Ser Ala Ser Tyr Glu Val Asp Phe Trp
    130                 135                 140

Gly Gly Arg Gln Ala Ala Tyr Arg Ser Ala Leu Glu Ser Leu Lys Ala
145                 150                 155                 160

Ser Glu Tyr Asp Arg Ala Thr Val Glu Leu Thr Leu Ser Gly Val
                165                 170                 175

Ala Asn Ser Tyr Leu Gln Val Leu Ala Leu Arg Glu Gln Gln Arg Ile
            180                 185                 190

Ala Arg Leu Asn Leu Asp Asn Ala Glu His Val Leu Arg Leu Val Glu
        195                 200                 205

Thr Arg His Ala Ala Gly Ser Ala Thr Ala Leu Glu Val Ala Gln Gln
    210                 215                 220

Ser Ser Leu Val Ala Ser Gln Arg Lys Gln Leu Pro Leu Leu Glu Gln
225                 230                 235                 240

Gln Ala His Glu Ala Leu Ile Thr Leu Ala Thr Leu Ile Gly Glu Pro
                245                 250                 255

Val Gln Ala Leu Gln Val Ala Glu Arg Pro Phe Asp Ser Leu Arg Trp
            260                 265                 270

Pro Glu Thr Gly Ala Gly Leu Pro Ser Glu Leu Leu Ser Arg Arg Pro
        275                 280                 285

Asp Ile Ala Asn Ala Glu Ala Gln Leu Ala Ala Gln Ala Asp Val
    290                 295                 300

Gln Val Ala Arg Ala Ala Leu Phe Pro Lys Leu Thr Leu Ser Ala Ser
305                 310                 315                 320

Leu Ser Ser Gly Ala Asn Arg Ala Ala Asp Thr Phe Arg Asn Pro Tyr
                325                 330                 335

Tyr Asn Leu Gly Ala Asn Leu Leu Ala Pro Ile Phe Asn His Gly Arg
            340                 345                 350

Leu Arg Ala Glu Arg Asp Arg Ser Leu Ala Arg Gln Glu Glu Leu Leu
        355                 360                 365

Glu Thr Tyr Arg Lys Ala Ile Leu Thr Ala Phe Ala Asp Thr Glu Arg
    370                 375                 380

Ser Leu Asn Ser Ile Asp Gly Leu Asp Arg Gln Leu His Trp Gln Gln
385                 390                 395                 400

Gln Glu Leu Glu Gln Ala Gln Arg Ala Phe Asp Leu Ser Asp Ser Arg
                405                 410                 415
```

Tyr Gln Ala Gly Ala Glu Thr Leu Leu Thr Val Leu Glu Thr Gln Arg
                420                 425                 430

Thr Leu Tyr Ala Ala Gln Asp Ala Ala Val Gln Leu Arg Leu Ala Arg
            435                 440                 445

Leu Gln Ala Ser Val Gly Leu Tyr Lys Ala Leu Gly Gly Gly Trp Gln
        450                 455                 460

Ser Asp Arg Gln Gly Leu Ala Arg Lys Asp
465                 470

<210> SEQ ID NO 23
<211> LENGTH: 501
<212> TYPE: DNA
<213> ORGANISM: Pseudomonas aeruginosa

<400> SEQUENCE: 23

| | | | | | | |
|---|---|---|---|---|---|---|
| ggtcgctcgc | gggagaggat | cggttggata | acttggcatc | gtgacgatga | cgctttgatt | 60 |
| gcaggacgat | gaaggccgct | tcgcgggatg | cccggcgatg | ctttccgttg | gaactgtcgg | 120 |
| ggtcgtcttg | ccgtcgcctc | cgccgacga | actacgaggt | gccgggaagt | gctatttcat | 180 |
| ttctcccggt | tttttatgaa | atacgcatcg | tagagttctg | atatttgccc | gctgggttat | 240 |
| ttagtcgatt | tgccgtgcca | ggtgatgggg | gttgtttata | agtattata | acttttgat | 300 |
| tatatattgt | ttatcaatta | gataggcgtg | tgatggctaa | atggctgcat | gttttccagg | 360 |
| ggttatctaa | attgaatttt | tcatgggggt | tttcttagtc | gttatatata | aagtcagact | 420 |
| cgccttttat | ttaaaagctg | ctatttctgg | attacatggt | gcggccgttc | ggtcgctgct | 480 |
| tgacaagagg | aatgtcggaa | a | | | | 501 |

<210> SEQ ID NO 24
<211> LENGTH: 501
<212> TYPE: DNA
<213> ORGANISM: Pseudomonas aeruginosa

<400> SEQUENCE: 24

| | | | | | | |
|---|---|---|---|---|---|---|
| agcccatgaa | aaaccgctaa | tcctggcagt | tcatcccact | ctttcggatt | agtaccattg | 60 |
| aatggctttc | cagactcatg | ggaagcctaa | aggagatata | tgaaatgaaa | gaactcaatg | 120 |
| acattgaagt | cacctgcgtt | tcgggtggaa | ctctttccgg | catgatcgta | ggcgccgtcg | 180 |
| acggcgccgc | gacgggcatg | gcaatcggcg | ggaaatgggg | cggtgccggc | ggcttcggct | 240 |
| tcggcgctct | ttcccagttg | gtcggcctga | tcgtgccaac | cgcaatgggc | gctattgccg | 300 |
| ggggcacggt | cggtctcttc | accaatgcag | agacggctgt | cggttacttg | gccaatacc | 360 |
| gggaaaactt | cggtcccggt | gatgtaggcc | gcaccaccat | ctaattagaa | aagtcgcact | 420 |
| ccggcacttc | atgcgtttga | actttcgcaa | gggtgtcgga | gtgtcatgca | agtattattc | 480 |
| gaatccagga | tccagccacc | a | | | | 501 |

<210> SEQ ID NO 25
<211> LENGTH: 501
<212> TYPE: DNA
<213> ORGANISM: Pseudomonas aeruginosa

<400> SEQUENCE: 25

| | | | | | | |
|---|---|---|---|---|---|---|
| caacgtggta | gtcaccgtca | ccgagggctc | ggtgaaggtc | cgcagcgaag | gctcgggcaa | 60 |
| cgacagcagc | ctgactcccg | gcatgcaggc | cagctactat | ccgggcctgc | tgcaaccgtt | 120 |
| ggtcgaggcc | gtggataccc | gccagacgct | agcctggcgc | gagggccgcc | tggtactcga | 180 |

-continued

```
cgacctgccc ctgtccaagg ccctgccgct gatcaaccgc tacctcgacg ctccgctggt    240
cctgggcgac aggagcgctg cgaaactgcg cattggcggg atctacagca cccgcgacat    300
ccgcagcctg gtcgacgccc tgccgaaagt cctgcccgtg gacctggaac atcgcgagga    360
cggcagcatc cgcatcagca gccgttacgc ccagctctga acccaggtta aatttagccg    420
ccctggcctc gtatatctgg cagtgcccag cctgccgatc cagcggcggc ggtctctcca    480
cgcaccggcc ggattcccga a                                              501
```

<210> SEQ ID NO 26
<211> LENGTH: 501
<212> TYPE: DNA
<213> ORGANISM: Pseudomonas aeruginosa

<400> SEQUENCE: 26

```
gctccgggt ggtcggcgac gaagcgctcg acggcgacga tcatcgacgc caggctgcct     60
ttcatgtccg ccgcgccgcg cccgcagagc atgccctggt cgtcgatcag ggcgtcgaag    120
ggttggtgct gccaggcctg cagcgggccg gtggggacca cgtcggtgtg cccggcgaag    180
cacagcaccg gccgtcgcc gccgcgccgt gcccagaagt tgtccacctc ctcgatgcgc     240
atcggctcca gggcgaagcc ggcggcttcc aggcggcgca tcatcagggc ctggcagtcg    300
gcgtcgagcg gcgtgacgga ggggcggcgg atcaactcgc aggcgagttc gagggtcggc    360
gagagactcg gcgaagaggc ggtcatgggg agggcatcct gagcgggtcg agcggaaagg    420
gggaatctta aagcataaac gtgggcgaag ggacgccgtt taggcgagcg gggccggccg    480
tcccgacgcc tcgcccgacc t                                              501
```

<210> SEQ ID NO 27
<211> LENGTH: 920
<212> TYPE: PRT
<213> ORGANISM: Bradyrhizobium japonicum

<400> SEQUENCE: 27

```
Met Arg Val Val Ala Val Leu Leu Leu Val Ser Ala Leu His Ala
 1               5                  10                  15

Gly Leu Trp Gly Val Leu Arg Asp Lys Glu Pro Ala Pro Asp Phe Arg
                20                  25                  30

Gly Leu Leu Pro Ser Val Ser Tyr Ala Pro Phe Glu Gly Ser Ala His
            35                  40                  45

Pro Asp Ile Asp Asn Ile Pro Thr Val Glu Lys Ile Arg Ala Asp Leu
50                  55                  60

Lys Thr Leu Ser Thr Met Thr Arg Ala Ile Arg Leu Tyr Ser Ser Thr
65                  70                  75                  80

Gly Gly Val Glu Leu Val Pro Ala Ile Ala Ala Glu Phe Gly Leu Lys
                85                  90                  95

Val Thr Val Gly Ala Trp Ile Asp Lys Asp Lys Asp Arg Asn Glu Arg
            100                 105                 110

Glu Ile Lys Ala Ala Ile Glu Leu Ala Arg Lys Asn Ser Asn Val Val
        115                 120                 125

Gly Val Val Gly Asn Glu Val Ile Tyr Arg Gly Glu Gln Lys Val
    130                 135                 140

Glu Asp Leu Ile Asp Met Ile Lys Lys Val Lys Gly Ser Val Arg Val
145                 150                 155                 160

Pro Val Thr Thr Gly Glu Ile Trp Asn Ile Trp Arg Asp Asn Pro Asp
                165                 170                 175
```

-continued

```
Leu Ala Ser Asn Val Asp Phe Ile Ala His Val Leu Pro Tyr Trp
            180                 185                 190
Glu Asn Phe Arg Ser Asp Gln Ala Val Asp Gln Ala Val Asp Arg Tyr
        195                 200                 205
Asn Leu Leu Arg Asn Leu Phe Pro Gly Lys Arg Ile Val Ile Ala Glu
    210                 215                 220
Phe Gly Trp Pro Ser Gln Gly Tyr Asn Leu Arg Asn Ala Asp Pro Gly
225                 230                 235                 240
Pro Phe Gln Gln Ala Leu Thr Leu Arg Asn Phe Val Ser Arg Ala Glu
            245                 250                 255
Ala Ile Gly Met Glu Tyr Asn Ile Val Glu Ala Ile Asp Gln Pro Trp
            260                 265                 270
Lys Phe Phe Glu Gly Gly Val Gly Pro Tyr Trp Gly Ile Leu Asn Ala
            275                 280                 285
Ser Arg Glu Pro Lys Phe Ala Trp Thr Gly Pro Val Glu Asn Pro Asp
        290                 295                 300
Tyr Trp Lys Leu Met Thr Ile Ala Leu Leu Val Gly Val Leu Leu Ser
305                 310                 315                 320
Leu Pro Ile Leu Arg Leu Gln Gln Pro Thr Ala Lys Gln Ala Phe Leu
            325                 330                 335
Leu Ser Ala Thr Ala Asn Gly Val Gly Ala Trp Ala Ala Thr Val Phe
            340                 345                 350
Ala Phe Trp Asn Gly His Tyr Phe Ile Phe Gly Ser Ala Phe Ala Leu
            355                 360                 365
Thr Leu Gly Met Ile Leu Leu Val Pro Leu Val Leu Ile Ala Met Ala
    370                 375                 380
Arg Ile Asp Glu Ile Ala Ala Val Ala Phe Gly Arg Pro Pro Gln Arg
385                 390                 395                 400
Leu Leu Ala Lys Ser Lys Pro Val Glu Asn Val Pro Glu Asn Tyr Tyr
            405                 410                 415
Pro Lys Val Ser Ile His Ile Pro Ala Tyr Phe Glu Pro Val Glu Met
            420                 425                 430
Leu Lys Gln Thr Leu Asp Ala Leu Ser Arg Leu Asn Tyr Pro Asn Tyr
            435                 440                 445
Glu Cys Val Val Ile Ile Asn Asn Thr Pro Asp Pro Ala Phe Trp Gln
    450                 455                 460
Pro Ile Gln Asp His Cys Arg Ala Leu Gly Glu Arg Phe Lys Phe Ile
465                 470                 475                 480
Asn Ala Glu Lys Val Gln Gly Phe Lys Ala Gly Ala Leu Arg Ile Ala
            485                 490                 495
Met Asp Arg Thr Ala Val Asp Ala Glu Ile Gly Ile Leu Asp Ala
            500                 505                 510
Asp Tyr Val Val Asp Pro Asp Trp Leu Lys Asp Leu Val Pro Ala Phe
        515                 520                 525
Ala Asp Pro Arg Val Gly Leu Val Gln Ala Pro Gln Glu His Arg Asp
        530                 535                 540
Gly Asp Leu Ser Ile Met His Tyr Ile Met Asn Gly Glu Tyr Ala Gly
545                 550                 555                 560
Phe Phe Asp Ile Gly Met Val Gln Arg Asn Glu Ala Asn Ala Ile Ile
            565                 570                 575
Val His Gly Thr Met Cys Leu Ile Arg Arg Ala Ala Met Asp Met Ala
            580                 585                 590
Gly Gly Trp Ser Ser Asp Thr Ile Cys Glu Asp Ser Asp Leu Gly Leu
```

```
                595             600             605
Ala Ile Gln Glu Leu Gly Trp Val Thr His Tyr Thr Asn His Arg Tyr
        610             615             620

Gly Gln Gly Leu Leu Pro Asp Thr Tyr Glu Ala Phe Lys Lys Gln Arg
625             630             635             640

His Arg Trp Ala Tyr Gly Gly Leu Gln Ile Val Lys Lys His Trp Arg
            645             650             655

His Phe Leu Pro Gly Arg Ser Arg Leu Thr Pro Asp Gln Lys Arg Glu
                660             665             670

Tyr Gly Leu Gly Trp Leu Asn Trp Leu Gly Ala Glu Ser Leu Gly Val
            675             680             685

Val Val Ala Leu Leu Asn Leu Val Trp Val Pro Ile Val Ala Phe Ala
        690             695             700

Asp Ile Ala Ile Pro Asp Lys Ile Leu Thr Leu Pro Ile Ile Gly Ala
705             710             715             720

Phe Val Val Ser Leu Ala His Phe Leu Ser Met Tyr Arg Ala Arg Val
                725             730             735

Ala Ile Lys Pro Gly Gln Met Leu Gly Ala Met Ile Ala Ala Met Ser
            740             745             750

Val Thr Val Asp Gly Val Ala Arg Gly Arg Ala Gly Thr Asp His Arg
        755             760             765

Ala His Arg Leu Arg Ala His Leu Gln Gly Arg Pro Val Gln Asp Val
        770             775             780

Asp Arg Val Pro Gly Val Leu Gly Gly Arg Asp Arg Pro Ala Pro
785             790             795             800

Asp Arg Arg Arg Arg Ala Asp Arg Leu Gln Gln Phe Pro Ala Asp His
                805             810             815

Arg Asp Leu His Leu Arg Arg Ala Gly Ala Lys Pro Ala Val
            820             825             830

Pro Gly Arg Gly Arg His Arg His Pro Arg Ala Gln Pro His Gln Leu
            835             840             845

Val Pro Val Leu Ala Arg Gln Arg Asp Pro His Arg Arg Ala Asp Trp
        850             855             860

Pro Ala Pro Gly Arg Pro Ala Asp Pro Arg Arg His Ala Ala Ser Arg
865             870             875             880

Ala Glu Arg Gly Gln Ala Arg Gly Glu Leu Thr Ala Gly Trp Leu Leu
                885             890             895

Gly Ala Gly Glu Thr Ser Ala Pro Pro Ser His Arg Gln Arg Ser Glu
            900             905             910

Trp Ile Ala Gly Arg Gln Ser Gly
        915             920

<210> SEQ ID NO 28
<211> LENGTH: 654
<212> TYPE: PRT
<213> ORGANISM: Agrobacterium tumefaciens

<400> SEQUENCE: 28

Met Tyr Phe Ser Ala Glu Gly Asp Val Gln Ser Val Leu Tyr Val Asn
  1               5              10              15

Leu Thr Ile Ala Ile Gly Ala Ile Leu Phe Ala Leu Leu Ala Asp Pro
             20              25              30

Arg Lys Met Val Asp Arg Leu Ala Phe Ser Ile Ile Met Leu Leu Ser
         35              40              45
```

```
Leu Gly Val Tyr Ile Val Trp Arg Ala Thr Asp Thr Leu Pro Pro Leu
    50                  55                  60

Glu Phe Ser Leu Glu Thr Leu Trp Cys Tyr Thr Tyr Phe Thr Phe Glu
65                  70                  75                  80

Leu Ile Ser Val Leu Tyr Ala Met Gly Ser Ile Leu Ile Leu Leu Arg
                85                  90                  95

Arg Thr Asp Trp Ser Ala Val Ala Asp Gln Gly Glu Ala Tyr Leu Ala
                100                 105                 110

Gly Asn Pro His Ala Pro Leu Val Asp Val Phe Ile Cys Thr Tyr Asn
                115                 120                 125

Glu Pro Leu Asn Val Leu Glu Lys Ser Ile Ile Ala Ala Gln Ala Met
    130                 135                 140

Asp Tyr Pro Arg Leu Arg Val Phe Val Cys Asp Asp Thr Arg Arg Ala
145                 150                 155                 160

Glu Val Arg Thr Tyr Cys Glu Ala Val Gly Val Asn Tyr Val Thr Arg
                165                 170                 175

Pro Asp Asn Lys His Ala Lys Ala Gly Asn Leu Asn Asn Ala Leu Leu
                180                 185                 190

His Thr Asn Ala Leu Glu Glu Val Ser Asp Phe Ile Met Val Leu Asp
            195                 200                 205

Ala Asp Phe Ala Pro Gln Ala Asn Phe Leu Arg Arg Val Thr Gly Leu
    210                 215                 220

Phe Ser Asp Pro Lys Val Ala Val Gln Thr Pro Gln Phe Tyr Phe
225                 230                 235                 240

Asn Ser Asp Pro Ile Gln His Asn Leu Gly Ile Asp Lys Ser Phe Val
                245                 250                 255

Asp Asp Gln Arg Val Phe Phe Asp Val Phe Gln Pro Ala Lys Asp Ala
                260                 265                 270

Val Gly Cys Ala Phe Cys Val Gly Thr Ser Phe Val Val Arg Arg Ala
                275                 280                 285

Ala Val Asn Gly Ile Gly Gly Phe Pro Ser Asp Ala Leu Ser Glu Asp
    290                 295                 300

Met Leu Leu Thr Tyr Arg Leu Met Glu Arg Gly Tyr Val Thr Arg Trp
305                 310                 315                 320

Leu Asn Glu Lys Leu Ser Val Gly Leu Ser Ala Glu Gly Val Pro Glu
                325                 330                 335

Tyr Ile Thr Gln Arg Thr Arg Trp Cys Leu Gly Thr Ile Gln Ile Gly
                340                 345                 350

Leu Leu Arg Thr Gly Pro Leu Trp Arg Gly Asn Phe Thr Leu Thr Gln
            355                 360                 365

Arg Leu His Tyr Leu His Gly Leu Phe Cys Trp Leu Ser Lys Pro Phe
    370                 375                 380

Ile Leu Cys Leu Leu Leu Ala Pro Ser Ile Tyr Trp Leu Thr Gly Val
385                 390                 395                 400

Ser Ala Leu Gln Ala Asp Glu Leu Met Phe Met Lys Leu Gly Leu Ser
                405                 410                 415

Ser Leu Ala Leu Phe Trp Thr Tyr Thr Trp Ile Ser Gly Lys Arg
                420                 425                 430

Thr Leu Pro Leu Phe Thr Glu Val Thr His Ala Leu Thr Ala Val Pro
            435                 440                 445

Ile Thr Ile Thr Leu Phe Gln Ala Ile Arg Lys Pro Phe Gly Arg Pro
450                 455                 460

Phe Lys Val Thr Glu Lys Gly Gly Asp Arg Ser Gln Val Arg Val His
```

```
                465                 470                 475                 480
            Leu Pro Thr Ala Ile Phe Phe Ala Phe Val Thr Leu Ser Ser Ala Val
                            485                 490                 495
            Ser Ile Val Leu Ala Val Tyr Gly Leu Asp Ala Pro Ser Glu Leu Ser
                        500                 505                 510
            Ser Arg Asp Cys Leu Asn Leu Ile Trp Ser Ala Val Ala Met Val Ile
                        515                 520                 525
            Ala Phe Thr Ser Phe Ile Cys Cys Ile Glu Leu Pro Arg Phe Gly Lys
                        530                 535                 540
            Glu Glu Met Ile Gly Val Asp Phe Arg Gly Gln Leu Arg Ser Ala Ser
            545                 550                 555                 560
            Ser Thr Arg Pro Val Arg Ile Thr Gly Leu Ser Thr Glu Asn Ile Thr
                            565                 570                 575
            Leu Ala Ala Val Pro Ser Ser Asp Val Thr Asp Val Phe Val Pro
                        580                 585                 590
            Glu Ala Gly Trp Met Arg Ile Ser Pro Ala Glu His Ala Gln Asn Ser
                        595                 600                 605
            Gly Lys Phe Asp Ile His Pro Ser Asp Glu Gln Arg Ser Ile Leu
                610                 615                 620
            Arg Leu Leu Phe Arg Lys Ala Pro Glu Asn Val Ala Glu Gln Gly Asp
            625                 630                 635                 640
            Leu Met Lys Ser Met Arg Ile Leu Leu Ala Arg Ala Phe Gly
                            645                 650
```

<210> SEQ ID NO 29
<211> LENGTH: 2592
<212> TYPE: DNA
<213> ORGANISM: Pseudomonas putida
<220> FEATURE:
<221> NAME/KEY: CDS
<222> LOCATION: (1)...(2589)

<400> SEQUENCE: 29

```
atg tct tca cgt aaa ttc ggc ctg aac ctg gta gtg gtg ctg gcc atc      48
Met Ser Ser Arg Lys Phe Gly Leu Asn Leu Val Val Val Leu Ala Ile
1               5                   10                  15 gcc gca ctg ttc acc ggg ttc tgg gca ctg atc aac cgc ccg gtc tcc      96
Ala Ala Leu Phe Thr Gly Phe Trp Ala Leu Ile Asn Arg Pro Val Ser
                20                  25                  30 gcc ccc gcc tgg cca gaa cag atc tct ggc ttt tcg tat tcg ccg ttc     144
Ala Pro Ala Trp Pro Glu Gln Ile Ser Gly Phe Ser Tyr Ser Pro Phe
            35                  40                  45 cgc ctg ggc gaa agc cca cag aag ggt cag tac ccc act gac gac gaa     192
Arg Leu Gly Glu Ser Pro Gln Lys Gly Gln Tyr Pro Thr Asp Asp Glu
        50                  55                  60 atg cgc cag gac ctg gag caa ctg agc aaa ctg acc gac agc atc cgt     240
Met Arg Gln Asp Leu Glu Gln Leu Ser Lys Leu Thr Asp Ser Ile Arg
65                  70                  75                  80 atc tat acc gtg gaa ggc acc cag gcc gac gtc ccg cgc ctg gcc gag     288
Ile Tyr Thr Val Glu Gly Thr Gln Ala Asp Val Pro Arg Leu Ala Glu
                85                  90                  95 gag ttc ggc ctg cgg gtg acg ctg ggg ata tgg atc agc ccg gac ctg     336
Glu Phe Gly Leu Arg Val Thr Leu Gly Ile Trp Ile Ser Pro Asp Leu
                100                 105                 110 gag cgc aac gag cgc gaa att gcc acg gcc atc cag ctg gcc aac acg     384
Glu Arg Asn Glu Arg Glu Ile Ala Thr Ala Ile Gln Leu Ala Asn Thr
            115                 120                 125 tcg cgc agc gtg gtg cgg gtg gtg gtc ggc aac gag gcg ctg ttc cgt     432
```

```
                Ser Arg Ser Val Val Arg Val Val Gly Asn Glu Ala Leu Phe Arg
                    130                 135                 140 gaa gaa gtc aca ccg gaa aac ctg atc aaa tac ctg gac cgc gta cgc        480
Glu Glu Val Thr Pro Glu Asn Leu Ile Lys Tyr Leu Asp Arg Val Arg
145                 150                 155                 160 gca gcc gtg aag gtg ccc gtg acc acc agt gaa cag tgg cac atc tgg        528
Ala Ala Val Lys Val Pro Val Thr Thr Ser Glu Gln Trp His Ile Trp
                165                 170                 175 aag gaa cat cct gag ctg gcc agg cac gtc gac ctg att gcc gcg cac        576
Lys Glu His Pro Glu Leu Ala Arg His Val Asp Leu Ile Ala Ala His
                180                 185                 190 atc ctg ccc tac tgg gag ttc gtg ccg atg aag gat tcg gtc gag ttc        624
Ile Leu Pro Tyr Trp Glu Phe Val Pro Met Lys Asp Ser Val Glu Phe
                195                 200                 205 gtc ctc gag cgc gcc cgt gaa ctg aag cac cag ttc ccg cgc aaa cct        672
Val Leu Glu Arg Ala Arg Glu Leu Lys His Gln Phe Pro Arg Lys Pro
                210                 215                 220 ctg ctg ctg tcg gaa gtc ggc tgg ccg agc aac ggc cgc atg cgc ggt        720
Leu Leu Leu Ser Glu Val Gly Trp Pro Ser Asn Gly Arg Met Arg Gly
225                 230                 235                 240 ggt gcc gat gcc aca cag gcc gac cag gcc atc tac ttg cgc acc ctg        768
Gly Ala Asp Ala Thr Gln Ala Asp Gln Ala Ile Tyr Leu Arg Thr Leu
                245                 250                 255 gtc aat acc ctc aac cgc cgt ggc tac aac tac ttt gtc att gaa gcc        816
Val Asn Thr Leu Asn Arg Arg Gly Tyr Asn Tyr Phe Val Ile Glu Ala
                260                 265                 270 tat gac caa ccc tgg aag gcc agc gac gaa gga tcg gta ggc gcc tac        864
Tyr Asp Gln Pro Trp Lys Ala Ser Asp Glu Gly Ser Val Gly Ala Tyr
                275                 280                 285 tgg ggc gtc tac aac gcc gag cgc cag cag aag ttc aac ttc gac ggc        912
Trp Gly Val Tyr Asn Ala Glu Arg Gln Gln Lys Phe Asn Phe Asp Gly
290                 295                 300 ccc gtg gtg gcg atc ccg cag tgg cgg gcc ctg gca gtg gcg tcg gtg        960
Pro Val Val Ala Ile Pro Gln Trp Arg Ala Leu Ala Val Ala Ser Val
305                 310                 315                 320 gtg ctg gca atg atc gcc ttg atg gtg ctg ttc atc gat ggc tcg gcc       1008
Val Leu Ala Met Ile Ala Leu Met Val Leu Phe Ile Asp Gly Ser Ala
                325                 330                 335 ctg cgc cag cgt ggc cgt acc ttc ctg acg ttc atc acc ttc ctg tgc       1056
Leu Arg Gln Arg Gly Arg Thr Phe Leu Thr Phe Ile Thr Phe Leu Cys
                340                 345                 350 ggg tcg gtg ctg gtg tgg atc gcc tac gac tac agc cag caa tac agc       1104
Gly Ser Val Leu Val Trp Ile Ala Tyr Asp Tyr Ser Gln Gln Tyr Ser
                355                 360                 365 acc tgg ttc agc ctg acc gtg ggc gtg ctg ctg gcc ctc ggc gcg ctg       1152
Thr Trp Phe Ser Leu Thr Val Gly Val Leu Leu Ala Leu Gly Ala Leu
                370                 375                 380 ggt gtg ttc atc gtg ctc ctc acc gag gcc cac gaa ctg gcc gag gcg       1200
Gly Val Phe Ile Val Leu Leu Thr Glu Ala His Glu Leu Ala Glu Ala
385                 390                 395                 400 gtc tgg ata cac aag cgc cgc cgc gag ttc ctg ccc gtg cag gcc gac       1248
Val Trp Ile His Lys Arg Arg Arg Glu Phe Leu Pro Val Gln Ala Asp
                405                 410                 415 act gcc tac cgg ccc aag gtg tcg gtg cat gtg ccg tgc tac aac gag       1296
Thr Ala Tyr Arg Pro Lys Val Ser Val His Val Pro Cys Tyr Asn Glu
                420                 425                 430 cca cct gag atg gtg aaa cag acc ctg gac gcc ctg gcc gcc ctg gac       1344
Pro Pro Glu Met Val Lys Gln Thr Leu Asp Ala Leu Ala Ala Leu Asp
                435                 440                 445
```

```
tac ccc gac tac gaa gtg ctg gtg atc gac aac aac acc aag gac ccg      1392
Tyr Pro Asp Tyr Glu Val Leu Val Ile Asp Asn Asn Thr Lys Asp Pro
    450                 455                 460 gcc gtg tgg gag ccg ctc aag gcc cac tgc gaa aag ctt ggc gag cgc      1440
Ala Val Trp Glu Pro Leu Lys Ala His Cys Glu Lys Leu Gly Glu Arg
465                 470                 475                 480 ttc aag ttc ttc cac gtc gcg cca ctg gcc ggc ttc aag ggt ggc gcg      1488
Phe Lys Phe Phe His Val Ala Pro Leu Ala Gly Phe Lys Gly Gly Ala
                485                 490                 495 ctg aat tac ctg atc ccg cac acg gca aag gac gcc gaa gtg atc gcg      1536
Leu Asn Tyr Leu Ile Pro His Thr Ala Lys Asp Ala Glu Val Ile Ala
                500                 505                 510 gta atc gac tcg gac tac tgc gtc gac cgc aac tgg ctc aag cac atg      1584
Val Ile Asp Ser Asp Tyr Cys Val Asp Arg Asn Trp Leu Lys His Met
            515                 520                 525 gtg ccg cac ttc gcc gac ccg aaa att gcc gtg gtg cag tca ccg cag      1632
Val Pro His Phe Ala Asp Pro Lys Ile Ala Val Val Gln Ser Pro Gln
530                 535                 540 gat tac cgt gac cag cac gaa agc gcc ttc aag aag ctg tgc tac agc      1680
Asp Tyr Arg Asp Gln His Glu Ser Ala Phe Lys Lys Leu Cys Tyr Ser
545                 550                 555                 560 gaa tac aag ggc ttc ttc cac atc ggt atg gtc acc cgc aac gac cgt      1728
Glu Tyr Lys Gly Phe Phe His Ile Gly Met Val Thr Arg Asn Asp Arg
                565                 570                 575 gac gcg atc atc cag cac ggc acc atg acc atg acc cgg cgc agt gtg      1776
Asp Ala Ile Ile Gln His Gly Thr Met Thr Met Thr Arg Arg Ser Val
                580                 585                 590 ctg gaa gaa ctg ggc tgg gcc gag tgg tgc atc tgc gag gac gcc gaa      1824
Leu Glu Glu Leu Gly Trp Ala Glu Trp Cys Ile Cys Glu Asp Ala Glu
            595                 600                 605 ctg ggc ctg cgc gtg ttc gag aaa ggc ctg tcc gcc gcc tac gcc cac      1872
Leu Gly Leu Arg Val Phe Glu Lys Gly Leu Ser Ala Ala Tyr Ala His
610                 615                 620 aac agc tac ggc aag ggc ctg atg ccc gac acc ttc atc gac ttc aag      1920
Asn Ser Tyr Gly Lys Gly Leu Met Pro Asp Thr Phe Ile Asp Phe Lys
625                 630                 635                 640 aag caa cgc ttc cgc tgg gcc tac ggc gcc atc cag atc atc aag cac      1968
Lys Gln Arg Phe Arg Trp Ala Tyr Gly Ala Ile Gln Ile Ile Lys His
                645                 650                 655 cac gcc ggc gcg ctg ctc cgc ggc aaa ggc agc cag ctg acc cgt ggc      2016
His Ala Gly Ala Leu Leu Arg Gly Lys Gly Ser Gln Leu Thr Arg Gly
                660                 665                 670 cag cgc tac cac ttc ctg gcc ggc tgg cta ccg tgg atc gcc gat ggc      2064
Gln Arg Tyr His Phe Leu Ala Gly Trp Leu Pro Trp Ile Ala Asp Gly
            675                 680                 685 atg aac atc ttc ttc acc atc ggc gcg ctg ttg tgg tcg gcg gcg atg      2112
Met Asn Ile Phe Phe Thr Ile Gly Ala Leu Leu Trp Ser Ala Ala Met
690                 695                 700 atc atc gtg ccg cat cgg gtc gat ccg ccc ctg atg atc ttc gcc atc      2160
Ile Ile Val Pro His Arg Val Asp Pro Pro Leu Met Ile Phe Ala Ile
705                 710                 715                 720 ccg ccg ctg gcg ctg ttc ttc ttc aag gtc ggc aag atc atc ttc ctg      2208
Pro Pro Leu Ala Leu Phe Phe Phe Lys Val Gly Lys Ile Ile Phe Leu
                725                 730                 735 tac cgc cga gcg gtg ggg gtg aac ctc aag gat gcc ttc gca gct gcg      2256
Tyr Arg Arg Ala Val Gly Val Asn Leu Lys Asp Ala Phe Ala Ala Ala
                740                 745                 750 ctg gcc ggg ctg gca ctg tcg cac acc atc gcc aag gcg gta ctg tat      2304
Leu Ala Gly Leu Ala Leu Ser His Thr Ile Ala Lys Ala Val Leu Tyr
                755                 760                 765
```

```
ggt ttc ttc acc agc agc atg ccg ttc ttc cgc acg ccg aag aac gct    2352
Gly Phe Phe Thr Ser Ser Met Pro Phe Phe Arg Thr Pro Lys Asn Ala
770                 775                 780 gac agc cat ggg ttg ctg gtg gcg att tcc gaa gcc cgt gaa gag ctg    2400
Asp Ser His Gly Leu Leu Val Ala Ile Ser Glu Ala Arg Glu Glu Leu
785                 790                 795                 800 ttc atc atg gtg ctg ctg tgg ggc gcg gcg ttg ggt atc tac ctg gtg    2448
Phe Ile Met Val Leu Leu Trp Gly Ala Ala Leu Gly Ile Tyr Leu Val
                805                 810                 815 cag ggg ctg ccg agt tcg gac atg cgc ttc tgg gtg gcg atg ttg ctg    2496
Gln Gly Leu Pro Ser Ser Asp Met Arg Phe Trp Val Ala Met Leu Leu
            820                 825                 830 gtg cag tcg ttg cct tat gtg gca gcg ctg gtg atg gcg ttc ctg tcg    2544
Val Gln Ser Leu Pro Tyr Val Ala Ala Leu Val Met Ala Phe Leu Ser
        835                 840                 845 tcg ctg ccc aag ccc gca gaa aag gct gcc caa gcg cag cag gct        2589
Ser Leu Pro Lys Pro Ala Glu Lys Ala Ala Gln Ala Gln Gln Ala
    850                 855                 860 tga                                                                 2592
```

<210> SEQ ID NO 30
<211> LENGTH: 863
<212> TYPE: PRT
<213> ORGANISM: Pseudomonas putida

<400> SEQUENCE: 30

```
Met Ser Ser Arg Lys Phe Gly Leu Asn Leu Val Val Leu Ala Ile
1               5                   10                  15

Ala Ala Leu Phe Thr Gly Phe Trp Ala Leu Ile Asn Arg Pro Val Ser
                20                  25                  30

Ala Pro Ala Trp Pro Glu Gln Ile Ser Gly Phe Ser Tyr Ser Pro Phe
            35                  40                  45

Arg Leu Gly Glu Ser Pro Gln Lys Gly Gln Tyr Pro Thr Asp Asp Glu
    50                  55                  60

Met Arg Gln Asp Leu Glu Gln Leu Ser Lys Leu Thr Asp Ser Ile Arg
65                  70                  75                  80

Ile Tyr Thr Val Glu Gly Thr Gln Ala Asp Val Pro Arg Leu Ala Glu
                85                  90                  95

Glu Phe Gly Leu Arg Val Thr Leu Gly Ile Trp Ile Ser Pro Asp Leu
            100                 105                 110

Glu Arg Asn Glu Arg Glu Ile Ala Thr Ala Ile Gln Leu Ala Asn Thr
    115                 120                 125

Ser Arg Ser Val Val Arg Val Val Gly Asn Glu Ala Leu Phe Arg
130                 135                 140

Glu Glu Val Thr Pro Glu Asn Leu Ile Lys Tyr Leu Asp Arg Val Arg
145                 150                 155                 160

Ala Ala Val Lys Val Pro Val Thr Thr Ser Glu Gln Trp His Ile Trp
                165                 170                 175

Lys Glu His Pro Glu Leu Ala Arg His Val Asp Leu Ile Ala Ala His
            180                 185                 190

Ile Leu Pro Tyr Trp Glu Phe Val Pro Met Lys Asp Ser Val Glu Phe
    195                 200                 205

Val Leu Glu Arg Ala Arg Glu Leu Lys His Gln Phe Pro Arg Lys Pro
210                 215                 220

Leu Leu Leu Ser Glu Val Gly Trp Pro Ser Asn Gly Arg Met Arg Gly
225                 230                 235                 240
```

```
                                -continued

Gly Ala Asp Ala Thr Gln Ala Asp Gln Ala Ile Tyr Leu Arg Thr Leu
                245                 250                 255

Val Asn Thr Leu Asn Arg Arg Gly Tyr Asn Tyr Phe Val Ile Glu Ala
            260                 265                 270

Tyr Asp Gln Pro Trp Lys Ala Ser Asp Glu Gly Ser Val Gly Ala Tyr
        275                 280                 285

Trp Gly Val Tyr Asn Ala Glu Arg Gln Gln Lys Phe Asn Phe Asp Gly
    290                 295                 300

Pro Val Val Ala Ile Pro Gln Trp Arg Ala Leu Ala Val Ala Ser Val
305                 310                 315                 320

Val Leu Ala Met Ile Ala Leu Met Val Leu Phe Ile Asp Gly Ser Ala
                325                 330                 335

Leu Arg Gln Arg Gly Arg Thr Phe Leu Thr Phe Ile Thr Phe Leu Cys
            340                 345                 350

Gly Ser Val Leu Val Trp Ile Ala Tyr Asp Tyr Ser Gln Gln Tyr Ser
        355                 360                 365

Thr Trp Phe Ser Leu Thr Val Gly Val Leu Ala Leu Gly Ala Leu
    370                 375                 380

Gly Val Phe Ile Val Leu Leu Thr Glu Ala His Glu Leu Ala Glu Ala
385                 390                 395                 400

Val Trp Ile His Lys Arg Arg Glu Phe Leu Pro Val Gln Ala Asp
                405                 410                 415

Thr Ala Tyr Arg Pro Lys Val Ser Val His Val Pro Cys Tyr Asn Glu
            420                 425                 430

Pro Pro Glu Met Val Lys Gln Thr Leu Asp Ala Leu Ala Ala Leu Asp
        435                 440                 445

Tyr Pro Asp Tyr Glu Val Leu Val Ile Asp Asn Asn Thr Lys Asp Pro
    450                 455                 460

Ala Val Trp Glu Pro Leu Lys Ala His Cys Glu Lys Leu Gly Glu Arg
465                 470                 475                 480

Phe Lys Phe Phe His Val Ala Pro Leu Ala Gly Phe Lys Gly Gly Ala
                485                 490                 495

Leu Asn Tyr Leu Ile Pro His Thr Ala Lys Asp Ala Glu Val Ile Ala
            500                 505                 510

Val Ile Asp Ser Asp Tyr Cys Val Asp Arg Asn Trp Leu Lys His Met
        515                 520                 525

Val Pro His Phe Ala Asp Pro Lys Ile Ala Val Gln Ser Pro Gln
    530                 535                 540

Asp Tyr Arg Asp Gln His Glu Ser Ala Phe Lys Lys Leu Cys Tyr Ser
545                 550                 555                 560

Glu Tyr Lys Gly Phe Phe His Ile Gly Met Val Thr Arg Asn Asp Arg
                565                 570                 575

Asp Ala Ile Ile Gln His Gly Thr Met Thr Met Thr Arg Arg Ser Val
            580                 585                 590

Leu Glu Glu Leu Gly Trp Ala Glu Trp Cys Ile Cys Glu Asp Ala Glu
        595                 600                 605

Leu Gly Leu Arg Val Phe Glu Lys Gly Leu Ser Ala Ala Tyr Ala His
    610                 615                 620

Asn Ser Tyr Gly Lys Gly Leu Met Pro Asp Thr Phe Ile Asp Phe Lys
625                 630                 635                 640

Lys Gln Arg Phe Arg Trp Ala Tyr Gly Ala Ile Gln Ile Ile Lys His
                645                 650                 655
```

-continued

| | | | | | | | | | | | | |
|---|---|---|---|---|---|---|---|---|---|---|---|---|
|His|Ala|Gly|Ala|Leu|Leu|Arg|Gly|Lys|Gly|Ser|Gln|Leu|Thr|Arg|Gly|
| | | |660| | | | |665| | | | |670| | |

| | | | | | | | | | | | |
|---|---|---|---|---|---|---|---|---|---|---|---|
|Gln|Arg|Tyr|His|Phe|Leu|Ala|Gly|Trp|Leu|Pro|Trp|Ile|Ala|Asp|Gly|
| | | |675| | | | |680| | | | |685| | |

| | | | | | | | | | | | |
|---|---|---|---|---|---|---|---|---|---|---|---|
|Met|Asn|Ile|Phe|Phe|Thr|Ile|Gly|Ala|Leu|Leu|Trp|Ser|Ala|Ala|Met|
| | | |690| | | | |695| | | | |700| | |

|Ile|Ile|Val|Pro|His|Arg|Val|Asp|Pro|Pro|Leu|Met|Ile|Phe|Ala|Ile|
|---|---|---|---|---|---|---|---|---|---|---|---|---|---|---|---|
|705| | | | |710| | | | |715| | | | |720|

|Pro|Pro|Leu|Ala|Leu|Phe|Phe|Lys|Val|Gly|Lys|Ile|Ile|Phe|Leu|
|---|---|---|---|---|---|---|---|---|---|---|---|---|---|---|
| | | | |725| | | | |730| | | | |735|

|Tyr|Arg|Arg|Ala|Val|Gly|Val|Asn|Leu|Lys|Asp|Ala|Phe|Ala|Ala|Ala|
|---|---|---|---|---|---|---|---|---|---|---|---|---|---|---|---|
| | | |740| | | | |745| | | | |750| | |

|Leu|Ala|Gly|Leu|Ala|Leu|Ser|His|Thr|Ile|Ala|Lys|Ala|Val|Leu|Tyr|
|---|---|---|---|---|---|---|---|---|---|---|---|---|---|---|---|
| | |755| | | | |760| | | | |765| | | |

|Gly|Phe|Phe|Thr|Ser|Ser|Met|Pro|Phe|Phe|Arg|Thr|Pro|Lys|Asn|Ala|
|---|---|---|---|---|---|---|---|---|---|---|---|---|---|---|---|
| | |770| | | | |775| | | | |780| | | |

|Asp|Ser|His|Gly|Leu|Leu|Val|Ala|Ile|Ser|Glu|Ala|Arg|Glu|Glu|Leu|
|---|---|---|---|---|---|---|---|---|---|---|---|---|---|---|---|
|785| | | | |790| | | | |795| | | | |800|

|Phe|Ile|Met|Val|Leu|Leu|Trp|Gly|Ala|Ala|Leu|Gly|Ile|Tyr|Leu|Val|
|---|---|---|---|---|---|---|---|---|---|---|---|---|---|---|---|
| | | | |805| | | | |810| | | | |815| |

|Gln|Gly|Leu|Pro|Ser|Ser|Asp|Met|Arg|Phe|Trp|Val|Ala|Met|Leu|Leu|
|---|---|---|---|---|---|---|---|---|---|---|---|---|---|---|---|
| | | |820| | | | |825| | | | |830| | |

|Val|Gln|Ser|Leu|Pro|Tyr|Val|Ala|Ala|Leu|Val|Met|Ala|Phe|Leu|Ser|
|---|---|---|---|---|---|---|---|---|---|---|---|---|---|---|---|
| | | |835| | | | |840| | | | |845| | |

|Ser|Leu|Pro|Lys|Pro|Ala|Glu|Lys|Ala|Ala|Gln|Ala|Gln|Gln|Ala|
|---|---|---|---|---|---|---|---|---|---|---|---|---|---|---|
| | |850| | | | |855| | | | |860| | | |

```
<210> SEQ ID NO 31
<211> LENGTH: 2529
<212> TYPE: DNA
<213> ORGANISM: Pseudomonas syringae
<220> FEATURE:
<221> NAME/KEY: CDS
<222> LOCATION: (1)...(2526)

<400> SEQUENCE: 31
```

| | | | | | | | | | | | | | | | | |
|---|---|---|---|---|---|---|---|---|---|---|---|---|---|---|---|---|
|atg|tcg|ata|tac|cgc|atg|gag|cac|agt|tta|gac|atg|aat|aaa|aaa|ata| |48|
|Met|Ser|Ile|Tyr|Arg|Met|Glu|His|Ser|Leu|Asp|Met|Asn|Lys|Lys|Ile| | |
|1| | | |5| | | | |10| | | | |15| | | |

|tca|gac|gct|cca|atc|tgg|ccg|gtc|aac|tca|ttc|aaa|tcc|gtc|gtg|acc| |96|
|---|---|---|---|---|---|---|---|---|---|---|---|---|---|---|---|---|---|
|Ser|Asp|Ala|Pro|Ile|Trp|Pro|Val|Asn|Ser|Phe|Lys|Ser|Val|Val|Thr| | |
| | | |20| | | | |25| | | | |30| | | | |

|aaa|gtc|ccg|gac|tgg|cct|gac|agc|atc|tcg|ggc|ctt|gcc|tat|aac|ccc| |144|
|---|---|---|---|---|---|---|---|---|---|---|---|---|---|---|---|---|---|
|Lys|Val|Pro|Asp|Trp|Pro|Asp|Ser|Ile|Ser|Gly|Leu|Ala|Tyr|Asn|Pro| | |
| | |35| | | | |40| | | | |45| | | | | |

|ttt|cgt|ccc|gga|caa|agt|ccc|tac|aag|cac|atc|tat|ccg|acc|cgc|gag| |192|
|---|---|---|---|---|---|---|---|---|---|---|---|---|---|---|---|---|---|
|Phe|Arg|Pro|Gly|Gln|Ser|Pro|Tyr|Lys|His|Ile|Tyr|Pro|Thr|Arg|Glu| | |
| | |50| | | | |55| | | | |60| | | | | |

|caa|atc|aaa|gaa|gac|ttg|ctg|ctg|atc|cgc|ccg|ttg|act|cga|cat|gta| |240|
|---|---|---|---|---|---|---|---|---|---|---|---|---|---|---|---|---|---|
|Gln|Ile|Lys|Glu|Asp|Leu|Leu|Leu|Ile|Arg|Pro|Leu|Thr|Arg|His|Val| | |
|65| | | | |70| | | | |75| | | | |80| | |

|aga|acc|tac|tcg|gtc|gag|cag|acg|ctg|gcc|tgt|att|ccc|gaa|ata|gcc| |288|
|---|---|---|---|---|---|---|---|---|---|---|---|---|---|---|---|---|---|
|Arg|Thr|Tyr|Ser|Val|Glu|Gln|Thr|Leu|Ala|Cys|Ile|Pro|Glu|Ile|Ala| | |
| | | | |85| | | | |90| | | | |95| | | |

|gaa|gaa|ctc|ggc|atg|agt|gtc|aca|ctc|ggc|ata|tgg|ata|ggc|tgg|gac| |336|
|---|---|---|---|---|---|---|---|---|---|---|---|---|---|---|---|---|---|
|Glu|Glu|Leu|Gly|Met|Ser|Val|Thr|Leu|Gly|Ile|Trp|Ile|Gly|Trp|Asp| | |
| | | | |100| | | | |105| | | | |110| | | |

|gaa|aaa|cgc|aat|gat|cgg|gaa|ctg|atc|gag|ggc|gtg|aag|ctt|gcc|aat| |384|
|---|---|---|---|---|---|---|---|---|---|---|---|---|---|---|---|---|---|

-continued

```
Glu Lys Arg Asn Asp Arg Glu Leu Ile Glu Gly Val Lys Leu Ala Asn
        115                 120                 125 cag tat ccc agc gtc cgg cgt ctg atc atc gga aat gaa aca tta ctg      432
Gln Tyr Pro Ser Val Arg Arg Leu Ile Ile Gly Asn Glu Thr Leu Leu
130                 135                 140 cgc aat gac gtc acc gtc agc caa ctg atc gat tac atg caa acg gca      480
Arg Asn Asp Val Thr Val Ser Gln Leu Ile Asp Tyr Met Gln Thr Ala
145                 150                 155                 160 cga caa ggt gtc aac gtt ccg att tca acc tca gag gga tgg caa cag      528
Arg Gln Gly Val Asn Val Pro Ile Ser Thr Ser Glu Gly Trp Gln Gln
                165                 170                 175 tgg cac gat acg ccg gaa ctg gct gat cac gca gac ttc atc gcg gcg      576
Trp His Asp Thr Pro Glu Leu Ala Asp His Ala Asp Phe Ile Ala Ala
            180                 185                 190 cat gtc ttg cca ttc agg gag ttc gtt cca gtc acc cag gca ggc tct      624
His Val Leu Pro Phe Arg Glu Phe Val Pro Val Thr Gln Ala Gly Ser
        195                 200                 205 gca gtt ctc gca cgg gcg aac gaa ttg agg ctg atg ttt ccc gaa aaa      672
Ala Val Leu Ala Arg Ala Asn Glu Leu Arg Leu Met Phe Pro Glu Lys
210                 215                 220 ccg ctg ata ctt tcc gag att ggc tgg cca gac aaa ggc aac ttc aga      720
Pro Leu Ile Leu Ser Glu Ile Gly Trp Pro Asp Lys Gly Asn Phe Arg
225                 230                 235                 240 aga cgc acc acc gcc tac gtc gcc gaa cag tca att tac ctg cgc agc      768
Arg Arg Thr Thr Ala Tyr Val Ala Glu Gln Ser Ile Tyr Leu Arg Ser
                245                 250                 255 cag ctc gcg ctg ttg aac cag agt ggc ctc gac tac ttt gtc agg gag      816
Gln Leu Ala Leu Leu Asn Gln Ser Gly Leu Asp Tyr Phe Val Arg Glu
            260                 265                 270 gca ttt gat caa caa tgg aaa act gag gaa ggg ttg ccg ggg cct cac      864
Ala Phe Asp Gln Gln Trp Lys Thr Glu Glu Gly Leu Pro Gly Pro His
        275                 280                 285 tgg ggc ctg ttc gat gcc cag cga aag ata aag tta cca ctg caa ggc      912
Trp Gly Leu Phe Asp Ala Gln Arg Lys Ile Lys Leu Pro Leu Gln Gly
290                 295                 300 cca gtg aaa ata cgg gcc agc tgg cga tca gaa gtt ccg aga ttg gtc      960
Pro Val Lys Ile Arg Ala Ser Trp Arg Ser Glu Val Pro Arg Leu Val
305                 310                 315                 320 gcc gat tgg cag ccc gac aac tgg cga aca acc gta ttg att ttt gct     1008
Ala Asp Trp Gln Pro Asp Asn Trp Arg Thr Thr Val Leu Ile Phe Ala
                325                 330                 335 gcg ttg tac aca tta ttg gta ggc gtt ggc ata agt tac gca cag ccc     1056
Ala Leu Tyr Thr Leu Leu Val Gly Val Gly Ile Ser Tyr Ala Gln Pro
            340                 345                 350 tta tcg atg tgg gtg gct ttg ccc atc gcc ttg gtg tgg gtg acc agc     1104
Leu Ser Met Trp Val Ala Leu Pro Ile Ala Leu Val Trp Val Thr Ser
        355                 360                 365 tta ctg atc ggc acg ggg ata cag ggt tac gag ttc ctc gaa tca tgc     1152
Leu Leu Ile Gly Thr Gly Ile Gln Gly Tyr Glu Phe Leu Glu Ser Cys
370                 375                 380 tgg gga ccg gag aaa ccg cga tct ttt cct ccg tta aga gct tac ccg     1200
Trp Gly Pro Glu Lys Pro Arg Ser Phe Pro Pro Leu Arg Ala Tyr Pro
385                 390                 395                 400 ggg ccg tta ccc aaa gtg tcc ata cac gta ccg tgc tac aac gaa cct     1248
Gly Pro Leu Pro Lys Val Ser Ile His Val Pro Cys Tyr Asn Glu Pro
                405                 410                 415 ccc gac atg gtg aag ctg acg ctc gac gca tta caa cgc ctg gac tat     1296
Pro Asp Met Val Lys Leu Thr Leu Asp Ala Leu Gln Arg Leu Asp Tyr
            420                 425                 430
```

-continued

```
ccg aac ttt gag gtt ctg atc atc gac aac aac act caa gac ccg gaa       1344
Pro Asn Phe Glu Val Leu Ile Ile Asp Asn Asn Thr Gln Asp Pro Glu
        435                 440                 445 gtc tgg gag ccc att gag cag tac tgc agg caa ctg gga cct cgc ttc       1392
Val Trp Glu Pro Ile Glu Gln Tyr Cys Arg Gln Leu Gly Pro Arg Phe
    450                 455                 460 cgg ctc ttt cat gtc aat cca ctt agc ggg ttc aag tcg ggc gca ctg       1440
Arg Leu Phe His Val Asn Pro Leu Ser Gly Phe Lys Ser Gly Ala Leu
465                 470                 475                 480 aac tac ctg ctg gac tac acc gcc aag gat gcc gaa ata gta gcg gcg       1488
Asn Tyr Leu Leu Asp Tyr Thr Ala Lys Asp Ala Glu Ile Val Ala Ala
                485                 490                 495 atc gat gct gat tat tgc gtg cac cgg cat tgg ctc aag cat atg gcc       1536
Ile Asp Ala Asp Tyr Cys Val His Arg His Trp Leu Lys His Met Ala
            500                 505                 510 ccc tat ttt gcg tgc ccg gat ata gcg gtt atc caa gta ccg caa gac       1584
Pro Tyr Phe Ala Cys Pro Asp Ile Ala Val Ile Gln Val Pro Gln Asp
        515                 520                 525 tac cgt gat ggc gac gac agc ctg ttc aaa cgt tgc tgc cag gcc gag       1632
Tyr Arg Asp Gly Asp Asp Ser Leu Phe Lys Arg Cys Cys Gln Ala Glu
    530                 535                 540 tat cgc gtt ttt ttc aat att ggc atg gtc atc cgc aac gac cac gac       1680
Tyr Arg Val Phe Phe Asn Ile Gly Met Val Ile Arg Asn Asp His Asp
545                 550                 555                 560 gca atc att cag cac ggc acc atg acc ctg att cgc aat tcg gtg ttg       1728
Ala Ile Ile Gln His Gly Thr Met Thr Leu Ile Arg Asn Ser Val Leu
                565                 570                 575 cag cga ctg cgc tgg gca gaa tgg agc atc tgc gaa gat gcc gag ctc       1776
Gln Arg Leu Arg Trp Ala Glu Trp Ser Ile Cys Glu Asp Ala Glu Leu
            580                 585                 590 gga ctg cgg ata ctg gag aac ggt ttt tcc acc ggc tat gtc gcc atc       1824
Gly Leu Arg Ile Leu Glu Asn Gly Phe Ser Thr Gly Tyr Val Ala Ile
        595                 600                 605 agc tat ggc aag gga ctg atc ccg gat aca ttc atg gac ttc aag aaa       1872
Ser Tyr Gly Lys Gly Leu Ile Pro Asp Thr Phe Met Asp Phe Lys Lys
    610                 615                 620 caa cgg tat cgc tgg gct tac ggt gtc atc cag ata ctc aaa cga cat       1920
Gln Arg Tyr Arg Trp Ala Tyr Gly Val Ile Gln Ile Leu Lys Arg His
625                 630                 635                 640 act gga agc ctg atc gca ggt acg tgc gag gcc ttg acg cca ata cag       1968
Thr Gly Ser Leu Ile Ala Gly Thr Cys Glu Ala Leu Thr Pro Ile Gln
                645                 650                 655 cgc tat cac ttc att gcc ggc tgg atg cct tgg att gca ggg gga ata       2016
Arg Tyr His Phe Ile Ala Gly Trp Met Pro Trp Ile Ala Gly Gly Ile
            660                 665                 670 aat tac ttt ctg gct atc gct gtg ctt ctc tgg tca atg gca atg atc       2064
Asn Tyr Phe Leu Ala Ile Ala Val Leu Leu Trp Ser Met Ala Met Ile
        675                 680                 685 att caa ccc gac aca ctc gaa cct gtg ccg tgg ata ttt tca tcc tca       2112
Ile Gln Pro Asp Thr Leu Glu Pro Val Pro Trp Ile Phe Ser Ser Ser
    690                 695                 700 tta ctg ttg atg ttt gtt ctg ggc gtt tgc aaa gcg atc agc ctt tat       2160
Leu Leu Leu Met Phe Val Leu Gly Val Cys Lys Ala Ile Ser Leu Tyr
705                 710                 715                 720 caa cga ttg gcc agc acc gac atc aaa gac gcc ttc gca gcc ata att       2208
Gln Arg Leu Ala Ser Thr Asp Ile Lys Asp Ala Phe Ala Ala Ile Ile
                725                 730                 735 gcg agc atg gcg ctg tac tcg gtt gta ggc aag gcc gtg ctt tca tcg       2256
Ala Ser Met Ala Leu Tyr Ser Val Val Gly Lys Ala Val Leu Ser Ser
            740                 745                 750
```

```
gca ttc acc tca gga tta ccg ttc ttt cgc act ccc aag cag acc tct    2304
Ala Phe Thr Ser Gly Leu Pro Phe Phe Arg Thr Pro Lys Gln Thr Ser
        755                 760                 765 ggc agc ggg ctc ggc aag gcc ctg ctg gac gtc cgg gaa gat ctg tac    2352
Gly Ser Gly Leu Gly Lys Ala Leu Leu Asp Val Arg Glu Asp Leu Tyr
    770                 775                 780 atg gcc gtg gtc tgg tgg gtc atg acg gta tcg ctg tgc ttc cga aaa    2400
Met Ala Val Val Trp Trp Val Met Thr Val Ser Leu Cys Phe Arg Lys
785                 790                 795                 800 gaa gct atc ggt ccg gac ctt gga ttc tgg gtg gcg ata atg ttc gcc    2448
Glu Ala Ile Gly Pro Asp Leu Gly Phe Trp Val Ala Ile Met Phe Ala
                805                 810                 815 cag tca ttg cct tac gta gcc gcc atg atc atg gca ata ctg tcg gct    2496
Gln Ser Leu Pro Tyr Val Ala Ala Met Ile Met Ala Ile Leu Ser Ala
            820                 825                 830 ctc gca aac cgc cct tca cgc tcc aca acc tga                        2529
Leu Ala Asn Arg Pro Ser Arg Ser Thr Thr
                835                 840

<210> SEQ ID NO 32
<211> LENGTH: 842
<212> TYPE: PRT
<213> ORGANISM: Pseudomonas syringae

<400> SEQUENCE: 32

Met Ser Ile Tyr Arg Met Glu His Ser Leu Asp Met Asn Lys Lys Ile
1               5                   10                  15

Ser Asp Ala Pro Ile Trp Pro Val Asn Ser Phe Lys Ser Val Val Thr
            20                  25                  30

Lys Val Pro Asp Trp Pro Asp Ser Ile Ser Gly Leu Ala Tyr Asn Pro
        35                  40                  45

Phe Arg Pro Gly Gln Ser Pro Tyr Lys His Ile Tyr Pro Thr Arg Glu
    50                  55                  60

Gln Ile Lys Glu Asp Leu Leu Leu Ile Arg Pro Leu Thr Arg His Val
65                  70                  75                  80

Arg Thr Tyr Ser Val Glu Gln Thr Leu Ala Cys Ile Pro Glu Ile Ala
                85                  90                  95

Glu Glu Leu Gly Met Ser Val Thr Leu Gly Ile Trp Ile Gly Trp Asp
            100                 105                 110

Glu Lys Arg Asn Asp Arg Glu Leu Ile Glu Gly Val Lys Leu Ala Asn
        115                 120                 125

Gln Tyr Pro Ser Val Arg Arg Leu Ile Ile Gly Asn Glu Thr Leu Leu
    130                 135                 140

Arg Asn Asp Val Thr Val Ser Gln Leu Ile Asp Tyr Met Gln Thr Ala
145                 150                 155                 160

Arg Gln Gly Val Asn Val Pro Ile Ser Thr Ser Glu Gly Trp Gln Gln
                165                 170                 175

Trp His Asp Thr Pro Glu Leu Ala Asp His Ala Asp Phe Ile Ala Ala
            180                 185                 190

His Val Leu Pro Phe Arg Glu Phe Val Pro Val Thr Gln Ala Gly Ser
        195                 200                 205

Ala Val Leu Ala Arg Ala Asn Glu Leu Arg Leu Met Phe Pro Glu Lys
    210                 215                 220

Pro Leu Ile Leu Ser Glu Ile Gly Trp Pro Asp Lys Gly Asn Phe Arg
225                 230                 235                 240

Arg Arg Thr Thr Ala Tyr Val Ala Glu Gln Ser Ile Tyr Leu Arg Ser
```

-continued

```
                    245                 250                 255
Gln Leu Ala Leu Leu Asn Gln Ser Gly Leu Asp Tyr Phe Val Arg Glu
            260                 265                 270
Ala Phe Asp Gln Gln Trp Lys Thr Glu Glu Gly Leu Pro Gly Pro His
        275                 280                 285
Trp Gly Leu Phe Asp Ala Gln Arg Lys Ile Lys Leu Pro Leu Gln Gly
        290                 295                 300
Pro Val Lys Ile Arg Ala Ser Trp Arg Ser Glu Val Pro Arg Leu Val
305                 310                 315                 320
Ala Asp Trp Gln Pro Asp Asn Trp Arg Thr Thr Val Leu Ile Phe Ala
                325                 330                 335
Ala Leu Tyr Thr Leu Leu Val Gly Val Gly Ile Ser Tyr Ala Gln Pro
            340                 345                 350
Leu Ser Met Trp Val Ala Leu Pro Ile Ala Leu Val Trp Val Thr Ser
        355                 360                 365
Leu Leu Ile Gly Thr Gly Ile Gln Gly Tyr Glu Phe Leu Glu Ser Cys
    370                 375                 380
Trp Gly Pro Glu Lys Pro Arg Ser Phe Pro Pro Leu Arg Ala Tyr Pro
385                 390                 395                 400
Gly Pro Leu Pro Lys Val Ser Ile His Val Pro Cys Tyr Asn Glu Pro
                405                 410                 415
Pro Asp Met Val Lys Leu Thr Leu Asp Ala Leu Gln Arg Leu Asp Tyr
            420                 425                 430
Pro Asn Phe Glu Val Leu Ile Ile Asp Asn Asn Thr Gln Asp Pro Glu
        435                 440                 445
Val Trp Glu Pro Ile Glu Gln Tyr Cys Arg Gln Leu Gly Pro Arg Phe
    450                 455                 460
Arg Leu Phe His Val Asn Pro Leu Ser Gly Phe Lys Ser Gly Ala Leu
465                 470                 475                 480
Asn Tyr Leu Leu Asp Tyr Thr Ala Lys Asp Ala Glu Ile Val Ala Ala
                485                 490                 495
Ile Asp Ala Asp Tyr Cys Val His Arg His Trp Leu Lys His Met Ala
            500                 505                 510
Pro Tyr Phe Ala Cys Pro Asp Ile Ala Val Ile Gln Val Pro Gln Asp
        515                 520                 525
Tyr Arg Asp Gly Asp Asp Ser Leu Phe Lys Arg Cys Cys Gln Ala Glu
    530                 535                 540
Tyr Arg Val Phe Phe Asn Ile Gly Met Val Ile Arg Asn Asp His Asp
545                 550                 555                 560
Ala Ile Ile Gln His Gly Thr Met Thr Leu Ile Arg Asn Ser Val Leu
                565                 570                 575
Gln Arg Leu Arg Trp Ala Glu Trp Ser Ile Cys Glu Asp Ala Glu Leu
            580                 585                 590
Gly Leu Arg Ile Leu Glu Asn Gly Phe Ser Thr Gly Tyr Val Ala Ile
        595                 600                 605
Ser Tyr Gly Lys Gly Leu Ile Pro Asp Thr Phe Met Asp Phe Lys Lys
    610                 615                 620
Gln Arg Tyr Arg Trp Ala Tyr Gly Val Ile Gln Ile Leu Lys Arg His
625                 630                 635                 640
Thr Gly Ser Leu Ile Ala Gly Thr Cys Glu Ala Leu Thr Pro Ile Gln
                645                 650                 655
Arg Tyr His Phe Ile Ala Gly Trp Met Pro Trp Ile Ala Gly Gly Ile
            660                 665                 670
```

```
Asn Tyr Phe Leu Ala Ile Ala Val Leu Leu Trp Ser Met Ala Met Ile
        675                 680                 685

Ile Gln Pro Asp Thr Leu Glu Pro Val Pro Trp Ile Phe Ser Ser Ser
    690                 695                 700

Leu Leu Leu Met Phe Val Leu Gly Val Cys Lys Ala Ile Ser Leu Tyr
705                 710                 715                 720

Gln Arg Leu Ala Ser Thr Asp Ile Lys Asp Ala Phe Ala Ala Ile Ile
                725                 730                 735

Ala Ser Met Ala Leu Tyr Ser Val Val Gly Lys Ala Val Leu Ser Ser
            740                 745                 750

Ala Phe Thr Ser Gly Leu Pro Phe Phe Arg Thr Pro Lys Gln Thr Ser
        755                 760                 765

Gly Ser Gly Leu Gly Lys Ala Leu Leu Asp Val Arg Glu Asp Leu Tyr
    770                 775                 780

Met Ala Val Val Trp Trp Val Met Thr Val Ser Leu Cys Phe Arg Lys
785                 790                 795                 800

Glu Ala Ile Gly Pro Asp Leu Gly Phe Trp Val Ala Ile Met Phe Ala
                805                 810                 815

Gln Ser Leu Pro Tyr Val Ala Ala Met Ile Met Ala Ile Leu Ser Ala
            820                 825                 830

Leu Ala Asn Arg Pro Ser Arg Ser Thr Thr
        835                 840
```